United States Patent
Terrett et al.

(10) Patent No.: US 10,710,994 B2
(45) Date of Patent: Jul. 14, 2020

(54) OXADIAZOLE TRANSIENT RECEPTOR POTENTIAL CHANNEL INHIBITORS

(71) Applicant: Genentech, Inc., South San Francisco, CA (US)

(72) Inventors: Jack Alexander Terrett, South San Francisco, CA (US); Huifen Chen, South San Francisco, CA (US); Lea Constantineau-Forget, Montreal (CA); Robin Larouche-Gauthier, Montreal (CA); Luce Lépissier, Montreal (CA); Francis Beaumier, Montreal (CA); Martin Déry, Montreal (CA); Chantal Grand-Maître, Montreal (CA); Claudio Sturino, Montreal (CA); Matthew Volgraf, South San Francisco, CA (US); Elisia Villemure, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/355,352

(22) Filed: Mar. 15, 2019

(65) Prior Publication Data

US 2019/0284179 A1    Sep. 19, 2019

Related U.S. Application Data

(60) Provisional application No. 62/644,987, filed on Mar. 19, 2018, provisional application No. 62/676,057, filed on May 24, 2018, provisional application No. 62/725,488, filed on Aug. 31, 2018, provisional application No. 62/812,806, filed on Mar. 1, 2019.

(51) Int. Cl.

| | |
|---|---|
| *A61P 23/00* | (2006.01) |
| *A61P 11/00* | (2006.01) |
| *A61P 29/00* | (2006.01) |
| *A61P 25/00* | (2006.01) |
| *C07D 471/04* | (2006.01) |
| *C07D 473/30* | (2006.01) |
| *C07D 487/04* | (2006.01) |
| *C07D 413/14* | (2006.01) |
| *C07D 498/04* | (2006.01) |
| *C07D 513/04* | (2006.01) |
| *A61K 31/427* | (2006.01) |

(52) U.S. Cl.
CPC .......... *C07D 413/14* (2013.01); *A61K 31/427* (2013.01); *A61P 11/00* (2018.01); *A61P 23/00* (2018.01); *A61P 25/00* (2018.01); *A61P 29/00* (2018.01); *C07D 471/04* (2013.01); *C07D 473/30* (2013.01); *C07D 487/04* (2013.01); *C07D 498/04* (2013.01); *C07D 513/04* (2013.01)

(58) Field of Classification Search
CPC ........... A61P 23/00; A61P 11/00; A61P 29/00; A61P 25/00; C07D 471/04; C07D 473/30; C07D 487/04; C07D 413/14; C07D 498/04; C07D 513/04; A61K 31/427

See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 5,004,697 A | 4/1991 | Pardridge et al. |
| 5,112,596 A | 5/1992 | Malfroy-Camine |
| 5,268,164 A | 12/1993 | Kozarich et al. |
| 5,506,206 A | 4/1996 | Kozarich et al. |
| 5,686,416 A | 11/1997 | Kozarich et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0162695 A1 | 8/2003 | Schatzberg et al. |
| 2004/0131692 A1 | 7/2004 | Kreuter et al. |
| 2004/0204354 A1 | 10/2004 | Nelson et al. |
| 2005/0089473 A1 | 4/2005 | Black et al. |
| 2005/0124533 A1 | 6/2005 | Schatzberg et al. |
| 2015/0376173 A1 | 12/2015 | Paek et al. |

(Continued)

FOREIGN PATENT DOCUMENTS

| | | |
|---|---|---|
| EP | 0102324 A2 | 3/1984 |
| EP | 0133988 A1 | 8/1984 |
| EP | 0438230 A2 | 7/1991 |
| WO | 2008/119741 A2 | 10/2008 |
| WO | 2011/114184 A1 | 9/2011 |
| WO | 2017/060488 A1 | 4/2017 |
| WO | 2018/096159 A1 | 5/2018 |
| WO | 2018/162607 A1 | 9/2018 |

OTHER PUBLICATIONS

RN1309344-12-4, registry entry compound, Jun. 14, 2011.*
RN1309116-79-7, registry entry compound, Jun. 13, 2011.*
Ackley, David C., et al. Optimization in Drug Discovery: In Vitro Methods "Metabolic Stability Accessed by LIver Microsomes and Hepatocytes" Yan, Zhengyin, ed., Totowa, New Jersey: Humana Press,:151-162 (Jan. 1, 2004).

(Continued)

*Primary Examiner* — Sun Jae Yoo
(74) *Attorney, Agent, or Firm* — Robert C. Hall

(57) ABSTRACT

The invention relates to compounds of formula I:

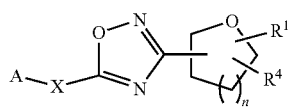

and pharmaceutically acceptable salts thereof wherein A, X, $R^1$, $R^4$ and n are as defined herein. In addition, the present invention relates to methods of manufacturing and methods of using the compounds of formula I as well as pharmaceutical compositions containing such compounds. The compounds may be useful in treating diseases and conditions mediated by TRPA1, such as pain.

38 Claims, No Drawings

(56) References Cited

OTHER PUBLICATIONS

Agopyan, N., et al., "TPRV1 receptors mediate particulate matter-induced apoptosis" Am J Physiol Lung Cell Mol Physiol 286:L563-L562 (Oct. 30, 2003).
Agopyan, N., et al., "Vanilloid receptor activation by 2- and 10-μm particles induces responses leading to apoptosis in human airway epithelial cells" Toxicol Appl Pharm 192:21-35 (May 28, 2003).
Ansel's Pharmaceutical Dosage Forms and Drug Delivery Systems (Table of Contents only, in 6 pages), Allen et al., 8th edition, Philadelphia, PA: Lippincott Williams & Wilkins, (2004).
Asai, Hideaki, et al., "Heat and mechanical hyperalgesia in mice model of cancer pain" Pain 117:19-29 (May 3, 2005).
Barton, N.J., et al., "Attenuation of experimental arthritis in TRPV1R knockout mice" Exp Mol Pathol 81:166-170 (Jun. 16, 2006).
Bobo et al., "Convection-enhanced delivery of macromolecules in the brain" PNAS Sci. USA 91:2076-2080 ( 1994).
Boleskei, Kata, et al., "Investigation of the role of TRPV1 receptors in acute and chronic nociceptive processes using gene-deficient mice" PAIN 117:368-376 (Jun. 27, 2005).
Bundgaard et al., "(C) Means to Enhance Penetration (1) Prodrugs as a means to improve the delivery of peptide drugs" Adv Drug Deliver Rev 8:1-38 ( 1992).
Bundgaard, A Textbook of Drug Design and Development; Chapter 5 "Design and Application of Prodrugs":113-191 ( 1991).
Bundgaard, "Design of prodrugs: Bioreversible derivatives for various functional groups and chemical entities" Design of Prodrugs: 1 ( 1985).
Bundgaard, "Formation of Prodrugs of Amines, Amindes, Ureides and Imides" Methods in Enzymology 112:347 ( 1985).
CAS Registry Database, 1069804-72-3, Nov. 2, 2008.
CAS Registry Database, 1309241-92-6, Jun. 13, 2011.
CAS Registry Database, 1381342-13-7, abstract (Database Registry [Online] Chemical Abstracts Service, Columbus, Ohio, US; Jul. 4, 2012 Database accession No. 1381342-13-7 abstract), pp. 1 Jul. 4, 2012.
CAS Registry Database, 887037-04-9, abstract (Database Registry [online] Chemical Abstracts Service, Columbus, Ohio, US; Jun. 7, 2006, Database accession No. 887037-04-9 abstract) Jun. 7, 2006.
Chan, C.L.H., et al., "Sensory fibres expressing capsaicin receptor TRPV1 in patients with crectal hypersensitivity and faecal urgency" LANCET 361:385-391 (Feb. 1, 2003).
Coffey, S. Rodd's Chemistry of Carbon Compounds Coffey, S., Second edition, Elsevier B.V.: Elsevier B.V., vol. I-IV ( 2008).
Database PubChem Compound [Online] NCBI, Sep. 8, 2005, Database accession No. CID 3437423 abstract).
de Yebenes et al., "Continuous Intracerebroventricular Infusion of Dopamine and Dopamine Agonists Trhough a Totally Implanted Drug Delivery System in Animal Models of Parkinson's Disease" Movement Disorders 2(3):143-158 ( 1987).
Derong Ding et al., "Exploration of the structure-activity relationship of 1,2,4-oxadiazole antibiotics" Bioorg Med Chem Lett 25(21):4854-4857 (Nov. 1, 2015).
Dinis, Paulo, et al., "Anandamide-Evoked Activation of Vanilloid Receptor 1 Contributes to the Development of Bladder Hyper-reflexia and Noviceptive Transmission to Spinal Dorsal Horn NEurons in Cystitis" J Neurol Sci 24(50):11253-11263 (Dec. 15, 2004).
Eppstein, D. et al., "Biological activity of liposome-encapsulated murine interferon y is mediated by a cell membrane receptor" PNAS 82(11):3688-3692 (Jun. 1, 1985).
Fleisher et al., "Improved oral drug delivery: solubility limitations overcome by the use of prodrugs" Adv Drug Deliver Rev 19:115-130 ( 1996).
Gennaro et al. Remington: The Science and Practice of Pharmacy (Press), Philadelphia: Lippincott, Williams & Wilkins, ( 2000).
Geppetti, P., et al., "Activation and sensitisation of the vanilloid receptor: role in gastrointestinal inflammation and function" Brit J Pharmacol 141:1313-1320 (Mar. 29, 2004).
Ghilardi, J.R., et al., "Selective Blockade of the Capsaicin Receptor TRPV1 Attenuates Bone Cancer Pain" J Neurol Sci 25(12):3126-3131 (Mar. 23, 2005).
Gill et al., "Direct Brain Infusion of Glial Cell Line-Derived Neurotrophic Factor in Parkinson Disease" Nature Med. 9:589-595 (Mar. 31, 2003).
Goadsby, P. J., "Post-triptan Era for the Treatment of Acute Migraine" Curr Pain Head Reports 8:393-398 (Jan. 1, 2004).
Harbaugh, "Intracerebroventricular cholinergic drug administraction in Alzheimer's disease: preliminary results of a double-blind study" J. Neural. Transm. 24 Supply.:271-277 (1987).
HO Fiesers' Reagents for Organic Synthesis (Table of Contents, in 5 pages), Hoboken, New Jersey: John Wiley & Sons, Inc., vol. 23 ( 2007).
Honore, P., et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats" J Pharmacol Exp Ther 314(1):410-421 (Apr. 14, 2005).
Hwang et al., "Hepatic uptake and degradation of unilamellar sphingomyelin/cholesterol liposomes: A kinetic study" PNAS Sci. USA 77(7):4030-4034 ( 1980).
"International Preliminary Report on Patentability—PCT/EP2017/080571":pp. 1-28 (Feb. 7, 2018).
"International Search Report—PCT/EP2017/080571":pp. 1-5 (Jan. 26, 2017).
"International Search Report/Written Opinion—PCT/US2019/022659":pp. 1-15 (Jun. 24, 2019).
Kakeya et al., "Studies on Prodrugs of Cephalosporins.I. ///superscript:1)/// Synthesis and Biological Properties of Glycyloxbenzoyloxymethyl and Glycylaminobenzoyloxymethyl Esters of 7β-[2-(2-Aminothiazol-4yl)-(Z)-2-methoxyiminoacetamido]-3-3-methyl-3-cephem-4-carboxylic Acide" Chem. Pharm. Bull. 32(2):692-698 ( 1984).
Kimball, E.S., et al., "Vanilloid receptor 1 antagonists attenuate disease severity in dextran sulphate sodium-induced colitis in mice" Neurogastroent Motil 16:811-818 (Jan. 5, 2004).
Kosugi, Masafumi, et al., "Activation of TRPA1 Channel Facilitates Excitatory Synaptic Transmission in Substantia Gelatinosa Neurons of the Adult Rat Spinal Cord" J Neurol Sci 27(16):4443-4451 (Apr. 18, 2007).
Kremeyer, Barbara, et al., "A Gain-of-Function Mutation in TRPA1 Causes Familial Episodic Pain Syndrome" Neuro 66:671-680 (Jun. 10, 2010).
Lalloo, Umesh G., et al., "Capsazepine inhibits cough induced by capsaicin and citric acid but not by hypertonic saline in guinea pigs" J Appl Physiol:1082-1087 (May 23, 1995).
Langer et al., "Biocompatibility of polymeric delivery systems for macromolecules" J Biomed Mater Res 15:267-277 ( 1981).
Menendez, L., et al., "Analgesic effect of capsazepine and resiniferatoxin on bone cancer pain in mice" Neurosci Lett 393:70-73 (Sep. 19, 2005).
Monge et al., "The Reaction of 2-Indolecarbohydrazones With Ethoxycarbonylchloride. New Syntheses of 2,3-Dihydro-2-oxy-1,3,4-oxadiazoles and 1,2,3,4-Tetrahydro-4-oxo-5H-pyridazino [4,5-b]indoles" J Heterocyclic Chem 21(2):397-400 (Jan. 1, 1984).
Musser et al., "Synthesis of 2-/2,3-Dihydro-2-oxo-1,3,4-oxadiazol-5-yl) Benzo Heterocycles. A Novel Series of Orally Active Antial-lergic Agents" J. Med. Chem. 27:121-125 (Jan. 1, 1984).
Neuwelt, E. A. Implications of the Blood-Brain Barrier and Its Manipulation Neuwelt, E.A., ed., Plenum Publishing Corporation-Springer, vol. vols. 1-2:1-434, (Jan. 1, 1989).
Nielsen, N., et al., "Glycolamide Esters as Biolabile Prodrugs of Carboxylic Acid Agents: Synthesis, Stability, Bioconversion, and Physicochemical Properties" J Pharmacol Sci 77(4):285 (Apr. 1, 1988).
Notari, Robert, et al. Methods of Enzymology: Drug and Enzyme Targeting "Theory and Practice of Prodrug Kinetics" Widder, Kenneth J., eds, First edition, Waltham, MA: Academic Press, vol. 112:309-396 (Jun. 11, 1985).
Papanastassiou et al., "The Potential for Efficacy of the Modified (ICP 34.5) Herpes Simplex Virus HSV1716 Following Intratumoural Injection into Human Malignant Glioma: A Proof of Principle Study" Gene Ther 9:398-406 (Apr. 2, 2002).

(56) References Cited

OTHER PUBLICATIONS

Patel, S., et al., "I 2 mediated synthesis of 5-substituted-3-methyl/benzyl-1-3,4-oxadiazol-2(3H)-ones via sequential condensation/oxidative cyclization and rearrangement" Bioorg Chem 14(24):5683-5689 (Jan. 1, 2016).

Pomonis, J.D., et al., "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain" J Pharmacol Exp Ther 306(1):387-393 (Apr. 31, 2003).

Remington's Pharmaceutical Sciences (Table of Contents, total in 6 pages), Osol et al., 15th edition, Easton, PA: Mack Publishing Company, ( 1975).

Robinson et al., "Discovery of the Hemifumarate and (α-L-Alanyloxy)methyl Ether as Prodrugs of an Antirheumatic Oxindole: Prodrugs for the Enolic OH Group" J. Med. Chem. 39:10-18 ( 1996).

Rowe. R. C. et al. Handbook of Pharmaceutical Excipients, [GB] "Chemical Industry Press" (in Chinese with English Abstract),:137-139, 530-532,667-669.

Sanchez, Maria, et al., "Expression of the transient receptor potential vanilloid 1 (TRPV1) in LNCaP and PC-3 prostate cancer cells and in human prostate tissue" Eur J Pharmacol 515:20-27 (Apr. 8, 2005).

Schenkel et al., "Optimization of a Novel Quinazolinone-Based Series of Transient Receptor Potential A1 (TRA1) Antagonists Demostrating Potent in Vivo Activity" J Med Chem 59(6):2794-2809 (Mar. 24, 2016).

Sculptoreanu, A., et al., "Protein kinase C contributes to abnormal capsaicin responses in DRG nuerons from cats with feline interstitial cystits" Neurosci Lett 381:42-46 (Jan. 28, 2005).

Sidman, K., et al., "Controlled Release of Macromolecules and Pharmaceuticals from Synthetic Polypeptides Based on Glutamic Acid" Biopolymers 22:547-556 ( 1983).

Sugimoto, O., et al., "The use of a Mitsunobu reagent for the formation of heterocycles: a simple method for the preparation of 3-alkyl-e-aryl-1,3,4-oxadiazol-2(3H)-ones from carboxylic acids" Chem Commun 50(55):7314-7317 (Jan. 1, 2014).

Szabo, A., et al., "Role of Transient Receptor Potential Vanilloid 1 Receptors in Adjuvant-Induced Chronic Arthritis: In Vivo Study Using Gene-Deficient Mice" J Pharmacol Exp Ther 314(1):111-119 (Apr. 5, 2005).

Wael, et al., "Synthesis and Antimicrobial Activity of New 1,2,3-Triazolopyrimide Derivatives and Their Glycoside and Acyclic Nucleoside Analogs" J Heterocyclic Chem 49(3):607-612 (May 1, 2012).

Walker, Katherine, et al., "The VR1 Antagonist Capsazepine Reverses Mechanical Hyperalgesia in Models of Inflammatory and Neuropathic Pain" J Pharmacol Exp Ther 304(1):56-62 (Jan. 1, 2003).

Wei, Hong, et al., "Spinal transient receptor potential ankyrin 1 channel contributes to central pain hypersensistivity in various pathophysiological conditions in the rat" Pain 152:582-591 (Nov. 29, 2010).

Wei, Hong, et al., "Spiral TRPA1 ion channels contribute to cutaneous neurogenic inflammation in the rat" Neurosci Lett 479:253-256 (May 23, 2010).

Xu, L., et al., "Discovery and Modification of in Vivo Active Nrf2 Hits Identifictaion and Structure-Activity Relationship study" J Med Chem 58(14):5419-5439 (Jul. 23, 2015).

Yiangou, Y., et al., "Vanilloid receptor 1 immunoreactivity in inflamed human bowel" LANCET 357:1338-1339 (Apr. 28, 2001).

\* cited by examiner

OXADIAZOLE TRANSIENT RECEPTOR POTENTIAL CHANNEL INHIBITORS

CROSS REFERENCE TO RELATED APPLICATIONS

This application claims priority to U.S. Provisional Application No. 62/644,987 filed Mar. 19, 2018, U.S. Provisional Application No. 62/676,057 filed May 24, 2018, U.S. Provisional Application No. 62/725,488 filed Aug. 31, 2018, and U.S. Provisional Application No. 62/812,806 filed Mar. 1, 2019, all of which is hereby incorporated by reference in their entirety.

FIELD OF THE INVENTION

The present invention relates to oxadiazole compounds, their manufacture, pharmaceutical compositions containing them and their use as Transient Receptor Potential (TRP) cation channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. Transient receptor potential cation channel, subfamily A, member 1 (TRPA1) is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a chemosensor.

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress (e.g., 4-hydroxynonenal and related compounds) activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., J. Neurosci 27, (2007) 4443-4451; Kremayer et al., Neuron 66 (2010) 671-680; Wei et al., Pain 152 (2011) 582-591); Wei et al., Neurosci Lett 479 (2010) 253-256)), providing additional rationale for the utility of small molecule TRPA1 inhibitors in the treatment of pain disorders.

SUMMARY OF THE INVENTION

In some embodiments, a compound of formula (I), stereoisomers thereof, tautomers thereof, and salts thereof are provided:

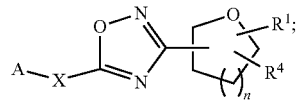

wherein:

A is: substituted or unsubstituted 6-6 fused bicyclic heteroaryl; substituted or unsubstituted 5-6 fused bicyclic heteroaryl; or substituted and unsubstituted 6-5 fused bicyclic heteroaryl;

X is; a bond; $C_{1-4}$ alkylene; —O—; —S—; —SO$_2$—; or —N(R$^a$)—;

n is: 0, 1, 2 or 3;

R$^a$ is H or $C_{1-6}$ alkyl which may be unsubstituted or substituted one or more times with halo;

R$^1$ is: H; or $C_{1-6}$ alkyl; and

R$^4$ is: substituted or unsubstituted phenyl; substituted or unsubstituted heteroaryl; or substituted or unsubstituted naphthyl;

or R$^1$ and R$^4$ may together form an unsubstituted or substituted $C_{3-6}$ cycloalkyl fused to a substituted or unsubstituted phenyl; substituted or unsubstituted heteroaryl; or substituted or unsubstituted naphthyl.

In other embodiments, the following compounds, stereoisomers thereof, and pharmaceutically acceptable salts thereof are provided:

Some other embodiments provide pharmaceutical compositions comprising a compound described above, or a pharmaceutically acceptable salt thereof, and a pharmaceutically acceptable carrier, diluent or excipient.

Some other embodiments provide a compound as described above, or a pharmaceutically acceptable salt thereof, for use in medical therapy.

Some other embodiments provide a compound as described above, or a pharmaceutically acceptable salt thereof, for the treatment or prophylaxis of a respiratory disorder.

Some other embodiments provide a compound as described above, or a pharmaceutically acceptable salt thereof, for the preparation of a medicament for the treatment or prophylaxis of a respiratory disorder.

Some other embodiments provide a method for treating a respiratory disorder in a mammal comprising, administering a therapeutically effective amount of a compound as described above, or a pharmaceutically acceptable salt thereof, to the mammal.

Some other embodiments provide a compound as described above, or a pharmaceutically acceptable salt thereof, for modulating TRPA1 activity.

Some other embodiments provide a compound as described above, or a pharmaceutically acceptable salt thereof, for the treatment or prophylaxis of a disease or condition mediated by TRPA1 activity.

Some other embodiments provide a use of a compound as described above, or a pharmaceutically acceptable salt thereof, for the preparation of a medicament for the treatment or prophylaxis of a disease or condition that is mediated by TRPA1 activity.

Some other embodiments provide a method for modulating TRPA1 activity, comprising contacting TRPA1 with a compound as described above, or a pharmaceutically acceptable salt thereof.

Some other embodiments provide a method for treating a disease or condition mediated by TRPA1 activity in a mammal, comprising administering a therapeutically effective amount of a compound as described above, or a pharmaceutically acceptable salt thereof, to the mammal.

DETAILED DESCRIPTION OF THE INVENTION

Definitions

Unless otherwise indicated, the following specific terms and phrases used in the description and claims are defined as follows:

The terms "moiety" and "substituent" refer to an atom or group of chemically bonded atoms that is attached to another atom or molecule by one or more chemical bonds thereby forming part of a molecule.

The term "substituted" refers to the replacement of at least one of hydrogen atom of a compound or moiety with another substituent or moiety. Examples of such substituents include, without limitation, halogen, —OH, —CN, oxo, alkoxy, alkyl, alkylene, aryl, heteroaryl, haloalkyl, haloalkoxy, cycloalkyl and heterocycle. For example, the term "alkyl substituted by halogen" refers to the fact that one or more hydrogen atoms of a alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms. Alkyl groups may be optionally substituted independently with one or more substituents described herein.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenylene" refers to linear or branched-chain divalent hydrocarbon radical of two to eight carbon atoms ($C_{2-8}$) with at least one site of unsaturation, i.e., a carbon-carbon double bond, wherein the alkenylene radical may be optionally substituted. Examples include, but are not limited to, ethylenylene or vinylene (—CH=CH—), allyl (—CH$_2$CH=CH—), and the like.

The term "alkoxy" denotes a group of the formula —O—R', wherein R' is an alkyl group. Alkoxy groups may be optionally substituted independently with one or more substituents described herein. Examples of alkoxy moieties include methoxy, ethoxy, isopropoxy, and tert-butoxy.

"Aryl" means a cyclic aromatic hydrocarbon moiety having a mono-, bi- or tricyclic aromatic ring of 5 to 16 carbon ring atoms. Bicyclic aryl ring systems include fused bicyclics having two fused five-membered aryl rings (denoted as 5-5), having a five-membered aryl ring and a fused six-membered aryl ring (denoted as 5-6 and as 6-5), and having two fused six-membered aryl rings (denoted as 6-6). The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted.

The term "heteroaryl" denotes an aromatic heterocyclic mono-, bi- or tricyclic ring system of 5 to 16 ring atoms, comprising 1, 2, 3 or 4 heteroatoms selected from N, O and S, the remaining ring atoms being carbon. In some aspects, monocyclic heteroaryl rings may be 5-6 membered. Bicyclic heteroaryl ring systems include fused bicyclics having two fused five-membered heteroaryl rings (denoted as 5-5), having a five-membered heteroaryl ring and a fused six-membered heteroaryl ring (denoted as 5-6 and 6-5), and having two fused six-membered heteroaryl rings (denoted as 6-6). The heteroaryl group can be optionally substituted as defined herein. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl or trifluoromethyl.

The term "heteroalkyl" refers to a straight- or branched-chain alkyl as defined herein having from 2 to 14 carbons, from 2 to 10 carbons, or from 2 to 6 carbons in the chain, one or more of which has been replaced by a heteroatom selected from S, O, P and N. Non-limiting examples of heteroalkyls include alkyl ethers, secondary and tertiary alkyl amines, amides, and alkyl sulfides.

"Cycloalkyl" means a saturated or partially unsaturated carbocyclic moiety having mono-, bi-(including bridged bicyclic) or tricyclic rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_6$) cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl), bicyclo[3.1.0]hexanyl, bicyclo[3.1.0]hexenyl, bicyclo[3.1.1]heptanyl, and bicyclo[3.1.1]heptenyl. The cycloalkyl moiety can be attached in a "spirocycloakyl" fashion such as "spirocyclopropyl":

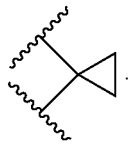

"Heterocycle" or "heterocyclyl" refers to a 4, 5, 6 and 7-membered monocyclic, 7, 8, 9 and 10-membered bicyclic (including bridged bicyclic) or 10, 11, 12, 13, 14 and 15-membered bicyclic heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In some aspects, the heterocycle is a heterocycloalkyl. In particular embodiments heterocycle or heterocyclyl refers to a 4, 5, 6 or 7-membered heterocycle. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure. Any of the heterocycle ring atoms can be optionally substituted with one or more substituents described herein. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, azabicyclo[2.2.1]heptanyl, azabicyclo[3.1.0]hexanyl, azabicyclo[3.1.1]heptanyl, octahydroindolyl, or tetrahydroquinolinyl.

The term "fused bicyclic" denotes a ring system including two fused rings, including bridged cycloalkyl and bridged heterocycloalkyl as defined elsewhere herein. The rings are each independently, aryl, heteroaryl, cycloalkyl, and heterocycle. In some aspects, the rings are each independently, $C_{5-6}$ aryl, 5-6 membered heteroaryl, $C_{3-6}$ cycloalkyl, and 4-6 membered heterocycle. Non-limiting examples of fused bicyclic ring systems include $C_{5-6}$ aryl-$C_{5-6}$ aryl, $C_{5-6}$ aryl-4-6 membered heteroaryl, and $C_{5-6}$ aryl-$C_{5-6}$ cycloalkyl.

The term "fused tricyclic" denotes a ring system including three fused rings. The rings are each independently, aryl, heteroaryl, cycloalkyl, and heterocycle. In some aspects, the rings are each independently, $C_{5-6}$ aryl, 5-6 membered heteroaryl, $C_{3-6}$ cycloalkyl, and 4-6 membered heterocycle. An non-limiting example of a fused tricyclic ring system is $C_{3-6}$ cycloakyl-$C_{3-6}$ cycloalkyl-$C_{5-6}$ aryl, for instance, $C_3$ cycloalkyl-$C_5$ cycloalkyl-$C_6$ aryl.

Unless otherwise indicated, the term "hydrogen" or "hydro" refers to the moiety of a hydrogen atom (—H) and not $H_2$.

In the description herein, if there is a discrepancy between a depicted structure and a name given to that structure, then the depicted structure controls. Additionally, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. As used herein, "pharmaceutically acceptable" refers to a carrier, diluent or excipient that is compatible with the other ingredients of the formulation and not deleterious to the recipient thereof. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetyl-cystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in compounds (l), (m) and (n) for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, a therapeutically effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

One embodiment of the present invention provides for compounds of formula I, stereoisomers thereof, tautomers thereof, and salts thereof:

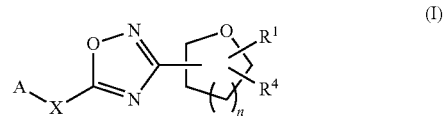

(I)

or a pharmaceutically acceptable salt thereof,
wherein:
A is: substituted or unsubstituted 6-6 fused bicyclic heteroaryl which may be partially saturated; substituted or unsubstituted 5-6 fused bicyclic heteroaryl which may be partially saturated; or substituted and unsubstituted 6-5 fused bicyclic heteroaryl which may be partially saturated;

X is: a bond; $C_{1-4}$ alkylene; —O—; —S—; —SO$_2$—; or —N(R$^a$)—;

n is: 0, 1, 2 or 3;

R$^a$ is H or $C_{1-6}$ alkyl which may be unsubstituted or substituted one or more times with halo;

R$^1$ is: H; or $C_{1-6}$alkyl; and

R$^4$ is: substituted or unsubstituted phenyl; substituted or unsubstituted heteroaryl; or substituted or unsubstituted naphthyl;

or R$^1$ and R$^4$ may together form an unsubstituted or substituted $C_{3-6}$cycloalkyl fused to a substituted or unsubstituted phenyl; substituted or unsubstituted heteroaryl; or substituted or unsubstituted naphthyl.

In some aspects, n is 0, 1 or 2. In some aspects, n is 0 or 1. In some aspects, n is 0. In some aspects, n is 1.

In some aspects, A is selected from:

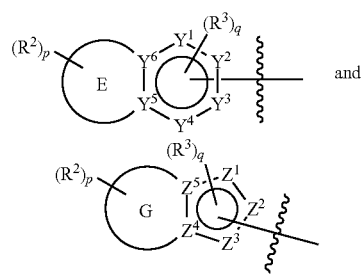

and wherein:

E is a five membered or a six membered heteroaryl ring wherein one ring carbon atom is optionally substituted with oxo;

G is a six membered heteroaryl ring having one ring carbon atom substituted with oxo;

one to three of Y$^1$, Y$^2$, Y$^3$, Y$^4$, Y$^5$ and Y$^6$ are nitrogen, and the other of Y$^1$, Y$^2$, Y$^3$, Y$^4$, Y$^5$ and Y$^6$ are carbon, and one of Y$^1$, Y$^2$, Y$^3$ and Y$^4$ may be —C(O)— or —C(S)—;

one or two of Z$^1$, Z$^2$, Z$^3$, Z$^4$ and Z$^5$ are nitrogen and the other of Z$^1$, Z$^2$, Z$^3$, Z$^4$ and Z$^5$ are carbon;

each R$^2$ is independently; H, —$C_{1-4}$ alkyl; —$C_{1-4}$ haloalkyl; —CN; halo; halo$C_{1-4}$alkoxy; $C_{1-4}$ alkoxy; —OH; —SO$_2$—$C_{1-4}$alkyl; —$C_{1-4}$CN, $C_{1-4}$ aldehyde; $C_{1-4}$ ketone; benzylamino; or NR$^{14}$R$^{15}$;

p is 0, 1 or 2;

each R$^3$ is independently: H; —$C_{1-4}$ alkyl; —$C_{1-4}$ haloalkyl; —CN; halo; or —NR$^{14}$R$^{15}$;

q is 0 or 1;

R$^{14}$ and R$^{15}$ are each independently: H; substituted or unsubstituted —$C_{1-4}$alkyl; substituted or unsubstituted —C(O)—$C_{1-4}$ alkyl; substituted or unsubstituted $C_{3-6}$ cycloalkyl; substituted or unsubstituted 3- to 6-membered heterocycloalkyl; substituted or unsubstituted 3- to 6-membered —$C_{1-4}$alkyl-heterocycloalkyl; substituted or unsubstituted —$C_{1-4}$ heteroalkyl; —C(O)NR$^{16}$R$^{17}$; substituted or unsubstituted —$C_{1-4}$ alkyl-C(O)NR$^{16}$R$^{17}$; substituted or unsubstituted phenyl; or substituted or unsubstituted benzyl;

or R$^{14}$ and R$^{15}$ together with the atoms to which they are attached may form a 4-, 5-, 6- or 7-membered ring that optionally includes one additional heteroatom selected from O, N and S; and R$^{16}$ and R$^{17}$ each are independently H and $C_{1-4}$ alkyl.

In some aspects, A is a fused heteroaryl moiety selected from:

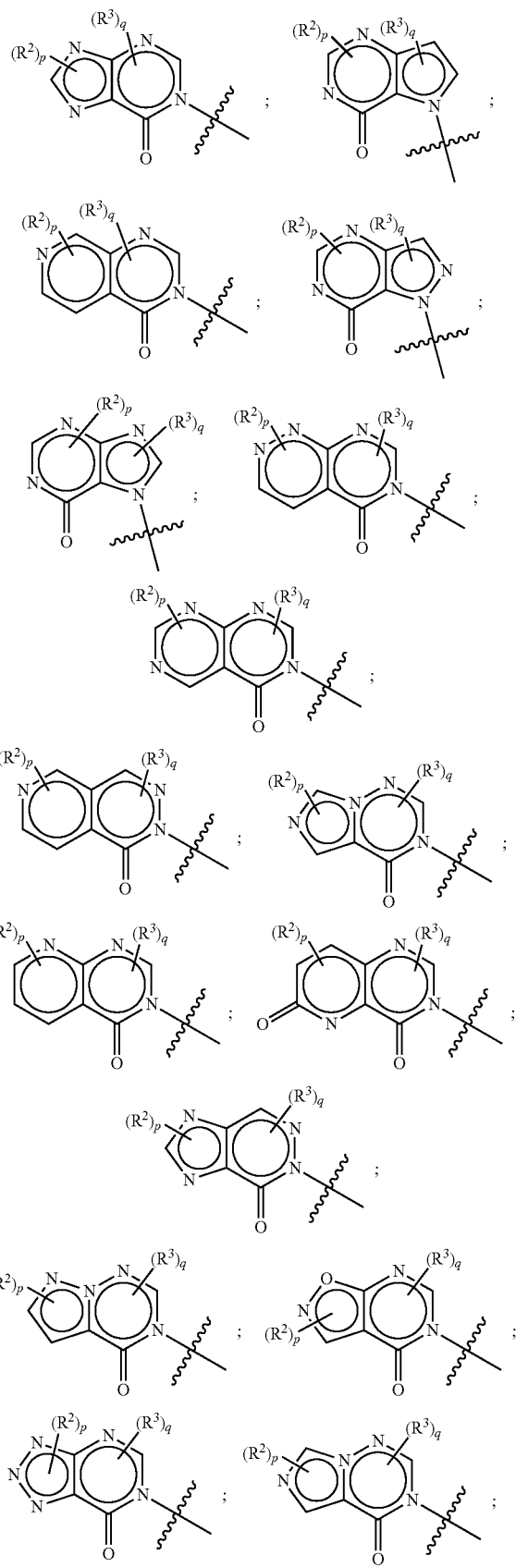

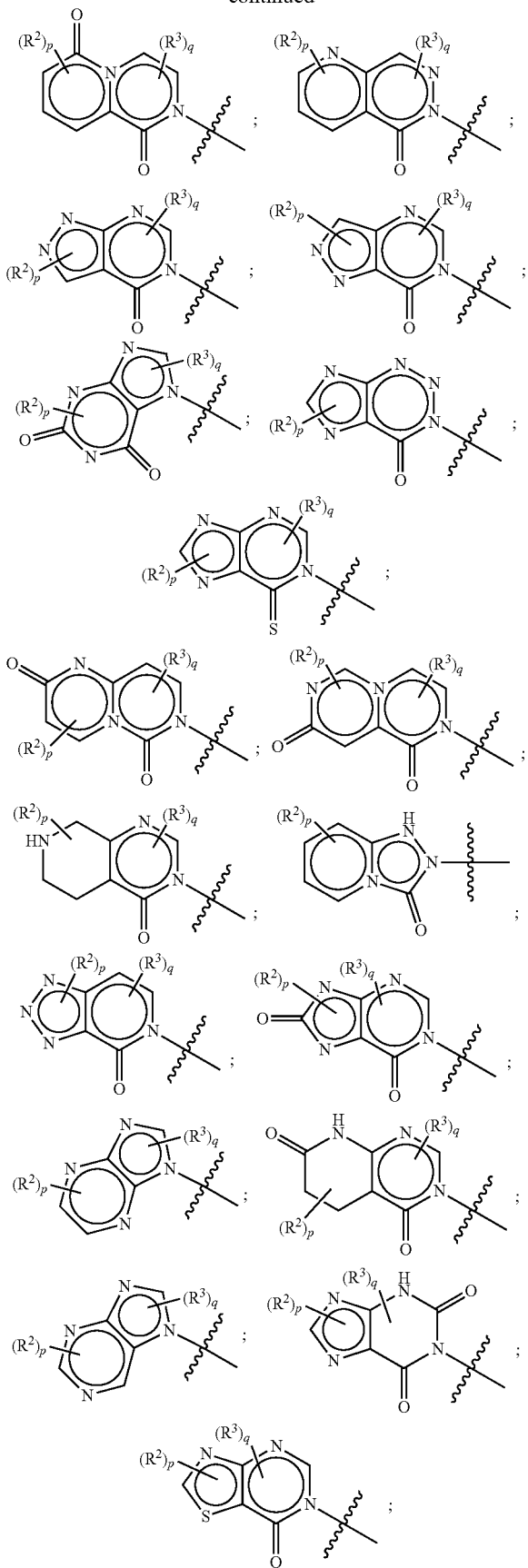

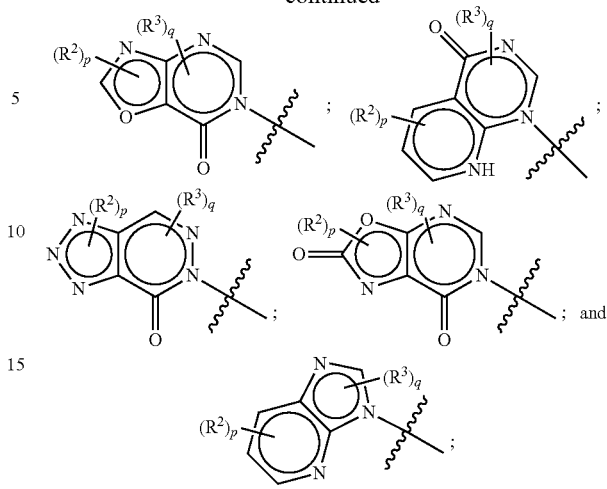

wherein:

each $R^2$ is independently: H; D; —$C_{1-4}$ alkyl; —$C_{1-4}$ haloalkyl; $C_{1-4}$ alkoxy; —CN, halo; —C(O)CH$_3$; —C(O)NR$^{16}$R$^{17}$; —NH$_2$; NHC$_{1-4}$ alkyl wherein the $C_{1-4}$ alkyl optionally comprises an oxygen heteroatom or an —OH substitutent; —NHC(O)—C$_{1-4}$alkyl; —NHCH$_2$C(O)N(C$_{1-4}$ alkyl)$_2$; benzylamino; and —NH—C$_{4-6}$ heterocyclo comprising an oxygen heteroatom;

each $R^3$ is independently: H; D: —$C_{1-4}$ alkyl; —$C_{1-4}$ haloalkyl; —CN; halo; or NR$^{14}$R$^{15}$;

p is 0, 1 or 2; and q is 0 or 1.

In some aspects, each $R^2$ is independently selected from H, -D, —$C_{1-4}$ alkyl, —$C_{1-4}$ haloalkyl, —CN, halo, —C(O)CH$_3$, —NH$_2$, NHC$_{1-4}$ alkyl wherein the $C_{1-4}$ alkyl optionally comprises an oxygen heteroatom or an —OH substitutent, —NHC(O)—$C_{1-4}$ alkyl, —NHCH$_2$C(O)N($C_{1-4}$ alkyl)$_2$, —C(O)—NH$_2$; and —NH—$C_{4-6}$ heterocyclo comprising an oxygen heteroatom. In some aspects, each $R^2$ is independently selected from H, D, —CH$_3$, —CN, -halo, —NH$_2$, —NHCH$_3$, NHCH$_2$CH$_3$, —NHCH$_2$CH$_2$CH$_2$OH, —NHCH$_2$CH$_2$OCH$_3$, —NHC(O)CH$_3$, —NHCH$_2$C(O)N(CH$_3$)$_2$,

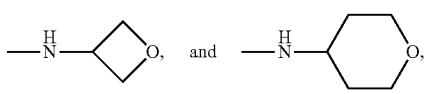

and p is 0 or 1. $R^3$ is selected from H, -D, —$C_{1-4}$ alkyl, —$C_{1-4}$ haloalkyl, —CN and halo. In some aspects, $R^3$ is selected from H, -D and —CN.

In some aspects, each $R^2$ is independently selected from H, -D, —$C_{1-4}$ alkyl, or —NH$_2$.

In some aspects, each $R^3$ is independently selected from H, -D, —$C_{1-4}$ alkyl, or —NH$_2$.

In some aspects, each $R^2$ is independently selected from H, -D, or —$C_{1-4}$ alkyl.

In some aspects, each $R^3$ is independently selected from H, -D, or —$C_{1-4}$ alkyl.

In some aspects, A is a fused heteroaryl moiety selected from:

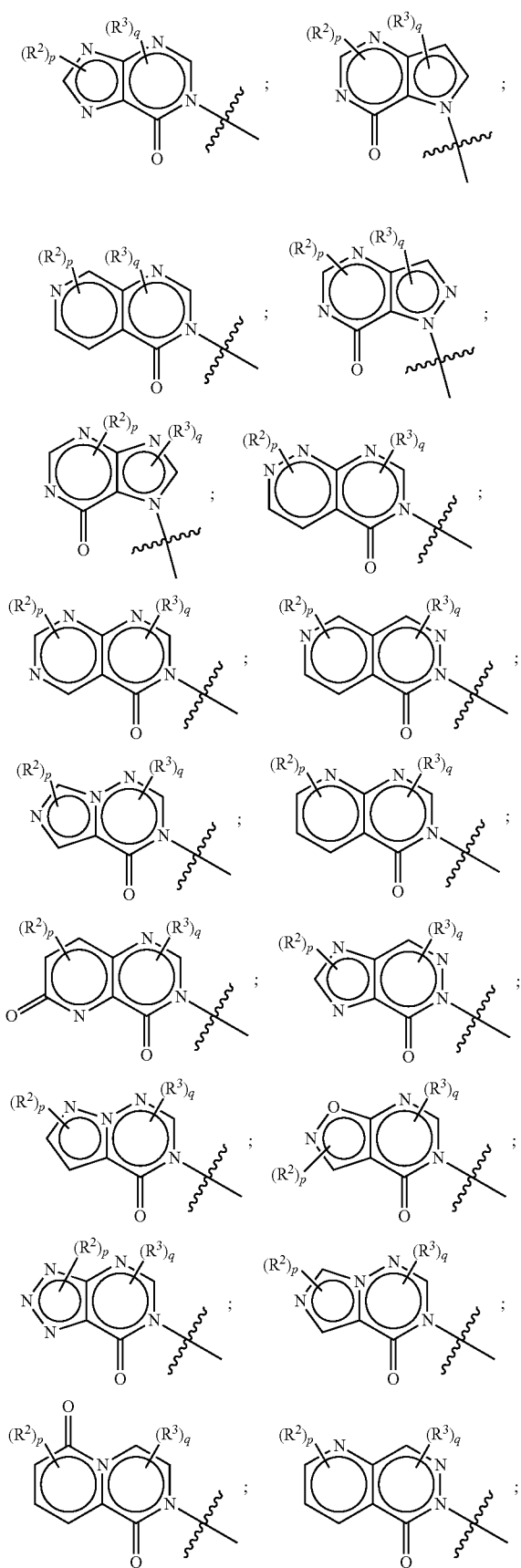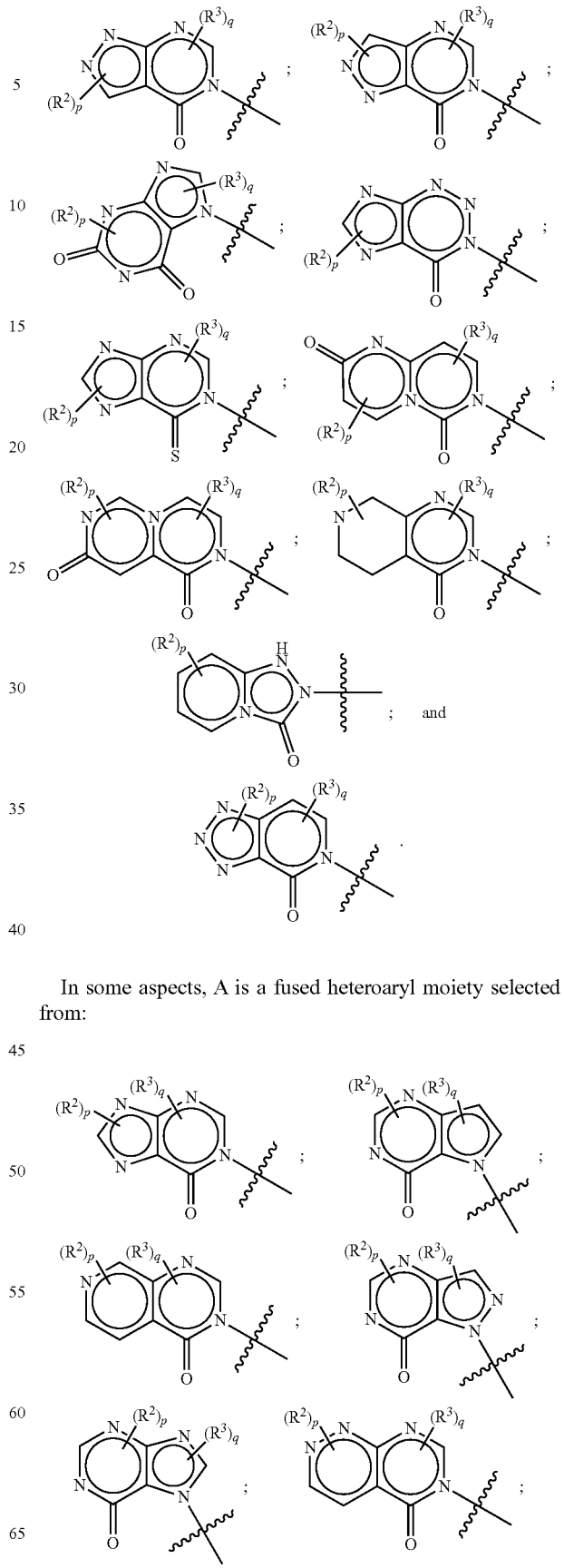
In some aspects, A is a fused heteroaryl moiety selected from:

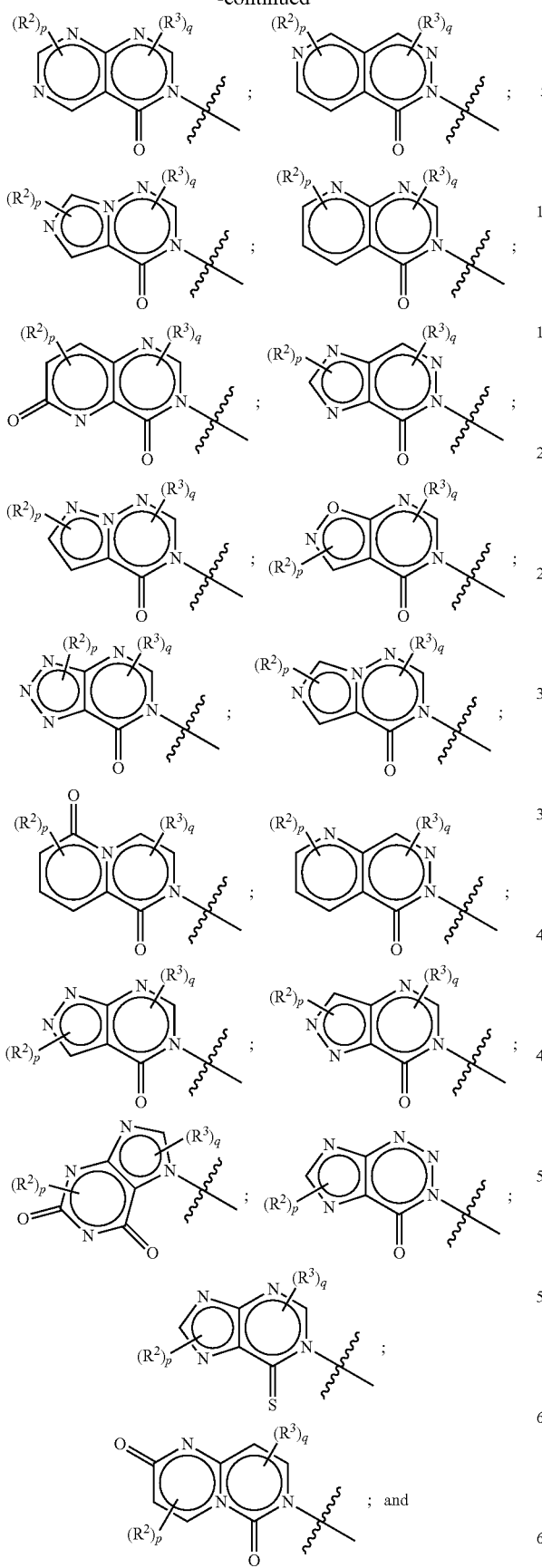
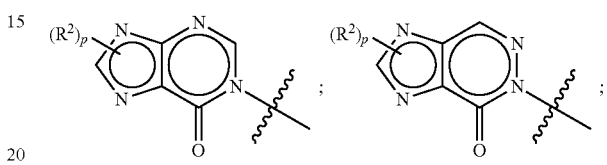
wherein $R^2$, $R^3$, p and q are as defined elsewhere herein.
In some aspects, A is selected from:
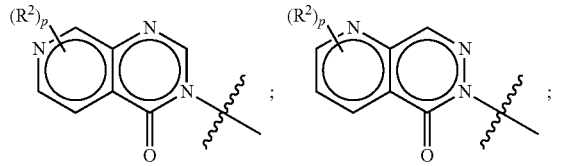
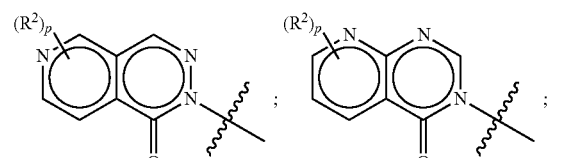
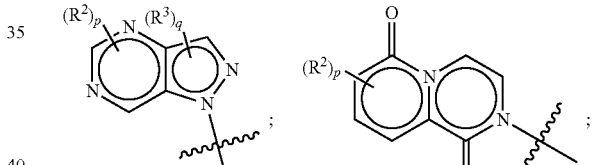
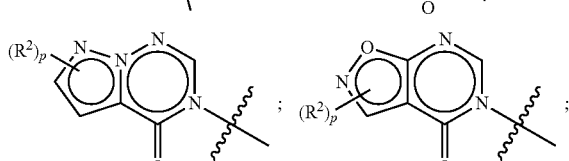
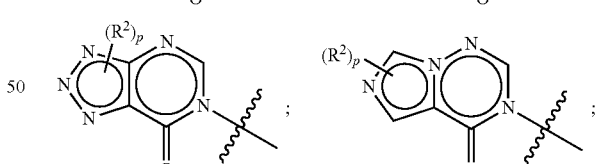
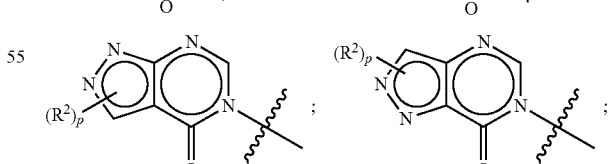
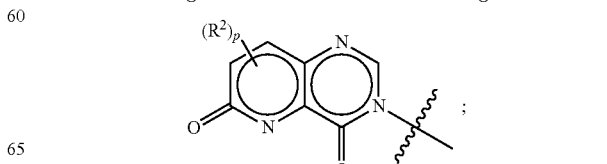
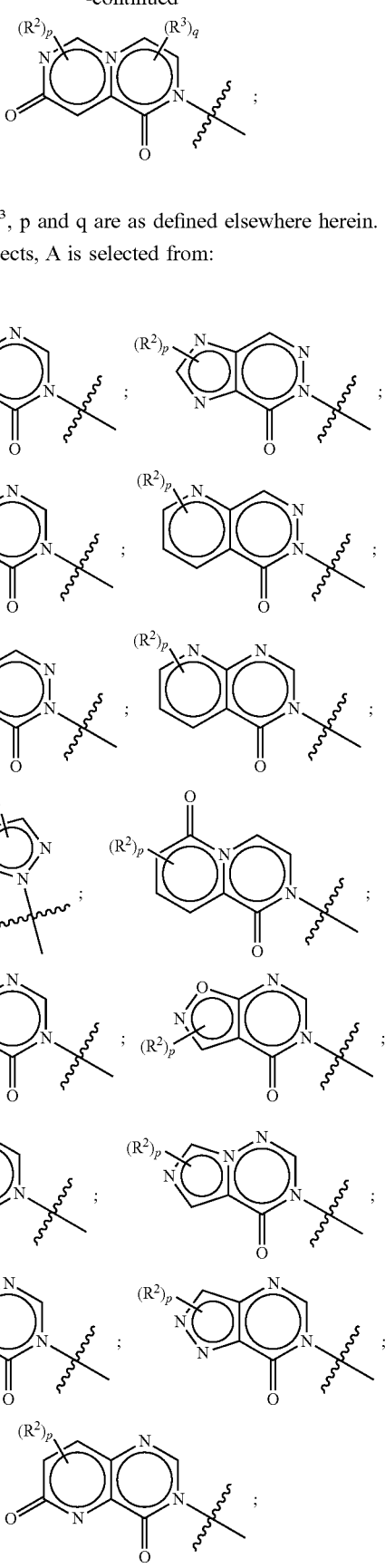

-continued
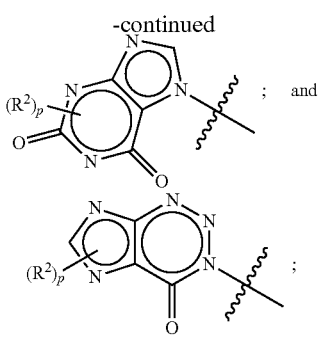
wherein $R^2$, $R^3$, p and q are as defined elsewhere herein.
In some aspects, A is selected from:
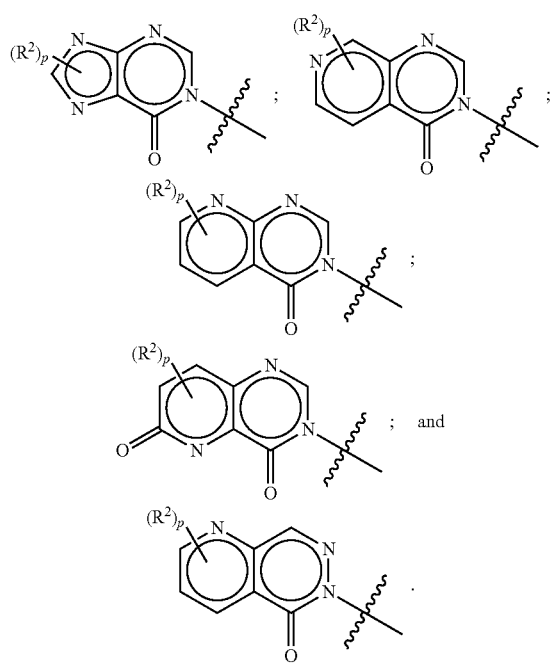
wherein $R^2$, $R^3$, p and q are as defined elsewhere herein.
In n some aspects, A is:
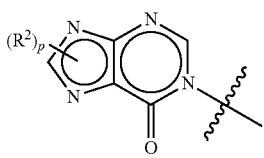
In some aspects, A is:
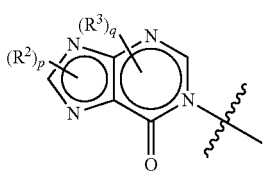
In some aspects, A is selected from:
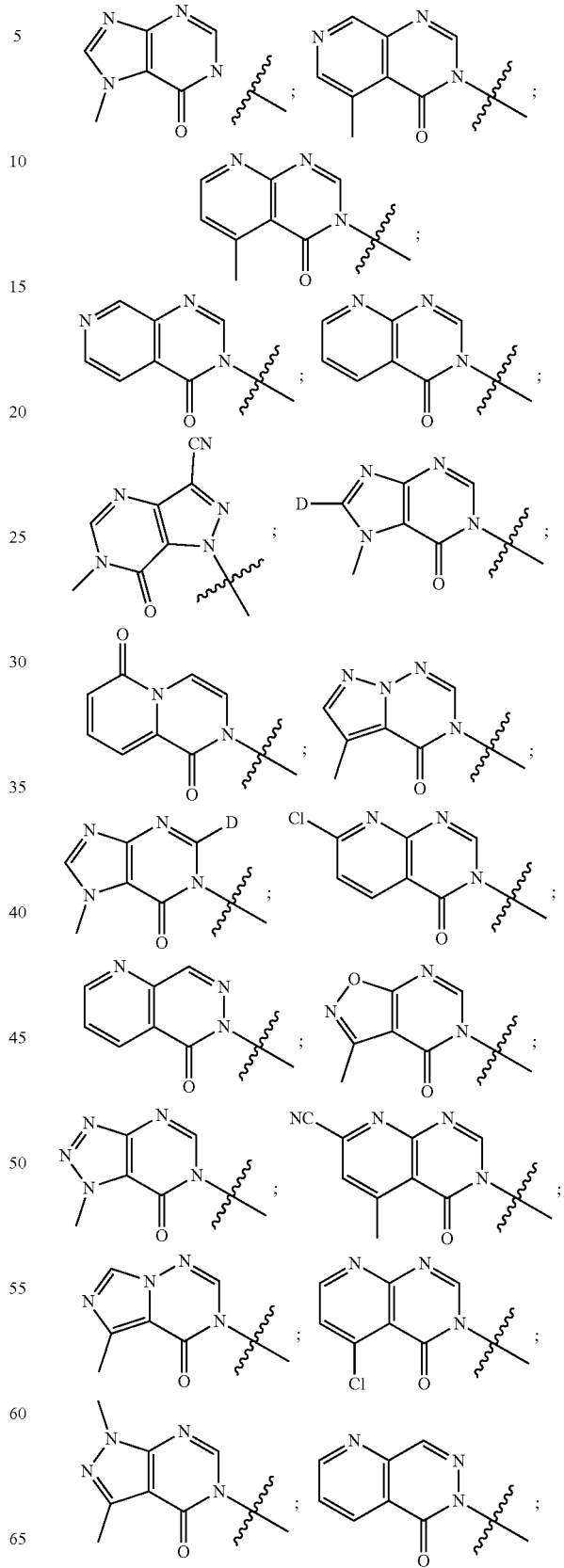

-continued
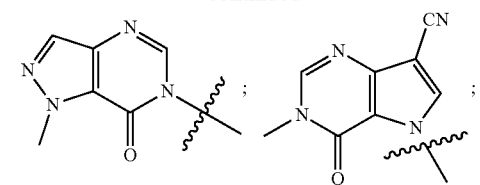
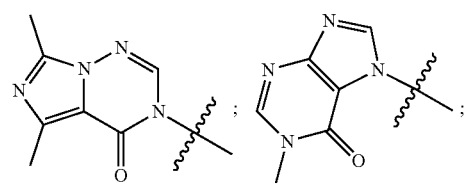
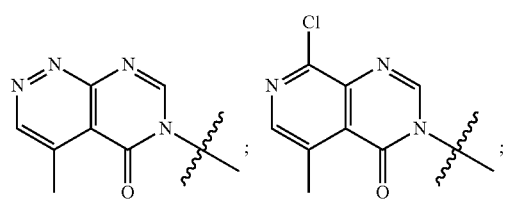
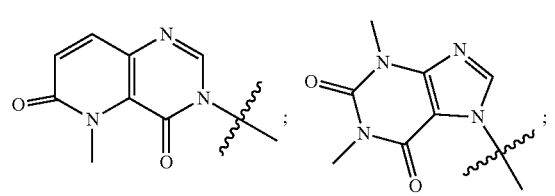
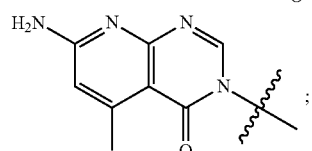
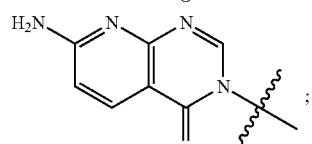
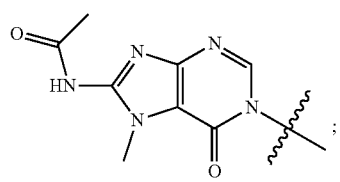
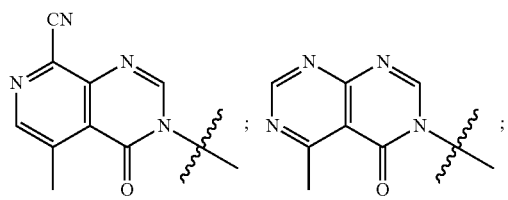
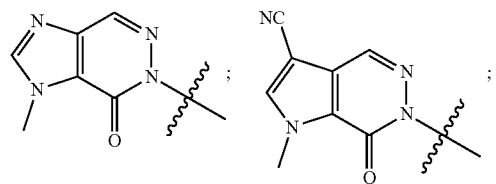
-continued
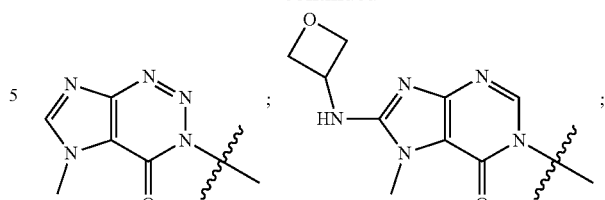
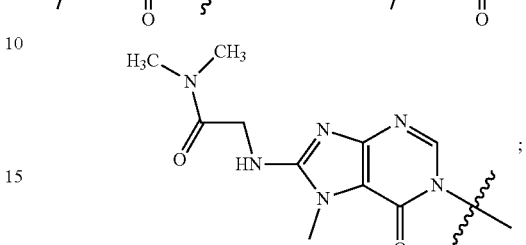
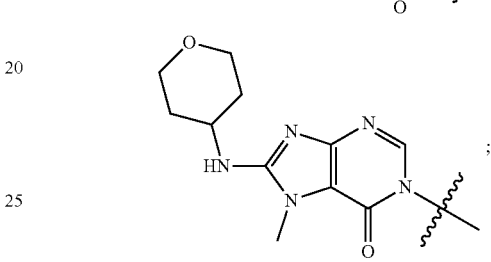
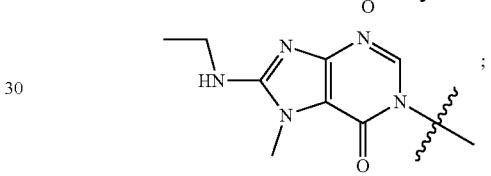
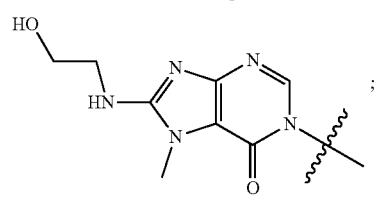
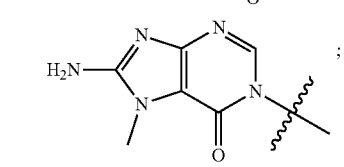
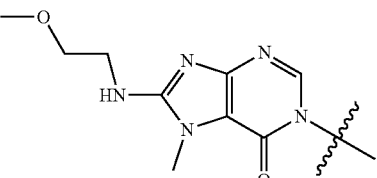
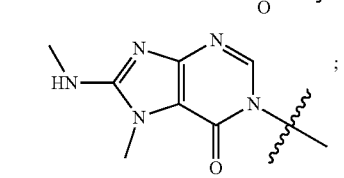
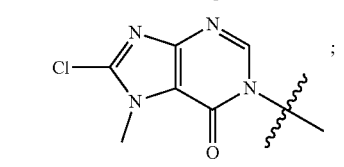

-continued
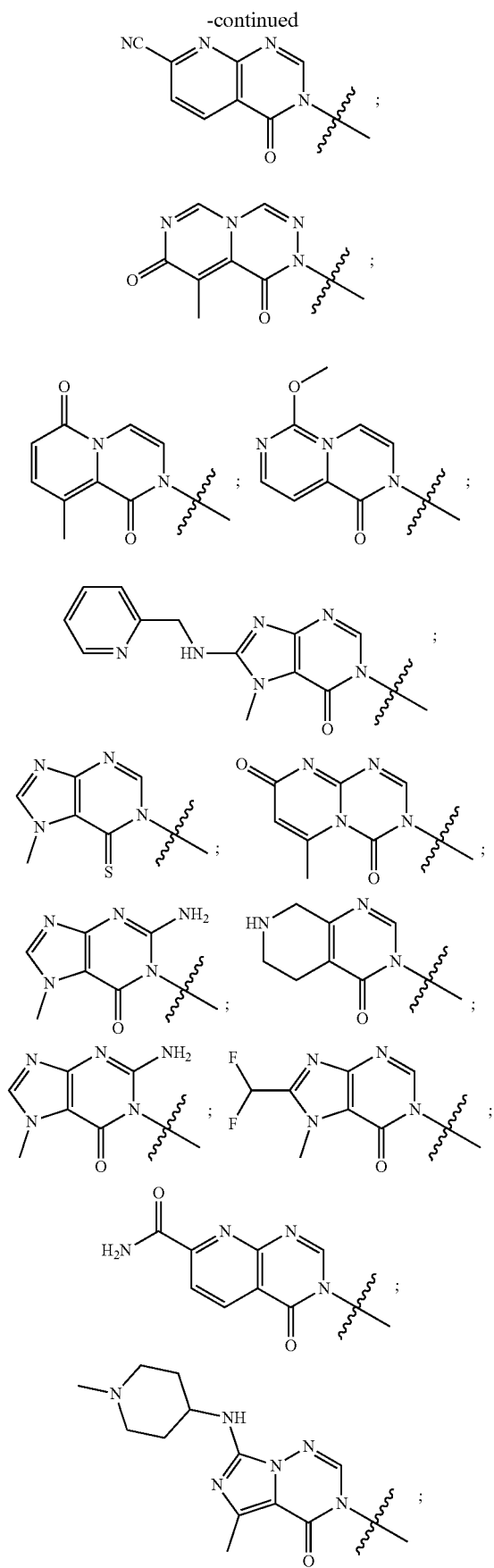
-continued
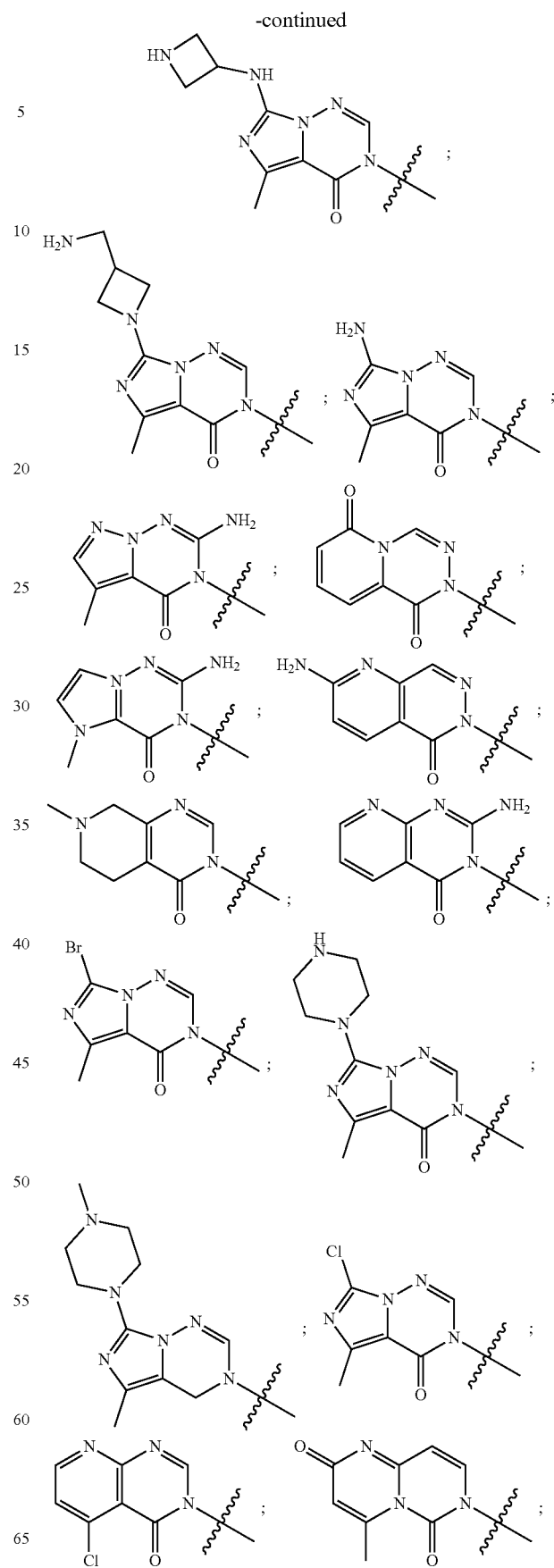

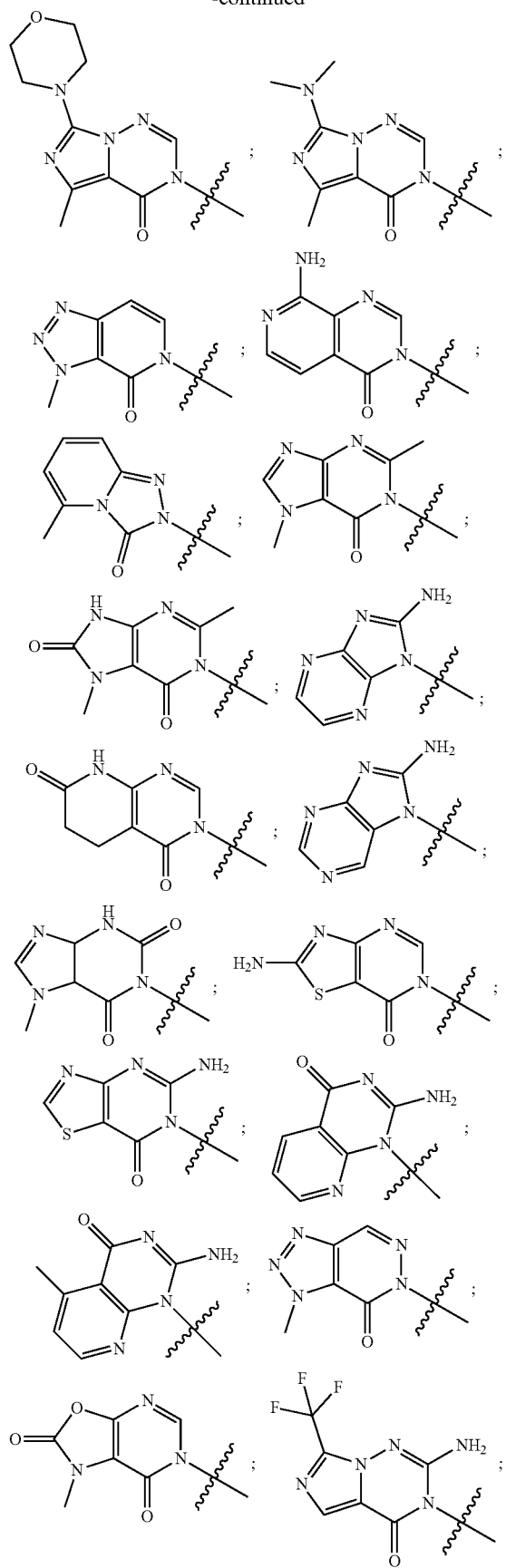
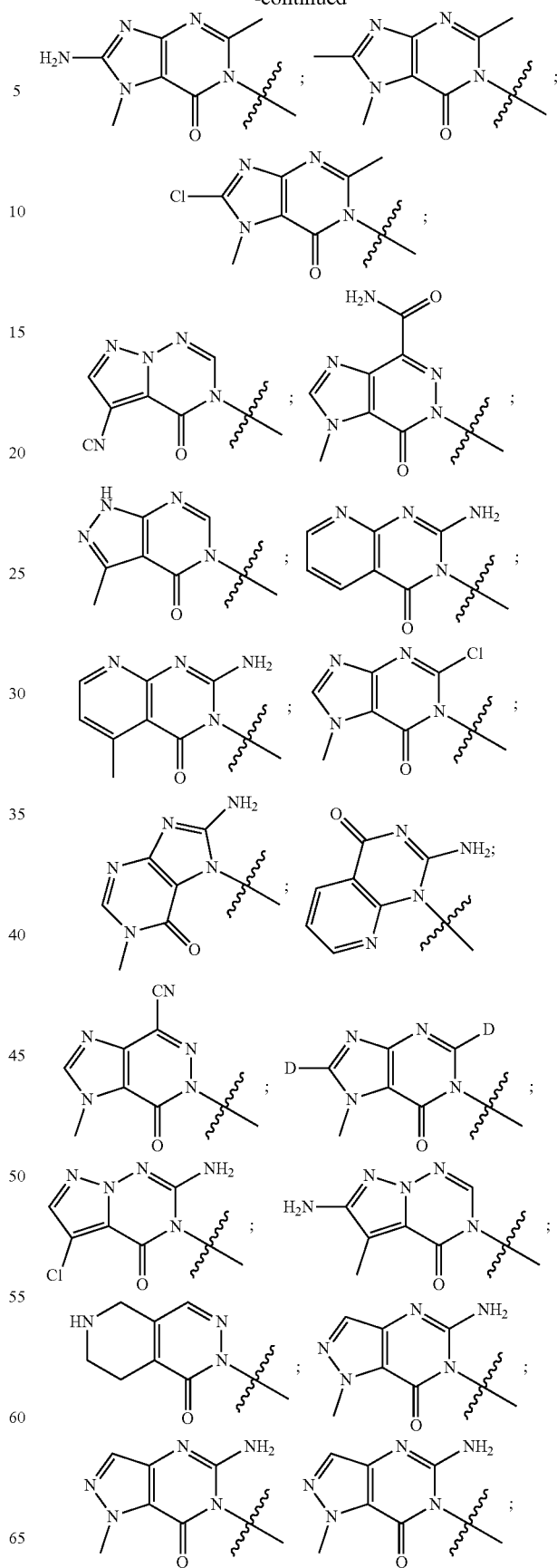

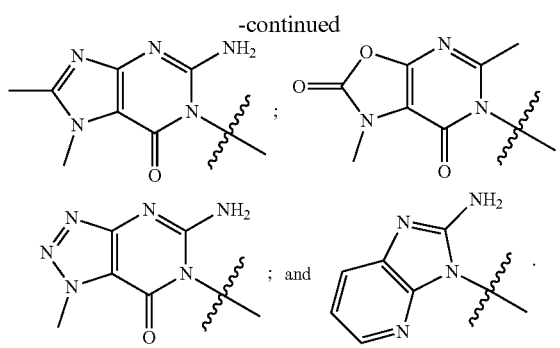
In some aspects, A is selected from:
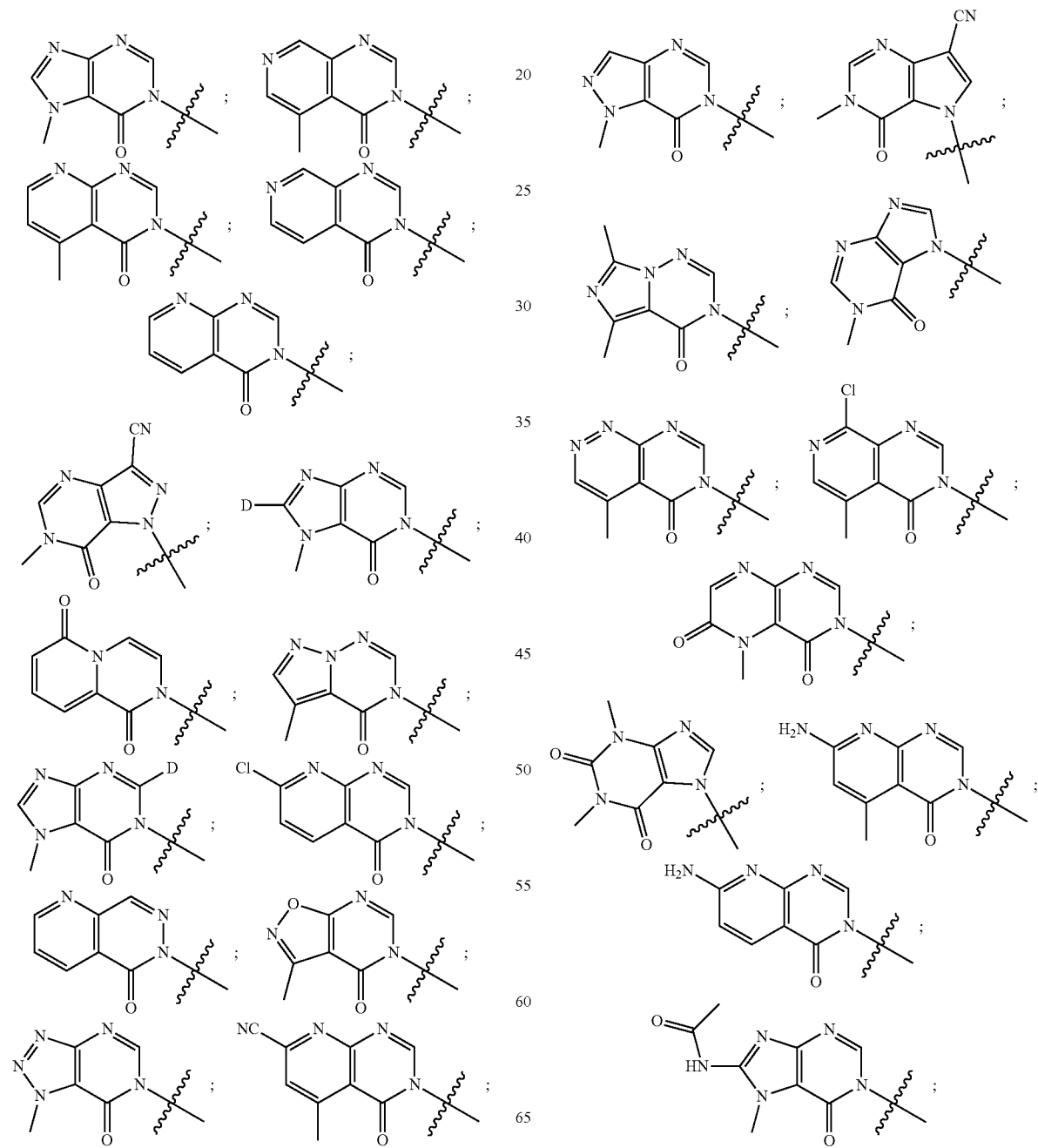

27
-continued
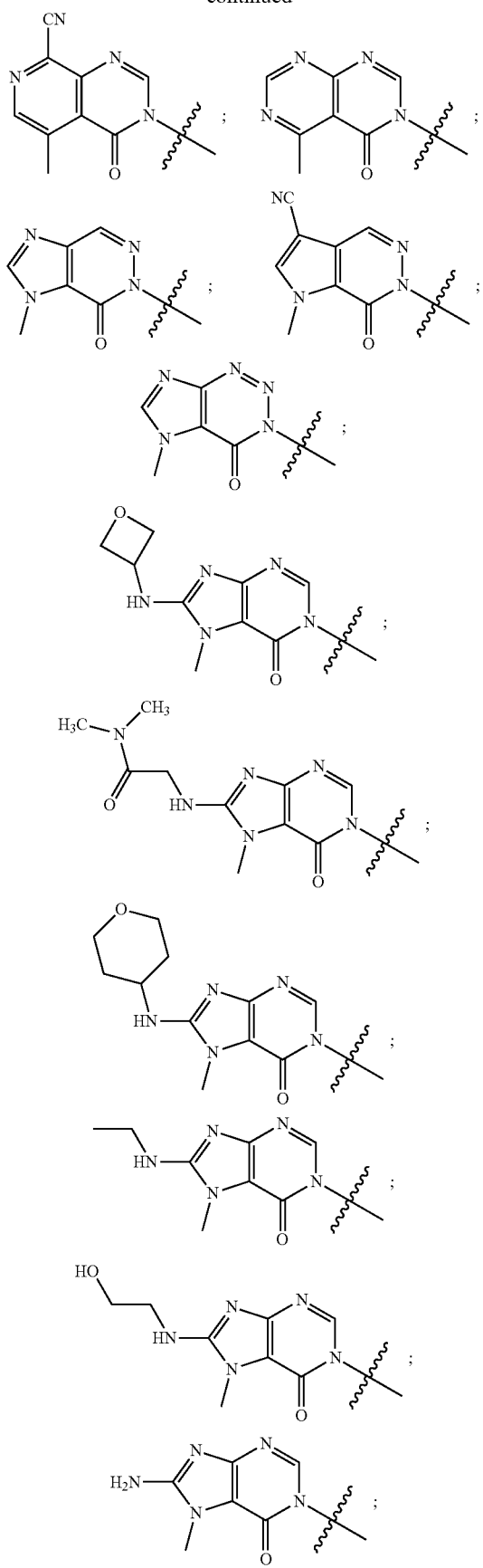
28
-continued
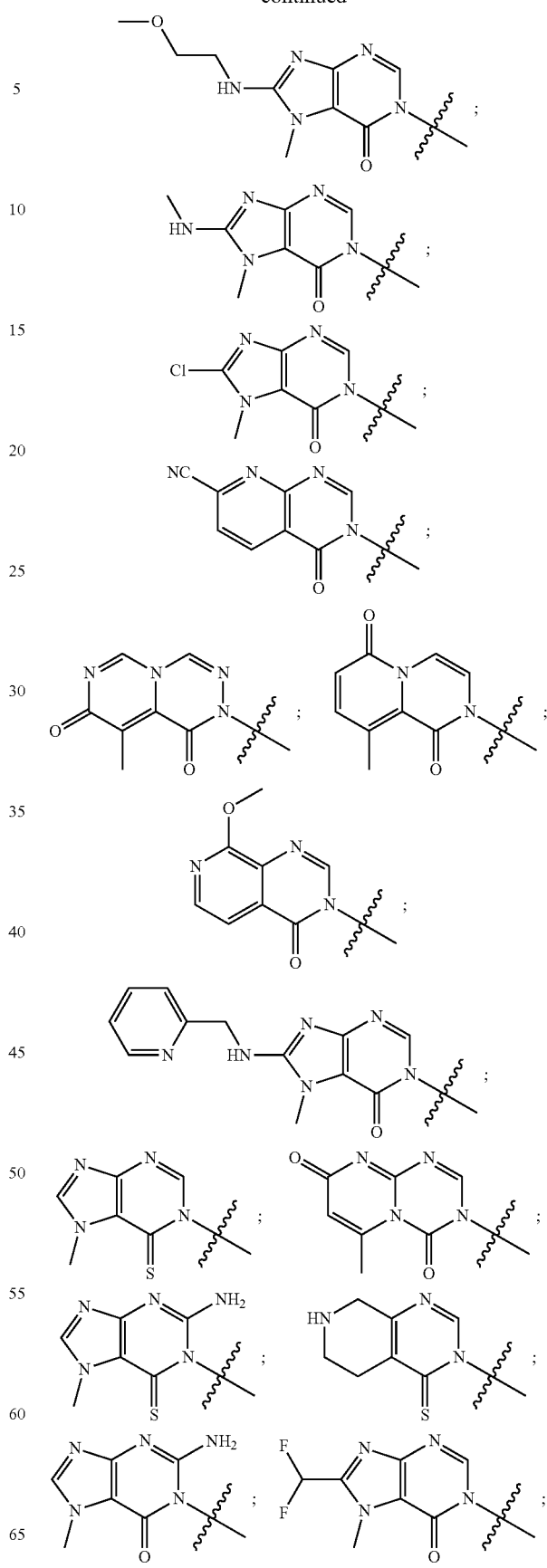

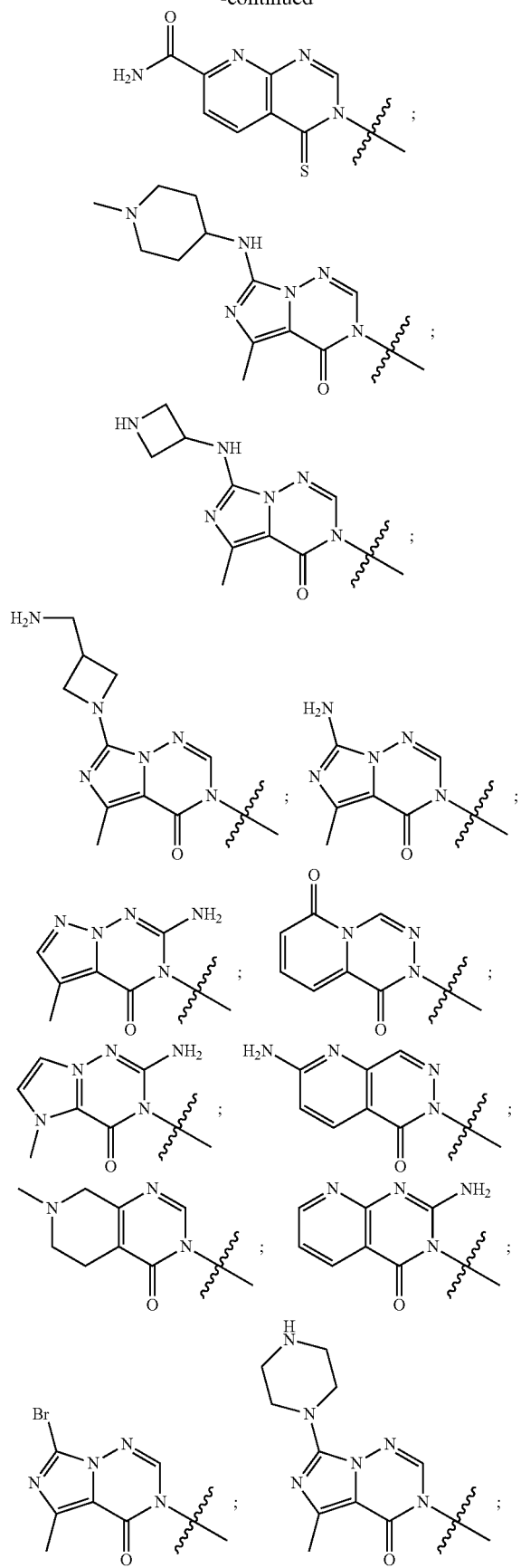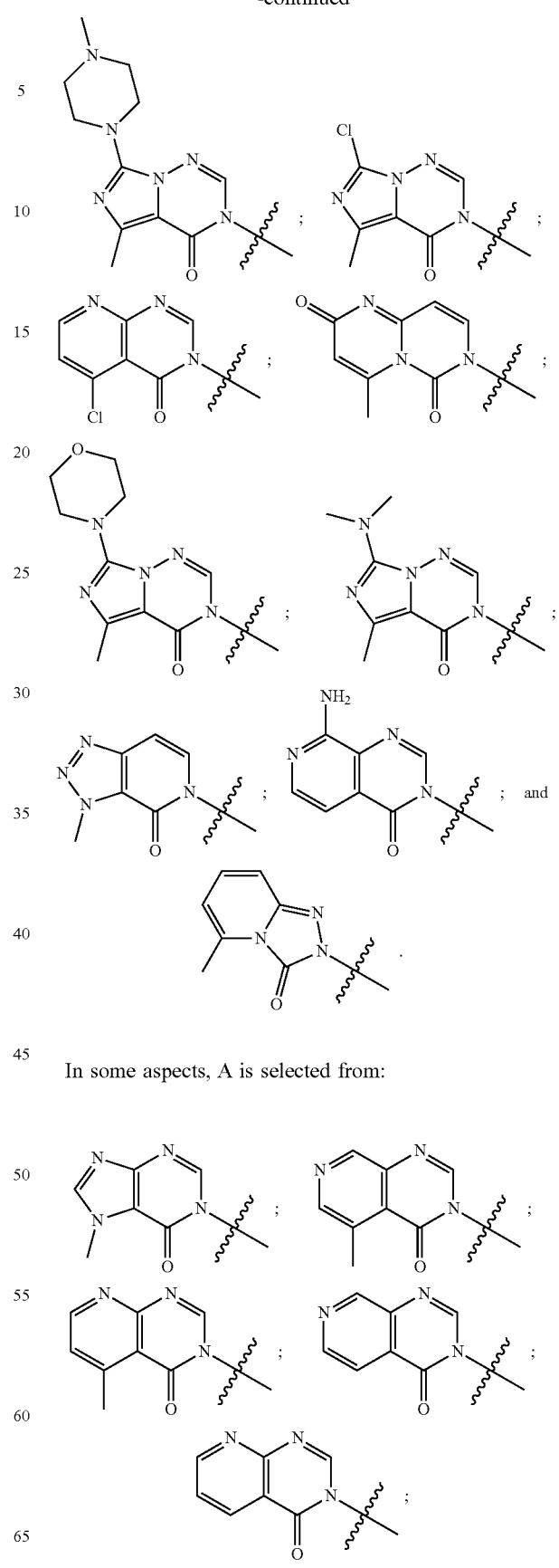
In some aspects, A is selected from:
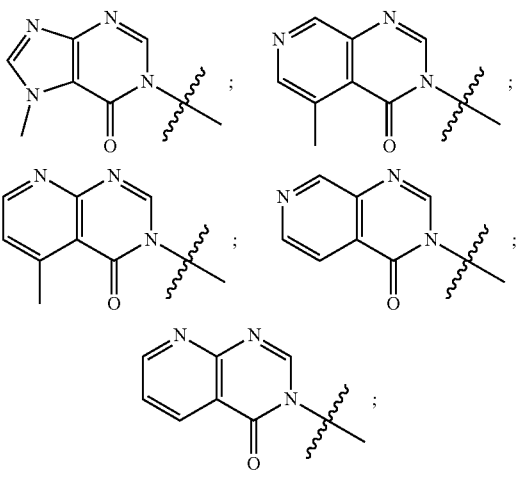

-continued
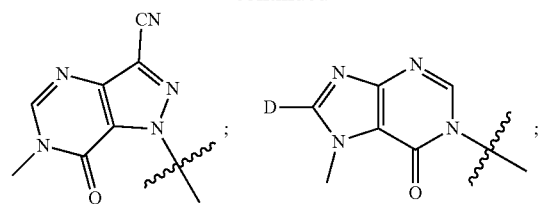
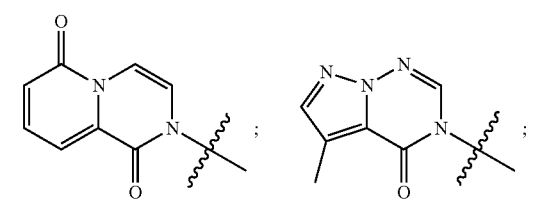
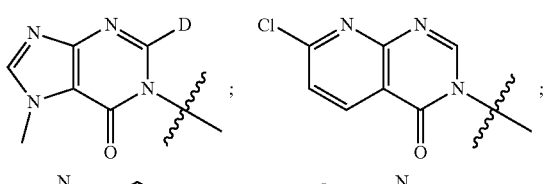
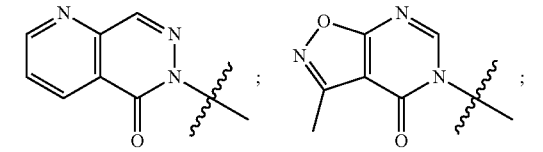
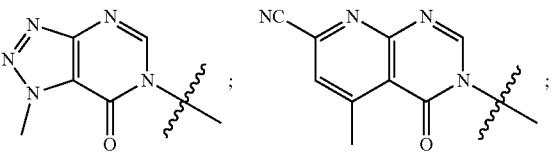
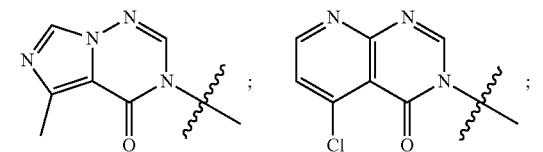
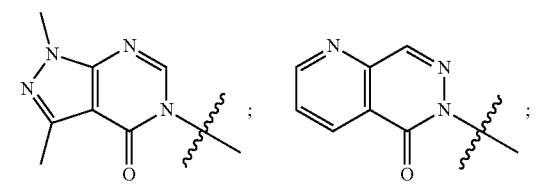
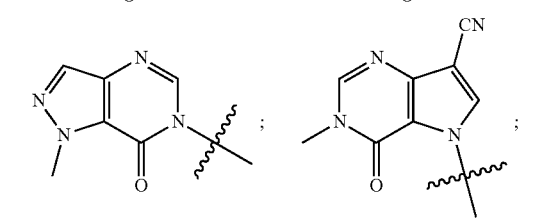
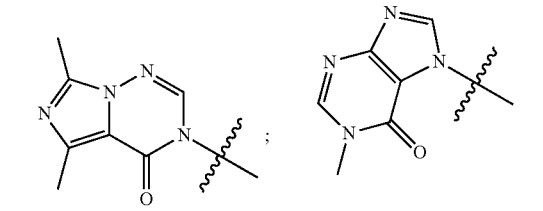
-continued
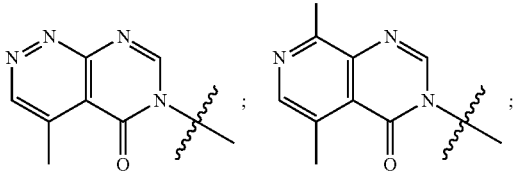
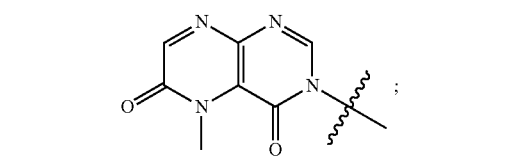
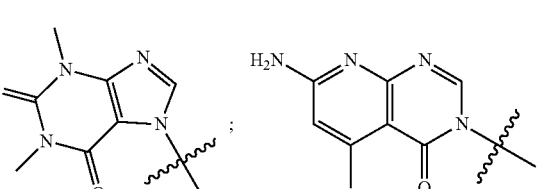
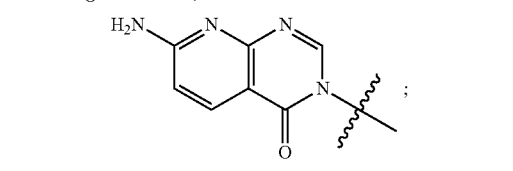
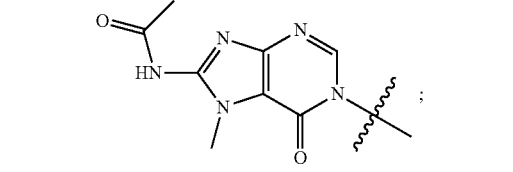
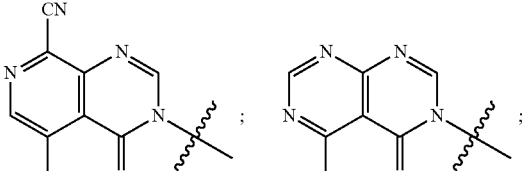
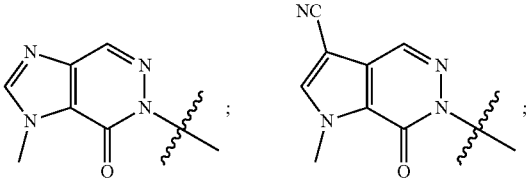
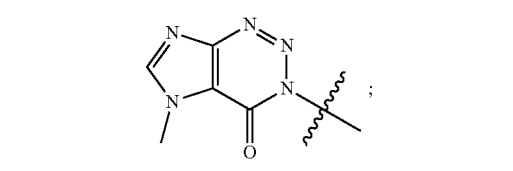
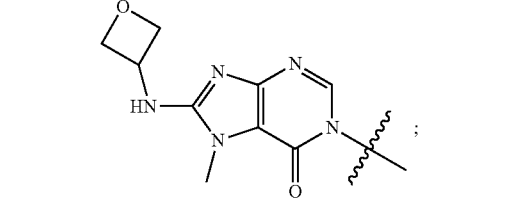

-continued
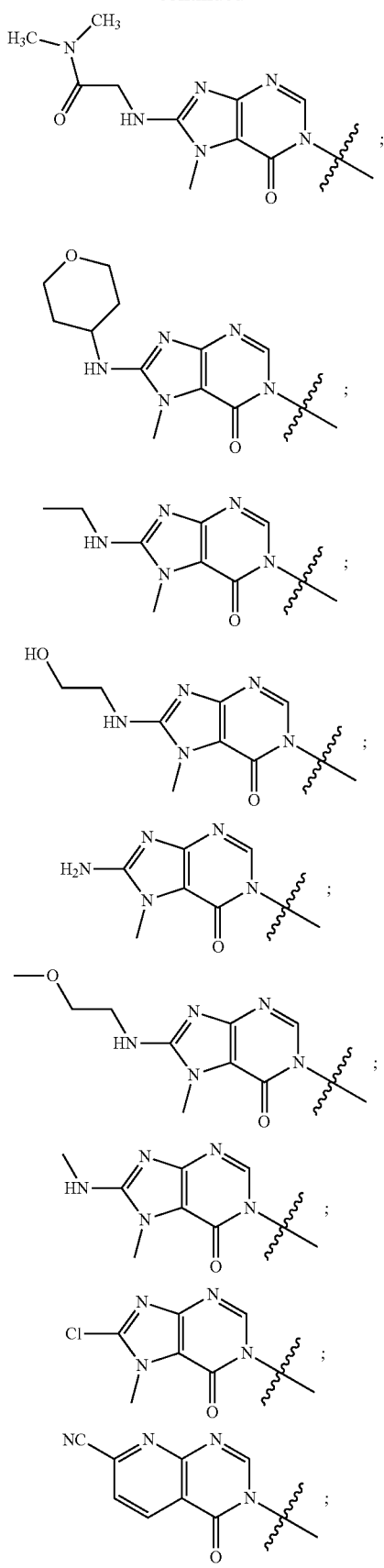
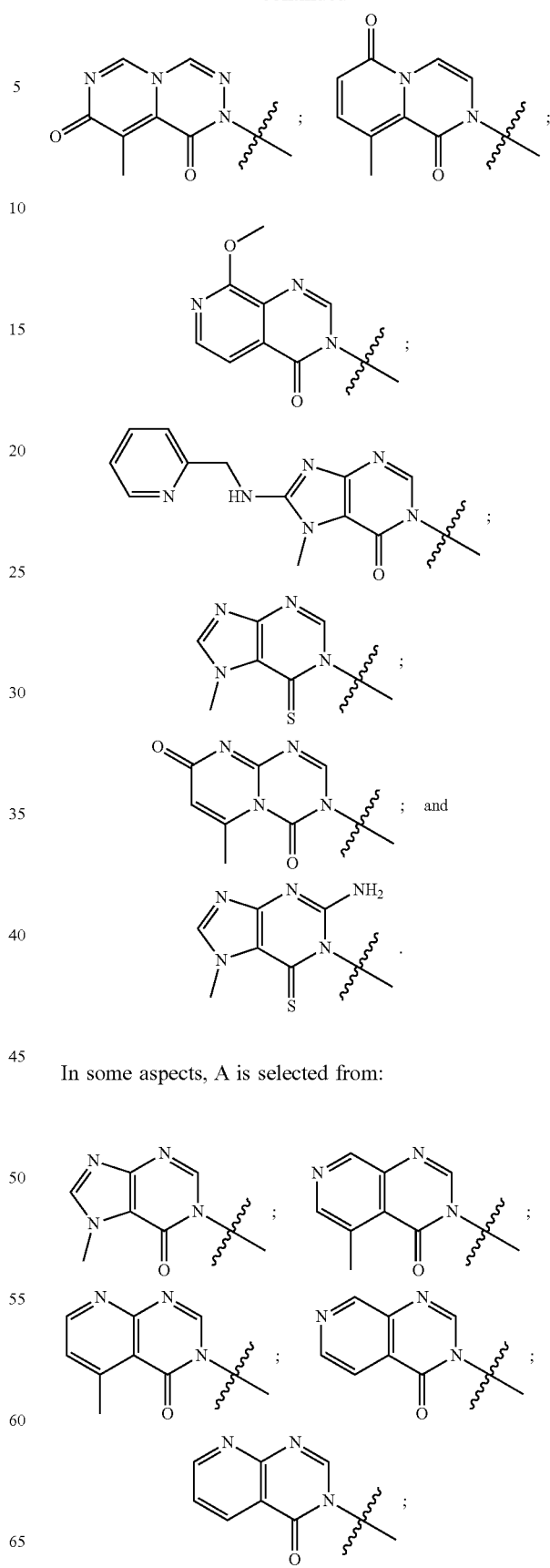
In some aspects, A is selected from:

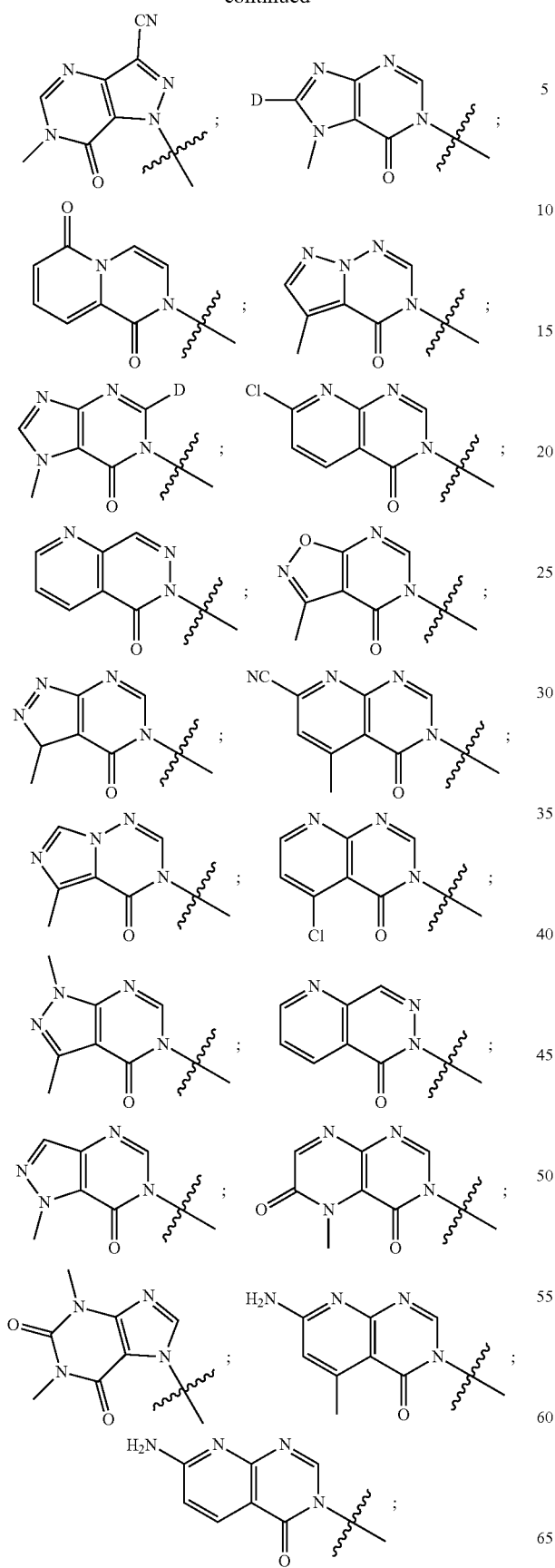
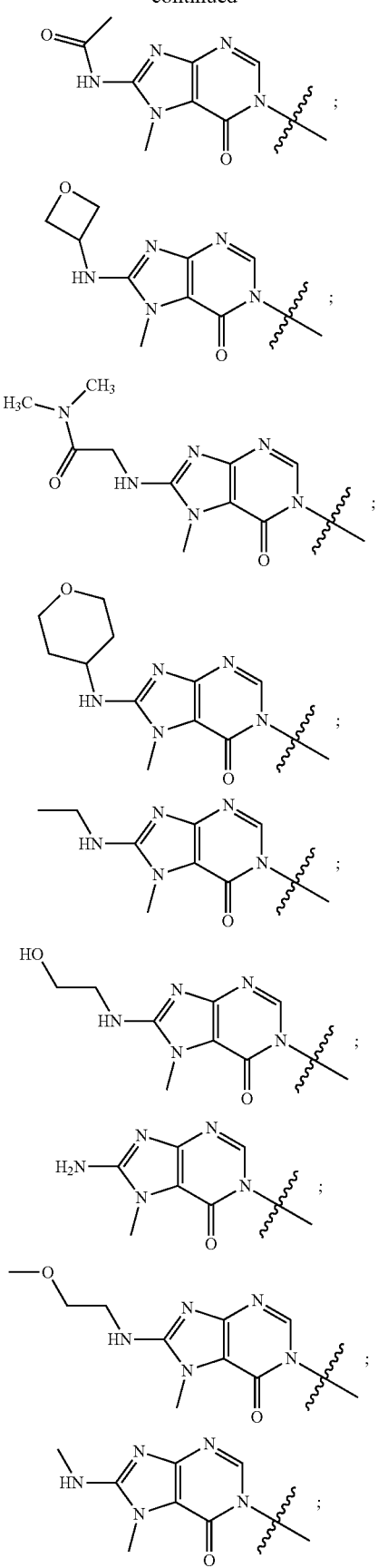

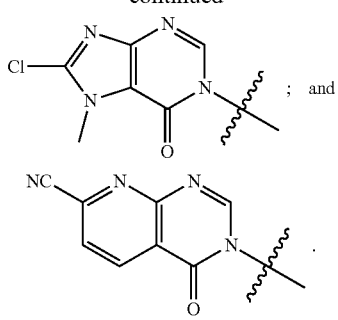; and

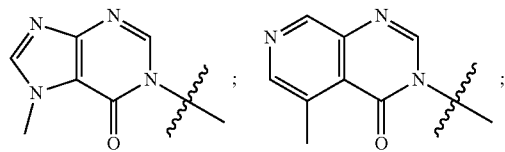

In some aspects, A is selected from:

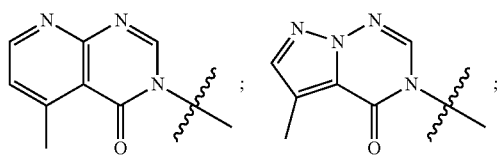

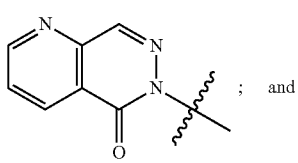; and

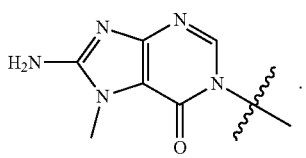

In some aspects, A is:

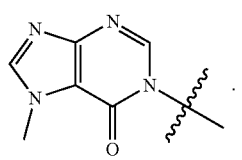 [SMILES: *n1cnc2ncn(C)c2c1=O]

In some aspects, A is:

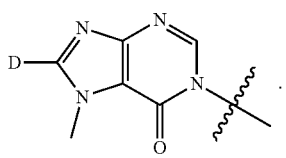 [SMILES: *n1cnc2nc([2H])n(C)c2c1=O]

In some aspects, A is:

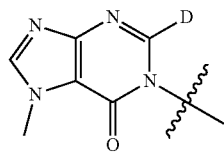

In some aspects, A is:

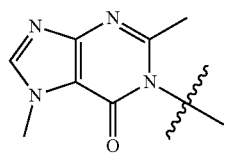

In some aspects, A is:

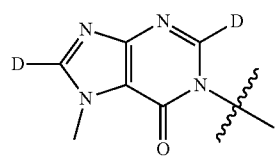

In some aspects, A is:

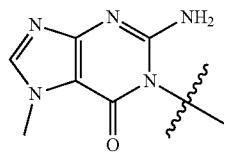

In some aspects, X is methylene.

$R^4$ is selected from substituted or unsubstituted phenyl, substituted or unsubstituted heteroaryl, and substituted or unsubstituted naphthyl. In some aspects, $R^4$ is:

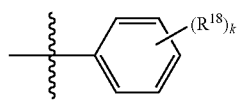

wherein each $R^{18}$ is independently selected from H, halogen, —OH, —$C_{1-4}$ alkyl, —$C_{1-4}$ haloalkyl, —CN, halo, $C_{1-4}$ haloalkoxy, $C_{1-4}$ alkoxy, —$SO_2$—$C_{1-4}$alkyl, —$C_{1-4}$CN, $C_{1-4}$ aldehyde, $C_{1-4}$ ketone, pentafluorosulfanyl, unsubstituted or substituted $C_{3-6}$cycloalkyl, unsubstituted or substituted phenyl, unsubstituted or substituted heteroaryl, fused aryl, and fused heteroaryl; and k is from 0 to 3. In some aspects, each $R^{18}$ is independently selected from H, Cl, —$OCHF_2$, —$OCF_3$, —$OCH_3$, and —CN. In certain embodiments $R^{18}$ is halo. In certain embodiments $R^{18}$ is chloro or fluoro. In certain embodiments k is 0, 1 or 2.

In some aspects, $R^4$ is selected from:
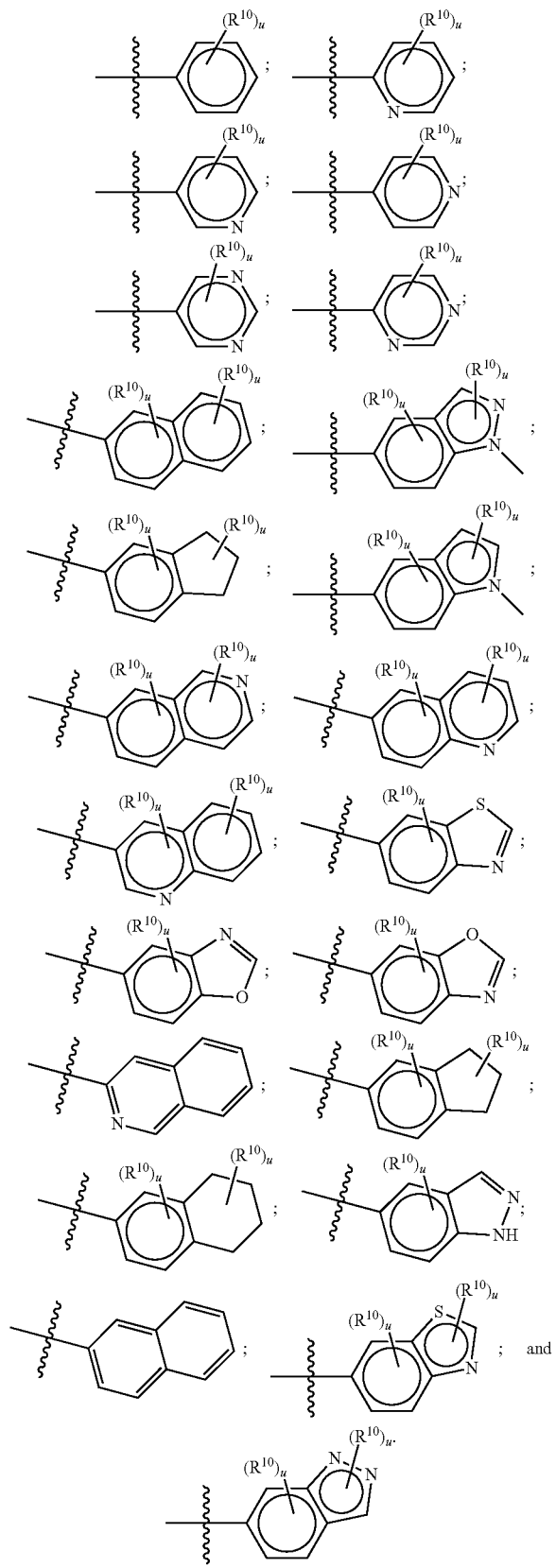
In some aspects, $R^4$ is selected from:
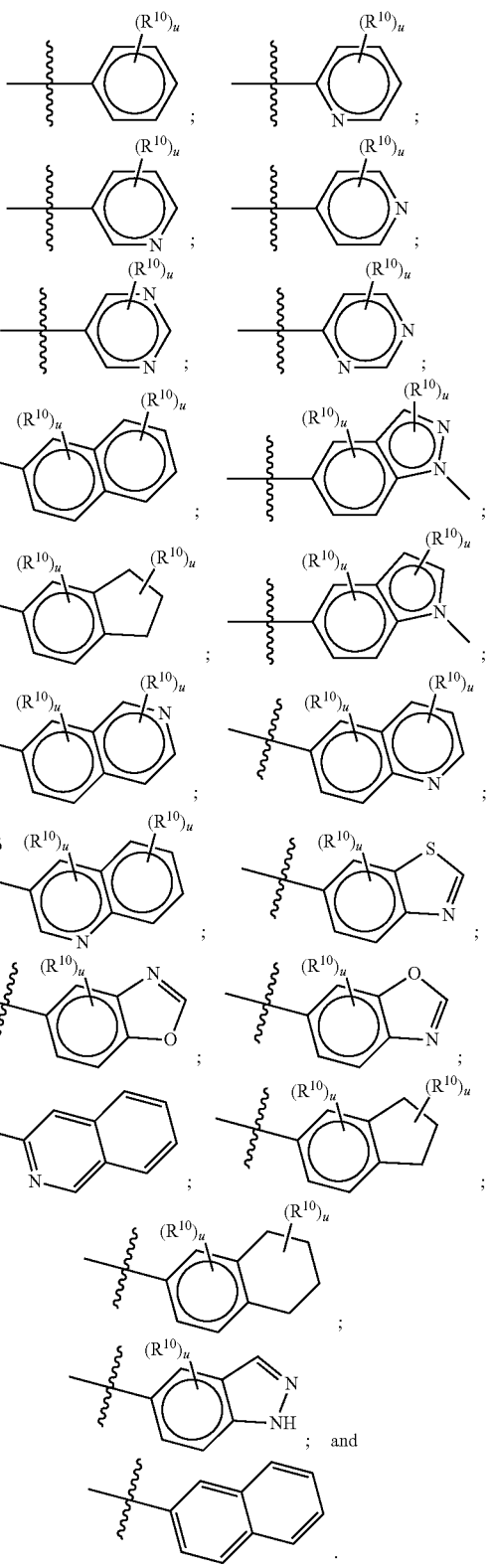
In such aspects, each $R^{10}$ is independently selected from H, halogen, —CN, —OH, $C_{1-4}$ alkyl, substituted or unsubstituted $C_{3-6}$ cycloalkyl, $C_{1-4}$ haloalkyl, $C_{1-4}$ haloalkoxy, $C_{1-4}$ alkoxy, —$SO_2$—$C_{1-4}$ alkyl, $C_{1-4}$ CN, $C_{1-4}$ aldehyde, $C_{1-4}$ ketone, —S—$C_{1-4}$ haloalkyl, pentafluorosulfanyl, unsubstituted or substituted $C_{3-6}$cycloalkyl, unsubstituted or substituted phenyl, unsubstituted or substituted or unsubstituted 5- to 6-membered heteroaryl, substituted or unsubstituted 4- to 6-membered hetercycloalkyl, substituted or unsubstituted phenyl, and substituted or unsubstituted naphthyl. Each u is independently selected from 0, 1, 2 and 3. In some aspects, each $R^{10}$ is independently selected from halogen, $C_1$ haloalkoxy, and $C_1$ alkoxy. In certain embodiments each $R^{10}$ is halo.

In some aspects wherein $R^1$ and $R^4$ together form an unsubstituted or substituted $C_{3-6}$cycloalkyl fused to a substituted or unsubstituted phenyl; substituted or unsubstituted heteroaryl; or substituted or unsubstituted naphthyl, such combined $R^1$ and $R^4$ may be of the formula

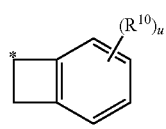

wherein * represents a spiro point of attachment and u and $R^{10}$ are as defined herein.

In some aspects, $R^4$ is selected from:

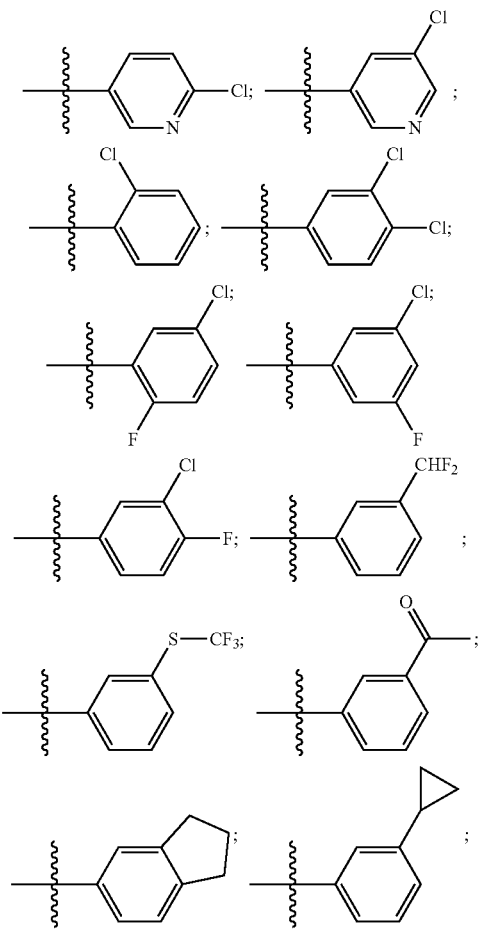

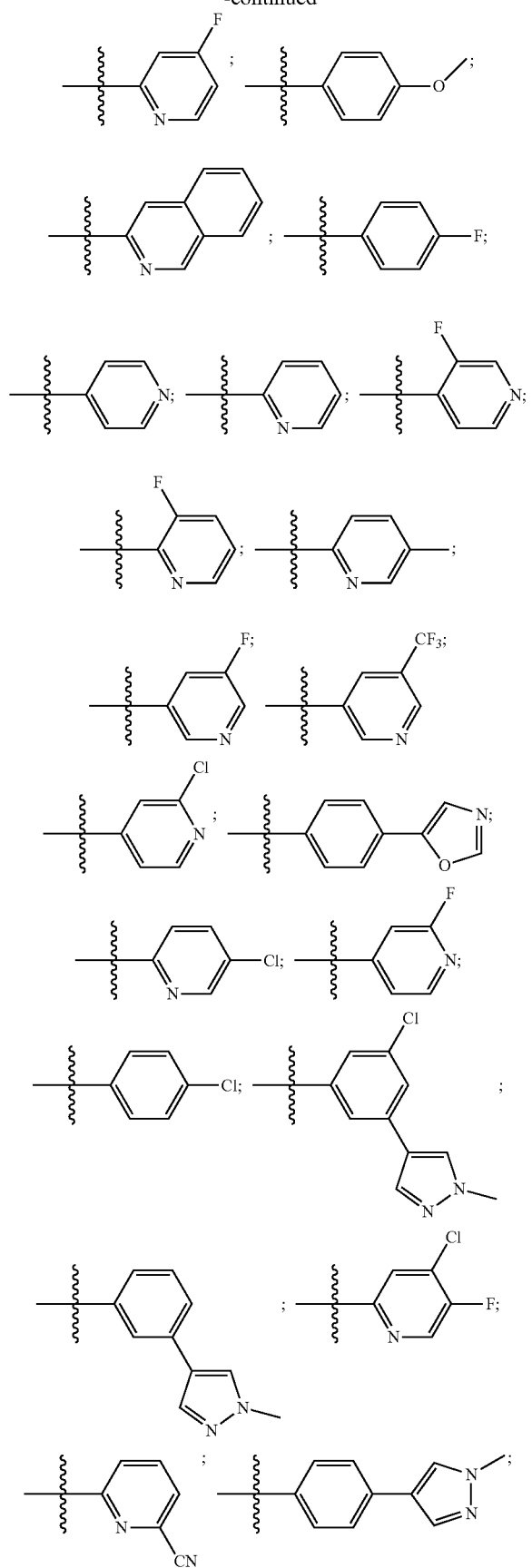
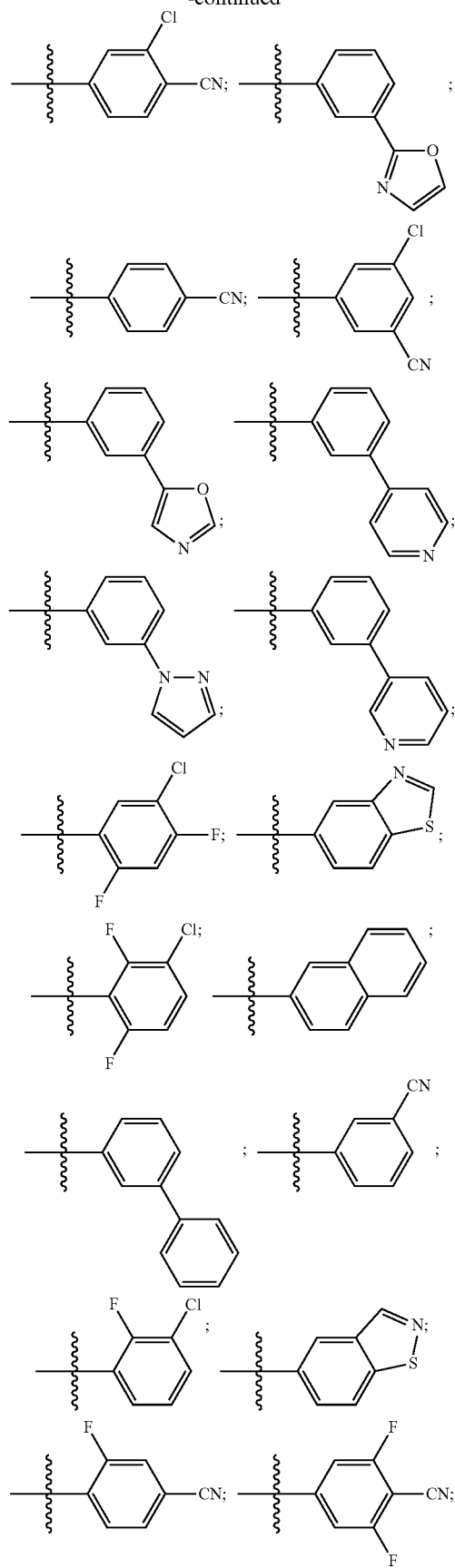

-continued
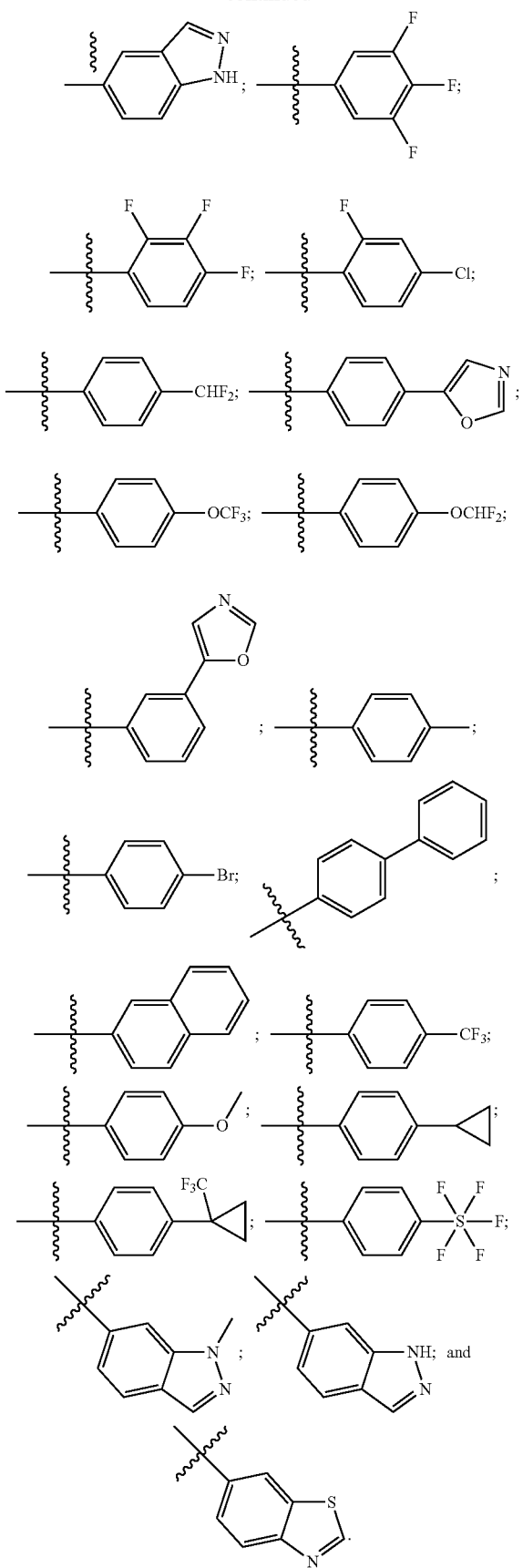
In some aspects, $R^4$ is selected from:
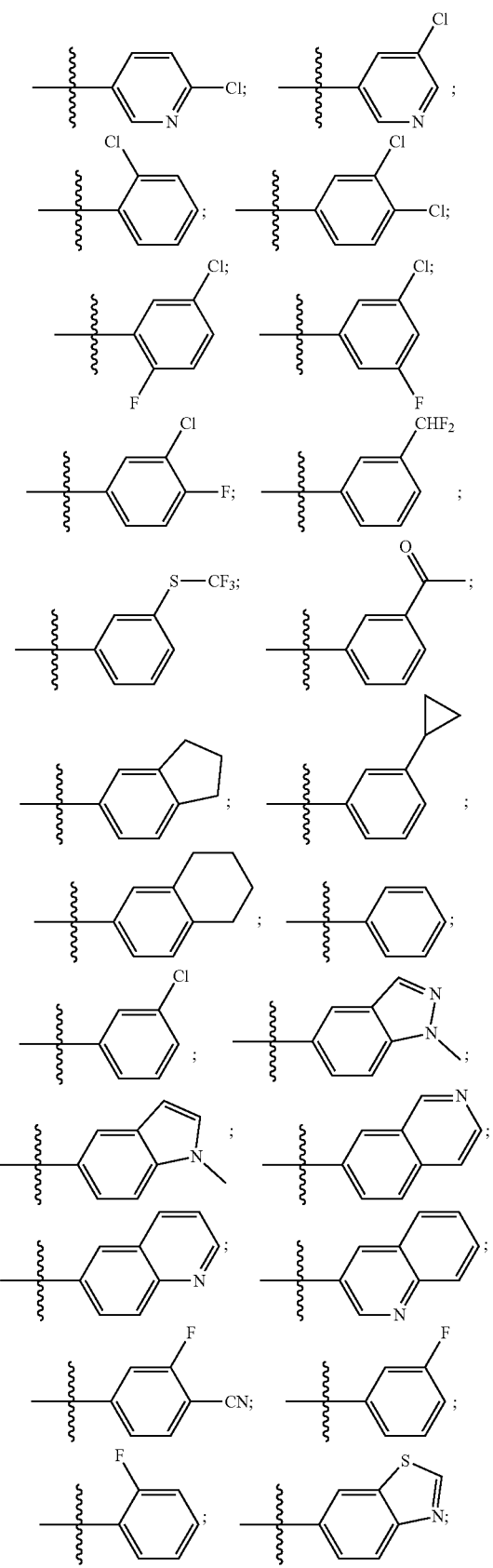

-continued
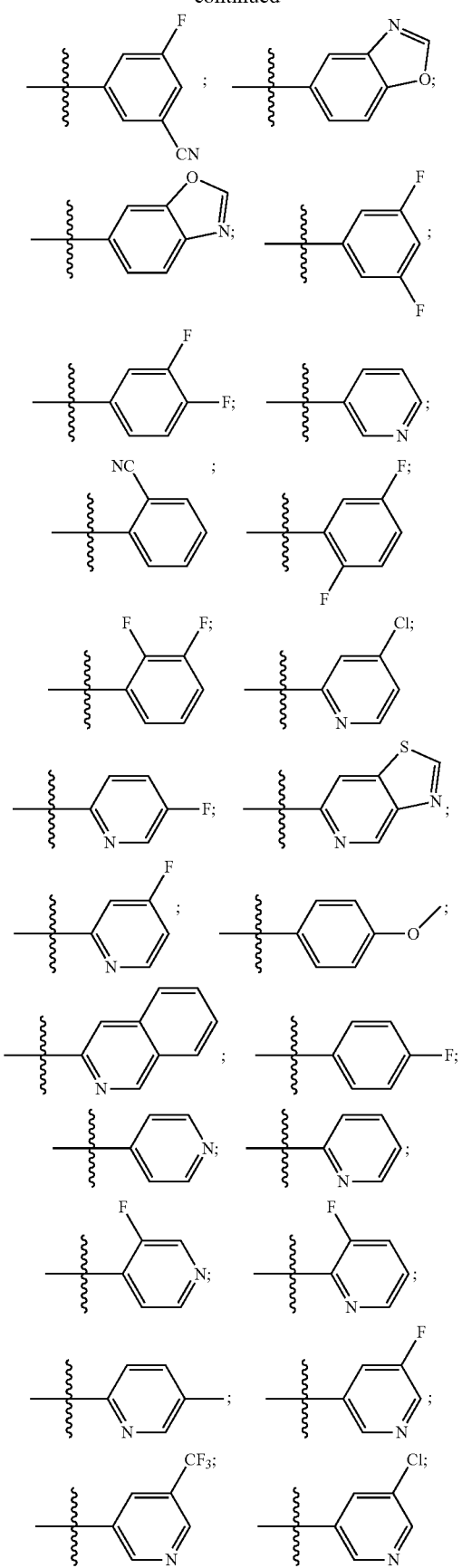
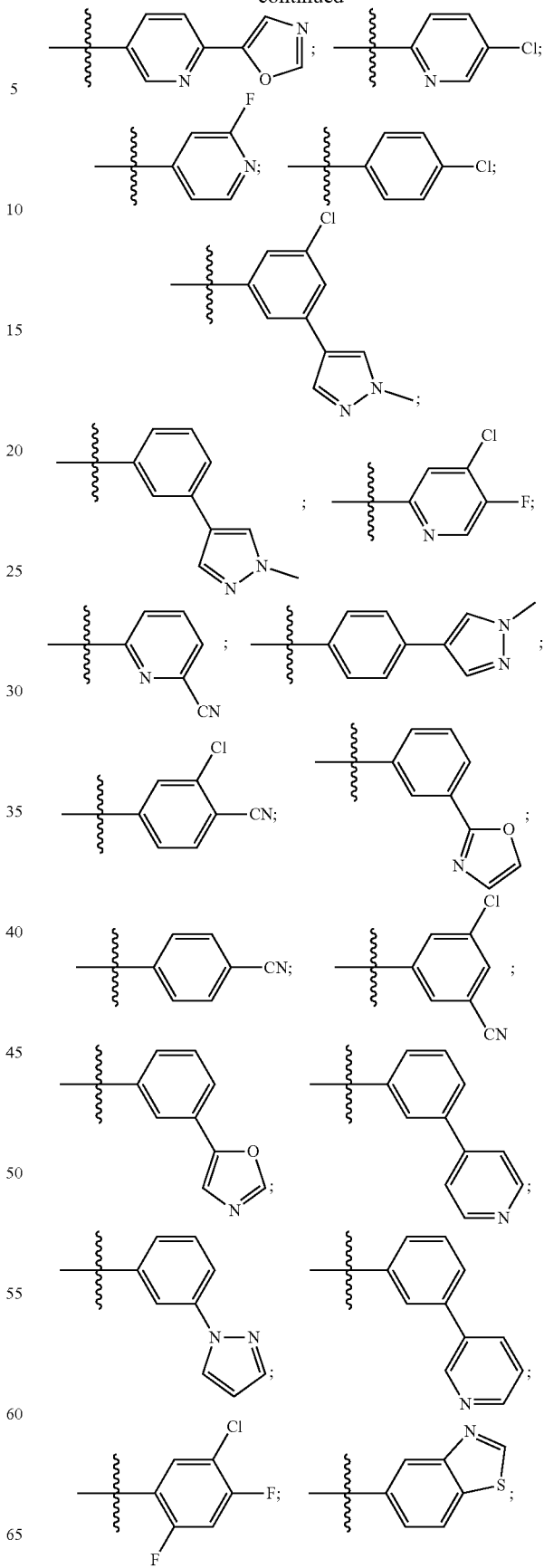

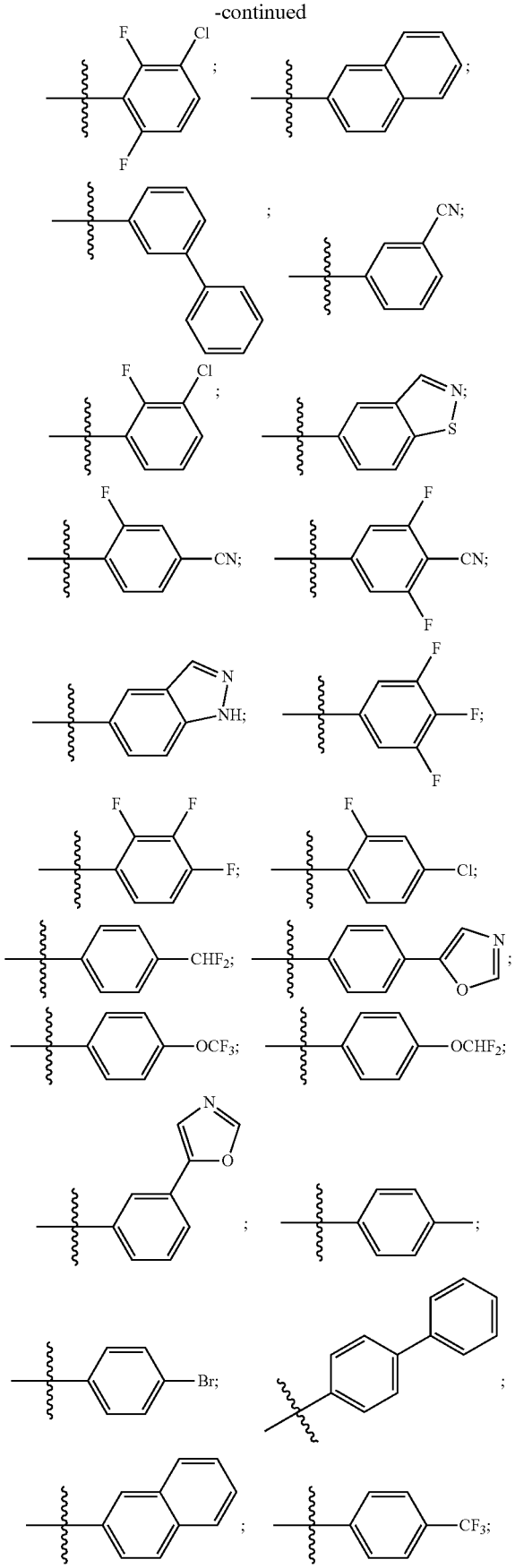

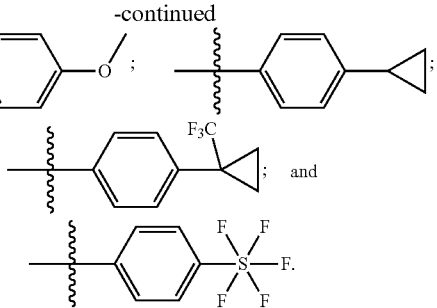

In some aspects, the compound of formula (I) may be of formula (II):

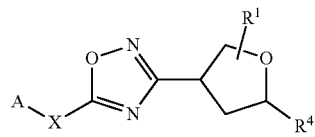

wherein A, X, $R^1$ and $R^4$ are as defined herein.

In some aspects, the compound of formula (I) may be of formula (IIIa) or formula (IIIb)

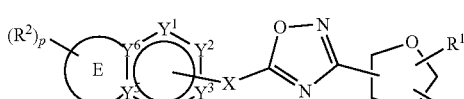

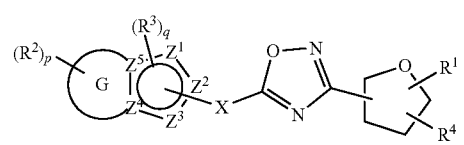

wherein E, G, $R^1$, $R^2$, $R^3$, $R^4$, X $Y^1$, $Y^2$, $Y^3$, $Y^4$, $Y^5$, $Y^6$, $fZ^1$, $Z^2$, $Z^3$, $Z^4$, $Z^5$, p and q are as defined herein.

In some aspects, X is $C_{1-4}$alkylene.
In some aspects, X is methylene.
In some aspects, $R^1$ is H.
In some aspects, $R^4$ is:

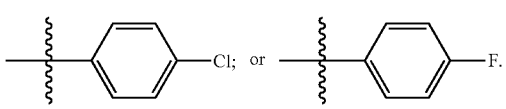

In some aspects, the compound of formula (I) may be of formula (IVa) or formula (IVb)

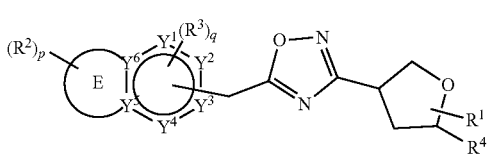

(IVb)

wherein E, G, R¹, R², R³, R⁴, Y¹, Y², Y³, Y⁴, Y⁵, Y⁶, fZ¹, Z², Z³, Z⁴, Z⁵, p and q are as defined herein.

In some aspects, the compound of formula (I) may be of formula (Va)

(Va)

wherein R¹, R², R⁴ and p are as defined herein.

In some aspects, the compound of formula (I) may be of formula (Vb)

(Vb)

wherein R¹, R², R³, R⁴, p and q are as defined herein.

In some aspects, the compound of formula (I) may be of formula (VIa) or (VIb)

(VIa)

(VIb)

wherein R¹, R², R⁴ and p are as defined herein.

In some aspects, the compound of formula (I) may be of formula (VIc) or (VId)

(VIc)

(VId)

wherein R¹, R², R³, R⁴, p and q are as defined herein.

In some aspects, the compound of formula (I) may be of formula (VIIa) or formula (VIIb)

(VIIa)

(VIIb)

wherein R¹, R², R⁴, R¹⁸, p and k are as defined herein.

In some aspects, the compound of formula (I) may be of formula (VIIc) or formula (VIIc)

(VIIc)

(VIId)

wherein R¹, R², R³, R¹⁸, p, q and k are as defined herein.

In certain embodiments of formula (I), the group A may be a group of the formula:

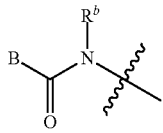

wherein:

B is a five membered heteroaryl selected from pyrrole, pyrazole, pyrazole, imidazole or triazole, each of which may be unsubstituted or substituted once with $R^a$, and wherein the pyrrole, pyrazole and imidazole each may be partially saturated; and $R^b$ is hydrogen, $C_{1-6}$alkyl which may be unsubstituted or substituted once with —$NR^{16}R^{17}$.

In certain embodiments, B is imidazolyl.

In certain embodiments, B is 1-methyl-imidazol-5-yl-.

In certain embodiments, B is triazolyl.

In certain embodiments, B is 5-methyl-1H-1,2,3-triazol-1-yl.

In certain embodiments, B is

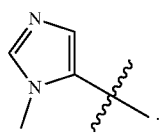 [SMILES: *c1cncn1C]

In certain embodiments, B is

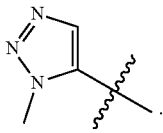

In certain embodiments, A is 2-amino-3-methylpyrimidin-4(3H)-one-5-yl.

In certain embodiments, A is:

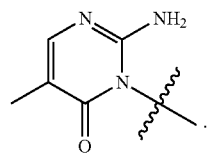 [SMILES: *n1c(N)ncc(C)c1=O]

In certain embodiments, $R^b$ is hydrogen.

In some aspects, the compound of formula (I), or pharmaceutically acceptable salts and stereoisomers thereof, is selected from the following:

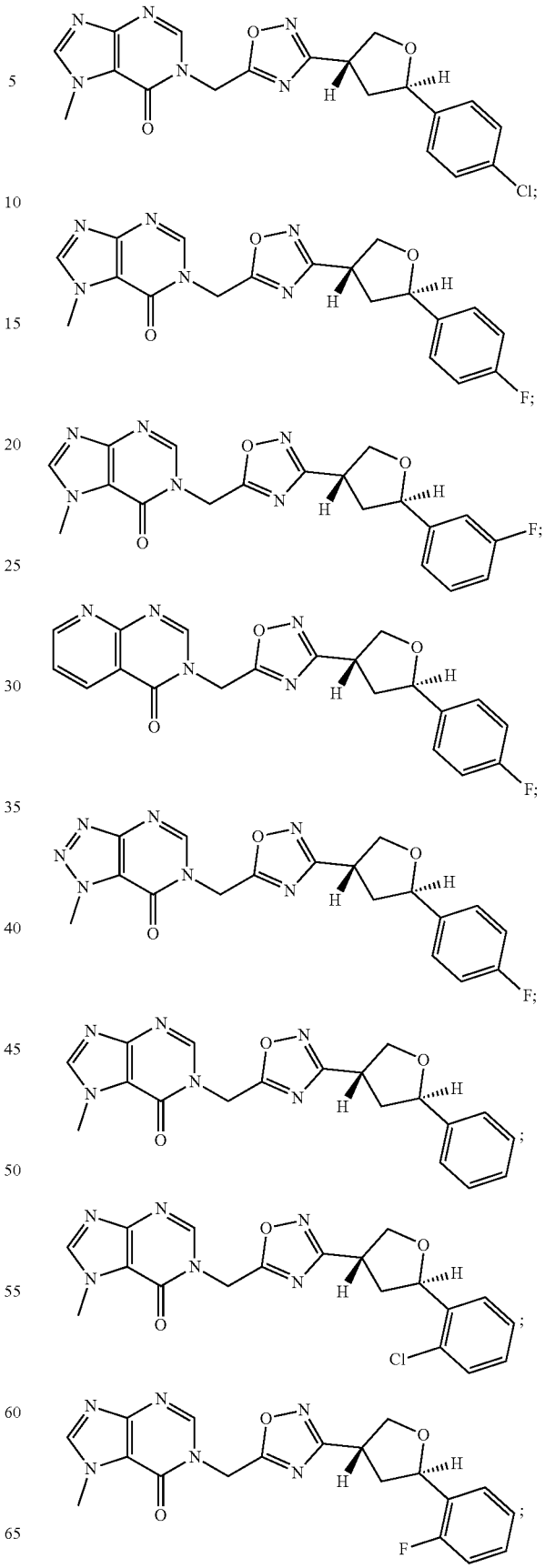

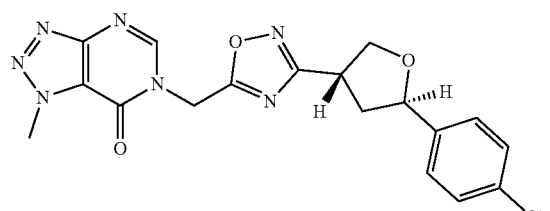
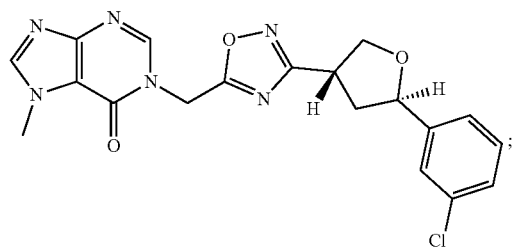
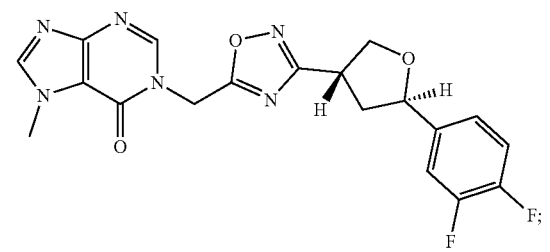
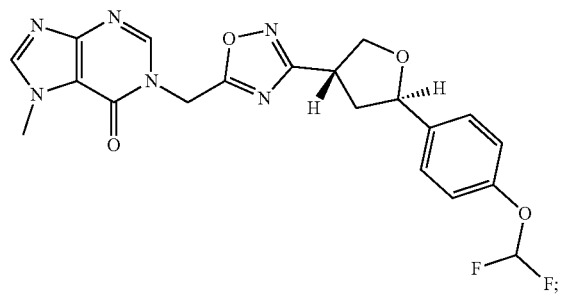
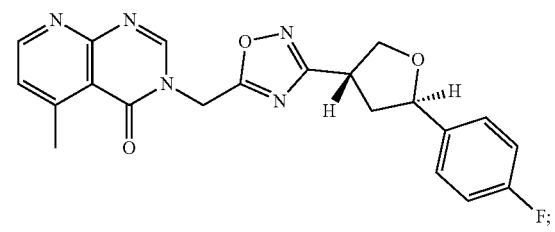
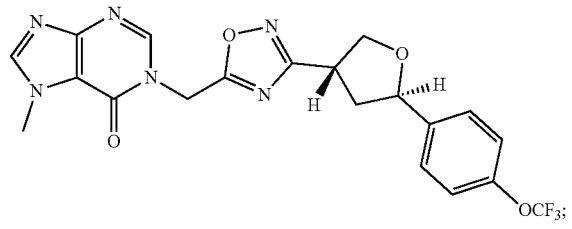
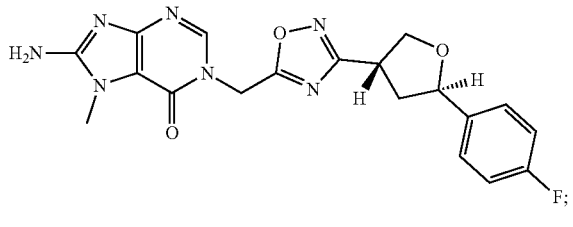
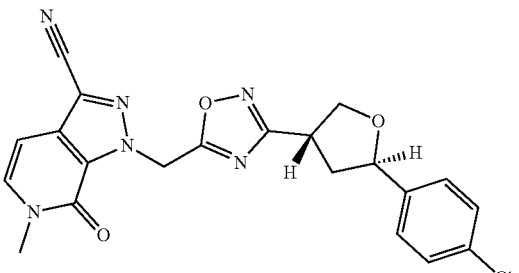
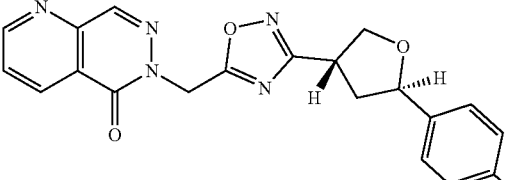
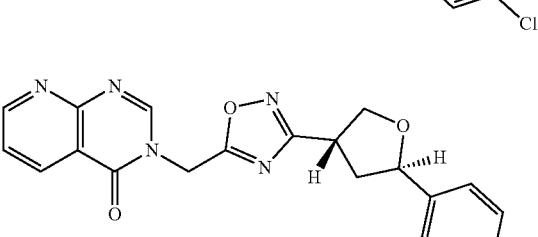
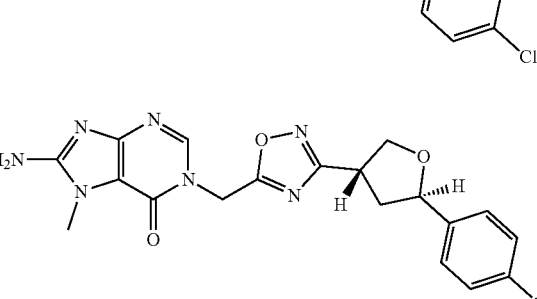
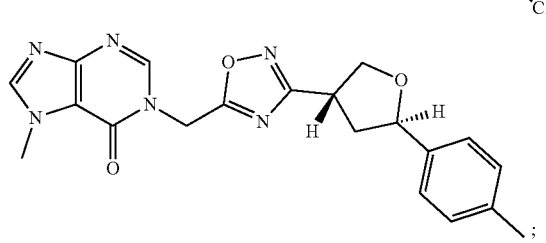
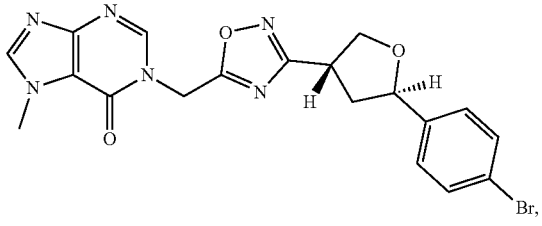

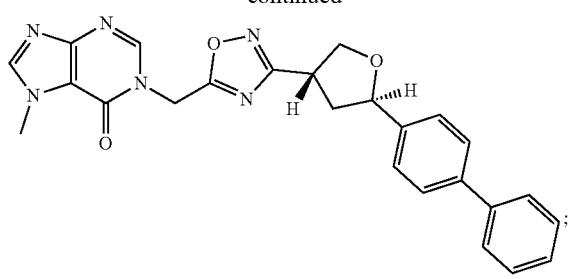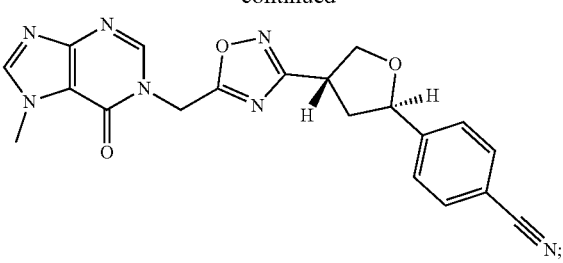

59
-continued
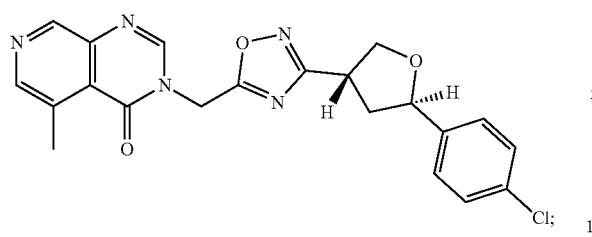
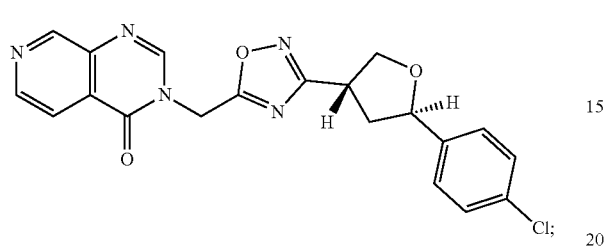
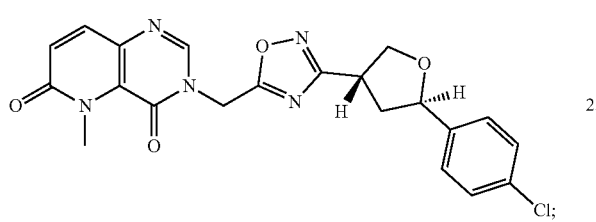
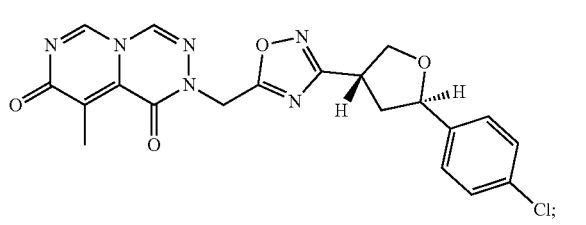
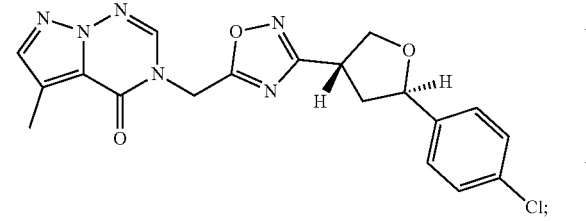
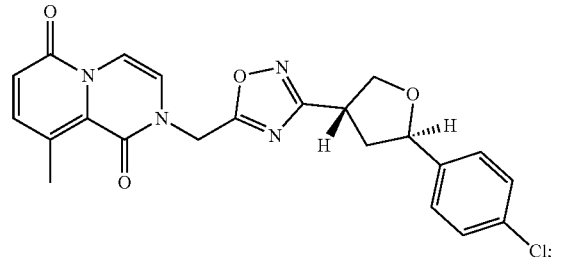
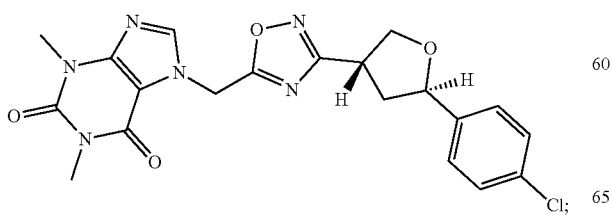
60
-continued
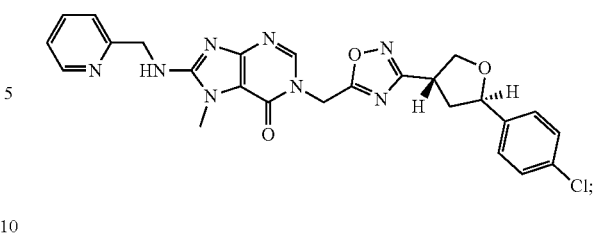
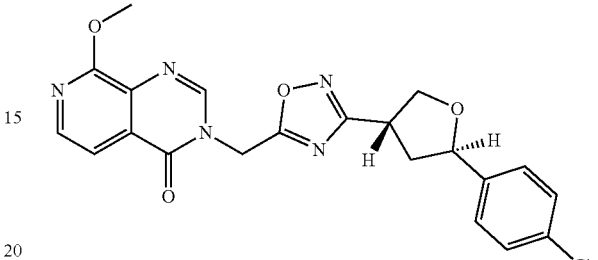

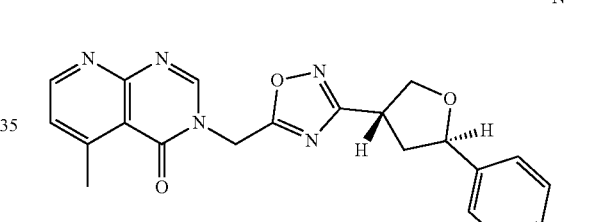
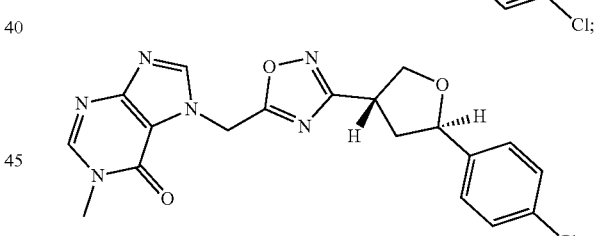
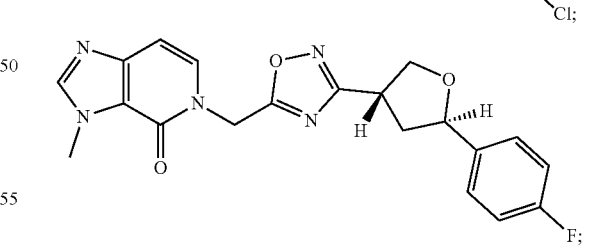
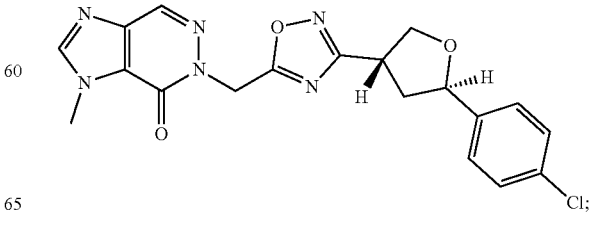

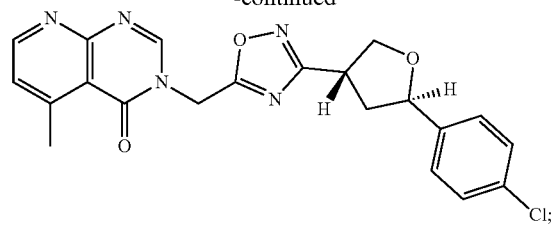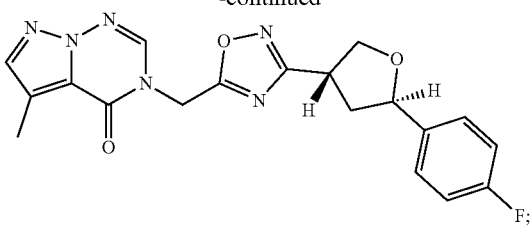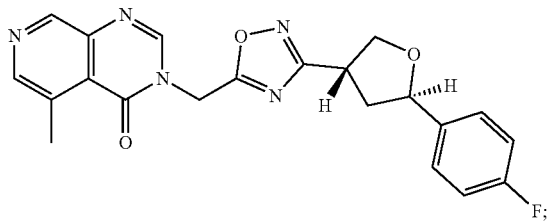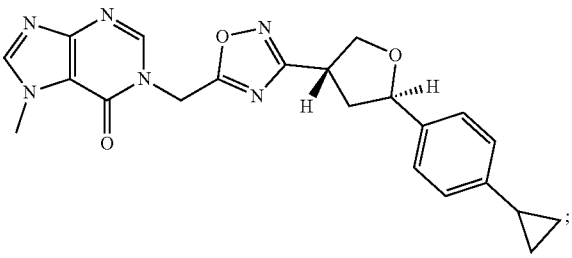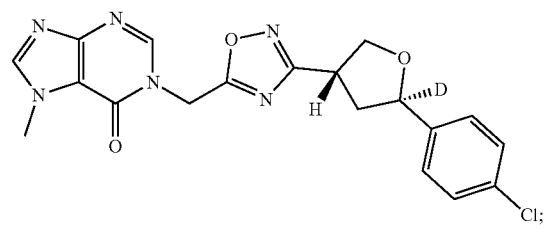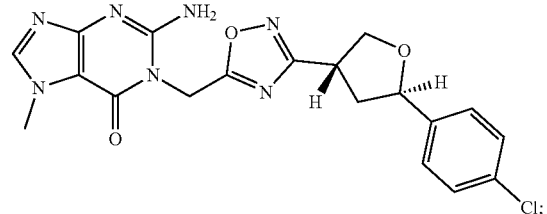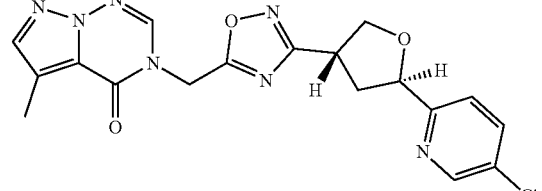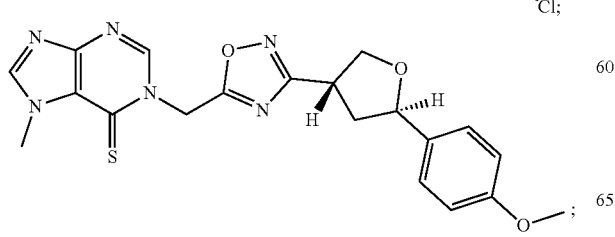

-continued
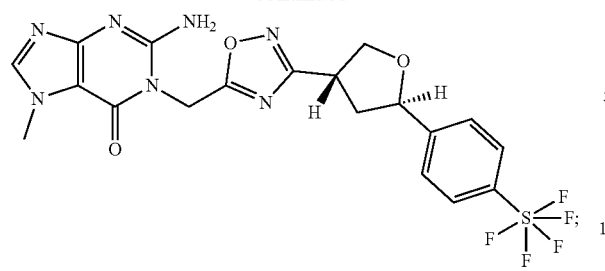
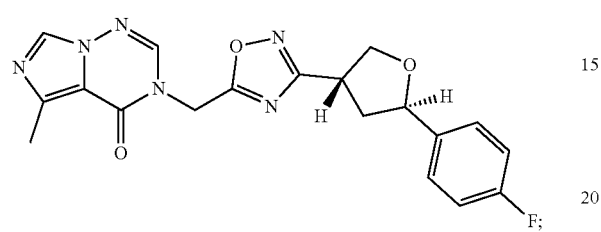
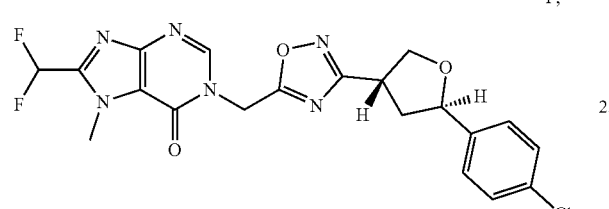
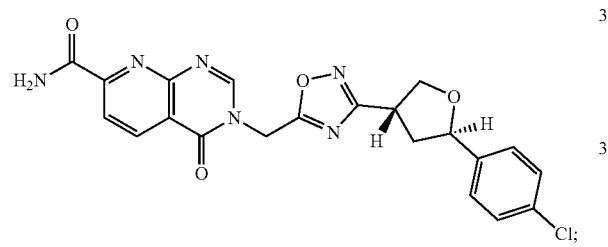
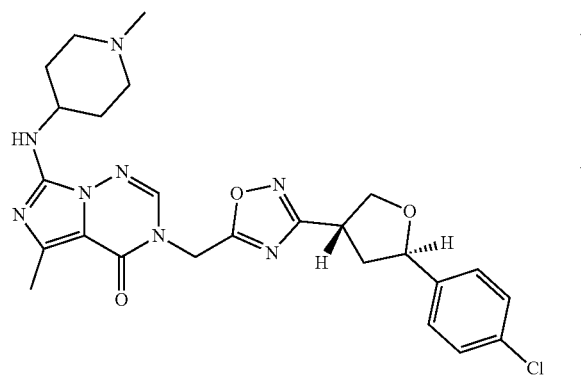
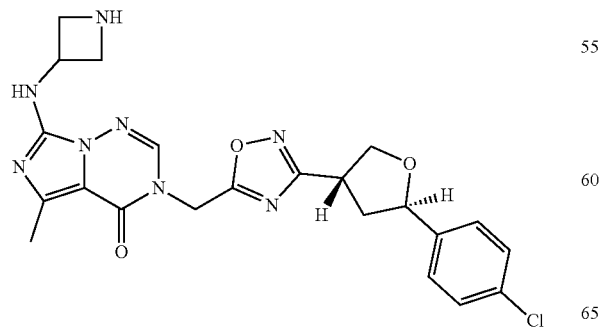
-continued
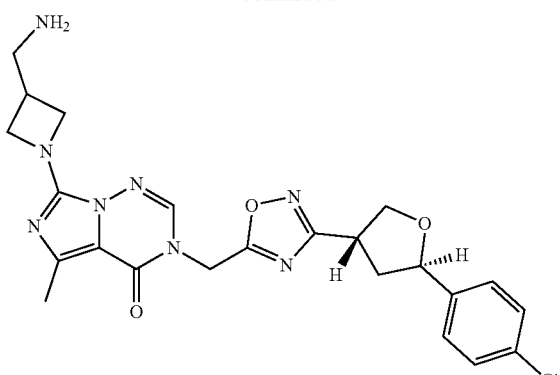
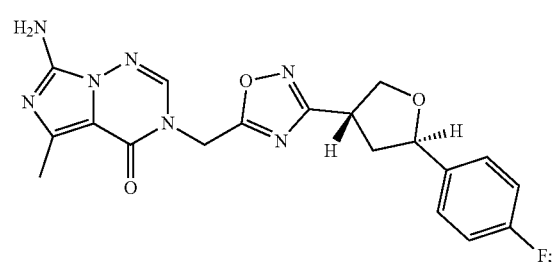
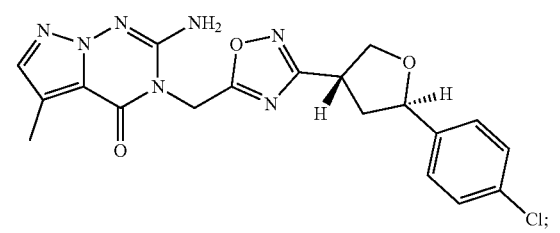
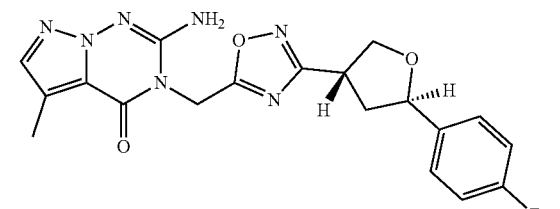
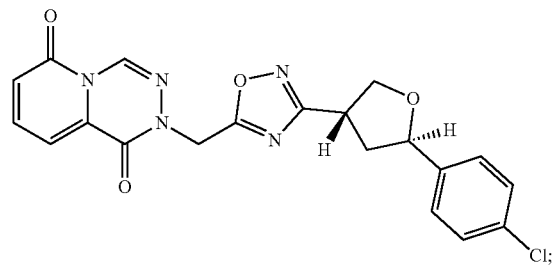
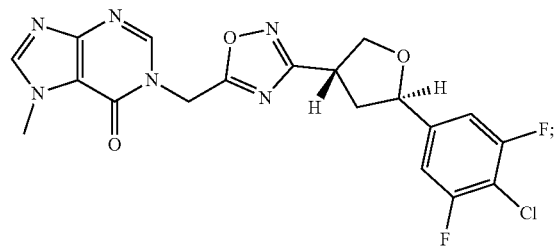

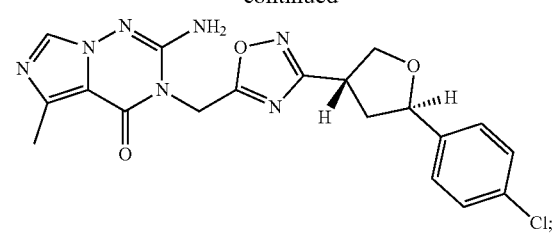
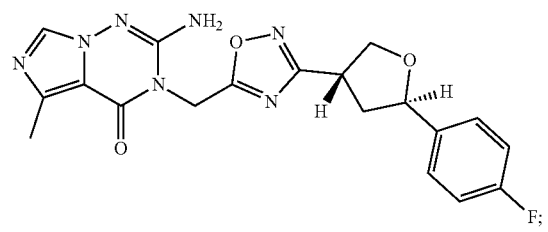
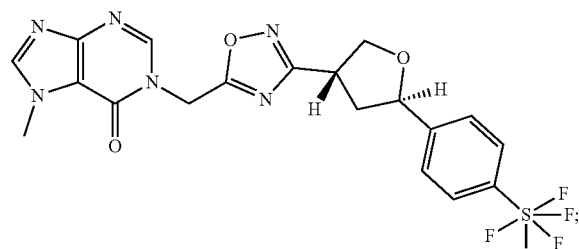
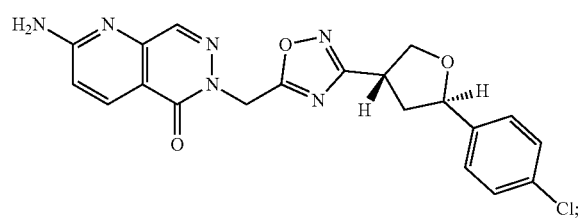
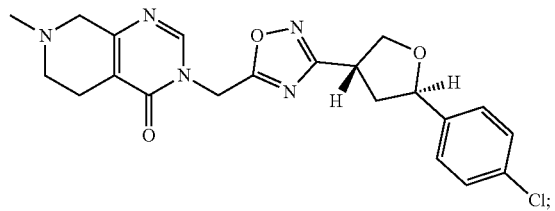
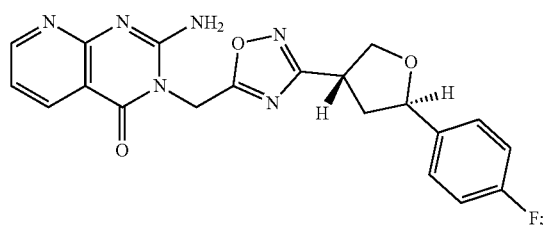
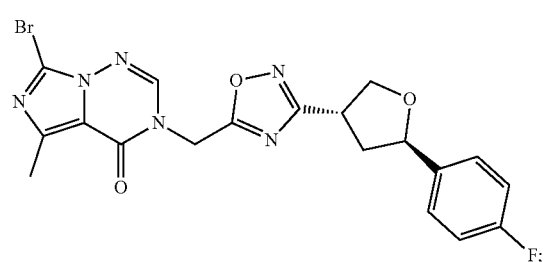
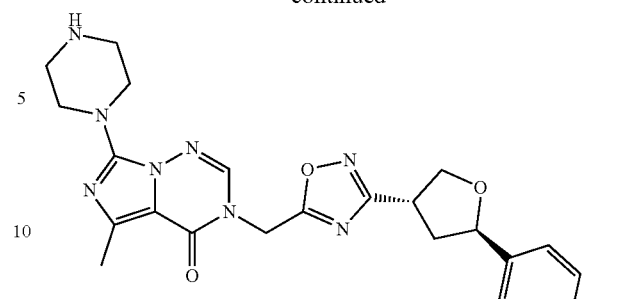
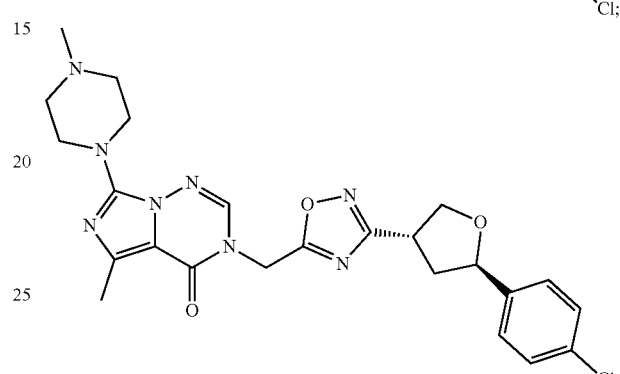
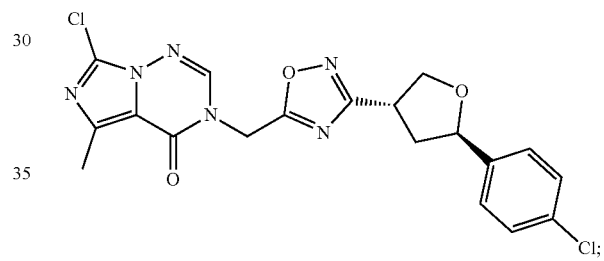
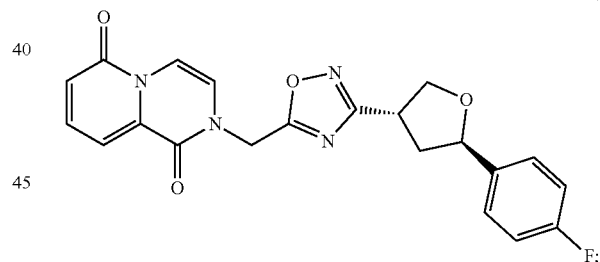
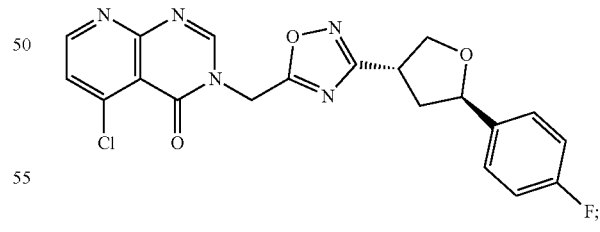
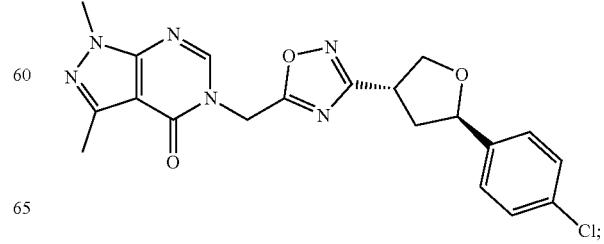

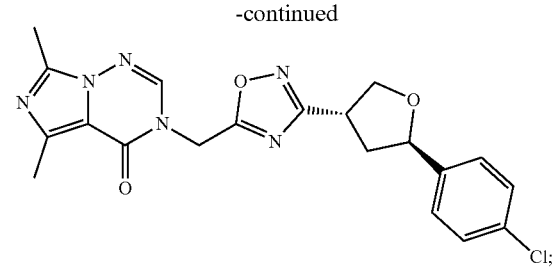
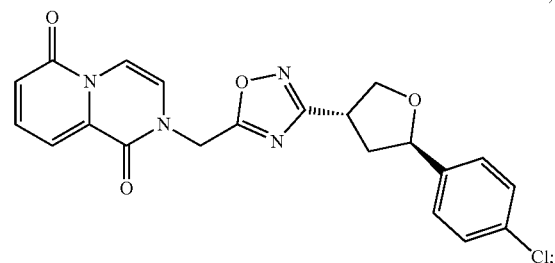
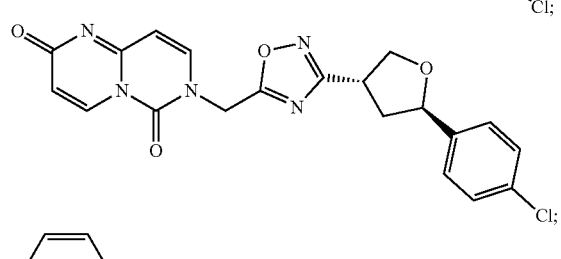
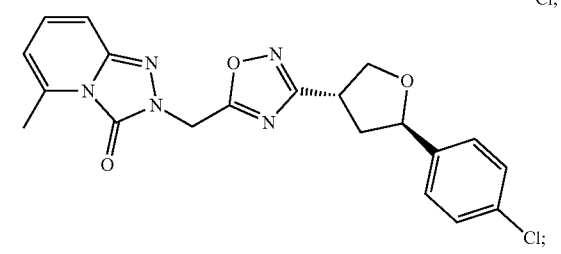
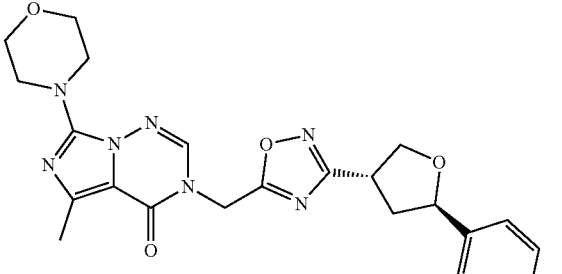
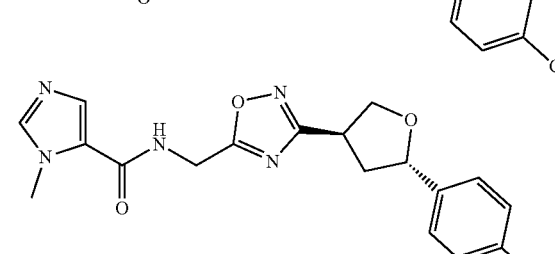
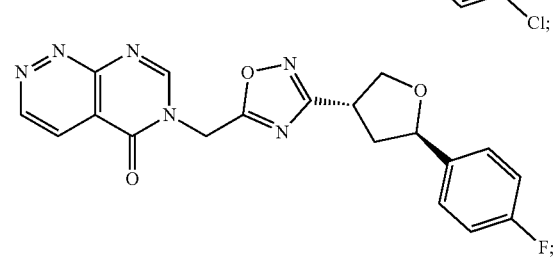
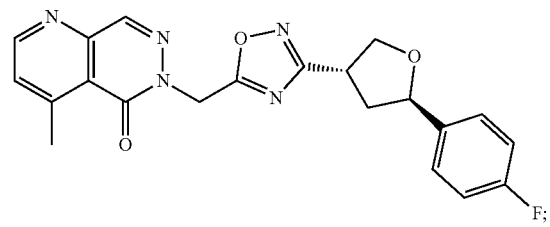
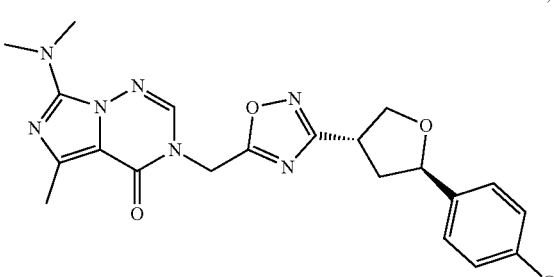
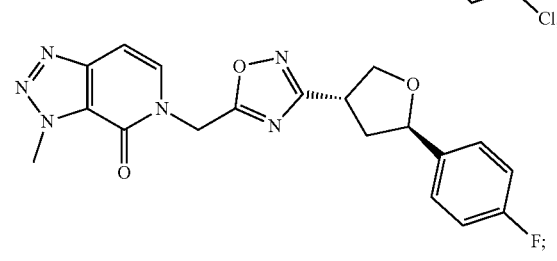
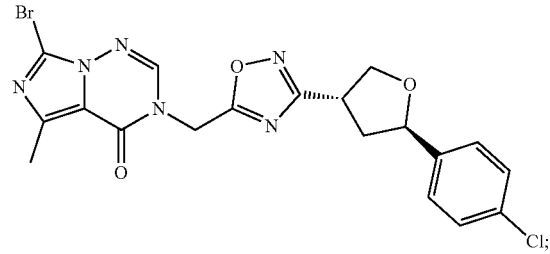
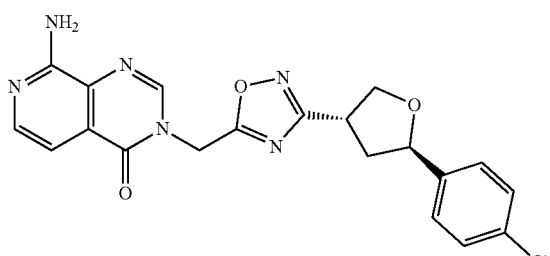
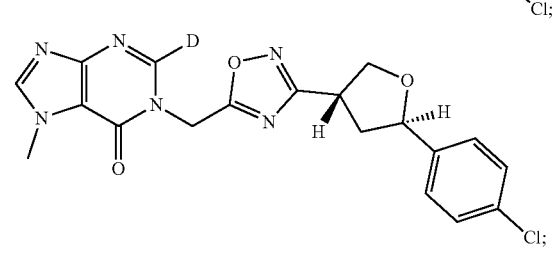
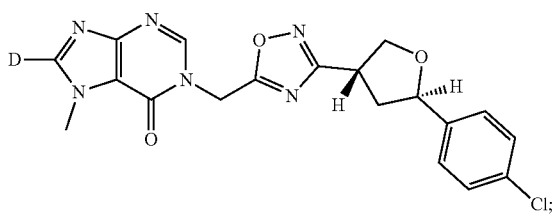

69
-continued
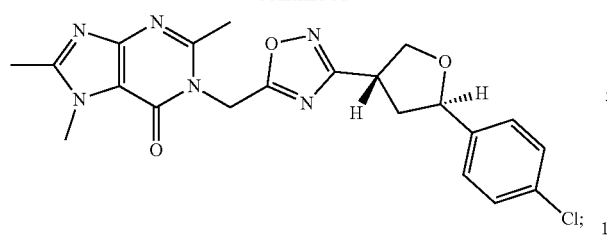
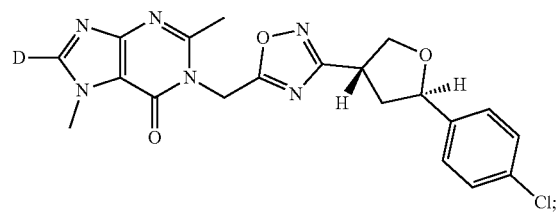
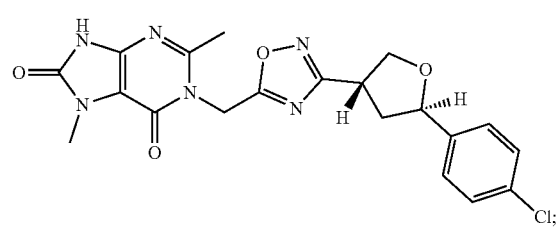
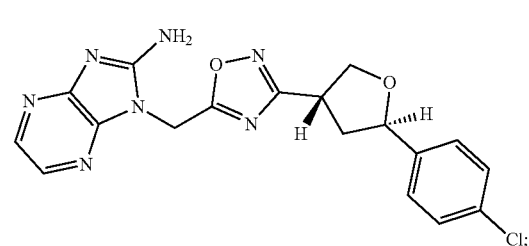
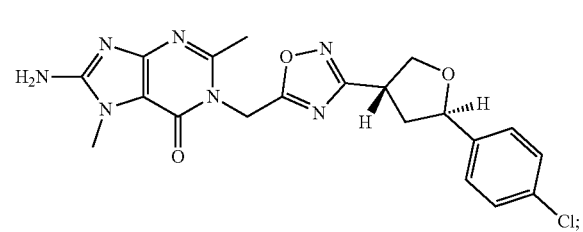
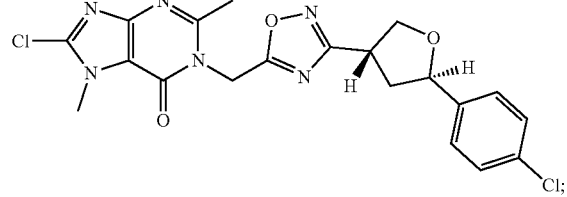
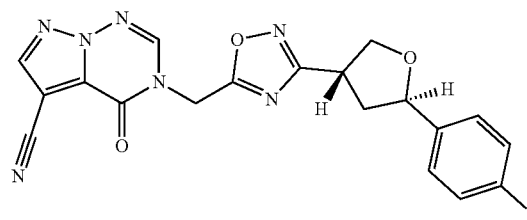
70
-continued
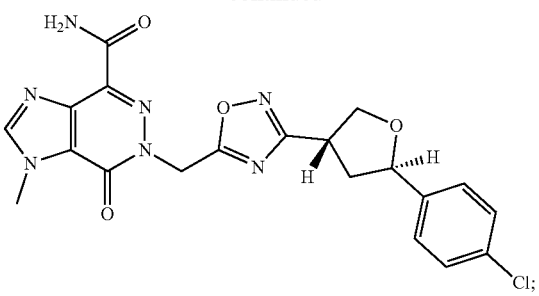
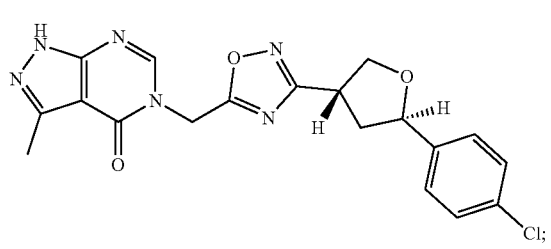
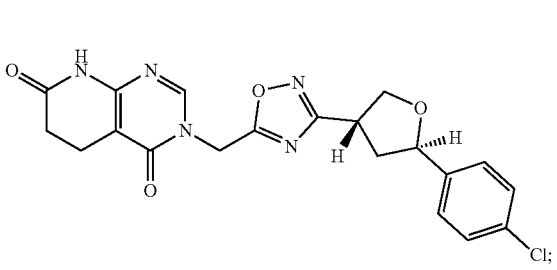
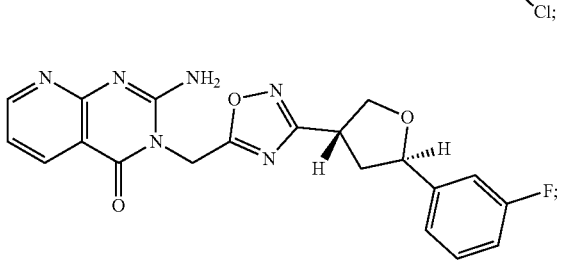
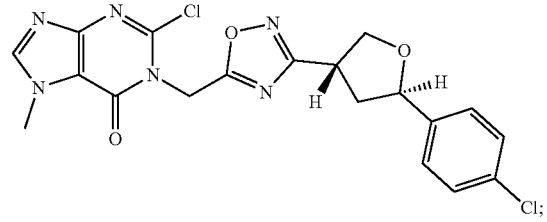
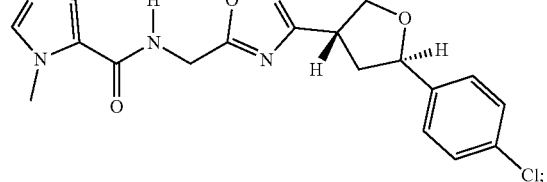
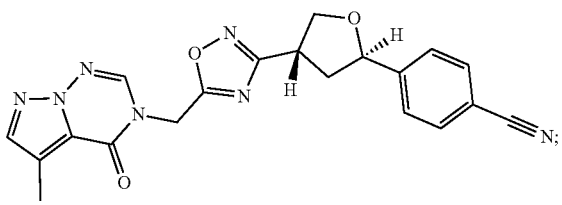

71
-continued
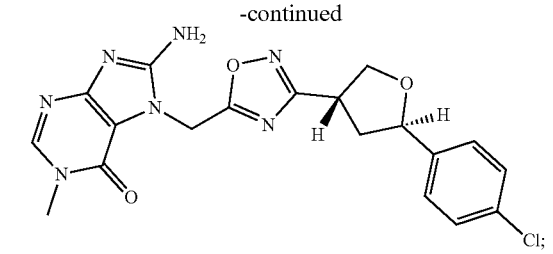
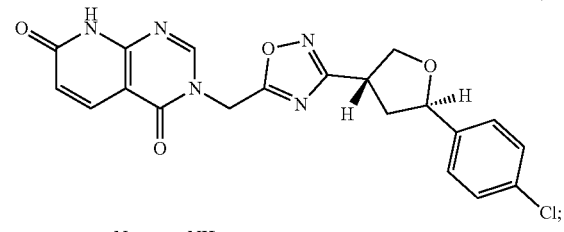
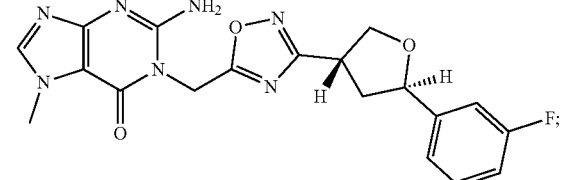
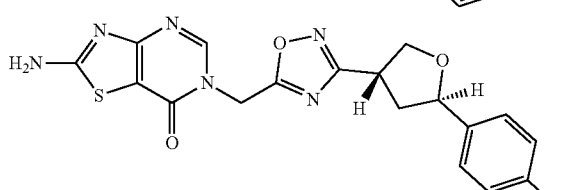
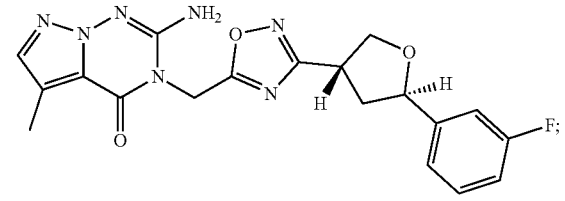
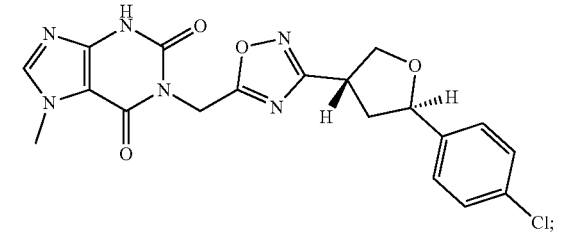
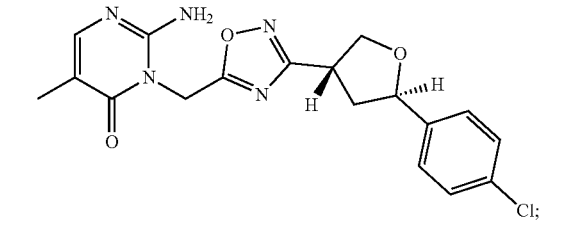
72
-continued
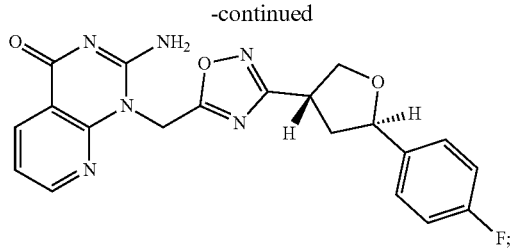
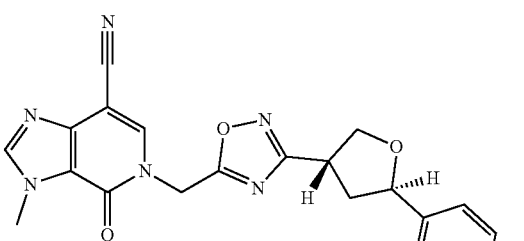
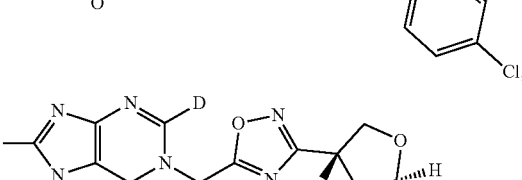
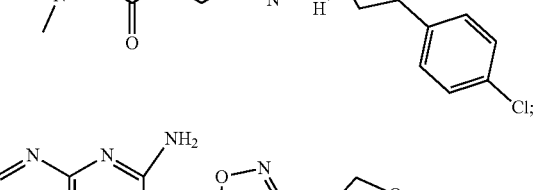
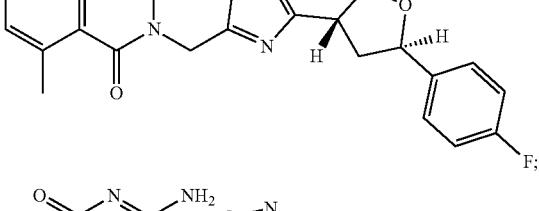
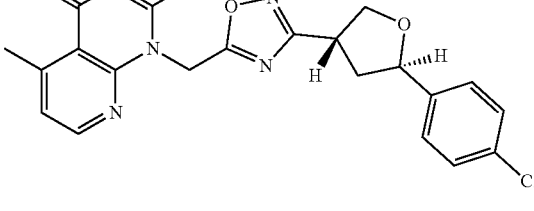
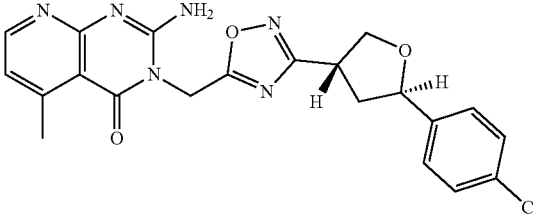
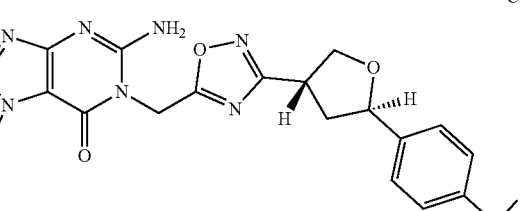

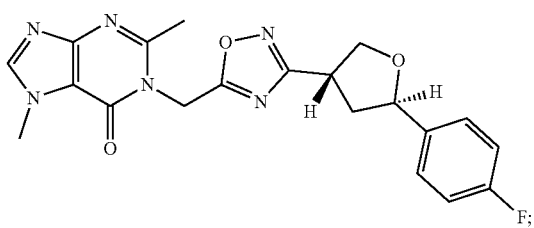
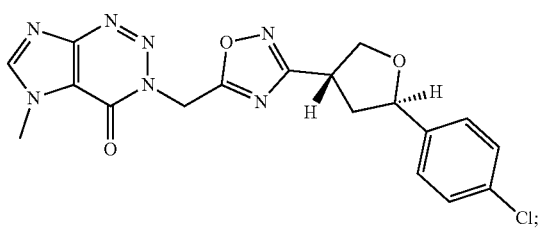
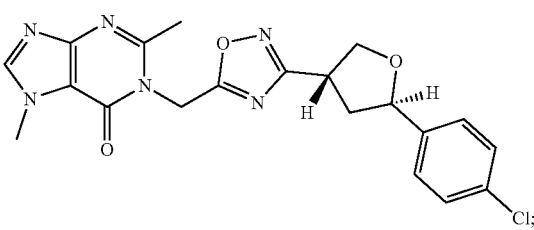
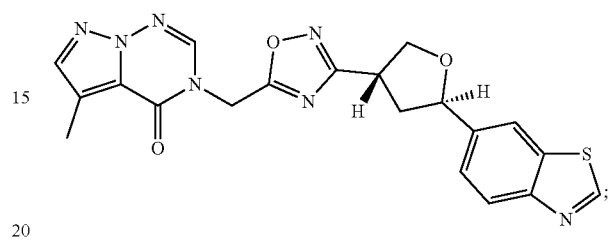
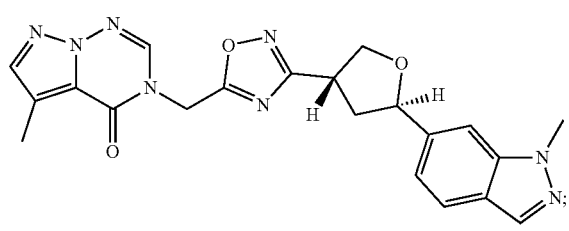
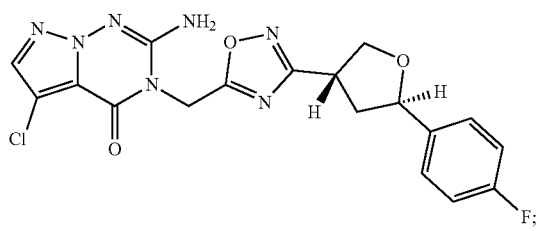
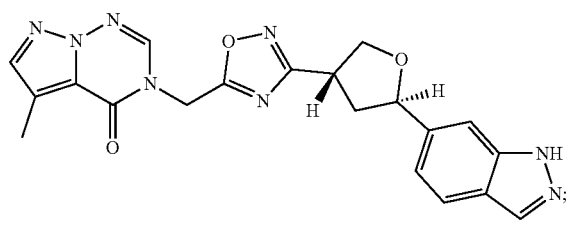
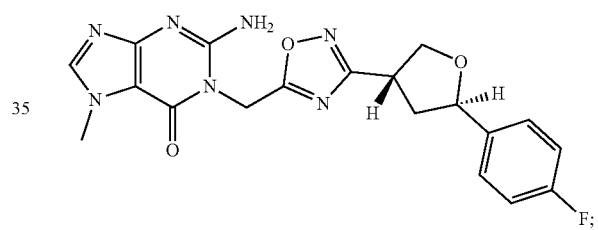
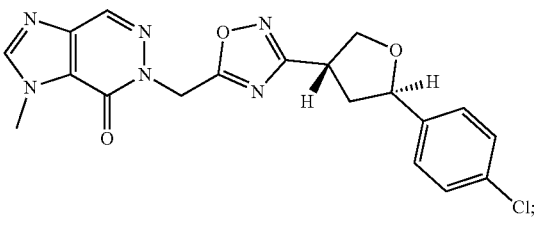
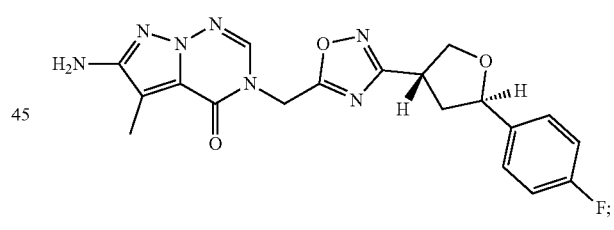
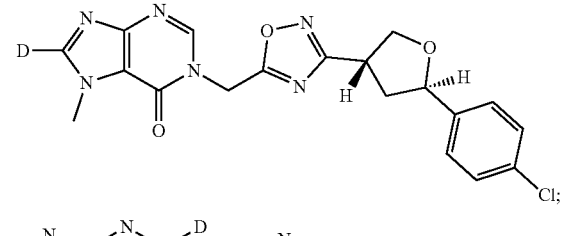
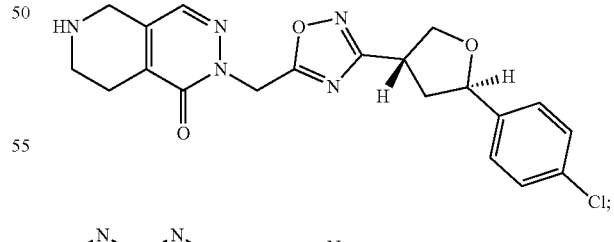
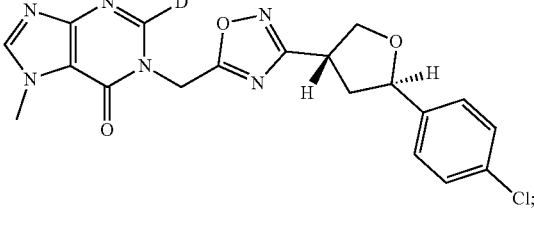
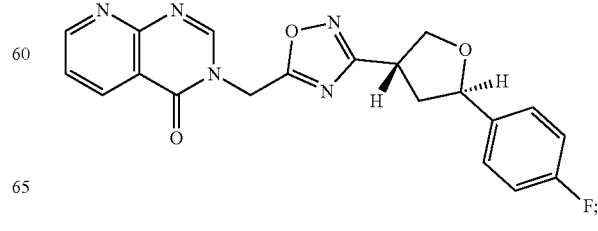

75

-continued

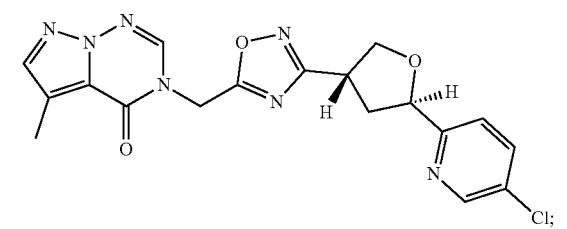

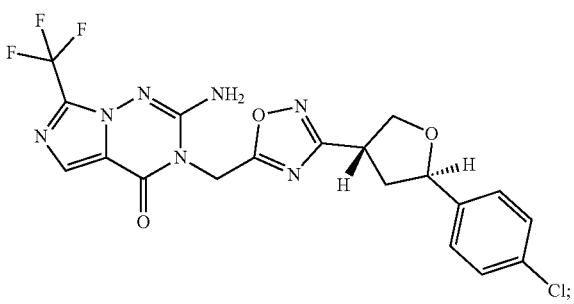

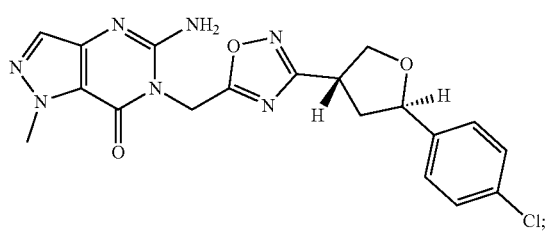

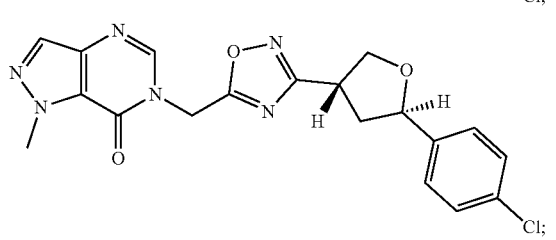

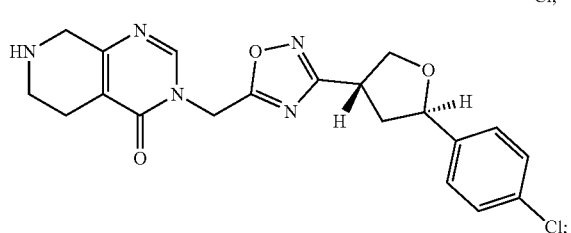

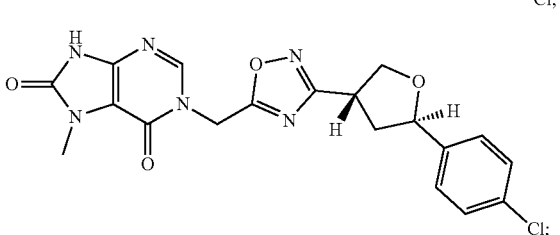

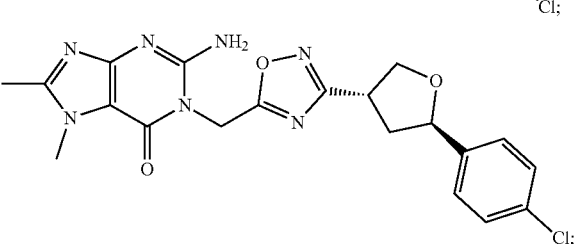

76

-continued

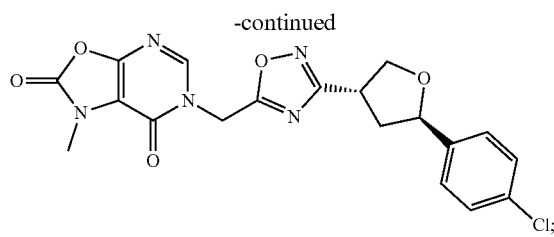

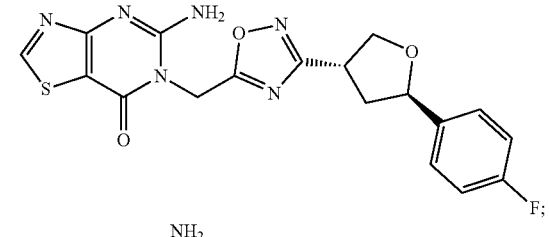

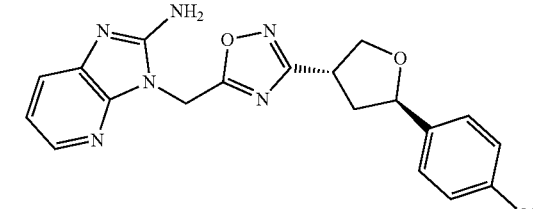

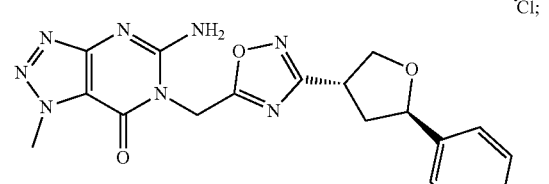

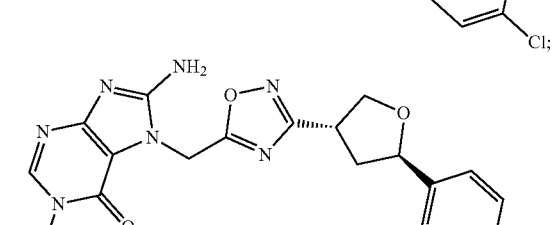

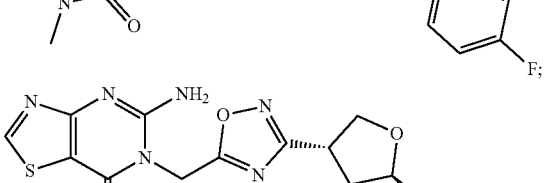

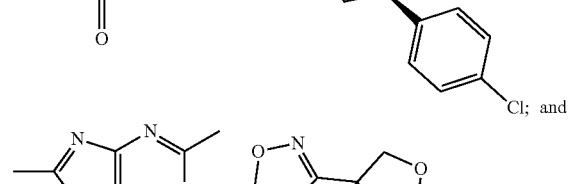

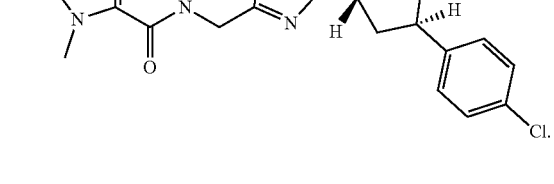

In another embodiment of the invention, the compounds of formula (I) are isotopically-labeled by having one or more atoms therein replaced by an atom having a different atomic mass or mass number. Such isotopically-labeled (i.e., radio-labeled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^2$H, may afford certain therapeutic advantages resulting from greater metabolic stability, for example, increased in vivo half-life or reduced dosage requirements. Accordingly, the term "hydrogen" or —H as used herein should be understood as encompassing deuterium and tritium.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I and a pharmaceutically acceptable carrier, diluent and/or excipient.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention may include phosphates, phosphate esters, alkyl phosphates, alkyl phosphate esters, acyl ethers, or other prodrug moieties as discussed below. In some embodiments, the prodrug moiety is:

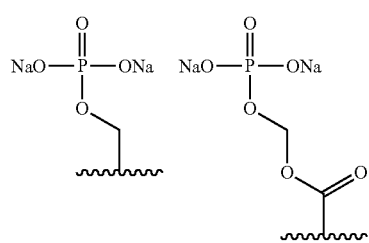

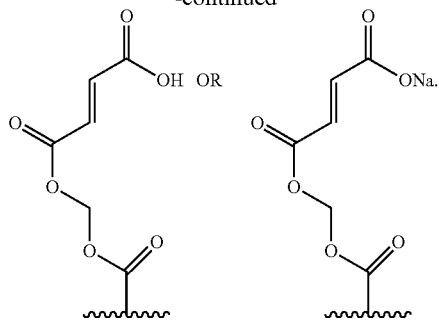

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxyl groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$) alkoxycarbonyloxymethyl, N—($C_{1-6}$)alkoxycarbonylaminomethyl, succinoyl, ($C_{1-6}$)alkanoyl, alpha-amino($C_{1-4}$) alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}$C or $^{3}$H) isotope of a compound of the invention, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

In another embodiment of the invention, processes for making the subject compounds are provided. Referring to Scheme I, there is shown a general synthetic procedure for making compounds of the invention, wherein $X^a$ is halo and may be the same or different in each occurrence, $R^a$ is aryl or $C_{1-6}$alkyl and may be the same or different in each occurrence, and $R^1$, $R^{18}$ and k are as defined herein.

Scheme 1

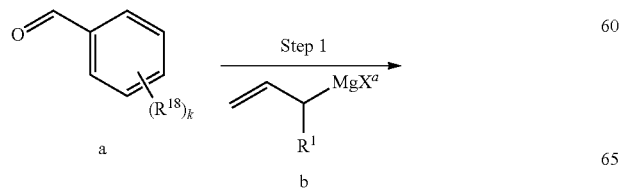

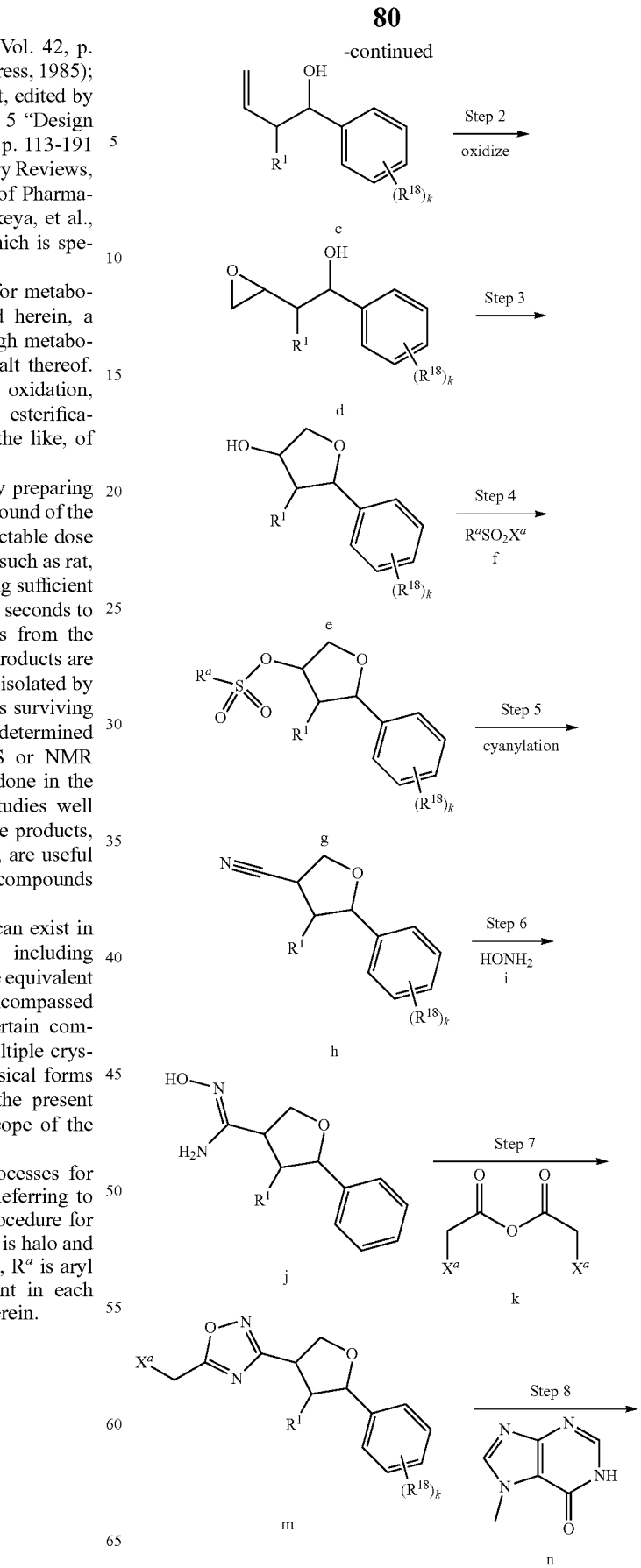

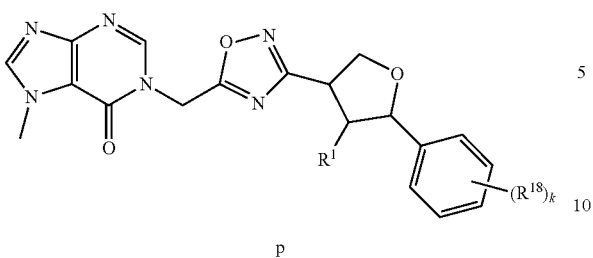

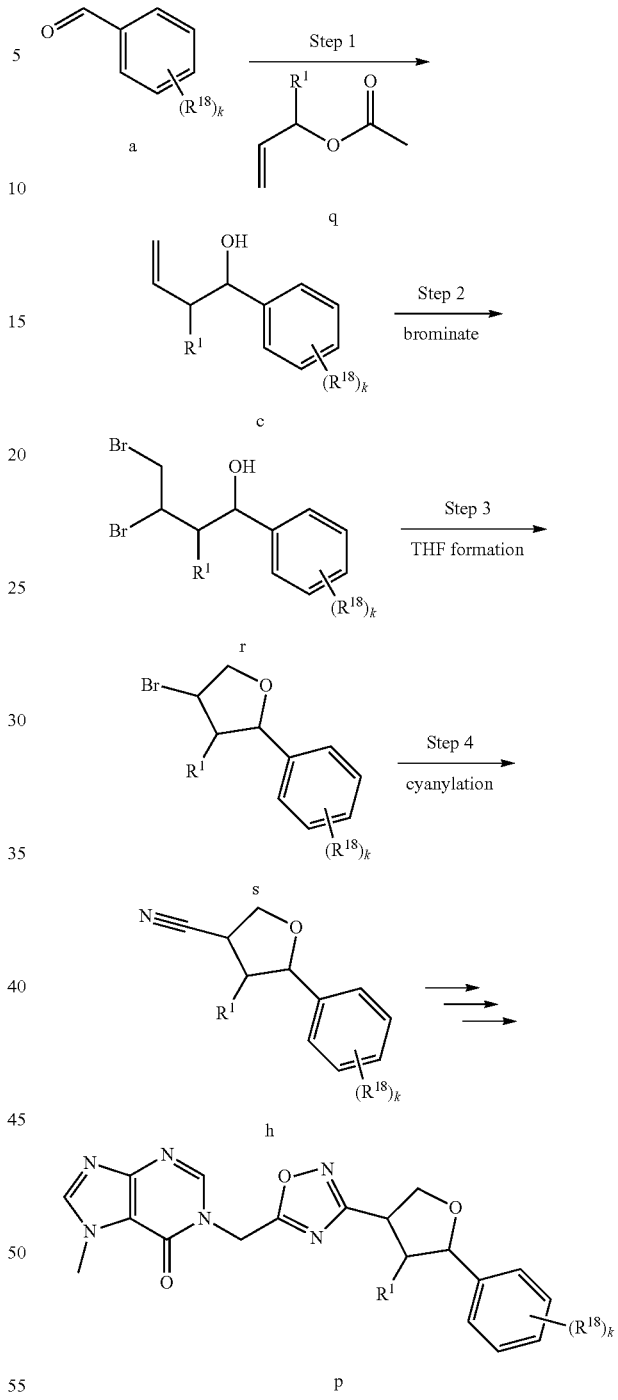

Scheme 2

In step 1 of Scheme 1, aryl aldehyde compound a is reacted with allyl Grignard reagent b to afford allyl aryl alcohol compound c. In certain embodiments $X^a$ may be halo, and $R^1$ may be hydrogen. The reaction of step 1 may be carried out under polar aprotic solvent conditions using THF or the like.

An oxidation is carried out in step 2 to oxidize the unsaturation in compound c to provide the epoxy aryl alcohol compound d. This reaction may be achieved using a mild oxidizing agent such as meta chloro perbenzoic acid in polar aprotic solvent such as dichloromethane.

In step 3 a rearrangement is effected y treatment of epoxide compound d with strong acid, such as sulfuric acid, to form aryl hydroxyl tetrahydrofuran compound e. This reaction may be carried out in a water soluble polar solvent such as dioxane.

In step 4 compound e is reacted with sulfonyl halide reagent f to afford aryl tetrahydrofuran sulfonate compound g. The reaction of step 4 may be achieved in the presence of amine catalyst in the presence of polar aprotic solvent such as dichloromethane. In certain embodiments $R^a$ may be methyl and $X^a$ may be chloro.

In step 5, compound g is treated with a cyanide reagent such as sodium or potassium cyanide, to displace the sulfonate group and provide aryl tetrahydrofuran nitrile compound h. This reaction may be carried out in polar, water miscible solvent such as dimethyl sulfoxide.

In step 6 nitrile compound h is treated with hydroxylamine to afford aryl tetrahydrofuran hydroxyl carboximidamide compound j. The reaction of step 6 may be carried out in alcohol solvent such as ethanol.

A ring formation occurs in step 7 by reaction of compound j with bis haloacetic anhydride reagent k to afford aryl oxadiazolyl tetrahydrofuran compound m. This reaction may be done in a polar aprotic solvent such as dichloroethane. In certain embodiments $X^a$ is chloro.

In step 8 an N-alkylation is carried out by reaction of imidazopyrimidone compound n with compound n to yield tetrahydrofuran oxadiazole compound 2, which is a compound of formula I in accordance with the invention. The reaction of step 8 may be carried out in the presence of potassium carbonate and trialkylammonium iodide in a solvent such as DMF.

Referring now to Scheme 2, another procedure making compounds of the invention is shown.

In step 1 of Scheme 2, aryl aldehyde compound a is reacted with allyl acetate reagent g to provide aryl allyl alcohol compound c. A chiral or assymetric synthesis reagent such as (R) or (S) BINAP (2,2'-bis(diphenylphosphino)-1,1'-binaphthyl) may be used in step 1 to impart desired stereochemistry to compound c. In this regard, the reaction of step 1 may be carried out in the presence of Cesium carbonate, 4-chloro-3-nitrobenzoic acid and/or halo cyclooctadiene iridium (I) dimer in an alcohol solvent such as isopropanol.

In step 2 compound c undergoes bromination to afford dibromo compound r. The reaction of step 2 may be carried out by treating compound c directly with bromine in polar aprotic solvent such as dichloromethane.

A cyclization is carried out in step 3 to afford aryl bromo tetrahydrofuran compound s. The reaction of step 3 may be achieved by treatment of compound r with potassium carbonate in alcohol solvent such as methanol.

In step 4, aryl bromo tetrahydrofuran compound s is treated with cyanate to form aryl tetrahydrofuran nitrile compound h. This reaction may be effected using potassium cyanate in dimethylsulfoxide or like solvent.

Using compound h, steps 6, 7 and 8 of Scheme 1 may then be carried out to afford tetrahydrofuran oxadiazole compound 2, which is a compound of formula I in accordance with the invention.

Many variations on the above procedures are possible within the scope of the invention and will suggest themselves to those skilled in the art. Several different bicyclic heteroaryl compounds may be used in place of imidazopyrimidone compound n, as will be made apparent by the experimental examples below. Chiral column separation techniques may be utilized on the final compound p as well as certain intermediates to provide particular desired stereoisomers, as described in the experimental examples below.

Pharmaceutical Compositions and Administration

In addition to one or more of the compounds provided above (including stereoisomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition" as used herein, is intended to encompass a product comprising the specified ingredients in the specified amounts, as well as any product which results, directly or indirectly, from combination of the specified ingredients in the specified amounts.

In one embodiment, the invention provides for pharmaceutical compositions or medicaments comprising a compound of formula I or an embodiment thereof, and its stereoisomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21st Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. Exp. Mol. Pathol. 2006, 81(2), 166-170), fibromyalgia, migraine and headache (e.g. cluster headache, sinus headache, or tension headache; see, Goadsby Curr. Pain Headache Reports 2004, 8, 393), sinusitis, oral mucositis, toothache, dental trauma, dental extractions, dental infections, burn (Bolcskei et al., Pain 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., Lancet, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., J Pharmacal Exp Ther., 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. J. Pharmacal. Exp. Ther. 2003, 306, 387; Walker, K. M. et al., J. Pharmacal. Exp. Ther. 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005, 117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., Br. J. Pharmacal. 2004, 141, 1313-20; Yiangou, Y. et al., Lancet2001, 357, 1338-39; Kimball, E. S. et al., Neurogastroenterol. Motif., 2004, 16, 811), osteoarthritis (Szabo, A. et al., J. Pharmacal. Exp. Ther. 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

For example, compounds of the invention can be administered to treat tracheobronchial and diaphragmatic dysfunctions including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacal. 2003, 192, 21-35), cough (e.g., acute or chronic cough, or cough caused by irritation from gastroesophageal reflux disease; see, Lalloo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., J Neurosci., 2004, 24, 11253-11263), interstitial cystitis (Sculptoreanu, A. et al., Neurosci Lett., 2005, 381, 42-46), inflammatory prostate disease, prostatitis (Sanchez, M. et al., Eur J Pharmacal., 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound as described herein to a subject in need thereof.

In another embodiment, the invention provides for a compound as described herein or a pharmaceutically acceptable salt thereof for modulating TRPA1 activity.

In another embodiment, the invention provides for a compound as described herein or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound as described herein to a subject in need thereof.

In another embodiment, the invention provides for a compound as described herein or a pharmaceutically acceptable salt thereof for the treatment or prophylaxis of a respiratory disorder.

In another embodiment, the invention provides for the use of a compound as described herein or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound as described herein or a pharmaceutically acceptable salt thereof to the mammal.

In another embodiment, the invention provides for a method for modulating TRPA1 activity, comprising contacting TRPA1 with a compound as described herein or a pharmaceutically acceptable salt thereof.

In another embodiment, the invention provides for a compound as described herein or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound as described herein or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound as described herein or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder. In some embodiments, the disease or condition is asthma.

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to the following.

Opiate analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine.

Non-opiate analgesics, e.g., acetomeniphen, and salicylates (e.g., aspirin).

Nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac.

Anticonvulsants, e.g., carbamazepine, oxcarbazepine, lamotrigine, valproate, topiramate, gabapentin and pregabalin.

Antidepressants such as tricyclic antidepressants, e.g., amitriptyline, clomipramine, despramine, imipramine and nortriptyline.

COX-2 selective inhibitors, e.g., celecoxib, rofecoxib, parecoxib, valdecoxib, deracoxib, etoricoxib, and lumiracoxib.

Alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline.

Barbiturate sedatives, e.g., amobarbital, aprobarbital, butabarbital, butabital, mephobarbital, metharbital, methohexital, pentobarbital, phenobartital, secobarbital, talbutal, theamylal and thiopental.

Tachykinin (NK) antagonist, particularly an NK-3, NK-2 or NK-1 antagonist, e.g., (aR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S).

Coal-tar analgesics, e.g., paracetamol.

Serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine.

Noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics.

Dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine.

Acetylcholinesterase inhibitors, e.g., donepezil.

5-HT3 antagonists, e.g., ondansetron.

Metabotropic glutamate receptor (mGluR) antagonists.

Local anaesthetics, e.g., mexiletine and lidocaine.

Corticosteroids, e.g., dexamethasone.

Antiarrhythimics, e.g., mexiletine and phenytoin.

Muscarinic antagonists, e.g., tolterodine, propiverine, tropsium chloride, darifenacin, solifenacin, temiverine and ipratropium.

Cannabinoids.

Vanilloid receptor agonists (e.g., resinferatoxin) or antagonists (e.g., capsazepine).

Sedatives, e.g., glutethimide, meprobamate, methaqualone, and dichloralphenazone.

Anxiolytics, e.g., benzodiazepines.

Antidepressants, e.g., mirtazapine.

Topical agents, e.g., lidocaine, capsacin and resiniferotoxin.

Muscle relaxants, e.g., benzodiazepines, baclofen, carisoprodol, chlorzoxazone, cyclobenzaprine, methocarbamol and orphrenadine.

Anti-histamines or H1 antagonists.

NMDA receptor antagonists.

5-HT receptor agonists/antagonists.

PDEV inhibitors.

Tramadol®.

Cholinergic (nicotinic) analgesics.

Alpha-2-delta ligands.

Prostaglandin E2 subtype antagonists.

Leukotriene B4 antagonists.

5-lipoxygenase inhibitors.

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Although certain exemplary embodiments are depicted and described herein, the compounds of the present invention can be prepared using appropriate starting materials according to the methods described generally herein and/or by methods available to one of ordinary skill in the art.

Intermediates and final compounds may be purified by either flash chromatography, and/or by reverse-phase preparative HPLC (high performance liquid chromatography), and/or by supercritical fluid chromatography. Unless otherwise noted, flash chromatography may be carried out using prepacked silica gel cartridges from either ISCO or Sili-Cycle on an ISCO CombiFlash® chromatography instrument (from Teledyne Isco, Inc.). Reverse-phase preparative HPLC may be performed using a (1) Polaris C-18 5 μM column (50×21 mm), or (2) XBridge Prep C-18 OBD 5 μM column (19×150 mm). Supercritical fluid chromatography may be carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 μM, (2) 4.6 cm×5 cm, 5 μM, or (3) 15 cm×21.2 mm, 5 μM.

Mass spectrometry (MS) may be performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) may be performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The following abbreviations may be used in the examples below:
BuOH n-Butyl alcohol
DMF Dimethylformamide
DMSO Dimethylsulfoxide
EtONa Sodium ethoxide
LCMS Liquid Chromatography Mass Spectroscopy
LDA Lithium diisopropylamide
LiHMDS Lithium bis(trimethylsilyl)amide
m-CPBA meta-Chloro perbenzoic acid
MeMgCl Methyl magnesium chloride
MeONa Sodium methoxide
n-BLi n-Butyllithium
PCMCl para-Methoxy benzyl chloride
SEMCl (2-Chloromethoxyethyl)trimethylsilane
TEA Triethylamine
TMSCHN$_2$ Trimethylsilyldiazomethane Preparation 1: 7-Methyl-1H-purin-6(7H)-one The Preparation 1 reaction scheme is as follows:

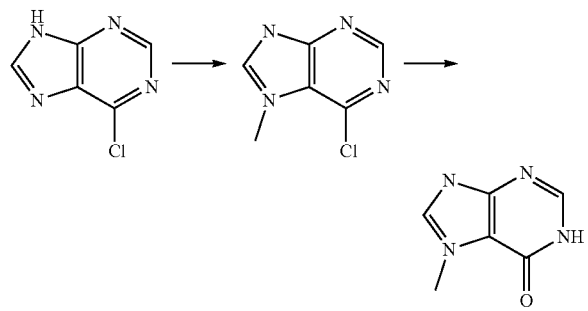

Step 1: Preparation of 6-chloro-7-methyl-7H-purine

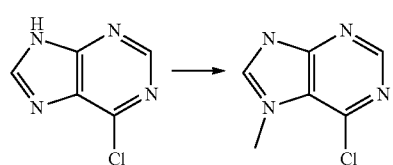

To a 1 L 3-necked round-bottom flask purged and maintained with an inert atmosphere of nitrogen was placed 6-chloro-9H-purine (15.4 g, 0.1 mol, 1 equiv) and tetrahydrofuran (155 mL) at 0° C. followed by the addition of MeMgCl (36.6 mL, 1.0M THF solution, 1.1 equiv) dropwise with stirring. The mixture was stirred at 0° C. for 30 min. To this was added iodomethane (42.6 g, 3 equiv) dropwise with stirring. The resulting solution was stirred at 50° C. in an oil bath for 5 h, quenched by the addition of 50 mL of aqueous NH$_4$Cl and extracted with dichloromethane (3×50 mL). The combined organic layers were washed with brine (2×50 mL) and concentrated under vacuum. The crude product was re-crystallized from CH$_2$Cl$_2$/petroleum ether in the ratio of 1:10 to afford desired product as a greenish solid (7 g, 42%).

Step 2: Preparation of 7-methyl-1H-purin-6(7H)-one

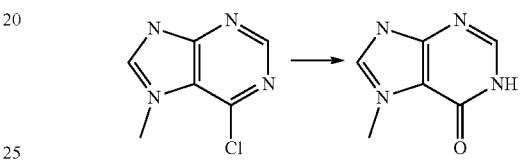

To a 1 L 3-necked round-bottom flask was placed 6-chloro-7-methyl-7H-purine (100 g, 590 mmol, 1 eq) and formic acid (1 L). The resulting solution was stirred at 70° C. for 3 h. The resulting mixture was concentrated under vacuum, and the residue was diluted with 500 mL of water. The resulting solution was extracted with 3×250 mL of ether/ethyl acetate (20:1) and the aqueous layers were concentrated under vacuum with toluene to remove water and formic acid. The residue was dissolved in water. The pH value of the solution was adjusted to 9 with NH$_3$.H$_2$O (25%) and the aqueous layer was concentrated under vacuum. The solids were collected by filtration, washed with water twice and dried to afford desired product (55 g, 62%) as yellow solid.

Preparation 2: 5-Methylpyrido[3,4-d]pyrimidin-4(3H)-one

The reaction scheme for Preparation 2 is as follows:

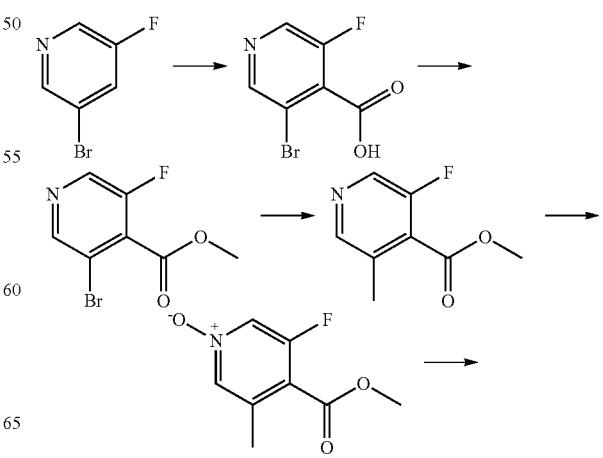

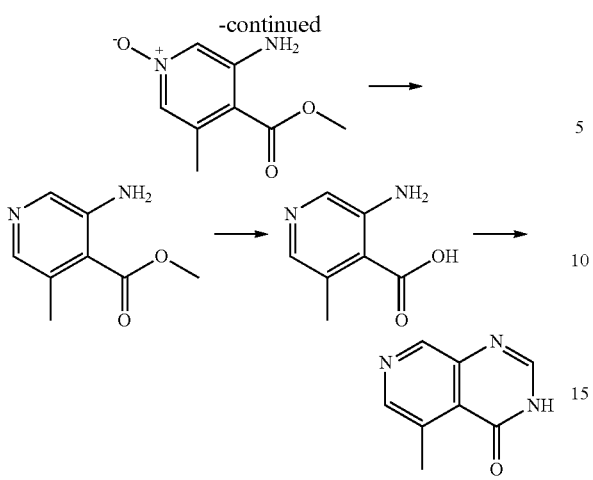

Step 1: Preparation of 3-bromo-5-fluoroisonicotinic acid

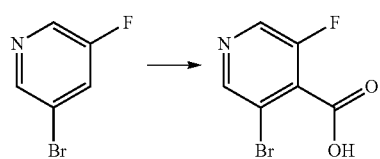 [SMILES: Fc1cncc(Br)c1 ; O=C(O)c1c(F)cncc1Br]

n-BuLi (250 mL, 0.62 mol, 2.5 equiv) was added dropwise into a solution of bis(propan-2-yl)amine (76 g, 0.75 mmol, 3 equiv) and tetrahydrofuran (1 L) at 0° C. under nitrogen. The mixture was stirred for 30 min at 0° C. To this was added 3-bromo-5-fluoropyridine (44 g, 0.25 mol, 1 equiv) dropwise with stirring at −70° C. The resulting solution was stirred for 1 h at −70° C. The reaction mixture was then poured into a mixture of dry ice in 500 mL of THF. The resulting mixture was stirred for 30 min and then concentrated under vacuum. The residue was dissolved in water. The pH value of the solution was adjusted to 3 with hydrogen chloride (1 mol/L). The mixture was extracted with ethyl acetate, dried over anhydrous sodium sulfate and concentrated under vacuum to give the product (40 g, 72%) as yellow solid.

Step 2: Preparation of methyl 3-bromo-5-fluoroisonicotinate

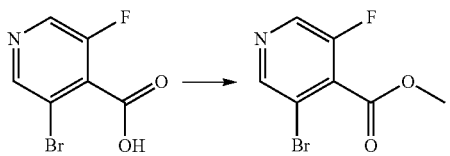

TMSCHN$_2$ (180 mL, 360 mmol, 2 equiv) was added into a solution of 3-bromo-5-fluoroisonicotinic acid (40 g, 182 mmol, 1 equiv), THF (240 mL), and MeOH (80 mL) dropwise with stirring at 0° C. under nitrogen. The resulting solution was stirred for 3 h at room temperature. The resulting mixture was concentrated under vacuum. The residue was purified by a silica gel column eluting with ethyl acetate/petroleum ether (1/9) to afford the title compound (35 g, 83%) as yellow oil.

Step 3: Preparation of methyl 3-fluoro-5-methylisonicotinate

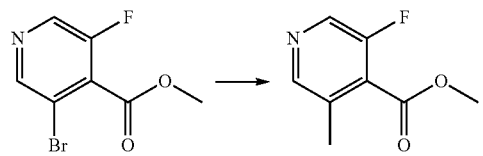

Zn(CH$_3$)$_2$ (225 mL, 0.22 mol, 1.5 equiv) was added into a mixture of 3-bromo-5-fluoroisonicotinate (35 g, 0.15 mol, 1 equiv), dioxane (1 L), and Pd(dppf)Cl$_2$ (11 g, 15 mmol, 0.1 equiv) at room temperature under nitrogen. The resulting solution was stirred for 3 h at 50° C. The reaction was then quenched by the addition of methanol. The solids were filtered out. The resulting mixture was concentrated under vacuum. The residue was dissolved in ethyl acetate, washed with brine, dried over anhydrous sodium sulfate and concentrated under vacuum. The residue was purified by silica column chromatography to give the product (17 g, 69%).

Step 4: Preparation of 3-fluoro-4-(methoxycarbonyl)-5-methylpyridine 1-oxide

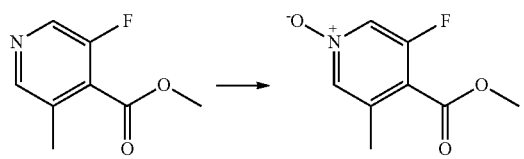

m-CPBA (96 g, 0.56 mol, 1.5 equiv) was added into a solution of methyl 5-fluoro-3-methylpyridine-4-carboxylate (63 g, 0.37 mol, 1 equiv) in dichloromethane (1.7 L) at 0° C. under nitrogen. The resulting mixture was stirred for 15 h at room temperature. The reaction was quenched by the addition of saturated solution of sodium bicarbonate, extracted with ethyl acetate, washed with saturated solution of Na$_2$S$_2$O$_3$ and brine, dried over anhydrous sodium sulfate, and concentrated under vacuum. The residue was purified by a silica gel column eluting with ethyl acetate/heptane (9/1) to afford the title compound (62 g, 89%) as a yellow solid.

Step 5: Preparation of 3-amino-4-(methoxycarbonyl)-5-methylpyridine 1-oxide

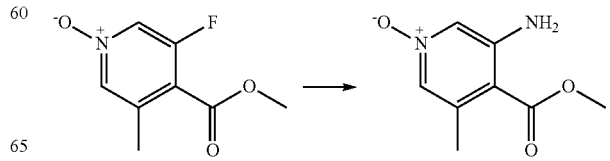

To a mixture of 3-fluoro-4-(methoxycarbonyl)-5-methylpyridine 1-oxide (62 g, 0.34 mol, 1 equiv) in DMSO (600 mL) was bubbled NH$_3$ (g) and the mixture was stirred for 12 h at 80° C. After completion, the mixture was diluted with water (1500 mL) and extracted with EA (800 mL×3). The combined organic layer was washed with brine twice. The resulting mixture was concentrated under vacuum to afford the title compound (62 g, crude) as a yellow solid, which was used in the next step without further purification.

Step 6: Preparation of methyl 3-amino-5-methylisonicotinate

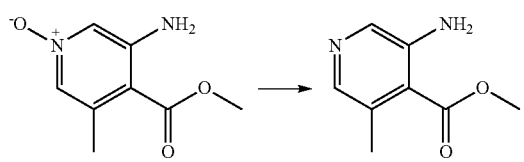

A mixture of 3-amino-4-(methoxycarbonyl)-5-methylpyridine 1-oxide (62 g, 0.34 mol, 1 equiv), methanol (400 mL), and Raney Nickel (10 g) was stirred for 30 min at room temperature under hydrogen atmosphere. The solids were filtered out. The resulting solution was concentrated under vacuum to afford the title compound (40 g, 71% for 2 steps) as a yellow solid.

Step 7: Preparation of 3-amino-5-methylisonicotinic acid

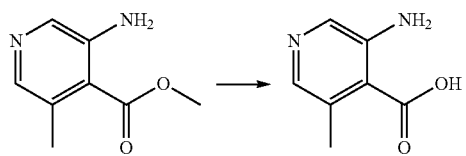

A mixture of methyl 3-amino-5-methylpyridine-4-carboxylate (40 g, 0.24 mol, 1 equiv), methanol (450 mL), water (90 mL), and sodium hydroxide (38 g, 0.96 mol, 4 equiv) was stirred for 12 h at room temperature. The pH value of the solution was adjusted to 3 with hydrogen chloride (1 mol/L). The resulting mixture was concentrated under vacuum. The residue was dissolved in ethanol. The solids were filtered out. The resulting filtrate was concentrated under vacuum to afford the title compound (35 g, 95%) as a yellow solid.

Step 8: Preparation of 5-methylpyrido[3,4-d]pyrimidin-4(3H)-one

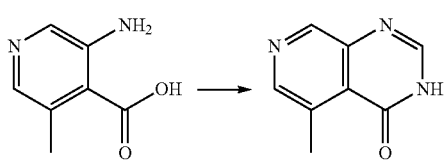

A mixture of 3-amino-5-methylpyridine-4-carboxylic acid (35 g, 0.23 mol, 1 equiv), ethanol (450 mL), and acetic acid, methanimidamide (35 g, 0.34 mol, 1.5 equiv) was stirred for 3 h at 80° C. The resulting mixture was concentrated under vacuum. The residue was purified by a silica gel column eluting with dichloromethane/methanol (5/1) to afford the title compound (22 g, 59%) as a yellow solid.

Preparation 3:
5-Methylpyrido[2,3-d]pyrimidin-4(3H)-one

The reaction scheme for Preparation 3 is shown below.

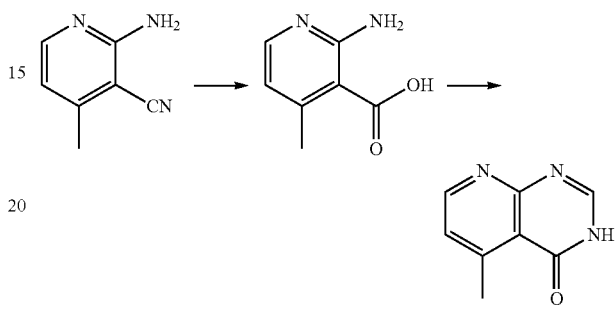

Step 1: Preparation of 2-amino-4-methylnicotinic acid

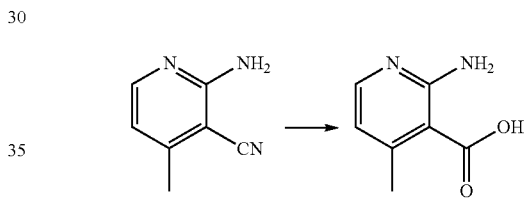

To a 2-L round-bottom flask was placed 2-amino-4-methylpyridine-3-carbonitrile (50 g, 375.51 mmol, 1.00 equiv.) and aqueous potassium hydroxide solution (20%, 700 mL). The resulting solution was stirred at 110° C. in an oil bath overnight and cooled to room temperature. The pH value of the mixture was adjusted to 3 with aqueous HCl solution (2 N). The mixture was concentrated under vacuum. The residue was washed with 2×400 mL of ethanol. The solid was filtered out. The filtrate was concentrated under vacuum to afford 40 g (crude) of 2-amino-4-methylpyridine-3-carboxylic acid as a yellow solid which was directly used in the next step.

Step 2: Preparation of 5-methylpyrido[2,3-d]pyrimidin-4(3H)-one

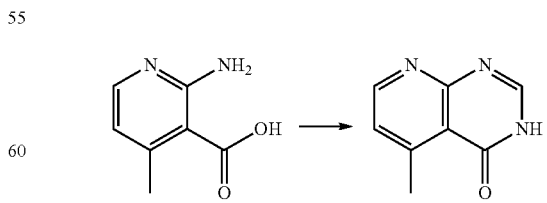

To a 1-L round-bottom flask was placed a solution of 2-amino-4-methylpyridine-3-carboxylic acid (40 g, 262.90 mmol, 1.00 equiv.) in ethanol (500 mL) and formamidine acetate (82.11 g, 788.69 mmol, 3.00 equiv.). The resulting solution was stirred at 100° C. in an oil bath overnight and cooled to room temperature. The solids were collected by filtration, washed with 3×100 mL of MeOH, and dried under vacuum to afford 21 g (50%) of 5-methyl-3H, 4H-pyrido[2,3-d]pyrimidin-4-one as a white solid.

Preparation 4: 5,7-Dimethyl-3H,4H-imidazo[4,3-f][1,2,4]triazin-4-one

The reaction scheme for Preparation 4 is shown below.

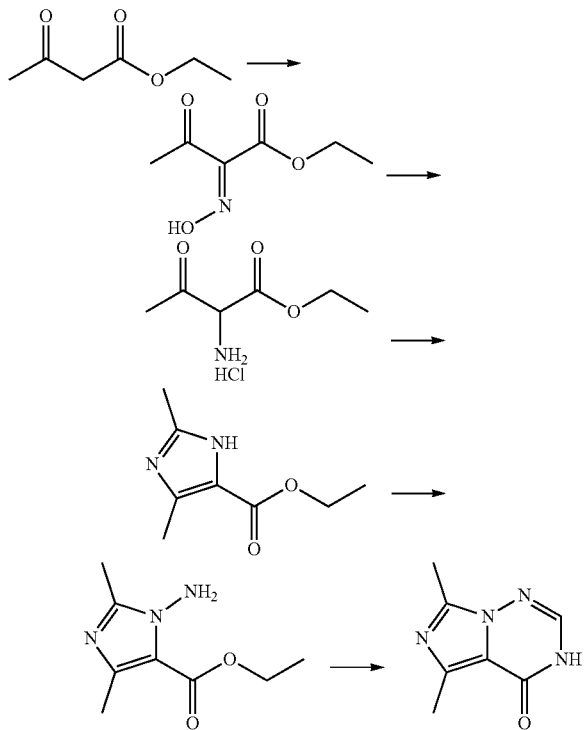

Step 1: Preparation of ethyl-2-(hydroxyimino)-3-oxobutanoate

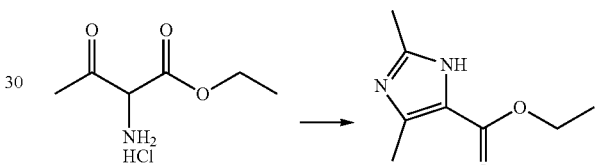

A solution of $NaNO_2$ (3.6 g, 52.18 mmol) in water (6 mL) was added dropwise into a mixture of ethyl 3-oxobutanoate (5.2 g, 39.96 mmol) and AcOH (6 mL) with stirring at 0° C. The resulting solution was stirred for 12 h at room temperature. The pH value of the solution was adjusted to 7 to 8 with sodium bicarbonate (saturated solution). The resulting solution was extracted with ethyl acetate, washed with brine, dried over anhydrous sodium sulfate and concentrated under vacuum. This resulted in the title compound (5.2 g, 82%) as colorless oil which was used for the next step without any further purification. LCMS [M+H⁺] 160.

Step 2: Preparation of ethyl 2-amino-3-oxobutanoate hydrochloride

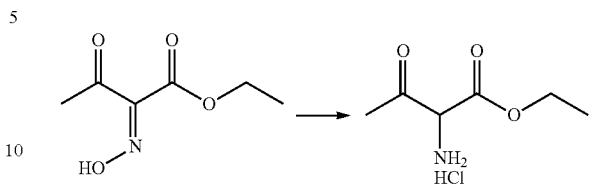

A mixture of ethyl-2-(hydroxyimino)-3-oxobutanoate (5.2 g, 32.68 mmol), ethanol (50 mL), concentrate hydrogen chloride (5 mL), and Pd/C (1 g, 10%) was stirred for 48 h at room temperature under hydrogen atmosphere. The solids were filtered out. The resulting mixture was concentrated under vacuum. This resulted in the title compound (5 g, 84%) as an off-white solid which was used for the next step without any further purification. LCMS [M+H⁺] 146.

Step 3: Preparation of ethyl 2,4-dimethyl-1H-imidazole-5-carboxylate

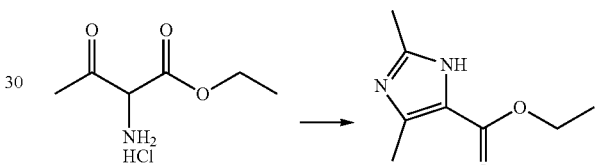

A solution of ethyl 2-amino-3-oxobutanoate hydrochloride (4.6 g, 25.33 mmol) in ethanol (10 mL) was added dropwise into a mixture of ethyl ethanecarboximidate hydrochloride (8.1 g, 65.54 mmol), ethanol (100 mL), and TEA (8.4 g, 83.01 mmol) with stirring at room temperature. The resulting solution was stirred for 12 h at room temperature. The resulting solution was diluted with ethyl acetate, washed with brine, dried over anhydrous sodium sulfate and concentrated under vacuum. The residue was purified on a silica gel column eluting with dichloromethane/methanol (10/1) to afford the title compound (1.3 g, 31%) as a light yellow solid. LCMS [M+H⁺] 169.

Step 4: Preparation of ethyl 1-amino-2,4-dimethyl-1H-imidazole-5-carboxylate

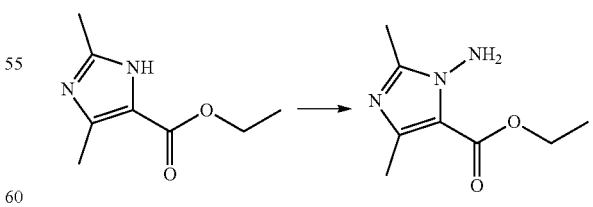

LiHMDS (8.5 mL, 1M in THF) was added dropwise into a mixture of ethyl 2,4-dimethyl-1H-imidazole-5-carboxylate (1.3 g, 7.73 mmol) and N,N-dimethylformamide (200 mL) with stirring at −10° C. in a dry ice bath under nitrogen. The resulting solution was stirred for 30 min at −10° C. To this was added amino diphenylphosphinate (2.2 g, 9.43 mmol) in portions at 0° C. The resulting solution was allowed to react, with stirring, for an additional 12 h at room temperature. The resulting solution was diluted with of water, extracted with ethyl acetate, washed with brine, dried over anhydrous sodium sulfate and concentrated under vacuum. The residue was purified by a silica gel column eluting with dichloromethane/methanol (10/1) to afford the title compound (1.0 g, 71%) as a light yellow solid. LCMS [M+H$^+$] 184.

Step 5: Preparation of 5,7-dimethyl-3H,4H-imidazo[4,3-f][1,2,4]triazin-4-one

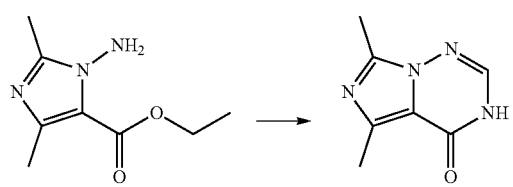

A mixture of ethyl 1-amino-2,4-dimethyl-1H-imidazole-5-carboxylate (1.0 g, 5.46 mmol), formamide (10 mL), and MeONa (3.0 mL, 5.4M in MeOH) was stirred for 1 h at 100° C. in an oil bath. The resulting solution was diluted with water. The pH value of the solution was adjusted to 5 with hydrogen chloride (1N). The solids were collected by filtration and dried under vacuum to afford 130 mg of white solid. The filtrate was purified on a C18 silica gel column eluting with CH$_3$CN/H$_2$O (10 mmol/L of NH$_4$HCO$_3$) increasing from 5% to 95% within 30 min. The fractions were collected and concentrated to afford 370 mg of white solid. This resulted in the title compound (total of 500 mg, 56%) as a white solid. LCMS [M+H$^+$] 165.

Preparation 5: Preparation of 6-methyl-7-oxo-1H,6H,7H-pyrazolo[4,3-d]pyrimidine-3-carbonitrile The reaction scheme for Preparation 5 is shown below.

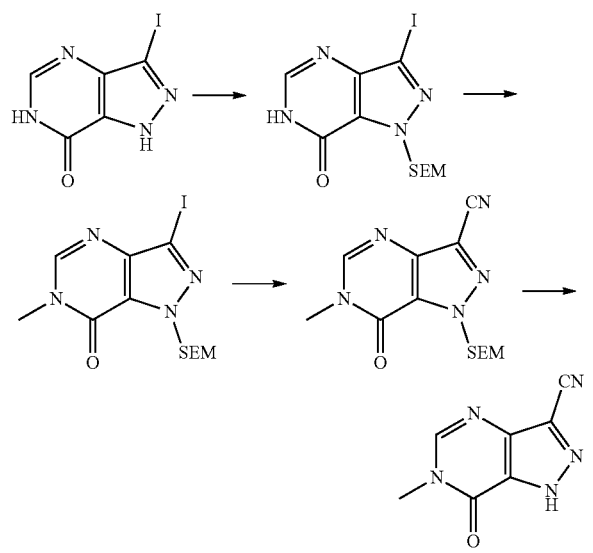

Step 1: Preparation of 3-iodo-1-[[2-(trimethylsilyl)ethoxy]methyl]-1H,6H,7H-pyrazolo[4,3-d]pyrimidin-7-one

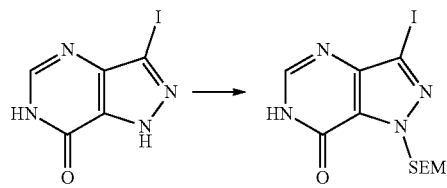 [SMILES: O=c1[nH]cnc2c(I)n[nH]c12 ; C[Si](C)(C)CCOCn1nc(I)c2nc[nH]c(=O)c21]

Sodium hydride (687 mg, 28.62 mmol) was added batchwise to a solution of 3-iodo-1H,6H,7H-pyrazolo[4,3-d]pyrimidin-7-one (1.5 g, 5.72 mmol) in N,N-dimethylformamide (50 mL) at 0° C. SEM-Cl (950 mg, 6.22 mmol) was added dropwise into the above solution after 20 min. The result solution was stirred for 12 h at room temperature and used for the next step without any further purification. LCMS [M+H$^+$] 393.

Step 2: Preparation of 3-iodo-6-methyl-1-[[2-(trimethylsilyl)ethoxy]methyl]-1H,6H,7H-pyrazolo[4,3-d]pyrimidin-7-one

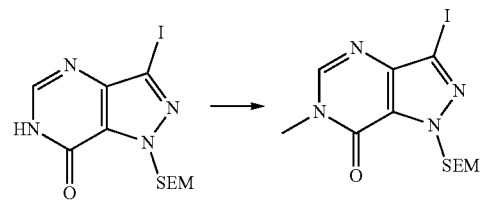 [SMILES: C[Si](C)(C)CCOCn1nc(I)c2nc[nH]c(=O)c21 ; Cn1cnc2c(I)nn(COCC[Si](C)(C)C)c2c1=O]

Sodium hydride (60 mg 2.50 mmol) was added into a solution of 3-iodo-1-[[2-(trimethylsilyl)ethoxy]methyl]-1H,6H,7H-pyrazolo[4,3-d]pyrimidin-7-one (~0.11M in DMF, 50 mL, prepared from step 1) at 0° C. After 20 min CH$_3$I (430 mg, 3.02 mmol) was added dropwise and the resulting mixture was stirred for 3 h at room temperature. The reaction solution was purified on a C18 silica gel column eluting with CH$_3$CN/H$_2$O (10 mmol/L NH$_4$HCO$_3$, 5% to 95%, over 30 min). This resulted in the title compound (250 mg, 24%) as a white solid. LCMS [M+H$^+$] 407.

Step 3: Preparation of 6-methyl-7-oxo-1-[[2-(trimethylsilyl)ethoxy]methyl]-1H,6H,7H-pyrazolo[4,3-d]pyrimidine-3-carbonitrile

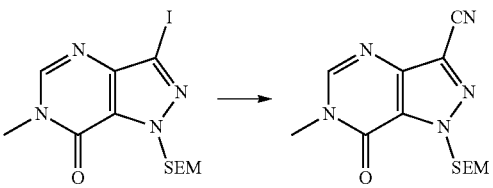 [SMILES: Cn1cnc2c(I)nn(COCC[Si](C)(C)C)c2c1=O ; Cn1cnc2c(C#N)nn(COCC[Si](C)(C)C)c2c1=O]

A mixture of 3-iodo-6-methyl-1-[[2-(trimethylsilyl)ethoxy]methyl]-1H,6H,7H-pyrazolo[4,3-d]pyrimidin-7-one (260 mg, 0.64 mmol), Zn(CN)$_2$ (148 mg, 1.26 mmol), Pd$_2$(dba)$_3$·CHCl$_3$ (66 mg, 0.06 mmol), dppf (71 mg, 0.13 mmol), and N,N-dimethylformamide (5 mL) was irradiated with microwave radiation for 1 h at 100° C. under nitrogen. The solids were filtered out. The filtrate was purified on a C18 silica gel column eluting with CH₃CN/H₂O (10 mmol/L NH₄HCO₃, 5% to 95%, over 30 min). This resulted in the title compound (150 mg, 77%) as a white solid. LCMS [M+H⁺] 306.

Step 4: Preparation of 6-methyl-7-oxo-1H,6H,7H-pyrazolo[4,3-d]pyrimidine-3-carbonitrile

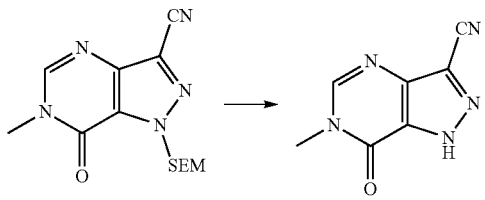 [SMILES: Cn1cnc2c(C#N)nn(COCC[Si](C)(C)C)c2c1=O ; Cn1cnc2c(C#N)n[nH]c2c1=O]

A mixture of 6-methyl-7-oxo-1-[[2-(trimethylsilyl)ethoxy]methyl]-1H,6H,7H-pyrazolo[4,3-d]pyrimidine-3-carbonitrile (120 mg, 0.39 mmol) and trifluoroacetic acid (3 mL) was stirred for 18 h at 60° C. The resulting mixture was concentrated under vacuum. This resulted in the title compound (60 mg, 87%) as a white solid. LCMS [M+H⁺] 176.

Preparation 6:
1-Methyl-6,7-dihydro-1H-purin-6-one

The overall Preparation 6 reaction scheme is as follows:

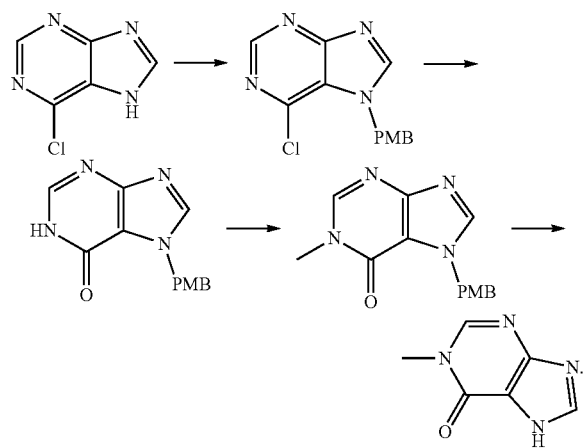

Step 1: Preparation of 6-chloro-7-[(4-methoxyphenyl)methyl]-7H-purine

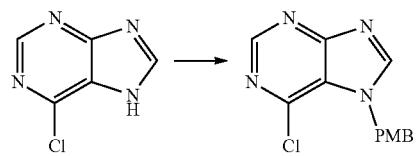

Sodium hydride (858 mg, 35.75 mmol) was added batchwise to a solution of 6-chloro-7H-purine (3 g, 19.41 mmol) in N,N-dimethylformamide (30 mL,). After 20 min PMBCl (6.1 g, 38.81 mmol) was added dropwise into the above mixture. The resulting solution was stirred for 4 h at room temperature, diluted with ethyl acetate, washed with brine, dried over anhydrous sodium sulfate, and concentrated under vacuum. The residue was purified on a silica gel column eluting with ethyl acetate/petroleum ether (1:1) to afford the title compound (2.3 g, 43%) as light yellow oil. LCMS [M+H⁺] 275.

Step 2: Preparation of 7-[(4-methoxyphenyl)methyl]-6,7-dihydro-1H-purin-6-one

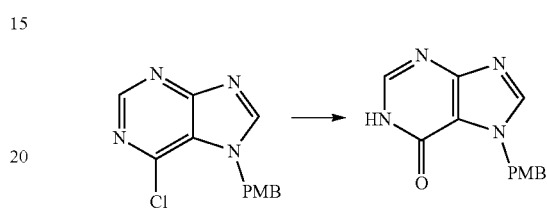

A mixture of 6-chloro-7-[(4-methoxyphenyl)methyl]-7H-purine (2.3 g, 8.37 mmol), 1,4-dioxane (3 mL), sodium hydroxide (1 g, 25.00 mmol) and water (25 mL) was stirred for 1.5 h at 90° C. The pH value of the solution was adjusted to 7 with HCl (2 M). The solids were collected by filtration to afford the title compound (1.95 g, 91%) as a white solid. LCMS [M+H⁺] 257.

Step 3: Preparation of 7-[(4-methoxyphenyl)methyl]-1-methyl-6,7-dihydro-1H-purin-6-one

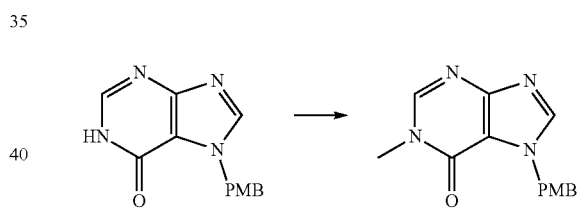

A mixture of 7-[(4-methoxyphenyl)methyl]-6,7-dihydro-1H-purin-6-one (1 g, 3.90 mmol), potassium carbonate (1.1 g, 7.80 mmol), N,N-dimethylformamide (12 mL) and CH₃I (666 mg, 4.69 mmol) was stirred for 1.5 h at room temperature. The solids were filtered out. The reaction mixture was purified on a C18 silica gel column eluting with CH₃CN/H₂O (10 mmol/L NH₄HCO₃, 5% to 95% over 30 min). This resulted in the title compound (700 mg, 66%) as a white solid. LCMS [M+H⁺] 271.

Step 4: Preparation of 1-methyl-6,7-dihydro-1H-purin-6-one

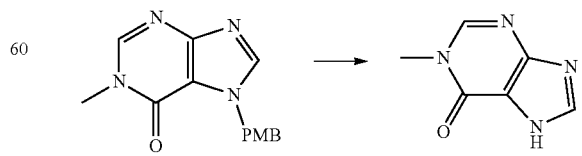

A mixture of 7-[(4-methoxyphenyl)methyl]-1-methyl-6,7-dihydro-1H-purin-6-one (700 mg, 2.590 mmol) and trifluoroacetic acid (10 mL) was stirred for 15 h at 70° C. The resulting mixture was concentrated under vacuum. This resulted in the title compound (700 mg, crude) as a white solid. LCMS [M+H⁺] 151.

Preparation 7: 4-Methylpyrimido[4,5-c]pyridazin-5(6H)-one

The overall Preparation 7 reaction scheme is as follows:

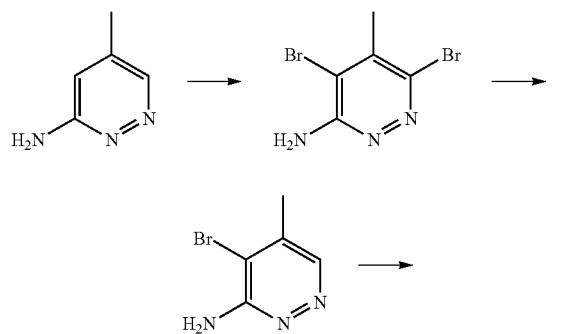

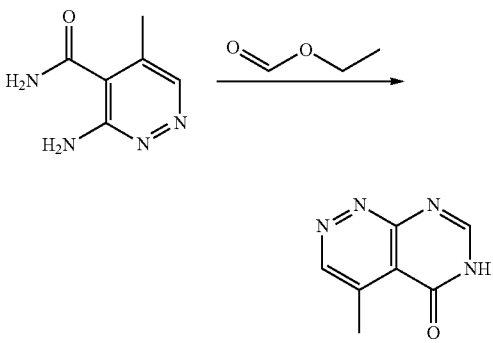

Step 1: Preparation of 4,6-dibromo-5-methylpyridazin-3-amine

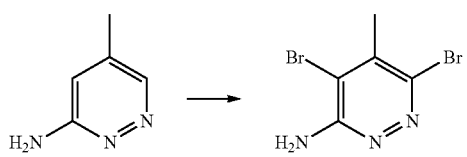

A solution of Br₂ (9.6 g, 60.07 mmol) in methanol (30 mL) was added dropwise into the mixture of 5-methyl-pyridazin-3-amine (3 g, 27.49 mmol), methanol (100 mL), and sodium bicarbonate (11.5 g, 136.89 mmol) at 0° C. The resulting solution was stirred for 2 h at room temperature, diluted with water, extracted with ethyl acetate, dried over sodium sulfate, and concentrated under vacuum. The residue was purified by a silica gel column eluting with ethyl acetate/petroleum ether (1/4) to afford the title compound (4.0 g, 55%) as a brown solid. LCMS [M+H⁺] 266.

Step 2: Preparation of 4-bromo-5-methylpyridazin-3-amine

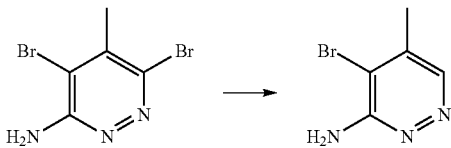

EtMgBr (2 mL, 15.15 mmol, 3M in THF) was added dropwise into a solution of 4,6-dibromo-5-methylpyridazin-3-amine (400 mg, 1.49 mmol) in tetrahydrofuran (8 mL) at 0-10° C. under nitrogen. The resulting solution was stirred for 35 min at 63° C. The reaction was quenched with water and concentrated under vacuum. The residue was purified on a C18 silica gel column eluting with CH₃CN/H₂O (10 mmol/L NH₄HCO₃, 5% to 95%, over 30 min). This resulted in the title compound (36 mg, 13%) as a white solid. LCMS [M+H⁺] 188.

Step 3: Preparation of 3-amino-5-methylpyridazine-4-carboxamide

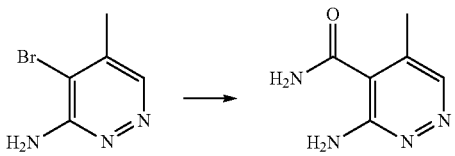

A mixture of 4-bromo-5-methylpyridazin-3-amine (80 mg, 425.47 mmol), NH₃/MeOH (7M) (4 mL), Pd(dppf)Cl₂ (31 mg, 0.04 mmol), TEA (128 mg, 1.26 mmol), and carbon monoxide was stirred overnight at 100° C. under 10 atm pressure. The reaction solution was purified on a C18 silica gel column eluting with CH₃CN/H₂O (10 mmol/L NH₄HCO₃, 5% to 95%, over 30 min). This resulted in the title compound (85 mg, crude) as a light yellow solid. LCMS [M+H⁺] 153.

Step 4: Preparation of 4-methylpyrimido[4,5-c]pyridazin-5(6H)-one

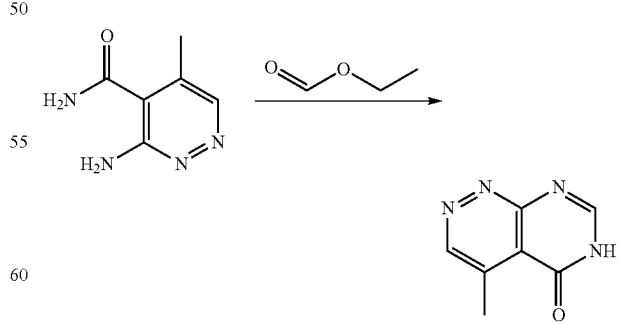

A mixture of 3-amino-5-methylpyridazine-4-carboxamide (150 mg, 0.98 mmol), ethanol (3 mL), EtONa (21%) (3.2 g, 0.04 mmol), ethyl formate (360 mg, 4.86 mmol) was stirred for 1 h at 80° C. under nitrogen. The resulting mixture was concentrated under vacuum. The pH value of the solution was adjusted to 8 with hydrogen chloride/H₂O (5%). The resulting mixture was concentrated under vacuum and diluted with ethanol. The solids were filtered out and the filtrate was concentrated under vacuum to afford the title compound (120 mg, 75%) as a brown solid. LCMS [M+H⁺] 163.

Preparation 8: 5-Methyl-4-oxo-3,4-dihydropyrido[2,3-d]pyrimidine-7-carbonitrile

The overall Preparation 8 reaction scheme is as follows:

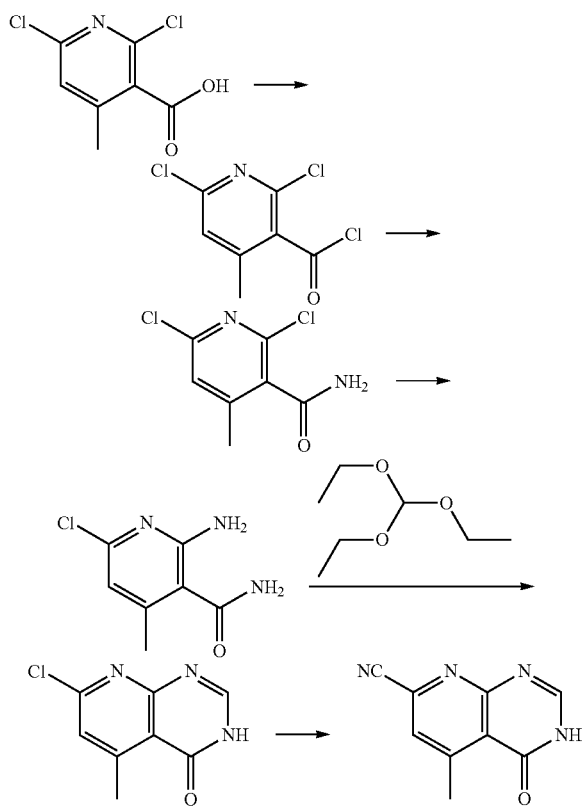

Step 1: Preparation of 2,6-dichloro-4-methylnicotinoyl chloride

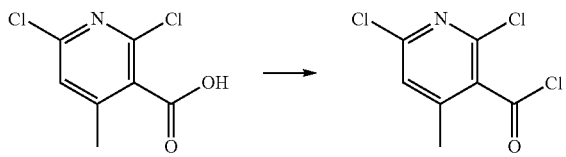

Oxalyl chloride (5.5 g, 43.33 mmol) was added dropwise into a solution of 2,6-dichloro-4-methylpyridine-3-carboxylic acid (3 g, 14.56 mmol), N,N-dimethylformamide (50 mg, 0.68 mmol), and dichloromethane (100 mL) at 0° C. The result solution was stirred overnight at room temperature and concentrated under vacuum. This resulted in the title compound (3.1 g, crude) as light yellow liquid.

Step 2: Preparation of 2,6-dichloro-4-methylnicotinamide

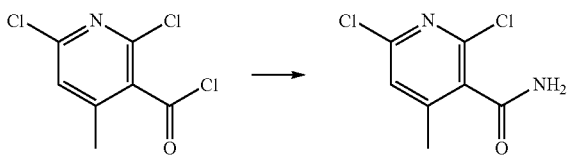

A solution of 2,6-dichloro-4-methylpyridine-3-carbonyl chloride (3.1 g, 13.81 mmol) in dichloromethane (15 mL) was added dropwise into a stirred solution NH₃/THF (0.5M) (42 mL) at 25° C. After being stirred for 1 h at room temperature the resulting mixture was concentrated under vacuum. The residue was purified by a silica gel column eluting with ethyl acetate/petroleum ether (1/1) to afford the title compound (1.5 g, 53%) as a white solid. LCMS [M+H⁺] 205.

Step 3: Preparation of 2-amino-6-chloro-4-methylnicotinamide

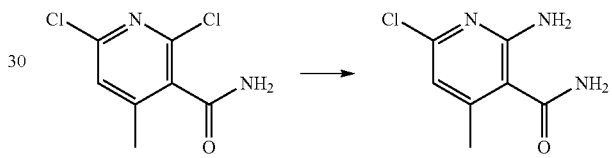

A mixture of 2,6-dichloro-4-methylpyridine-3-carboxamide (50 mg, 0.24 mmol), dioxane (2 mL, 23.60 mmol), and ammonia (30%, 0.5 mL) was stirred overnight at 130° C. The resulting mixture was concentrated under vacuum. The crude product was purified on a C18 silica gel column eluting with CH₃CN/H₂O (10 mmol/L NH₄HCO₃, 5% to 95%, over 30 min). This resulted in the title compound (25 mg, 55%) as a white solid. LCMS [M+H⁺] 186.

Step 4: Preparation of 7-chloro-5-methylpyrido[2,3-d]pyrimidin-4(3H)—

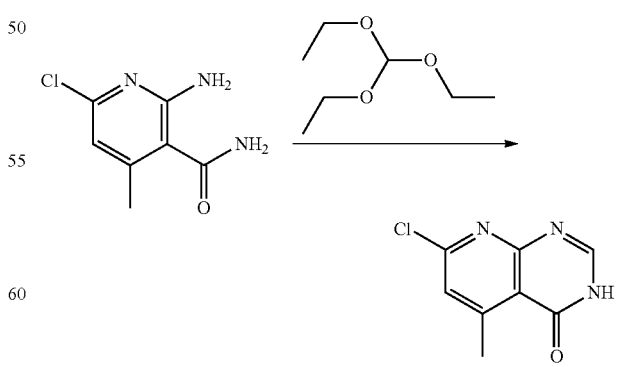

A mixture of 2-amino-6-chloro-4-methylpyridine-3-carboxamide (320 mg, 1.72 mmol) and (diethoxymethoxy)ethane (5 mL) was stirred overnight at 140° C. The solids were collected by filtration. This resulted in the title compound (180 mg, 53%) as a gray solid. LCMS [M+H+] 211.

Step 5: Preparation of 5-methyl-4-oxo-3,4-dihydropyrido[2,3-d]pyrimidine-7-carbonitrile

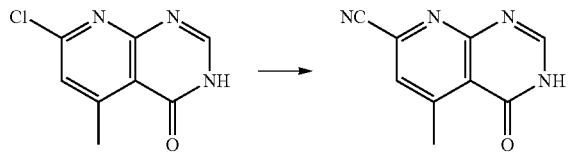

A mixture of 7-chloro-5-methyl-3H,4H-pyrido[2,3-d]pyrimidin-4-one (170 mg, 0.86 mmol), N,N-dimethylformamide (5 mL), Zn(CN)$_2$ (151 mg, 1.28 mmol), Pd$_2$(dba)$_3$·CHCl$_3$ (90 mg, 0.08 mmol,), and dppf (96 mg, 0.17 mmol) was stirred for 3 h at 100° C. under nitrogen. The solids were filtered out. The crude product was purified on a C18 silica gel column eluting with CH$_3$CN/H$_2$O (10 mmol/L NH$_4$HCO$_3$, 5% to 95%, over 30 min). This resulted in the title compound (100 mg, 62%) as a white solid. LCMS [M+H+] 187.

Preparation 9: 1-[(4-methoxyphenyl)methyl]-1H,6H,7H-imidazo[4,5-d]pyridazin-7-one The overall Preparation 9 reaction scheme is as follows:

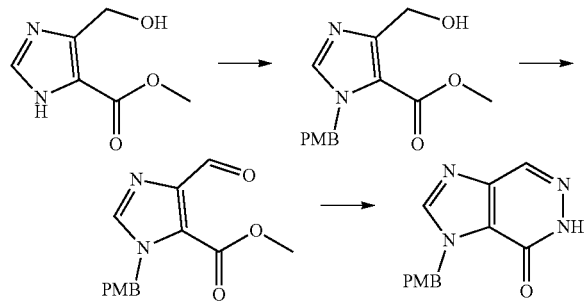

Step 1: Preparation of methyl 4-(hydroxymethyl)-1-(4-methoxybenzyl)-1H-imidazole-5-carboxylate

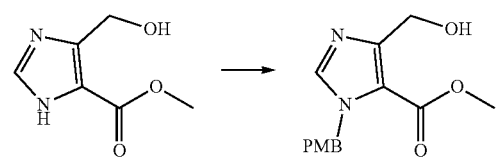

A mixture of methyl 4-(hydroxymethyl)-1H-imidazole-5-carboxylate (500 mg, 3.20 mmol), N,N-dimethylformamide (10 mL), potassium carbonate (885 mg, 6.40 mmol), PMBCl (para-methoxybenzyl chloride, 550 mg, 3.51 mmol) was stirred overnight at room temperature. The solids were filtered out. The resulting mixture was concentrated under vacuum. The residue was purified by a silica gel column eluting with dichloromethane/methanol (10/1) to afford the title compound (600 mg, 68%) as a greenish solid. LCMS [M+H+] 277.

Step 2: Preparation of methyl 4-formyl-1-(4-methoxybenzyl)-1H-imidazole-5-carboxylate

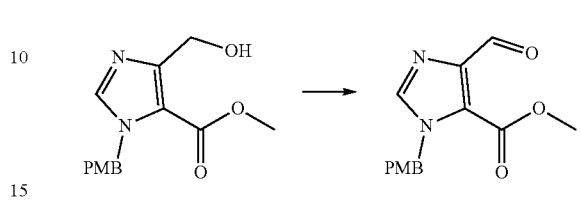

A mixture of methyl 4-(hydroxymethyl)-1-[(4-methoxyphenyl)methyl]-1H-imidazole-5-carboxylate (580 mg, 2.10 mmol), dichloromethane (20 mL), and Dess-Martin (888 mg, 2.09 mmol) was stirred for 1 h at room temperature. The solids were filtered out. The resulting mixture was concentrated under vacuum to afford the title compound (460 mg, 80%) as greenish oil. LCMS [M+H+] 275.

Step 3: Preparation of 1-[(4-methoxyphenyl)methyl]-1H,6H,7H-imidazo[4,5-d]pyridazin-7-one

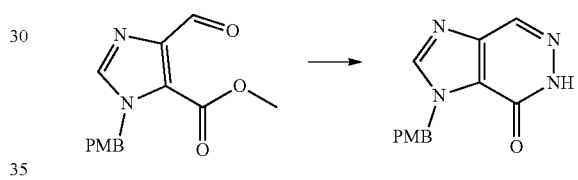

A mixture of methyl 4-formyl-1-[(4-methoxyphenyl)methyl]-1H-imidazole-5-carboxylate (460 mg, 1.68 mmol), ethanol (20 mL), and NH$_2$NH$_2$·H$_2$O (1.045 g, 20.88 mmol) was stirred for 1 h at 80° C. The resulting mixture was concentrated under vacuum. The residue was purified by a silica gel column eluting with dichloromethane/methanol (20/1) to give the title compound (400 mg, 93%) as a white solid. LCMS [M+H+] 257.

Preparation 10: 5-Methyl-4-oxo-3,4-dihydropyrido[3,4-d]pyrimidine-8-carbonitrile The overall reaction scheme for Preparation 10 is as follows:

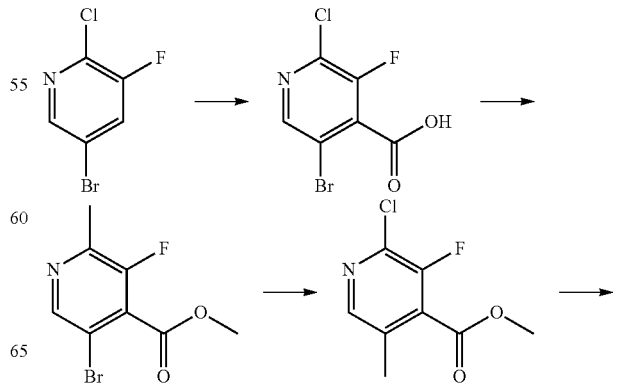

-continued

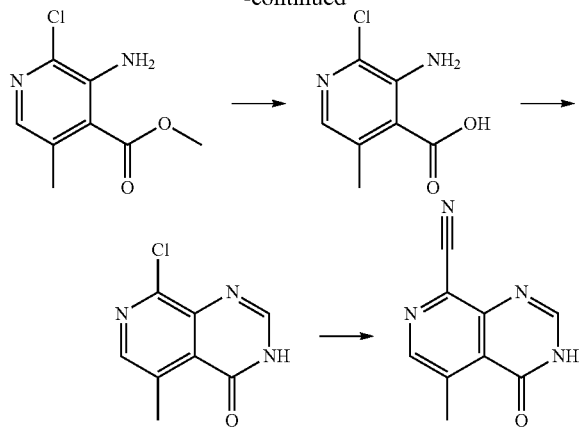

Step 1: Preparation of
5-bromo-2-chloro-3-fluoroisonicotinic acid

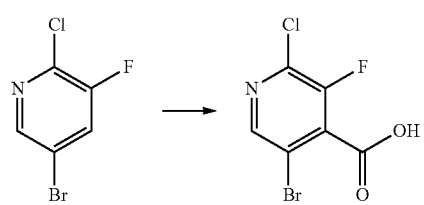

LDA (47.5 mL, 2.0 moL in THF) was added dropwise into a solution of 5-bromo-2-chloro-3-fluoropyridine (10 g, 47.52 mmol) in tetrahydrofuran (300 mL) at −78° C. under nitrogen. The resulting solution was stirred for 2 h at −78° C. The resulting mixture was poured into the CO$_2$ (solid) in THF. The reaction mixture was concentrated under vacuum. The pH value of the residue was adjusted to <7 with hydrogen chloride (2 M). The resulting mixture was extracted with ethyl acetate, washed with brine, dried over anhydrous sodium sulfate, and concentrated under vacuum. This resulted in the title compound (15 g, crude) as a white solid. LCMS [M−H$^+$] 254.

Step 2: Preparation of methyl
5-bromo-3-fluoro-2-methylisonicotinate

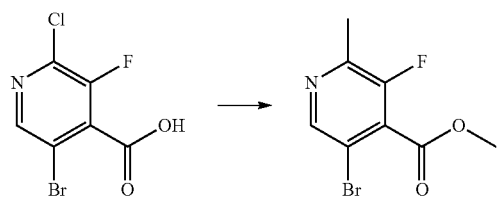

A mixture of 5-bromo-2-chloro-3-fluoropyridine-4-carboxylic acid (15 g, 59.0 mmol), tetrahydrofuran (100 mL), methanol (20 mL), TMSCHN$_2$ (60 mL, 2M in hexane) was stirred for 2 h at room temperature. The resulting mixture was concentrated under vacuum. This resulted in the title compound (12 g, crude) as oil which was used for the next step without any further purification. LCMS [M+H+] 248.

Step 3: Preparation of methyl
2-chloro-3-fluoro-5-methylisonicotinate

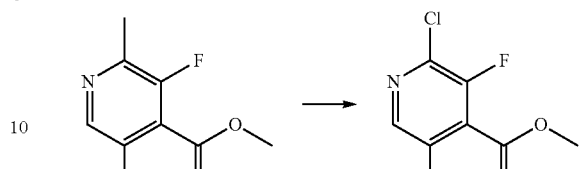

A mixture of methyl 5-bromo-2-chloro-3-fluoropyridine-4-carboxylate (5 g, 18.62 mmol), tricyclohexylphosphane (1.3 g, 4.60 mmol), palladium acetate (147 mg, 0.66 mmol), and toluene (60 mL) was stirred for 12 h at 100° C. under nitrogen. The resulting mixture was concentrated under vacuum. The residue was purified by a silica gel column eluting with ethyl acetate/petroleum ether (1:5) to afford the title compound (2.5 g, 66%) as a white solid. LCMS [M+H+] 204.

Step 4: Preparation of methyl
3-amino-2-chloro-5-methylisonicotinate

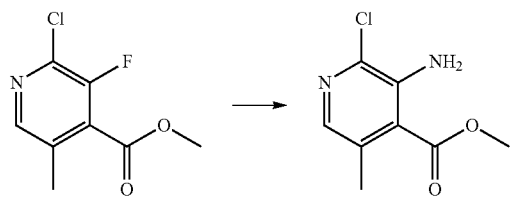

NH$_3$(g) (17.5 mL, 7 M in CH$_3$OH) was added dropwise into a solution of methyl 2-chloro-3-fluoro-5-methylpyridine-4-carboxylate (2.5 g, 12.28 mmol) in CH$_3$OH (50 mL). The resulting solution was stirred for 12 h at 100° C. and concentrated under vacuum. The residue was purified by a silica gel column eluting with ethyl acetate/petroleum ether (1:5) to afford the title compound (300 mg, 12%) as a white solid. LCMS [M+H$^+$] 201.

Step 5: Preparation of
3-amino-2-chloro-5-methylisonicotinic acid

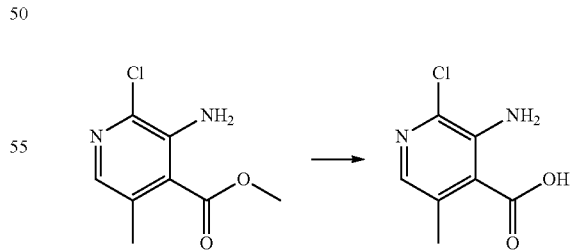

A mixture of methyl 3-amino-2-chloro-5-methylpyridine-4-carboxylate (300 mg, 1.5 mmol), water (2 mL), sodium hydroxide (200 mg, 5.00 mmol), and methanol (10 mL) was stirred for 2 h at 50° C. The resulting mixture was concentrated under vacuum. This resulted in the title compound (250 mg, crude) as a white solid which was used for the next step without any further purification. LCMS [M+H$^+$] 187.

Step 6: Preparation of 8-chloro-5-methylpyrido[3,4-d]pyrimidin-4(3H)-one

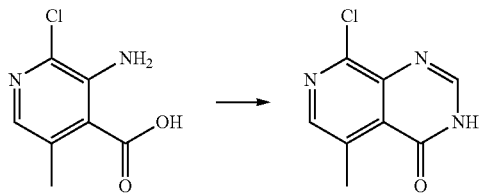

A mixture of 3-amino-2-chloro-5-methylpyridine-4-carboxylic acid (252 mg, 1.35 mmol), acetic acid; methanimidamide (600 mg, 5.80 mmol), and BuOH (15 mL) was stirred for 12 h at 120° C. The resulting mixture was concentrated under vacuum. The residue was purified by a silica gel column eluting with dichloromethane/methanol (20:1) to afford the title compound (140 mg, 53%) as a white solid. LCMS [M+H$^+$] 196.

Step 7: Preparation of 5-methyl-4-oxo-3,4-dihydropyrido[3,4-d]pyrimidine-8-carbonitrile

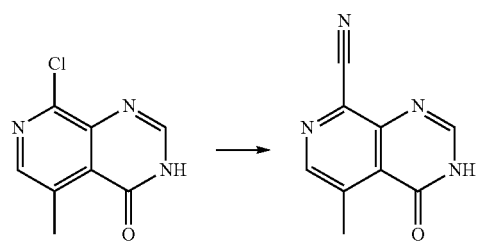

A mixture of 8-chloro-5-methyl-3H,4H-pyrido[3,4-d]pyrimidin-4-one (200 mg, 1.02 mmol), Pd$_2$(dba)$_3$ (100 mg, 0.10 mmol), dppf (200 mg, 0.36 mmol), zinc cyanide (120 mg, 1.00 mmol), and N,N-dimethylformamide (5 mL) was irradiated with microwave radiation for 1 h at 130° C. under nitrogen. The resulting mixture was concentrated under vacuum. The residue was purified by a silica gel column eluting with dichloromethane/methanol (10/1) to afford the title compound (140 mg, 74%) as a white solid. LCMS [M+H$^+$] 187.

Preparation 11: 5-Methylpyrimido[4,5-d]pyrimidin-4(3H)-one

The overall reaction scheme for Preparation 11 is as follows:

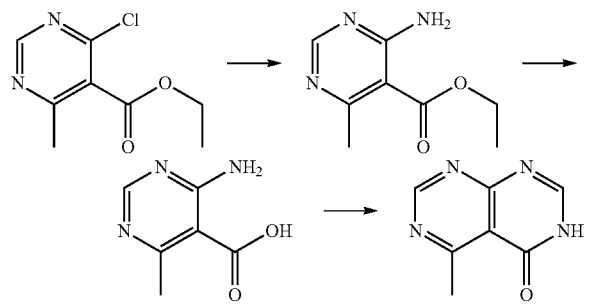

Step 1: Preparation of ethyl 4-amino-6-methylpyrimidine-5-carboxylate

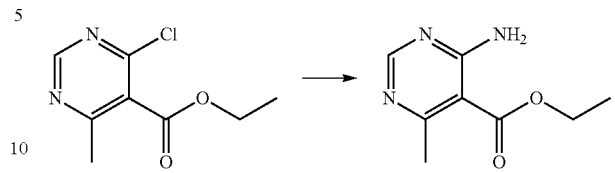

NH$_3$ (g) (8 mL, ~14% in ethanol) was added dropwise into a solution of ethyl 4-chloro-6-methylpyrimidine-5-carboxylate (800 mg, 4.00 mmol) in ethanol (10 mL). The resulting solution was stirred for 16 h at 120° C. The resulting mixture was concentrated under vacuum. The residue was purified by a silica gel column eluting with ethyl acetate/petroleum ether (1:5) to afford the title compound (700 mg, 97%) as a white solid. LCMS [M+H$^+$] 182.

Step 2: Preparation of 4-amino-6-methylpyrimidine-5-carboxylic acid

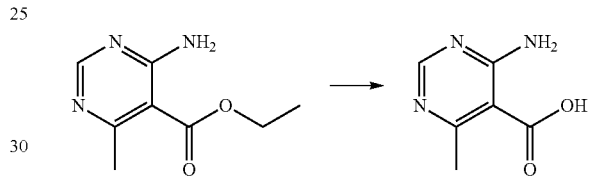

A mixture of ethyl 4-amino-6-methylpyrimidine-5-carboxylate (700 mg, 3.90 mmol), sodium hydroxide (464.4 mg, 11.60 mmol), water (6 mL), and methanol (30 mL) was stirred for 3 h at 50° C. The pH value of the solution was adjusted to 3 with hydrogen chloride (2M). The resulting mixture was concentrated under vacuum to afford the title compound (700 mg, crude) as a white solid. LCMS [M+H$^+$] 154.

Step 3: Preparation of 5-methylpyrimido[4,5-d]pyrimidin-4(3H)-one

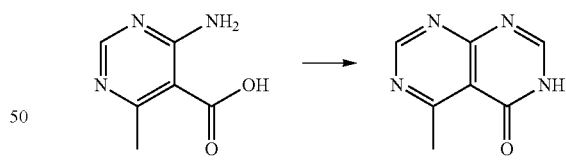

A mixture of 4-amino-6-methylpyrimidine-5-carboxylic acid (700 mg, 4.6 mmol), formamidine acetate (2 g, 19.40 mmol), and butan-1-ol (35 mL) was stirred for 3 days at 130° C. The reaction was diluted with water, extracted with ethyl acetate, washed with brine, dried over anhydrous sodium sulfate, and concentrated under vacuum. The residue was purified by a silica gel column eluting with dichloromethane/methanol (20/1) to afford the title compound (300 mg) as a light yellow solid. LCMS [M+H$^+$] 163.

Preparation 12: 5-(chloromethyl)-3-((3R,5R)-5-(4-chlorophenyl)tetrahydrofuran-3-yl)-1,2,4-oxadiazole The overall reaction scheme for Preparation 12 is as follows:

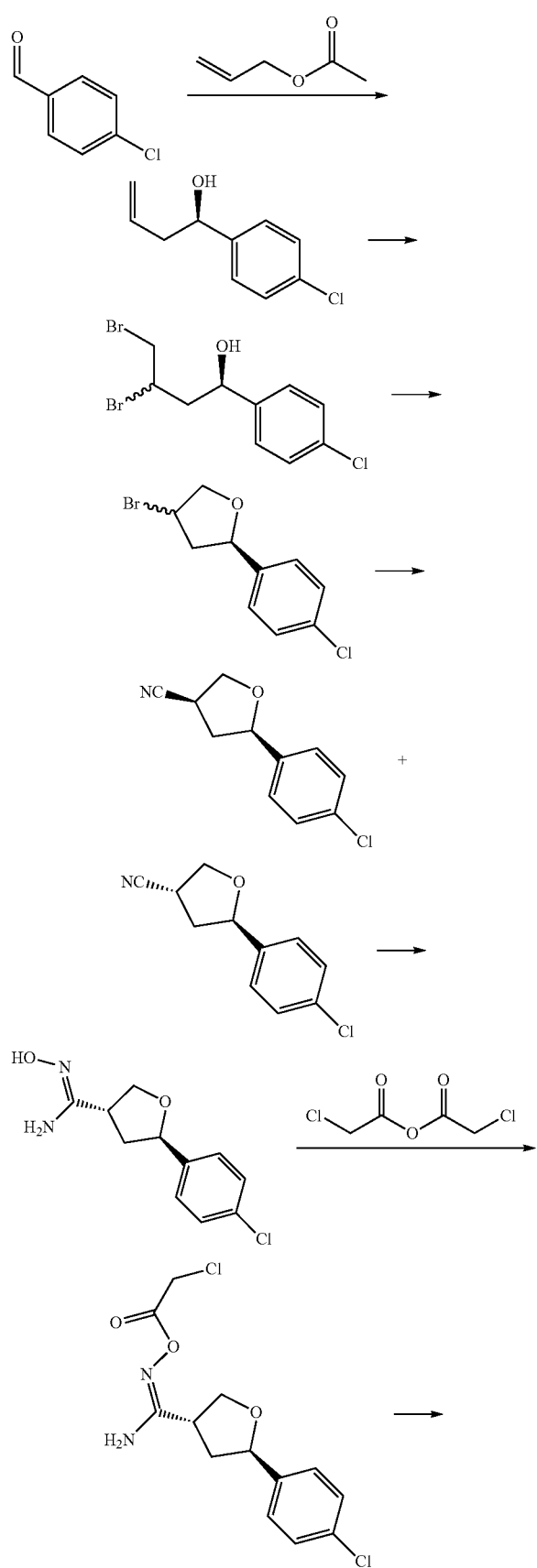

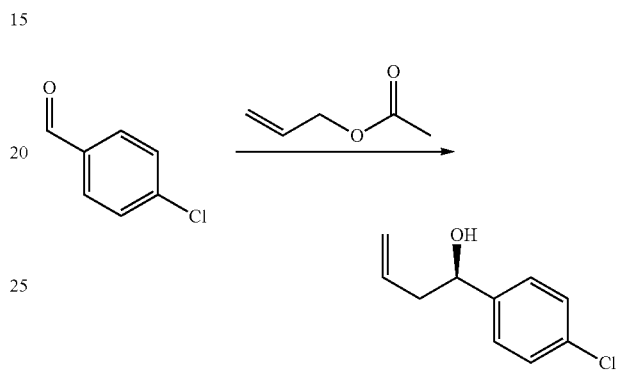

Step 1: Preparation of (R)-1-(4-chlorophenyl)but-3-en-1-ol

Four reactions were carried out in parallel: In a pressure vessel were added 4-fluorobenzaldehyde (100.0 g, 711.4 mmol, 1.00 eq), chloroiridium; (1Z, 5Z)-cycloocta-1,5-diene (14.3 g, 21.3 mmol, 0.03 eq), Cs2CO3 (46.3 g, 142.2 mmol, 0.2 eq) and 4-chloro-3-nitro-benzoic acid (14.3 g, 71.4 mmol, 0.1 eq), (R)-BINAP (22.1 g, 35.5 mmol, 0.05 eq). The flask was flushed with nitrogen before the addition of 1,4-dioxane (700.0 mL), allyl acetate (712.2 g, 7.11 mol, 10.0 eq) and i-PrOH (85.5 g, 1.42 mol, 108.9 mL, 2.00 eq). The reaction mixture was allowed to stir in a 112° C. oil bath for 20 h. TLC (Petroleum ether:Ethyl acetate=5:1, Rf=0.34) showed one new main spot appeared. The reaction mixtures were allowed to cool, combined, and then filtered to remove solid. The solid was rinsed with EtOAc (2×400.0 mL) and the filtrate was concentrated under reduced pressure. The crude residue was purified by column chromatography (SiO2, Petroleum ether/Ethyl acetate=5/1). To provide (R)-1-(4-chlorophenyl)but-3-en-1-ol (414.0 g, 2.27 mol, 79.6% yield) as a brown oil.

Step 2: Preparation of (1R)-3,4-dibromo-1-(4-chlorophenyl)butan-1-ol

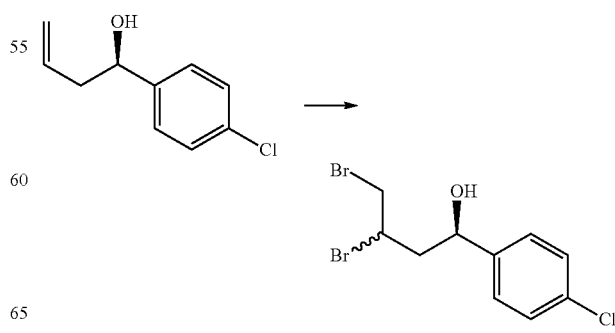

Three reactions were carried out in parallel: To a solution of Br$_2$ (126.7 g, 793.3 mmol, 40.9 mL, 1.05 eq) in DCM (480.0 mL) was added drop wise to a solution of (R)-1-(4-chlorophenyl)but-3-en-1-ol (138.0 g, 755.5 mmol, 1.00 eq) in DCM (480.0 mL) at −30° C. The resulting mixture was stirred for 1 h at −30° C. TLC (Petroleum ether:Ethyl acetate=5:1, R$_{f1}$=0.42, R$_{f2}$=0.31) showed the consumption of starting material and two new spots. The three reactions were then combined together for work up. The reactions were quenched by the addition of a saturated aqueous solution of Na$_2$S$_2$O$_3$ (3.00 L) and water (3.00 L). The flask was removed from the bath and was allowed to stir vigorously at 20° C. (orange color rapidly disappeared). The resulting mixture was extracted with DCM (2×2.50 L) and the combined organic layers were washed with brine (2.00 L×2), dried over Na$_2$SO$_4$, and concentrated under reduced pressure. The reaction was used to the next step without further purification. (1R)-3,4-dibromo-1-(4-chlorophenyl)butan-1-ol (743.0 g, crude) was obtained as a brown oil.

Step 3: Preparation of
(2R)-4-bromo-2-(4-chlorophenyl)tetrahydrofuran

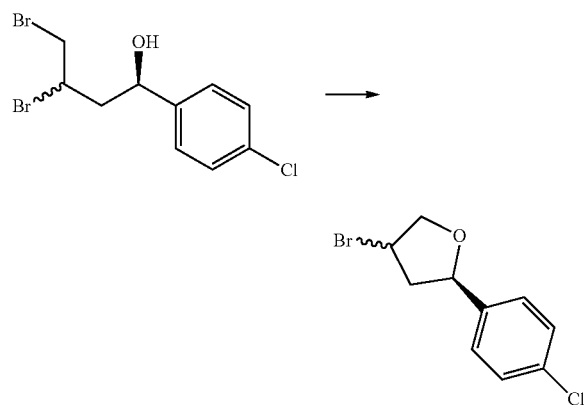

Three reactions were carried out in parallel: To a solution of (1R)-3,4-dibromo-1-(4-chlorophenyl)butan-1-ol (247.0 g, 721.2 mmol, 1.00 eq) in MeOH (1.70 L) was added K$_2$CO$_3$ (398.7 g, 2.89 mol, 4.00 eq) at 20° C. The reaction mixture was then stirred at 20° C. for 12 h. TLC (Petroleum ether:Ethyl acetate=5:1, R$_{f1}$=0.72, R$_{f2}$=0.56) showed the consumption of starting material. The three reactions were then combined for workup. The reaction mixtures were cooled and a saturated aqueous solution of NH$_4$Cl (1.50 L) was added followed by water (1.50 L). The mixture was transferred to a separatory funnel and was extracted with EtOAc (2×3.0 L). The combined organic layers were then washed with a mixture of water (3.00 L) and brine (3.00 L) and the combined organic layers were dried over anhydrous Na$_2$SO$_4$, filtered and concentrated under reduced pressure. The reaction was used to the next step without further purification. (2R)-4-bromo-2-(4-chlorophenyl)tetrahydrofuran (555.0 g, crude) was obtained as a brown oil.

Step 4: Preparation of (3R,5R)-5-(4-chlorophenyl)
tetrahydrofuran-3-carbonitrile

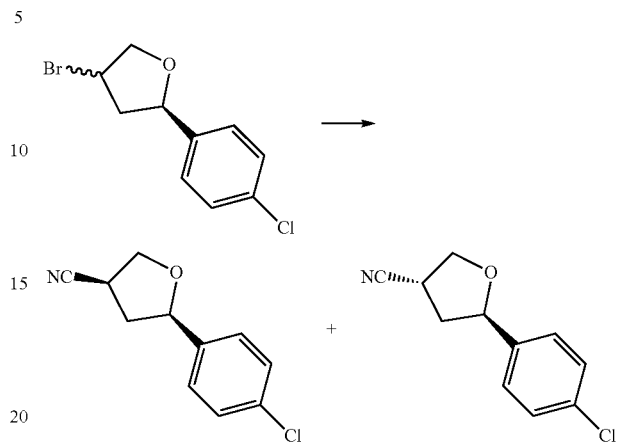

Three reactions were carried out in parallel: A mixture of (2R)-4-bromo-2-(4-chlorophenyl)tetrahydrofuran (170.0 g, 649.9 mmol, 1.00 eq) and KCN (112.3 g, 1.62 mol, 2.50 eq) in DMSO (1.20 mL) was degassed and purged with nitrogen three times, at which point the mixture was stirred at 60° C. for 20 hr under nitrogen atmosphere. TLC (petroleum ether: ethyl acetate=5/1, R$_{f1}$=0.51, R$_{f2}$=0.21) showed two new spots. The reaction was stopped by removing from oil bath and the three reactions were worked up together and combined. After cooling to 20° C., the mixture was diluted with EtOAc (200.0 mL) and solid was filtered on a fritted funnel and washed with additional EtOAc (140.0 mL). The filtrate was transferred to a 10.0 L separatory funnel followed by the addition of water (4.00 L) and brine (800.0 mL). The layers were separated and the aqueous layer was extracted with additional EtOAc (2×800.0 mL). The combined organic layers were then washed with a mixture of water (800.0 mL) and brine (800.0 mL), dried over anhydrous Na2SO4, filtered and concentrated under reduced pressure to give an orange oil. The residue was purified by column chromatography (SiO2, Petroleum ether/Ethyl acetate=50/1 to 5:1). (3R,5R)-5-(4-chlorophenyl)tetrahydrofuran-3-carbonitrile (102.0 g, 392.9 mmol, 20.1% yield, 80.0% purity) was obtained as yellow solid along with the diastereomer (120.0 g, 577.8 mmol, 29.6% yield) as a yellow solid.

Step 5: Preparation of (3R,5R,Z)-5-(4-chlorophenyl)-N'-hydroxytetrahydrofuran-3-carboximidamide

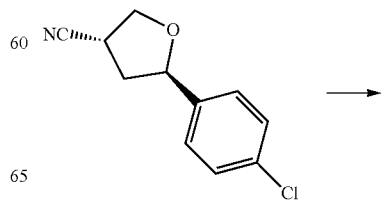

121

-continued

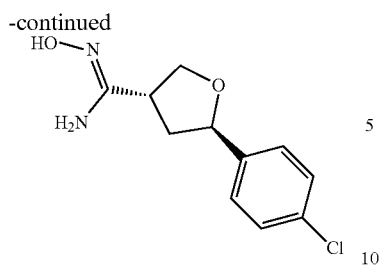

A mixture of (3R,5R)-5-(4-chlorophenyl)tetrahydrofuran-3-carbonitrile (102.0 g, 491.2 mmol, 1.00 eq) and hydroxylamine (40.5 g, 1.23 mol, 2.50 eq) in EtOH (600.0 mL) was degassed and purged with $N_2$ three times, and then the mixture was stirred at 83° C. for 2 hr under $N_2$ atmosphere at which point HPLC showed the reaction was complete. The reaction mixture was concentrated under reduced pressure to give a crude residue which was treated with 100.0 mL MTBE and stirred for 1 hr, at which point white solid appeared. The mixture was filtered and the filtrate was concentrated to provide (3R,5R,Z)-5-(4-chlorophenyl)-N'-hydroxytetrahydrofuran-3-carboximidamide (107.0 g, 444.5 mmol, 90.5% yield) as a white solid.

Step 6: Preparation of (3R,5R)—N'-(2-chloroacetoxy)-5-(4-chlorophenyl)tetrahydrofuran-3-carboximidamide

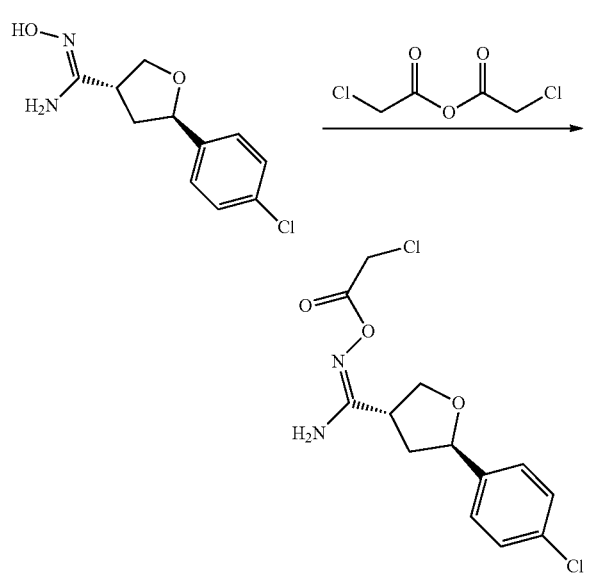

A mixture of (3R,5R,Z)-5-(4-chlorophenyl)-N'-hydroxytetrahydrofuran-3-carboximidamide (89.8 g, 525.5 mmol, 21.0 mL, 1.10 eq) in MTBE (800.0 mL) was added 2-chloroacetic anhydride (115.0 g, 477.8 mmol, 1 eq) at 0° C. and purged with $N_2$ three times, and then the mixture was stirred at 25° C. for 0.5 hr under $N_2$ atmosphere. HPLC showed the reaction was complete. The reaction mixture was added to a 500.0 mL saturated aqueous solution of $NaHCO_3$. The resulting mixture was extracted with EtOAc (3×250.0 mL) and the combined organic layers were dried with anhydrous $Na_2SO_4$, filtered and concentrated under reduced pressure. To the yellow oil 300.0 mL MTBE was added, the mixture was stirred 5 min, then cooled at −20° C. The

122 resulting solid was collected on a Büchner funnel, then rinsed with cold 150.0 mL MTBE (−20° C.) to give the desired product (3R,5R)—N'-(2-chloroacetoxy)-5-(4-chlorophenyl)tetrahydrofuran-3-carboximidamide (120.0 g, 378.3 mmol, 79.1% yield) as a white solid.

Step 7: Preparation of 5-(chloromethyl)-3-((3R,5R)-5-(4-chlorophenyl)tetrahydrofuran-3-yl)-1,2,4-oxadiazole

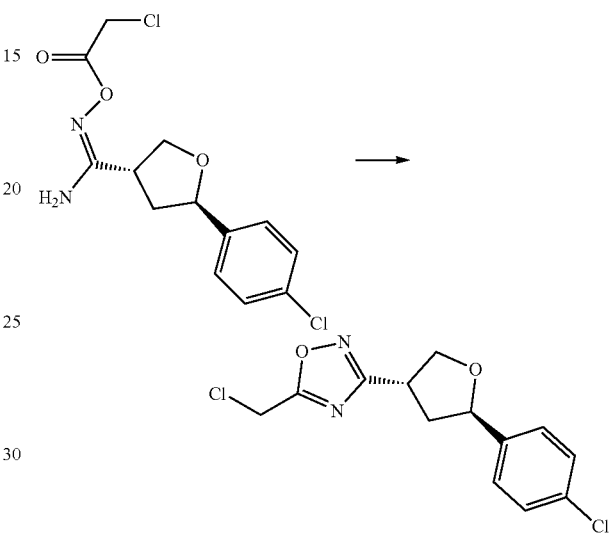

A mixture of (3R,5R)—N'-(2-chloroacetoxy)-5-(4-chlorophenyl)tetrahydrofuran-3-carboximidamide (135.0 g, 425.6 mmol, 1.00 eq) and activated 4 Å molecular sieves (135.0 g) in toluene (675.0 mL) was degassed and purged with $N_2$ three times, and then the mixture was stirred at 120° C. for 2 hr under $N_2$ atmosphere. HPLC and TLC (petroleum ether:ethyl acetate=1/1, $R_f$=0.60) showed the reaction was complete. The reaction mixture was filtered and the filtrate was concentrated. The crude residue was purified by column chromatography ($SiO_2$, Petroleum ether/Ethyl acetate=25/1 to 5:1) to provide 5-(chloromethyl)-3-((3R,5R)-5-(4-chlorophenyl)tetrahydrofuran-3-yl)-1,2,4-oxadiazole (82.0 g, 274.1 mmol, 64.4% yield) as a yellow oil.

Example 1: Preparation of 1-((3-((3R,5R)-5-(4-chlorophenyl)tetrahydrofuran-3-yl)-1,2,4-oxadiazol-5-yl)methyl)-7-methyl-1H-purin-6(7H)-one The overall Example 1 reaction scheme is as follows:

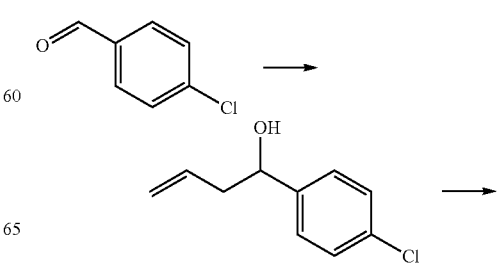

123

-continued

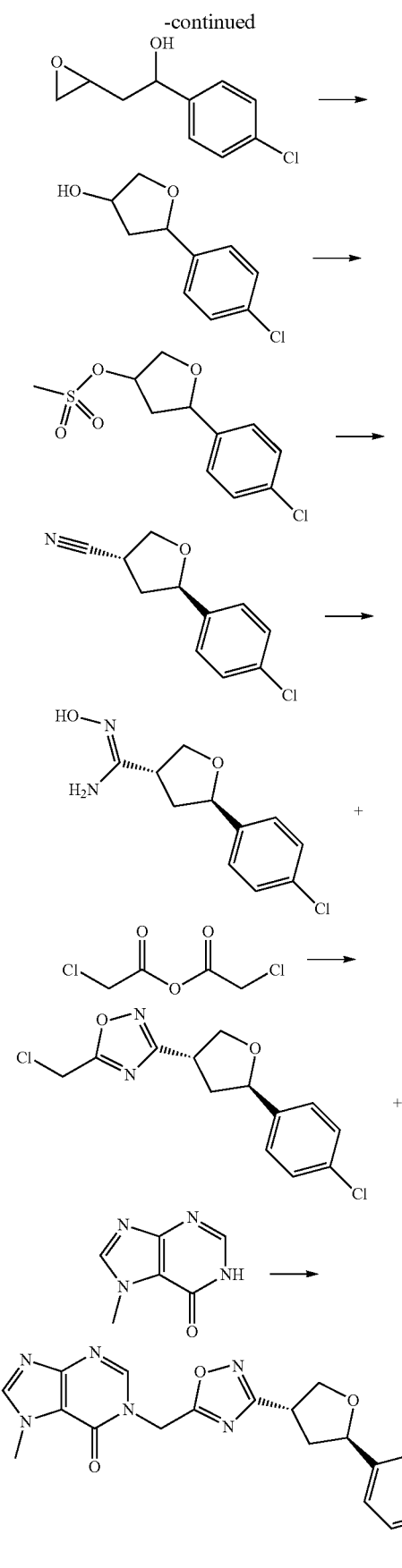

124

Step 1: Preparation of 1-(4-chlorophenyl)but-3-en-1-ol

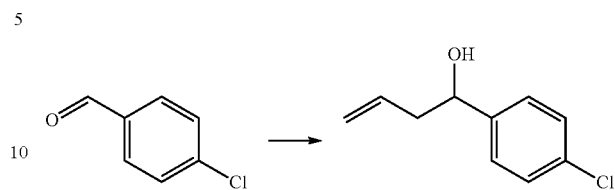

Allylmagnesium chloride (2.0 M in THF, 15.5 mL, 31.0 mmol) was added over 30 min to a solution of 4-chlorobenzaldehyde (3.43 mL, 28.2 mmol) in THF (28 mL) at 0° C. The resulting mixture was stirred at 0° C. 30 min, diluted with diethyl ether (25 mL) and the reaction was quenched with saturated aqueous NH$_4$Cl (25 mL) and H$_2$O (25 mL). The layers were separated and the aqueous layer was extracted with diethyl ether (3×50 mL). The combined organic layers were washed with brine (50 mL), dried over magnesium sulfate, filtered and concentrated under reduced pressure. The obtained residue was purified by SiO$_2$ chromatography (5 to 20% gradient of EtOAc in hexanes) to afford the title compound (2.71 g, 53%) as a colorless oil. $^1$H NMR (500 MHz, CDCl$_3$) δ 7.34-7.27 (m, 4H), 5.84-5.73 (m, 1H), 5.21-5.16 (m, 1H), 5.16-5.14 (m, 1H), 4.75-4.71 (m, 1H), 2.57-2.40 (m, 2H), 2.03 (d, J=3.3 Hz, 1H).

Step 2: Preparation of 1-(4-chlorophenyl)-2-(oxiran-2-yl)ethanol

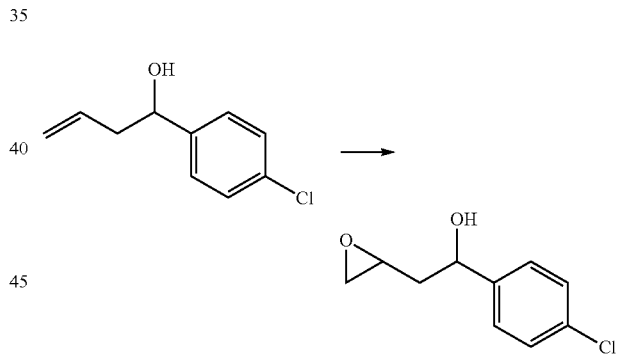

m-CPBA (77%, 3.31 g, 14.8 mmol) was added portion wise to a solution of 1-(4-chlorophenyl)but-3-en-1-ol (2.71 g, 14.8 mmol) in DCM (48 mL) at 0° C. The resulting mixture was allowed to warm to 20° C. and stirred for 18 h. The reaction mixture was cooled to 0° C., diluted with DCM and quenched with portion wise addition of Ca(OH)$_2$ (2.6 g, 29.6 mmol). The resulting mixture was stirred for 2 h at 20° C., the solid was filtered off and the filtrate was concentrated under reduced pressure to afford the title compound (2.79 g, 95%) a colorless oil. $^1$H NMR (500 MHz, CDCl$_3$, mixture of diastereoisomers) δ 7.35-7.29 (m, 4H), 4.96 (dd, J=8.3, 5.0 Hz, 0.5H), 4.92 (dd, J=9.0, 3.4 Hz, 0.5H), 3.19-3.13 (m, 0.5H), 3.05-2.99 (m, 0.5H), 2.83 (dd, J=4.7, 4.1 Hz, 0.5H), 2.77 (dd, J=4.8, 4.1 Hz, 0.5H), 2.62 (dd, J=4.8, 2.8 Hz, 0.5H), 2.54-2.46 (m, 1.5H), 2.14 (ddd, J=14.6, 9.0, 3.8 Hz, 0.5H), 2.06 (ddd, J=14.3, 4.9, 4.0 Hz, 0.5H), 1.85-1.74 (m, 1H).

Step 3: Preparation of 5-(4-chlorophenyl)tetrahydrofuran-3-ol

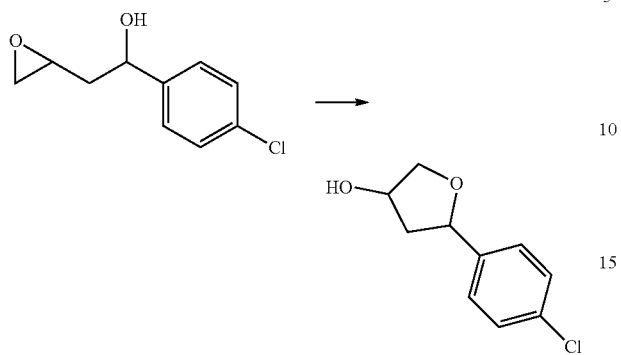

Sulfuric acid (98%, 0.68 mL, 12.5 mmol) was added to a mixture of 1-(4-chlorophenyl)-2-(oxiran-2-yl)ethanol (2.59 g, 13.0 mmol) in 1,4-dioxane (130 mL). The resulting mixture was stirred at 50° C. for 16 h. The reaction mixture was poured on crushed ice, neutralized by addition of saturated aqueous NaHCO₃ and extracted with DCM (3×150 mL). Combined organic layers were dried over magnesium sulfate, filtered and concentrated under reduced pressure. The obtained residue was purified by SiO₂ chromatography (10 to 50% gradient of EtOAc in hexanes) to afford the title compound (1.38 g, 53%) as a yellow oil. $^1$H NMR (500 MHz, CDCl₃, mixture of diastereoisomers) δ 7.37-7.26 (m, 4H), 5.13 (dd, J=10.2, 5.7 Hz, 0.56H), 4.91-4.86 (m, 0.44H), 4.67-4.55 (m, 1H), 4.24 (dd, J=9.9, 4.4 Hz, 0.56H), 4.07-4.03 (m, 0.44H), 3.93-3.87 (m, 1H), 2.70-2.62 (m, 0.44H), 2.35-2.29 (m, 0.56H), 1.93-1.84 (m, 1H), 1.75 (d, J=4.1 Hz, 0.56H), 1.63 (d, J=5.7 Hz, 0.44H)

Step 4: Preparation of 5-(4-chlorophenyl)tetrahydrofuran-3-yl methanesulfonate

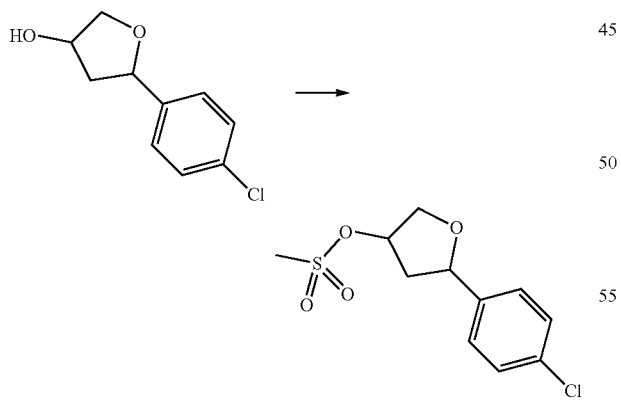

Methanesulfonyl chloride (0.50 mL, 6.41 mmol) was added to a solution of 5-(4-chlorophenyl)tetrahydrofuran-3-ol (980 mg, 4.93 mmol) and triethylamine (2.06 mL, 14.8 mmol) in DCM (25 mL) at 0° C. The resulting mixture was stirred for 15 min before saturated aqueous NaHCO₃ (25 mL) was added. The layers were separated and the aqueous layer was extracted with DCM (25 mL). The combined organic layers were washed with brine (25 mL), dried over magnesium sulfate, filtered and concentrated under reduced pressure to afford the title compound (1.36 g, 99%) as a colorless oil. $^1$H NMR (500 MHz, CDCl₃, mixture of diastereoisomers) δ 7.35-7.24 (m, 4H), 5.44-5.36 (m, 1H), 5.10 (dd, J=10.3, 5.5 Hz, 0.56H), 4.88 (t, J=7.5 Hz, 0.44H), 4.38-4.33 (m, 1H), 4.16-4.13 (m, 0.56H), 3.97 (dd, J=11.1, 4.5 Hz, 0.44H), 3.09 (s, 1.68H), 2.98 (s, 1.32H), 2.84-2.75 (m, 0.44H), 2.68-2.63 (m, 0.56H), 2.20-2.14 (m, 0.44H), 2.08-2.00 (m, 0.56H).

Step 5: Preparation of (3R,5R)-5-(4-chlorophenyl)tetrahydrofuran-3-carbonitrile

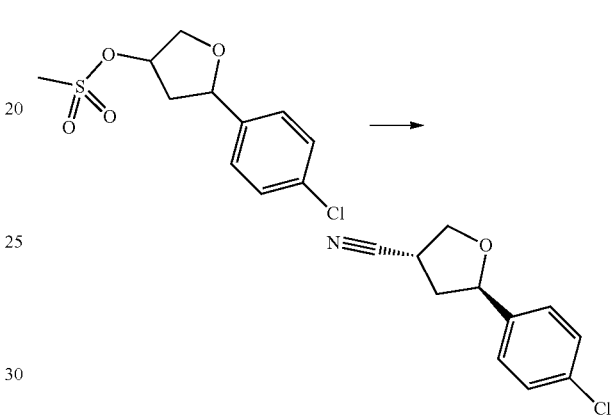

A mixture of 5-(4-chlorophenyl)tetrahydrofuran-3-yl methanesulfonate (1.36 g, 4.91 mmol) and potassium cyanide (1.60 g, 24.6 mmol) in DMSO (12 mL) was stirred for 1 h at 105° C. The reaction mixture was diluted with EtOAc and washed with saturated aqueous NaHCO₃, water and brine. The organic phase was dried over magnesium sulfate, filtered and concentrated under reduced pressure. The obtained residue was purified by SiO₂ chromatography (0 to 40% gradient of EtOAc in hexanes) to afford the title compound (213 mg, 21%) as a yellow oil (first eluting diastereoisomer) and the undesired cis-diastereoisomer (224 mg, 22%) as a yellow oil (second eluting diastereoisomer). Title compound: $^1$H NMR (500 MHz, CDCl₃) δ 7.35-7.32 (m, 2H), 7.26-7.23 (m, 2H), 5.09-5.02 (m, 1H), 4.38 (dd, J=8.9, 7.6 Hz, 1H), 4.09-4.03 (m, 1H), 3.28-3.19 (m, 1H), 2.68-2.61 (m, 1H), 2.18-2.11 (m, 1H). cis-diastereoisomer: $^1$H NMR (500 MHz, CDCl₃) δ 7.37-7.33 (m, 2H), 7.33-7.28 (m, 2H), 4.86 (dd, J=8.7, 6.7 Hz, 1H), 4.29 (dd, J=9.0, 5.4 Hz, 1H), 4.12 (dd, J=9.0, 7.7 Hz, 1H), 3.31-3.22 (m, 1H), 2.80-2.72 (m, 1H), 2.17-2.08 (m, 1H).

Step 6: Preparation of (3R,5R)-5-(4-chlorophenyl)-N'-hydroxytetrahydrofuran-3-carboximidamide

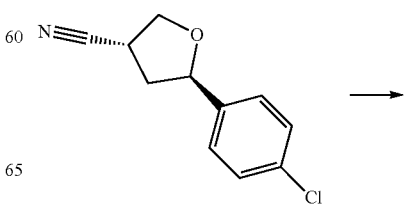

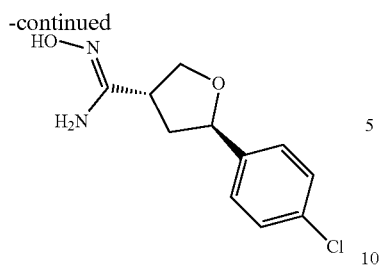

Hydroxylamine (50% in water, 0.31 mL, 5.13 mmol) was added to a solution of (3R,5R)-5-(4-chlorophenyl)tetrahydrofuran-3-carbonitrile (213. mg, 1.03 mmol) in EtOH (5.1 mL) and the resulting mixture was stirred at 80° C. for 1 h. The solvent was evaporated under reduced pressure and the residue co-evaporated with EtOH (2×) and with DCM (1×) to afford the title compound (231 mg, 94%) a thick colorless oil. LCMS [M+H$^+$] 241.

Step 7: Preparation of 5-(chloromethyl)-3-((3R,5R)-5-(4-chlorophenyl)tetrahydrofuran-3-yl)-1,2,4-oxadiazole

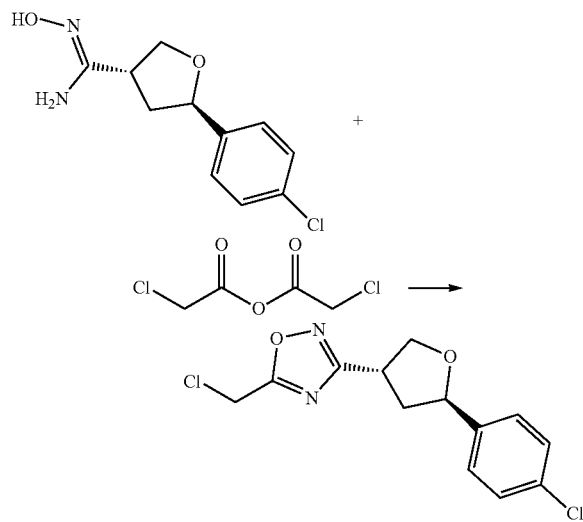

Chloroacetic anhydride (212 mg, 1.24 mmol) was added to a solution of (3R,5R)-5-(4-chlorophenyl)-N'-hydroxytetrahydrofuran-3-carboximidamide (231 mg, 0.960 mmol) in DCE (5 mL) at 20° C. The resulting mixture was stirred for 15 min, diisopropylethylamine (0.25 mL, 1.44 mmol) was added and the reaction mixture was concentrated under reduced pressure. The residue was diluted with toluene (5 mL) and the reaction mixture was stirred at 100° C. for 1 h. The reaction mixture was diluted with EtOAc (25 mL) and washed with saturated aqueous NaHCO$_3$, water and brine. The organic phase was dried over magnesium sulfate, filtered and concentrated under reduced pressure. The obtained residue was purified by SiO$_2$ chromatography (0 to 25% gradient of EtOAc in hexanes) to afford the title compound (235 mg, 82%) as a yellow oil. LCMS [M+H$^+$] 299. $^1$H NMR (500 MHz, CDCl$_3$) δ 7.35-7.29 (m, 4H), 5.14 (t, J=7.3 Hz, 1H), 4.69 (s, 2H), 4.47 (dd, J=8.8, 7.6 Hz, 1H), 4.10 (dd, J=8.8, 6.6 Hz, 1H), 3.79-3.73 (m, 1H), 2.72 (ddd, J=12.5, 7.0, 5.3 Hz, 1H), 2.23 (ddd, J=12.8, 9.0, 7.6 Hz, 1H).

Step 8: Preparation of 1-((3-((3R,5R)-5-(4-chlorophenyl)tetrahydrofuran-3-yl)-1,2,4-oxadiazol-5-yl)methyl)-7-methyl-1H-purin-6(7H)-one

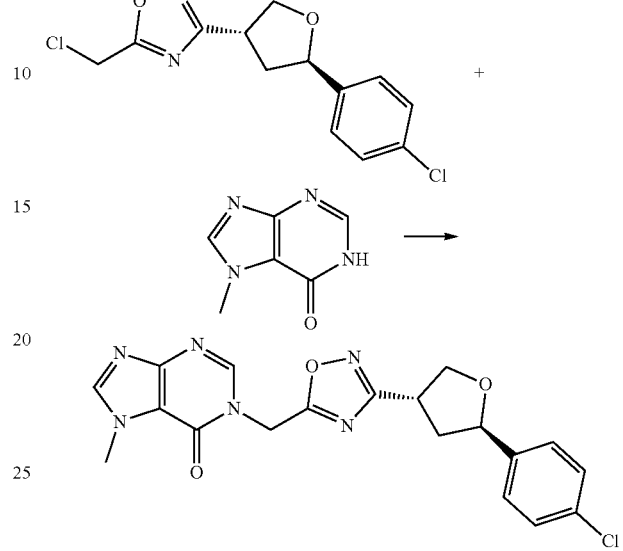

A mixture of racemic 5-(chloromethyl)-3-((3R,5R)-5-(4-chlorophenyl)tetrahydrofuran-3-yl)-1,2,4-oxadiazole (130. mg, 0.430 mmol), 7-methyl-1H-purin-6-one (98 mg, 0.650 mmol), tetrabutylammonium iodide (4 mg, 0.010 mmol) and potassium carbonate (180 mg, 1.30 mmol) in DMF (2 mL) was stirred at 20° C. for 2 h. Water (2 mL) was added to the reaction mixture, the solid was collected by filtration, washed with water and dried under vacuum to afford the title compound (152 mg, 85%) as a racemic mixture. The enantiomers were separated by SFC (column: Lux Cel-3, 10×250 mm, 5 μm, 40% MeOH, 10 mL/min, 150 bar, column temp: 40 C, run time 16 min) to afford the title compound (43 mg, 24%) as a white solid (first eluting enantiomer, RT=11.5 min) and the enantiomer of the title compound (43 mg, 24%) as a white solid (second eluting enantiomer, RT=13.5 min). Title compound: LCMS [M+H$^+$] 413. $^1$H NMR (500 MHz, DMSO-d6) δ 8.46 (s, 1H), 8.24 (s, 1H), 7.42-7.36 (m, 4H), 5.57 (s, 2H), 5.01 (t, J=7.3 Hz, 1H), 4.35 (dd, J=8.6, 7.4 Hz, 1H), 3.96 (s, 3H), 3.90 (dd, J=8.6, 6.3 Hz, 1H), 3.80-3.71 (m, 1H), 2.60-2.54 (m, 1H), 2.17-2.10 (m, 1H).

Example 2 Synthesis of 1-((3-((3R,5R)-5-(4-fluorophenyl)tetrahydrofuran-3-yl)-1,2,4-oxadiazol-5-yl)methyl)-7-methyl-1H-purin-6(7H)-one The overall Example 2 reaction scheme is as follows:

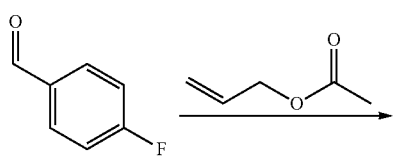

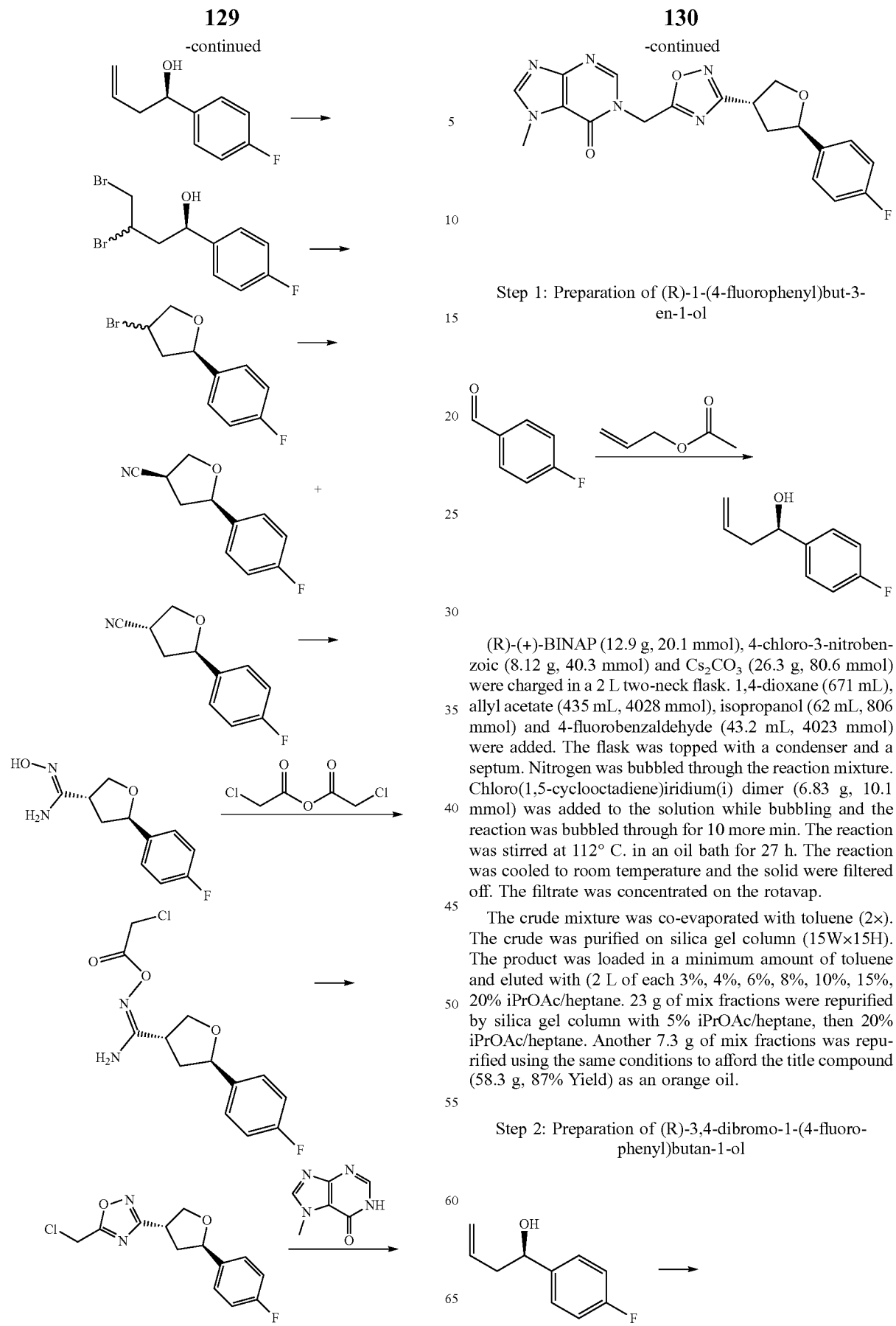

Step 1: Preparation of (R)-1-(4-fluorophenyl)but-3-en-1-ol (R)-(+)-BINAP (12.9 g, 20.1 mmol), 4-chloro-3-nitrobenzoic (8.12 g, 40.3 mmol) and Cs$_2$CO$_3$ (26.3 g, 80.6 mmol) were charged in a 2 L two-neck flask. 1,4-dioxane (671 mL), allyl acetate (435 mL, 4028 mmol), isopropanol (62 mL, 806 mmol) and 4-fluorobenzaldehyde (43.2 mL, 4023 mmol) were added. The flask was topped with a condenser and a septum. Nitrogen was bubbled through the reaction mixture. Chloro(1,5-cyclooctadiene)iridium(i) dimer (6.83 g, 10.1 mmol) was added to the solution while bubbling and the reaction was bubbled through for 10 more min. The reaction was stirred at 112° C. in an oil bath for 27 h. The reaction was cooled to room temperature and the solid were filtered off. The filtrate was concentrated on the rotavap.

The crude mixture was co-evaporated with toluene (2×). The crude was purified on silica gel column (15W×15H). The product was loaded in a minimum amount of toluene and eluted with (2 L of each 3%, 4%, 6%, 8%, 10%, 15%, 20% iPrOAc/heptane. 23 g of mix fractions were repurified by silica gel column with 5% iPrOAc/heptane, then 20% iPrOAc/heptane. Another 7.3 g of mix fractions was repurified using the same conditions to afford the title compound (58.3 g, 87% Yield) as an orange oil.

Step 2: Preparation of (R)-3,4-dibromo-1-(4-fluorophenyl)butan-1-ol

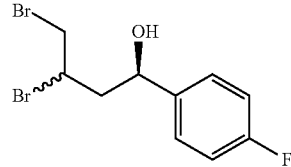

A solution of bromine (16.3 mL, 317 mmol) in DCM (302 mL) was added dropwise over 1 h30 to a solution of (1R)-1-(4-fluorophenyl)but-3-en-1-ol (50.2 g, 302 mmol) in DCM (755 mL) at −30° C.-−40° C. The reaction was stirred at −30° C. for 30 min. The reaction was quenched with saturated Na$_2$S$_2$O$_3$ (300 mL) and water (300 mL) and the reaction was stirred at room temperature for 30 min. The phases were separated and the aqueous layer was extracted (2×) with DCM. The combined organic layers were dried with MgSO$_4$, filtered and concentrated to afford the title compound (96.9 g, 98% Yield) as a crude brown oil.

Step 3: Preparation of (R)-4-bromo-2-(4-fluorophenyl)tetrahydrofuran

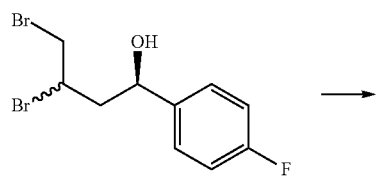

K$_2$CO$_3$ (166 g, 1189 mmol) was added to a solution of (1R)-3,4-dibromo-1-(4-fluorophenyl)butan-1-ol (96.9 g, 297 mmol) in MeOH (743 mL). A water bath at 20° C. was used to control the exotherm. The reaction was stirred at room temperature overnight. The reaction was cooled to 10° C. and saturated NH$_4$Cl (500 mL) was added followed by water (500 mL). The mixture was extracted with iPrOAc (3×), washed with water and brine. The combined organic layers were dried with MgSO$_4$, filtered and concentrated to afford the title compound (69.8 g, 96% Yield) as a crude brown oil.

Step 4: Preparation of (3R,5R)-5-(4-fluorophenyl)tetrahydrofuran-3-carbonitrile

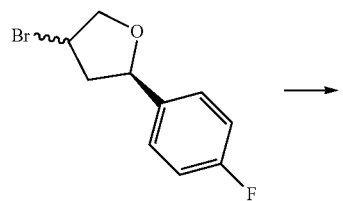

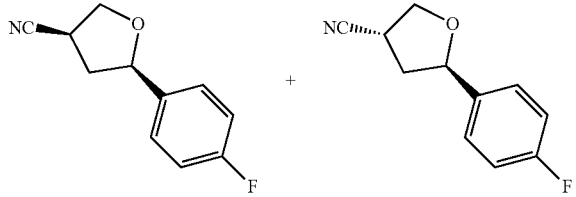

Potassium cyanide (57.4 g, 855 mmol) was added to a solution of (2R)-4-bromo-2-(4-fluorophenyl)tetrahydrofuran (69.8 g, 285 mmol) in DMSO (570 mL). The reaction mixture was stirred at 105° C. for 15 h. The reaction was allowed to cool down to room temperature. The excess KCN was removed by filtration and the solid were washed with iPrOAc. The reaction mixture was partitioned in water/iPrOAc and extracted with iPrOAc (3×). The combined organic extracts were washed with water (2×) and brine and they were dried over MgSO$_4$, filtered and concentrated. The crude mixture purified by silica gel chromatography using a column of 15 cm (width)×18 cm (height) eluting with 5%, 7%, 10%, 12%, 15%, 20%, 25%, 30%, 35%, 40% iPrOAc/heptane to afford the title trans nitrile (18.4 g, 34% Yield) as a clear yellow oil. The cis nitrile, (3S,5R)-5-(4-fluorophenyl)tetrahydrofuran-3-carbonitrile, was obtained (15.7 g, 29% Yield) as a clear yellow oil.

Step 5: Preparation of (3R,5R,Z)-5-(4-fluorophenyl)-N'-hydroxytetrahydrofuran-3-carboximidamide

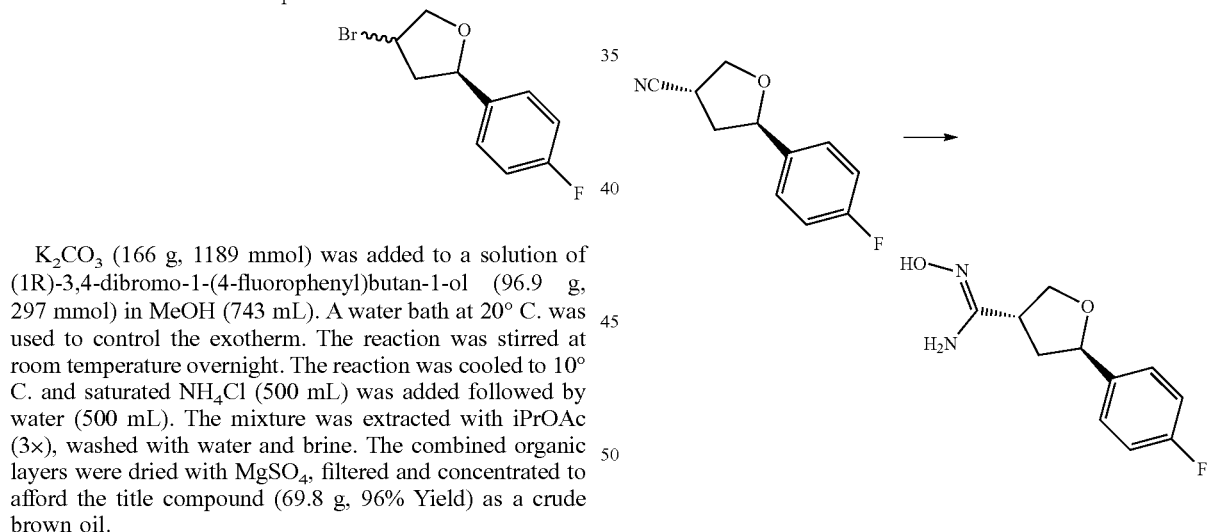

Hydroxylamine (50 mass % in water) (49.5 mL, 808 mmol) was added to a solution of (3R,5R)-5-(4-fluorophenyl)tetrahydrofuran-3-carbonitrile (48.3 g, 202 mmol) in EtOH (505 mL). The mixture was stirred at 80° C. for 2 h. The reaction mixture was concentrated on the rotavap. The mixture was purified on a pad of silica gel (10 cm wide×7 cm height) using 100% DCM (1.5 L) to elute the impurities, then 10% MeOH/DCM (2 L) to elute the product. Some product came out in the first fraction, the other fractions were clean. The first fraction was concentrated aside and repurified. 19.6 g of mix fractions were repurified by silica gel column with 100% DCM, then 10% MeOH/DCM to afford the title compound (36.4 g, 80% Yield) as a blue gray gum.

Step 6: Preparation of (3R,5R,Z)—N'-(2-chloroacetoxy)-5-(4-fluorophenyl)tetrahydrofuran-3-carboximidamide

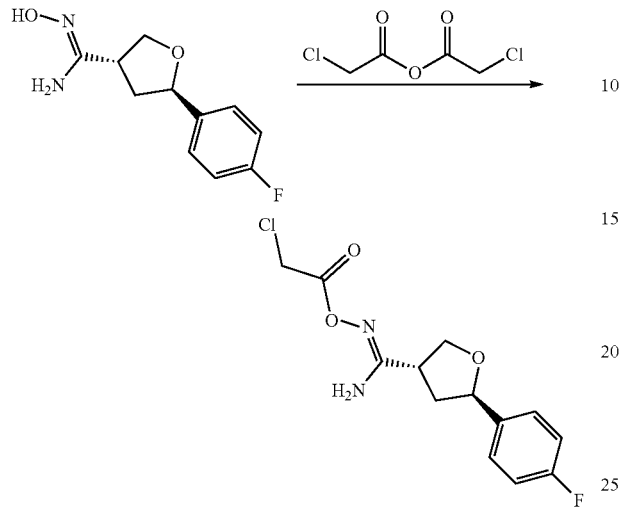

Chloroacetic anhydride (10.8 g, 60.1 mmol) was added portionwise to a solution of (3R,5R)-5-(4-fluorophenyl)-N'-hydroxy-tetrahydrofuran-3-carboxamidine (12.3 g, 54.6 mmol) in MTBE (137 mL) at 0° C. The reaction was stirred at room temperature for 20 min. The reaction mixture was cooled to 0° C., diluted with iPrOAc and partitioned with saturated NaHCO₃. The aqueous layer was extracted with iPrOAc (3×). The combined organic layers were washed with saturated NaHCO₃ again and brine, dried with MgSO₄, filtered and concentrated, but not completely. The solvent was swapped for MTBE and concentrated until an oily residue was obtained. The product was triturated with 150 mL of MTBE. The solution was cooled to −20° C., recovered by filtration and washed with MTBE at −20° C. The product was dried under vacuum to afford the title product (11.9 g, 73% Yield) as a white solid.

Step 7: Preparation of 5-(chloromethyl)-3-((3R,5R)-5-(4-fluorophenyl)tetrahydrofuran-3-yl)-1,2,4-oxadiazole

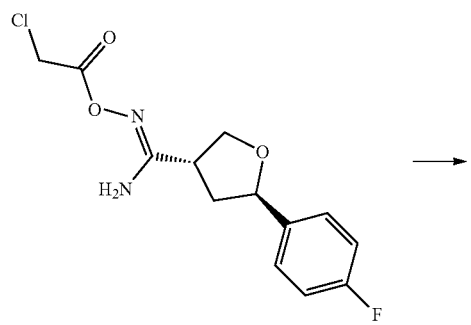

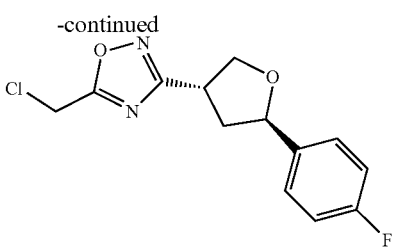

A mixture of [(Z)-[amino-[(3R,5R)-5-(4-fluorophenyl)tetrahydrofuran-3-yl]methylene]amino]2-chloroacetate (36.0 g, 120 mmol) and 4 Å Molecular Sieves Powder (40 g, preactivated in the oven) in toluene (479 mL) was stirred at 115° C. for 8 h. The reaction mixture was cooled to room temperature. The molecular sieves was removed by filtration and washed with iPrOAc. The filtrate was concentrated on the rotavap. The crude mixture was purified by silica gel column with 0-50% iPrOAc/heptane to afford the title compound (32.1 g, 95% Yield) as a clear oil.

Step 8: Preparation of 1-((3-((3R,5R)-5-(4-fluorophenyl)tetrahydrofuran-3-yl)-1,2,4-oxadiazol-5-yl)methyl)-7-methyl-1H-purin-6(7H)-one

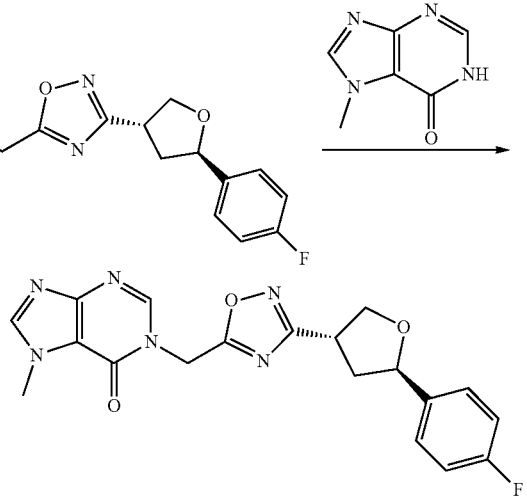

7-methyl-1H-purin-6-one (23.9 g, 159 mmol) and K₂CO₃ (47.6 g, 341 mmol) were added to a solution of 5-(chloromethyl)-3-[(3R,5R)-5-(4-fluorophenyl)tetrahydrofuran-3-yl]-1,2,4-oxadiazole (32.1 g, 114 mmol) in DMF (227 mL) at 0° C. The mixture was stirred at 0° C. for 6 h. The reaction was allowed to warm-up to room temperature overnight. EtOH (95 mL) was added at 0° C. followed by water (950 mL). The solid was recovered by filtration on a fritted funnel and washed with water at 0° C. The solid was dried under vacuum for 15 min. The solid was dissolved in DCM, dried with MgSO₄, filtered and concentrated. Once a paste is obtained on the rotavap, DCM was swapped for iPrOAc and co-evaporated 2× with 100 mL of iPrOAc. The residue was triturated with 415 mL of iPrOAc, cooled to 0° C., recovered by filtration and washed with cold iPrOAc and dried under vacuum to afford the title compound (40.5 g, 90% Yield) as an off-white solid.

135

Step 9: Recrystallization of 1-((3-((3R,5R)-5-(4-fluorophenyl)tetrahydrofuran-3-yl)-1,2,4-oxadiazol-5-yl)methyl)-7-methyl-1H-purin-6(7H)-on 1-((3-((3R,5R)-5-(4-fluorophenyl)tetrahydrofuran-3-yl)-1,2,4-oxadiazol-5-yl)methyl)-7-methyl-1H-purin-6(7H)-on (40 g, 101 mmol) was placed in 1 L reactor and EtOH/water (7:3, 720 mL) (18 volumes) was added. The mixture was heated to 75° C. The material slowly dissolved over 40 min. At this point the material was seeded with a suspension of crude material (1 g suspended in EtOH/water 1:1, 20 mL). The obtained suspension was left to age at 75° C. for 30 min. At this point the suspension was slowly cooled down to 25° C. over 2 h, and then left at 25° C. for another 1 h. The material was filtered through a filter funnel; the solid was washed with EtOH/water (1:1, 100 mL). The solid was dried in the air, and then the material was left in the vacuum oven (60° C. overnight) with slight stream of nitrogen to afford the title compound (36.2 g, 91% yield) as a white crystalline solid.

Example 3: 2-amino-3-((3-((3R,5R)-5-(4-fluorophenyl)tetrahydrofuran-3-yl)-1,2,4-oxadiazol-5-yl)methyl)-5-methylpyrazolo[5,1-f][1,2,4]triazin-4(3H)-one

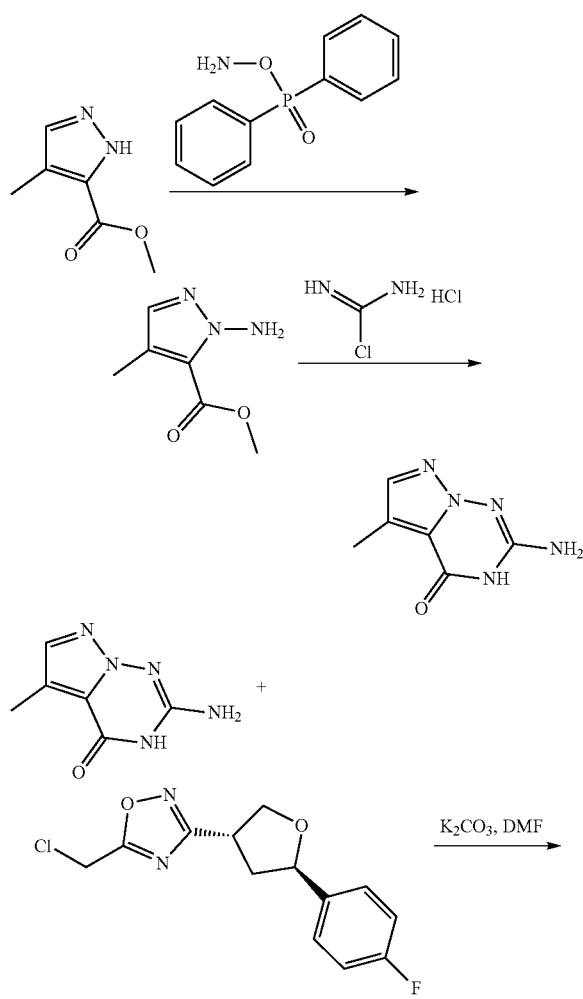

136

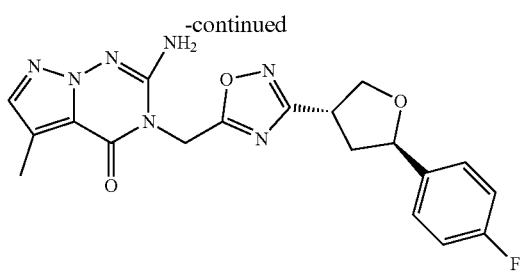

Step 1: Preparation of methyl 1-amino-4-methyl-1H-pyrazole-5-carboxylate

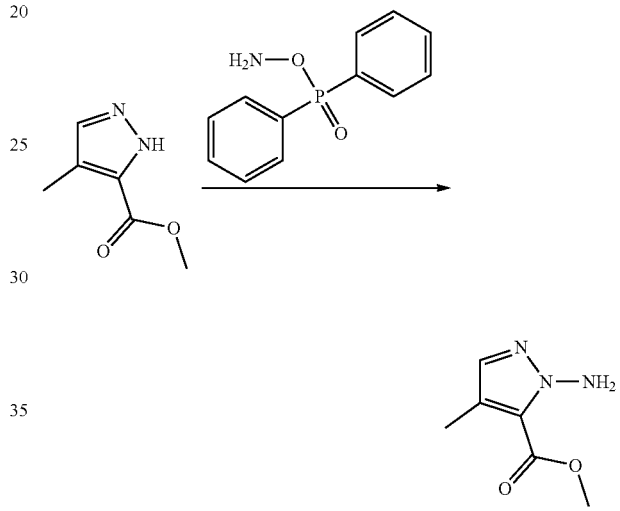

LiHMDS (1M in THF) (14.3 mL, 14.3 mmol) was added over 5 min to a solution of ethyl 4-methyl-1H-pyrazole-5-carboxylate (2.00 g, 13.0 mmol) in DMF (130 mL) at −20° C. The resulting mixture was stirred for 15 min at 0° C. before o-(diphenylphosphinyl)hydroxylamine (3.63 g, 15.6 mmol) was added in one portion. The reaction mixture became very thick rapidly after a white precipitate appeared and was stirred occasionally by hand for 1 h at rt. The reaction was diluted with water until the precipitate was completely dissolved and stirred at RT for 15 min. The reaction mixture was concentrated to dryness and diluted with about 150 mL of 2:1 DCM/EtOAc. The solid was removed by filtration, the cake was washed further with 2:1 DCM/EtOAc, the filtrate was concentrated under reduced pressure and co-evaporated 2× with heptane. The residue was purified by flash column chromatography (DCM load, 100 g biotage $SiO_2$, 0-4% gradient of MeOH in DCM over 17 CV) to afford ethyl 2-amino-4-methyl-pyrazole-3-carboxylate (1.54 g, 9.10 mmol, 70% yield) as a light yellow oil. LCMS: purity=98%, MH$^+$=169.8. $^1$H NMR (400 MHz, CDCl$_3$) δ 7.14 (d, J=0.4 Hz, 1H), 5.62 (br s, 2H), 4.39 (q, J=7.1 Hz, 2H), 2.23 (d, J=0.6 Hz, 3H), 1.40 (t, J=7.1 Hz, 3H).

Step 2: Preparation of 2-amino-5-methylpyrazolo[5,1-f][1,2,4]triazin-4(3H)-one

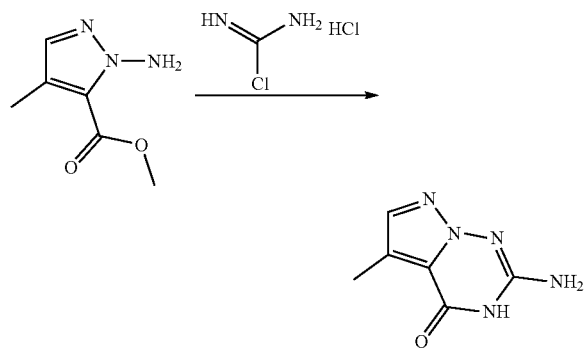

N,N-diisopropylethylamine (1.16 mL, 6.65 mmol) was added to a mixture of ethyl 2-amino-4-methyl-pyrazole-3-carboxylate (450. mg, 2.66 mmol) and chloroformamidine hydrochloride (611 mg, 5.32 mmol) in DCM (10 mL). The reaction mixture was heated under MW irradiation at 150° C. for 2 h. The solution was cooled to rt and the precipitate was filtered off and washed with DCM to afford 2-amino-5-methyl-3H-pyrazolo[5,1-f][1,2,4]triazin-4-one (432 mg, 2.62 mmol, 98% yield) as beige powder. LCMS: purity=85%, MH+=166.3. 1H NMR (400 MHz, DMSO-D6) 11.25 (s, 1H), 7.32 (s, 1H), 6.13 (s, 1H), 2.26 (t, 4H)

Step 3: Preparation of 2-amino-3-((3-((3R,5R)-5-(4-fluorophenyl)tetrahydrofuran-3-yl)-1,2,4-oxadiazol-5-yl)methyl)-5-methylpyrazolo[5,1-f][1,2,4]triazin-4(3H)-one

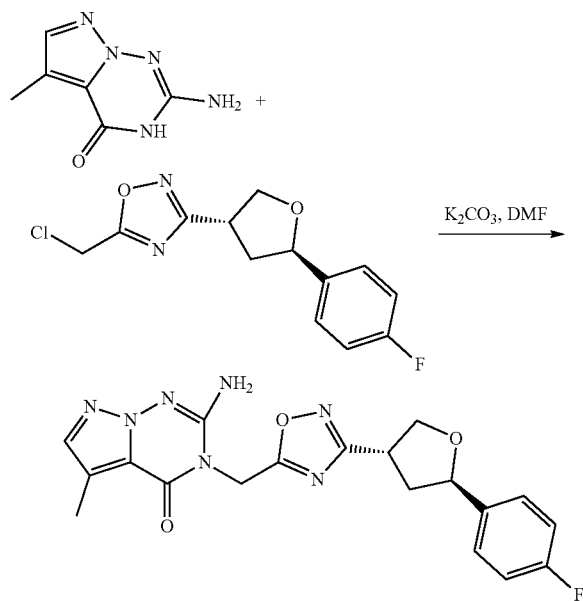

To a solution of 5-(chloromethyl)-3-[5-(4-fluorophenyl)tetrahydrofuran-3-yl]-1,2,4-oxadiazole (40.0 mg, 0.140 mmol, prepared from Example 6) in DMF (0.42 mL) was added 2-amino-5-methyl-3H-pyrazolo[5,1-f][1,2,4]triazin-4-one (28.0 mg, 0.170 mmol) followed by potassium carbonate (39.1 mg, 0.280 mmol). The reaction mixture was stirred at rt for 2 h. Diluted with water, extracted with EtOAc, washed with NH4Cl, brine, dried over MgSO4, filtered and concentrated. The residue was purified by normal flash chromatography (12 g, SiO2, 0-10% MeOH in DCM). Fractions containing product were combined and evaporated in vacuo. The compound was dissolved in a mixture of acetonitrile and water, freezed dry and lyophilized to afford 2-amino-3-[[3-[5-(4-fluorophenyl)tetrahydrofuran-3-yl]-1,2,4-oxadiazol-5-yl]methyl]-5-methyl-pyrazolo[5,1-f][1,2,4]triazin-4-one (16.2 mg, 0.039 mmol, 28% yield) as white solid. LCMS: purity=96%, MH+=412.0. 1H NMR (400 MHz, dmso) 7.44-7.35 (m, 3H), 7.21-7.11 (m, 2H), 6.88 (s, 2H), 5.48 (s, 2H), 5.00 (t, J=7.4 Hz, 1H), 4.36 (dd, J=8.5, 7.4 Hz, 1H), 3.89 (dd, J=8.5, 6.3 Hz, 1H), 3.77 (dt, J=13.9, 6.9 Hz, 1H), 2.56 (ddd, J=12.4, 7.0, 5.1 Hz, 1H), 2.29 (d, J=0.4 Hz, 3H), 2.15 (ddd, J=12.7, 8.9, 7.8 Hz, 1H).

Example 4: Preparation of 2-amino-3-((3-((3R,5R)-5-(4-chlorophenyl)tetrahydrofuran-3-yl)-1,2,4-oxadiazol-5-yl)methyl)-5-methylpyrazolo[5,1-f][1,2,4]triazin-4(3H)-one

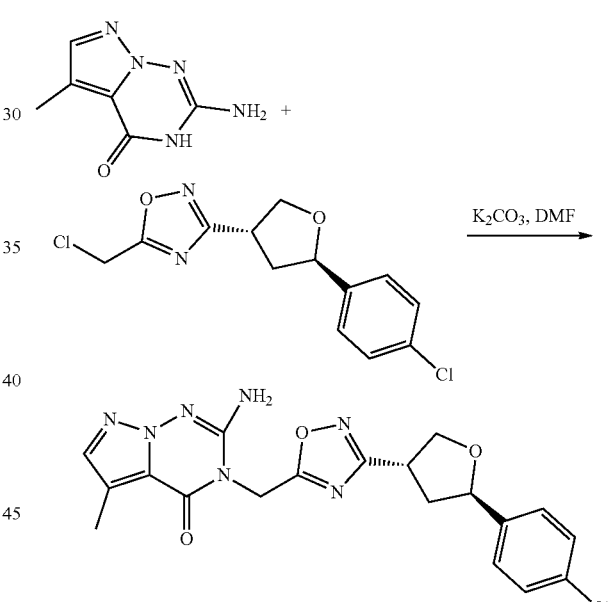

To a solution of 5-(chloromethyl)-3-[5-(4-chlorophenyl)tetrahydrofuran-3-yl]-1,2,4-oxadiazole (40.0 mg, 0.130 mmol, prepared in Example 1) in DMF (0.42 mL) was added 2-amino-5-methyl-3H-pyrazolo[5,1-f][1,2,4]triazin-4-one (26.5 mg, 0.160 mmol, prepared in Example 105) followed by potassium carbonate (37.0 mg, 0.270 mmol). The reaction mixture, was stirred at rt for 2 h. Diluted with water, extracted with EtOAc, washed with NH4Cl, brine, dried over MgSO4, filtered and concentrated. The residue was purified by flash (SiO2, 12 g, 0-10% MeOH in DCM).). Fractions containing product were combined and evaporated in vacuo. The compound was dissolved in a mixture of acetonitrile and water, freezed dry and lyophilized to afford 2-amino-3-[[3-[5-(4-chlorophenyl)tetrahydrofuran-3-yl]-1,2,4-oxadiazol-5-yl]methyl]-5-methyl-pyrazolo[5,1-f][1,2,4]triazin-4-one (21.7 mg, 0.051 mmol, 38% yield) as white solid. LCMS: purity=95%, MH+=428.1. 1H NMR (400

MHz, dmso) 7.44-7.35 (m, 5H), 6.87 (s, 2H), 5.48 (s, 2H), 5.01 (t, J=7.5 Hz, 1H), 4.36 (dd, J=8.5, 7.4 Hz, 1H), 3.90 (dd, J=8.6, 6.3 Hz, 1H), 3.77 (dd, J=14.9, 6.3 Hz, 1H), 2.57 (ddd, J=7.3, 6.2, 3.3 Hz, 1H), 2.29 (s, 3H), 2.20-2.08 (m, 1H).

Example 5: 1-((3-((3R,5R)-5-(4-chlorophenyl)tetrahydrofuran-3-yl)-1,2,4-oxadiazol-5-yl)methyl)-7-methyl-1,7-dihydro-6H-purin-6-one-2-d

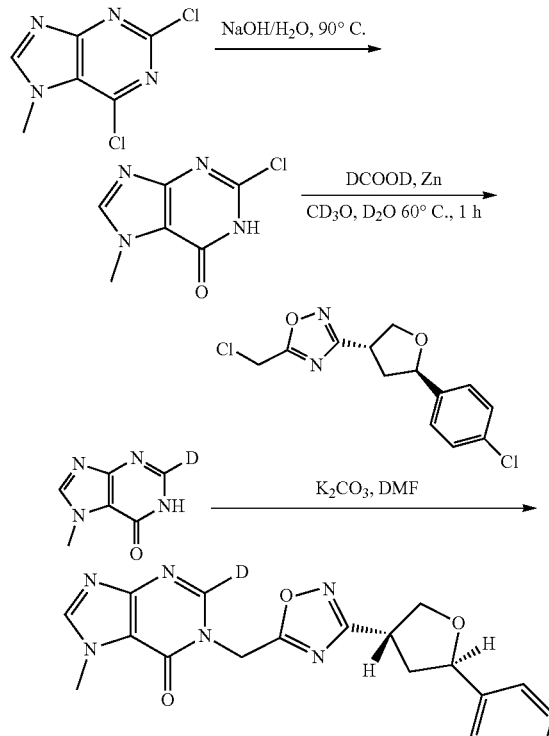

Step 1: Preparation of 2-chloro-7-methyl-1,7-dihydro-6H-purin-6-one

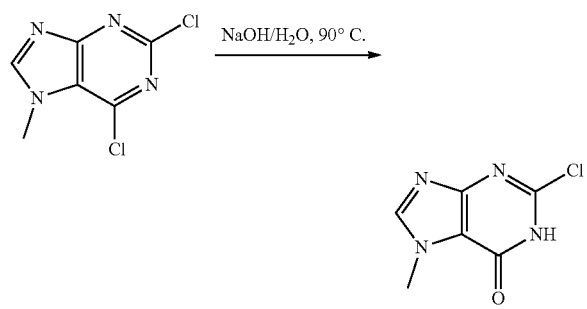

A solution of 2,6-dichloro-7-methylpurine (1.0 g, 4.93 mmol), and NaOH (0.99 g, 24.63 mmol) in Water (10 mL) was stirred at 900° C. for 1 hour. The reaction mixture was adjusted to pH 2 with HCl (10%). The solids were collected by filtration to afford the title compound as a white solid.

Step 2: Preparation of 7-methyl-1,7-dihydro-6H-purin-6-one-2-d

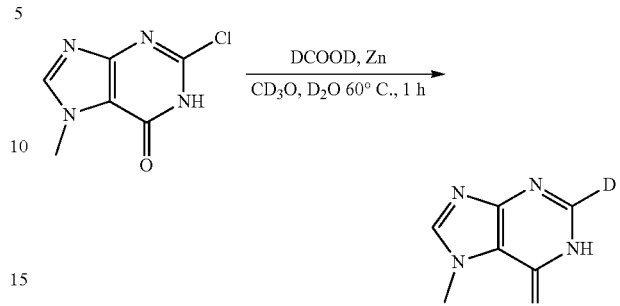

A mixture of 2-chloro-7-methyl-1H-purin-6-one (700.0 mg, 3.79 mmol), Zn (2465.06 mg, 37.92 mmol), and DCOOD (1820.35 mg, 37.92 mmol) in CD₃OD (10.0 g, 277.78 mmol) and D2O (5.0 g, 250 mmol) was stirred at 600° C. for 16 hours. The reaction mixture was diluted with MeOH (100 mL). The solid was filtrate and the filtrate was concentrated under reduced pressure. The residue was purified by C18 silica gel column eluting with CH3CN/H2O (10 mmol/L NH4HCO3, 5% to 95%, over 30 min) This resulted in the title compound (370 mg) as a white solid.

Step 3: Preparation of: 1-((3-((3R,5R)-5-(4-chlorophenyl)tetrahydrofuran-3-yl)-1,2,4-oxadiazol-5-yl)methyl)-7-methyl-1,7-dihydro-6H-purin-6-one-2-d

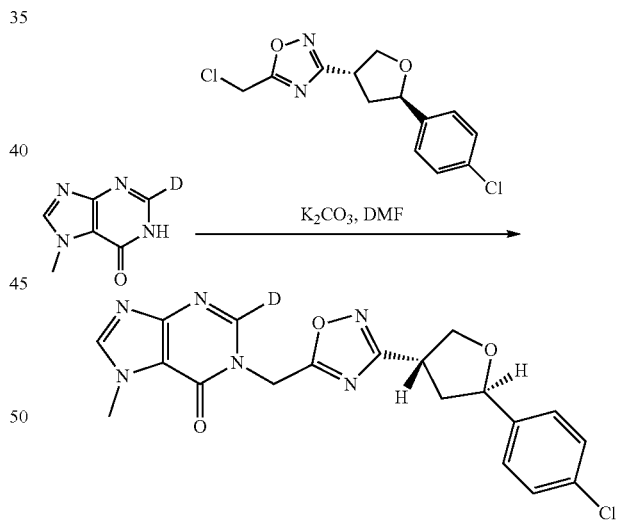

To a solution of 5-(chloromethyl)-3-[5-(4-chlorophenyl)tetrahydrofuran-3-yl]-1,2,4-oxadiazole (20.0 mg, 0.070 mmol, prepared according to a similar procedure as example 2) in DMF (0.5 mL) was added 2-deuterio-7-methyl-1H-purin-6-one (12.1 mg, 0.080 mmol) followed by potassium carbonate (18.5 mg, 0.130 mmol). The reaction mixture was stirred at room temperature for 16 h. The mixture was then diluted with water, extracted with EtOAc, washed with NH4Cl, brine, dried over MgSO4, filtered and concentrated. The residue was purified by flash (SiO2, 12 g, 0-10% MeOH in DCM). Fractions containing product were combined and evaporated in vacuo. The compound was dissolved in a mixture of acetonitrile and water, freezed dry and lyophilized to afford 1-[[3-[5-(4-chlorophenyl)tetrahydrofuran-3-yl]-1,2,4-oxadiazol-5-yl]methyl]-2-deuterio-7-methyl-purin-6-one (18.0 mg, 0.044 mmol, 65% yield) as white solid. LCMS: purity=96%, MH+=414.0. 1H NMR (400 MHz, dmso) 8.22 (s, 1H), 7.42-7.28 (m, 4H), 5.55 (s, 2H), 4.99 (t, J=7.4 Hz, 1H), 4.33 (dd, J=8.5, 7.4 Hz, 1H), 3.93 (s, 3H), 3.88 (dd, J=8.6, 6.3 Hz, 1H), 3.80-3.70 (m, 1H), 2.61-2.52 (m, 1H), 2.19-2.08 (m, 1H).

Example 6: 1-((3-((3R,5R)-5-(4-chlorophenyl)tetrahydrofuran-3-yl)-1,2,4-oxadiazol-5-yl)methyl)-7-methyl-1,7-dihydro-6H-purin-6-one-8-d

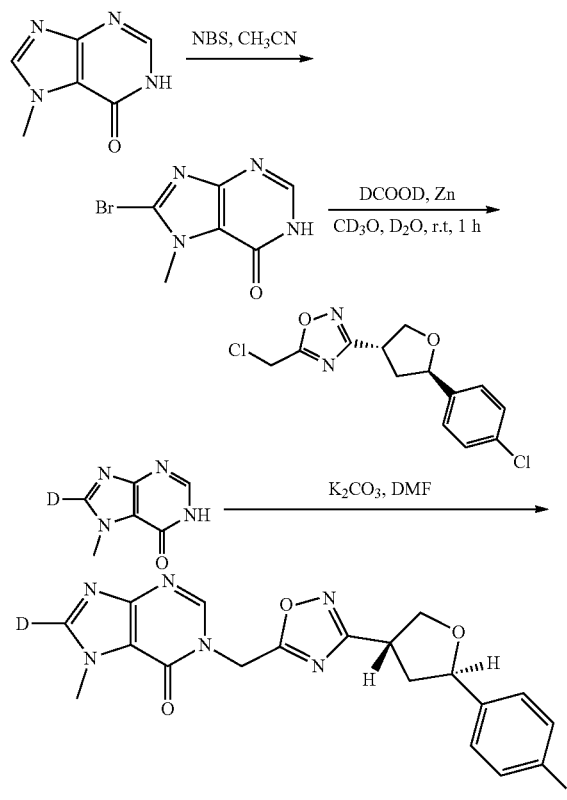

Step 1: Preparation of 8-bromo-7-methyl-1,7-dihydro-6H-purin-6-one

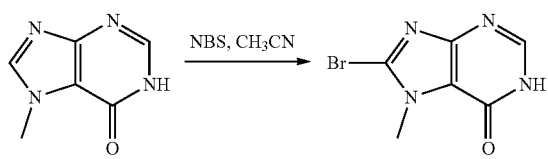

A mixture of 7-methyl-1H-purin-6-one (200.0 mg, 1.33 mmol) and NBS (284.53 mg, 1.6 mmol) in Acetonitrile (8 mL) was stirred overnight at 800° C. The solvent was concentrated under vacuum. The residue was purified by flash chromatography on silica gel eluting with CH2Cl2/MeOH (10:1) to afford the title compound as a white solid.

Step 2: Preparation of 7-methyl-1,7-dihydro-6H-purin-6-one-8-d

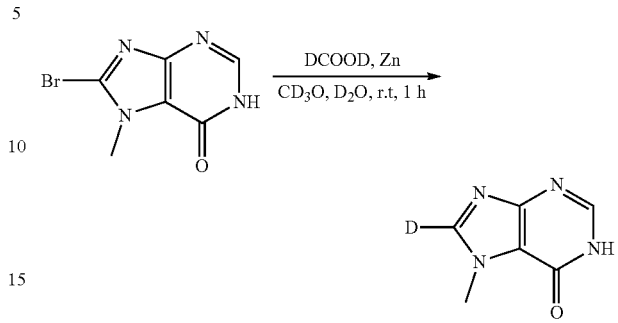

A mixture of 8-bromo-7-methyl-1H-purin-6-one (1.4 g, 6.11 mmol), D2O (5. mL, mmol), CD3OD (10. mL, mmol), Zn (3.91 g, 61.13 mmol), and DCOOD (2.93 g, 61.13 mmol) was stirred at room temperature for one hour. The solids were filtered out, the filtrate was purified by C18 silica gel column eluting with CH3CN/H2O (10 mmol/L NH4HCO3, 5% to 95%, over 30 min) This resulted in the title compound (510 mg) as a white solid.

Step 3: Preparation of 1-((3-((3R,5R)-5-(4-chlorophenyl)tetrahydrofuran-3-yl)-1,2,4-oxadiazol-5-yl)methyl)-7-methyl-1,7-dihydro-6H-purin-6-one-8-d

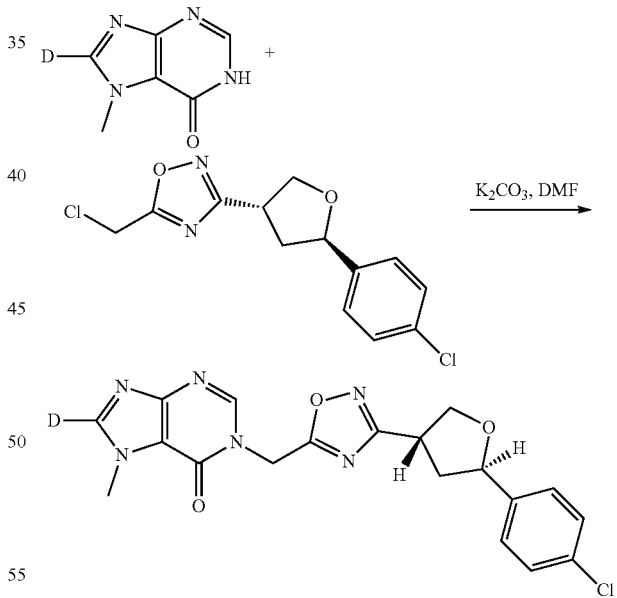

To a solution of 5-(chloromethyl)-3-[5-(4-chlorophenyl)tetrahydrofuran-3-yl]-1,2,4-oxadiazole (20.0 mg, 0.070 mmol, prepared according to a similar procedure as example 2) in DMF (0.5 mL) was added 8-deuterio-7-methyl-1H-purin-6-one (12.1 mg, 0.080 mmol) followed by potassium carbonate (18.5 mg, 0.130 mmol). The reaction mixture, was stirred at rt for 16 h. Diluted with water, extracted with EtOAc, washed with brine, dried over MgSO4, filtered and concentrated. The residue was purified by flash (SiO2, 12 g, 0-10% MeOH in DCM). Fractions containing product were combined and evaporated in vacuo. The compound was dissolved in a mixture of acetonitrile and water, freezed dry and lyophilized to afford 1-[[3-[5-(4-chlorophenyl)tetrahydrofuran-3-yl]-1,2,4-oxadiazol-5-yl]methyl]-8-deuterio-7-methyl-purin-6-one (12.0 mg, 0.029 mmol, 43% yield) as white solid. LCMS: purity=99%, MH+=414.0. 1H NMR (400 MHz, dmso) 8.44 (s, 1H), 7.47-7.28 (m, 4H), 5.56 (s, 2H), 4.99 (t, J=7.3 Hz, 1H), 4.33 (t, J=7.9 Hz, 1H), 3.93 (s, 3H), 3.88 (dd, J=8.5, 6.3 Hz, 1H), 3.79-3.70 (m, 1H), 2.61-2.51 (m, 1H), 2.19-2.08 (m, 1H).

Example 7: 1-((3-((3R, 5R)-5-(4-chlorophenyl)-tetrahydrofuran-3-yl)-1, 2, 4-oxadiazol-5-yl)methyl)-7-methyl-1H-purine-2,6(3H,7H)-dione The reaction scheme for Example 7 is as follows:

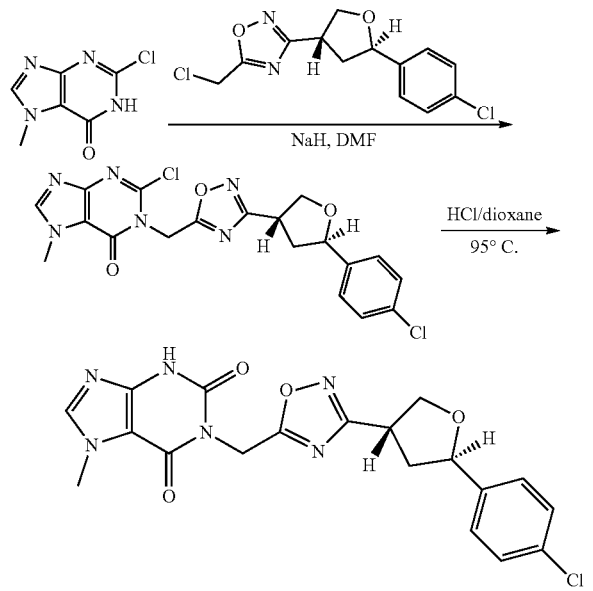

Step 1: Preparation of 2-chloro-1-((3-((3R, 5R)-5-(4-chlorophenyl)-tetrahydrofuran-3-yl)-1,2,4-oxadiazol-5-yl)methyl)-7-methyl-1H-purin-6(7H)-one

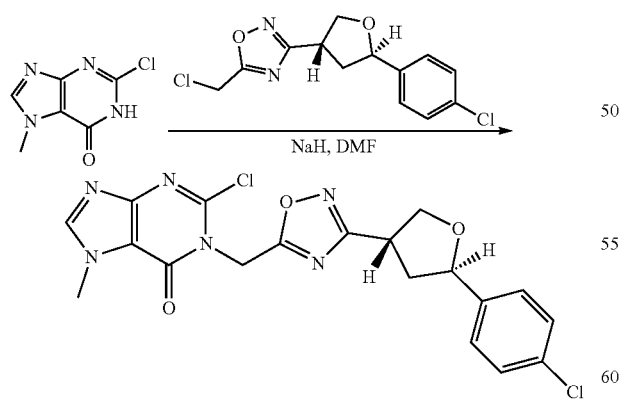

NaH (60%) (39.0 mg, 0.65 mmol) was added batchwise to a solution of 2-chloro-7-methyl-1H-purin-6-one (100.0 mg, 0.54 mmol) in DMF (3 mL) at room temperature under nitrogen and stirred for 1 hour. Then the solution of 5-(chloromethyl)-3-[(3R, 5R)-5-(4-chlorophenyl) tetrahydrofuran-3-yl]-1,2,4-oxadiazole (194.0 mg, 0.65 mmol, prepared according to a similar procedure as example 1) in DMF (3 mL) was added. The resulting solution was stirred at 50° C. overnight. The resulting solution was further purified by RP-HPLC to yield the title compound (91 mg, 38%) as a white solid.

Step 2: Preparation of 1-((3-((3R, 5R)-5-(4-chlorophenyl)-tetrahydrofuran-3-yl)-1, 2, 4-oxadiazol-5-yl)methyl)-7-methyl-1H-purine-2,6(3H,7H)-dione

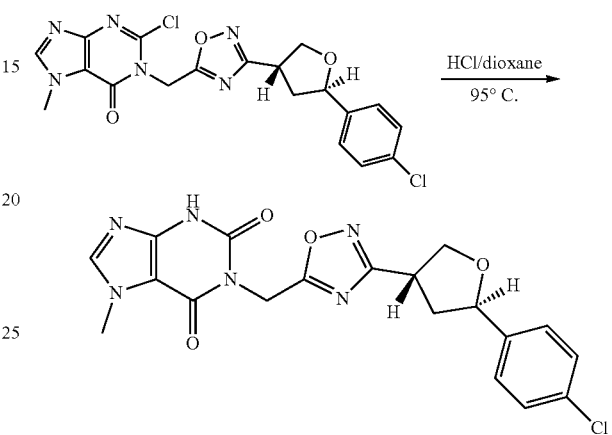

A solution of 2-chloro-1-[[3-[(3R, 5R)-5-(4-chlorophenyl) tetrahydrofuran-3-yl]-1, 2, 4-oxadiazol-5-yl] methyl]-7-methyl-purin-6-one (300.0 mg, 0.67 mmol) and HCl (36%) (0.5 mL, 0.67 mmol) in 1, 4-Dioxane (10 mL) was stirred at 95° C. for 4 hours. The residue was purified by RP-HPLC to yield the title compound (145 mg, 50%) as a white solid. LCMS [M+H$^+$]: 429.1. $^1$H NMR (400 MHz, DMSO-d$_6$) δ 12.21 (s, 1H), 8.03 (s, 1H), 7.40 (d, J=1.3 Hz, 4H), 5.31 (s, 2H), 5.02 (t, J=7.3 Hz, 1H), 4.36 (dd, J=8.6, 7.4 Hz, 1H), 3.91 (dd, J=8.6, 6.3 Hz, 1H), 3.87 (s, 3H), 3.77-3.73 (m, 1H), 2.1-2.56 (m, 1H), 2.20-2.06 (m, 1H).

Example 8: 1-((3-((3R,5R)-5-(4-chlorophenyl)tetrahydrofuran-3-yl)-1,2,4-oxadiazol-5-yl)methyl)-2,7-dimethyl-1H-purin-6(7H)-one The overall Example 8 reaction scheme is as follows:

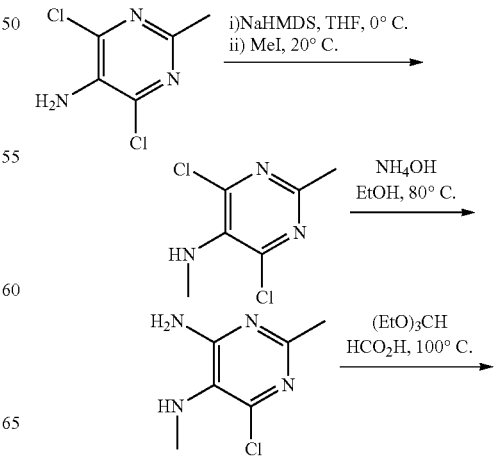

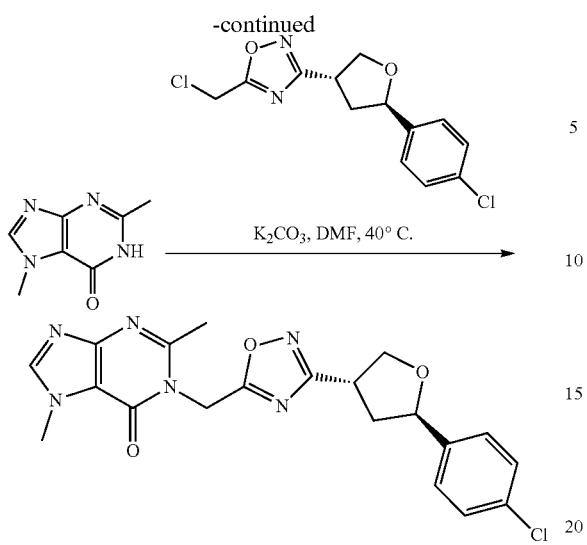

K₂CO₃, DMF, 40° C.

Step 1: Preparation of 4,6-dichloro-N,2-dimethylpyrimidin-5-amine

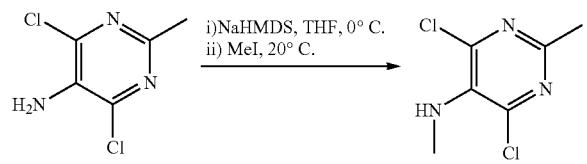

i) NaHMDS, THF, 0° C.
ii) MeI, 20° C.

To a 1 L RBF under nitrogen was added NaHMDS (1M in THF, 126 mL, 126 mmol) and THF (120 mL). The solution was cooled in an ice bath and when internal probe indicated 2° C., a solution of 4,6-dichloro-2-methylpyrimidin-5-amine (20.0 g, 112 mmol) in THF (120 mL) was canulated over 40 min. in order to keep internal temperature between 2 and 4° C. The reaction mixture was allowed to stir at 2° C. for 1 hour and iodomethane (8.2 mL, 131 mmol) was added over 5 min. The reaction mixture was stirred at 20° C. for 2 hours and the reaction was stopped by the addition of a saturated aqueous solution of NH₄Cl (350 mL), water (50 mL) and brine (50 mL). The resulting mixture was extracted with EtOAc (3×200 mL). The combined organic layers were washed with brine, dried over anhydrous Na₂SO₄, filtered and concentrated under reduced pressure to give crude 4,6-dichloro-N,2-dimethylpyrimidin-5-amine (supposed 21.6 g, 100% crude yield) as a brown oil which solidified upon standing at room temperature. LCMS showed a 88% purity and the crude material was used as is in the next reaction.

Step 2: Preparation of 6-chloro-N5,2-dimethylpyrimidine-4,5-diamine

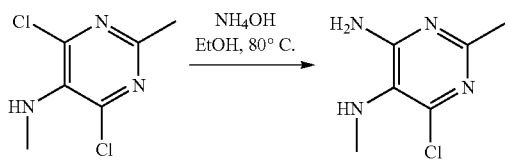

NH₄OH
EtOH, 80° C.

To a 500 mL pressure vessel was transferred crude 4,6-dichloro-N,2-dimethylpyrimidin-5-amine (21.6 g, 112 mmol) in Ethanol (70 mL). 28% aqueous NH₄OH (130 mL, 1924 mmol) was added, the flask was sealed and the mixture was stirred in a 80° C. oil bath for 18 hours. The reaction mixture was allowed to cool down at 20° C. and it was cooled in an ice bath. A golden solid slowly formed and the mixture was stirred at 0° C. for 2 hours. The suspension was filtered and the solid was washed with a mixture of cold EtOH (30 mL) and water (60 mL) to give 6-chloro-N5,2-dimethyl-pyrimidine-4,5-diamine (12.2 g, 70.7 mmol, 63% yield, 91% purity by LCMS) as a golden solid. The mother liquor was concentrated and the resulting solid was suspended in MeOH and water (~5:1). The mixture was heated to 70° C. and it was allowed to cool down at 20° C. The resulting suspension was filtered and the solid was washed with a minimum of cold MeOH to give a second crop of 6-chloro-N5,2-dimethylpyrimidine-4,5-diamine (1.40 g, 8.11 mmol, 7% yield, 97% purity by LCMS) as a beige solid.

Step 3: Preparation of 2,7-dimethyl-1H-purin-6(7H)-one

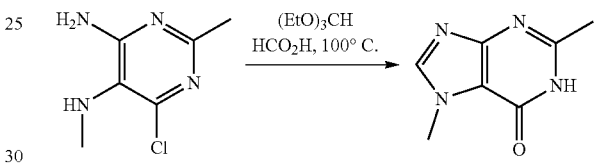

(EtO)₃CH
HCO₂H, 100° C.

To a solution of 6-chloro-2,N5-dimethylpyrimidine-4,5-diamine (3.50 g, 20.3 mmol) in triethyl orthoformate (15 mL) was added formic acid (2.80 g, 60.8 mmol). The resulting mixture was stirred at 100° C. overnight. The resulting mixture was concentrated. The crude product was washed with ethyl acetate to give 2,7-dimethyl-1H-purin-6(7H)-one (2.00 g, 60% yield) as a yellow solid. ¹H NMR (300 MHz, DMSO-d6) δ 12.14 (s, 1H), 8.07 (s, 1H), 3.93 (s, 3H), 2.32 (s, 3H).

Step 4: Preparation of 1-(((3-((3R,5R)-5-(4-chlorophenyl)tetrahydrofuran-3-yl)-1,2,4-oxadiazol-5-yl)methyl)-2,7-dimethyl-1H-purin-6(7H)-one

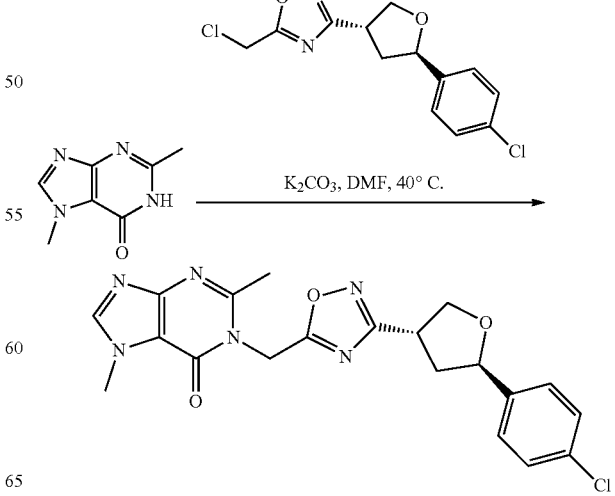

K₂CO₃, DMF, 40° C.

5-(chloromethyl)-3-[(3R,5R)-5-(4-chlorophenyl)tetrahydrofuran-3-yl]-1,2,4-oxadiazole (8.40 g, 28.1 mmol, prepared according to a similar procedure as example 1), 2,7-dimethyl-1H-purin-6(7H)-one (5.07 g, 30.9 mmol) and potassium carbonate (11.6 g, 84.2 mmol) were charged in a 200 mL RBF. DMF (56 mL) was added and the mixture was stirred in a 40° C. oil bath for 2 hours. Heat was removed and the reaction mixture was transferred to a separatory funnel containing EtOAc (100 mL) and water (500 mL). The mixture was extracted with EtOAc (3×100 mL). The combined organic layers were washed with a mixture of water (40 mL) and brine (40 mL), dried over anhydrous $Na_2SO_4$, filtered and concentrated under reduced pressure to give the crude product (77% purity by LCMS). The crude brown oil was dissolved in EtOAc (100 mL) and Heptane (60 mL) was added dropwise which led to the slow formation of a solid. The mixture was stirred at 0° C. for 30 min. and the solid was collected on a Büchner funnel, rinsed with heptane and air dried for 15 min. to give a first lot of 1-((3-((3R,5R)-5-(4-chlorophenyl)tetrahydrofuran-3-yl)-1,2,4-oxadiazol-5-yl)methyl)-2,7-dimethyl-1H-purin-6(7H)-one (8.0 g, 18.7 mmol, 67% yield, 92% purity by LCMS) as a yellow solid. The filtrate was concentrated and it was purified by reverse phase chromatography (C18, MeCN/10 mM $NH_4HCO_2$ in $H_2O$, pH 3.8, 0 to 60% gradient) to afford a second lot of 1-((3-((3R,5R)-5-(4-chlorophenyl)tetrahydrofuran-3-yl)-1,2,4-oxadiazol-5-yl)methyl)-2,7-dimethyl-1H-purin-6(7H)-one (950 mg, 2.23 mmol, 8% yield, >99% purity by LCMS) as a white solid.

The first lot of desired product (8.0 g, 92% purity by LCMS) was combined with a third lot obtained from a previous batch (1.3 g, 96% purity by LCMS). The material was dissolved in EtOAc (250 mL) and the solvent was displaced with iPrOH on the rotavap (3 cycles of iPrOH addition (50 mL)/evaporation of 50 mL of solvent). During the process, a solid crashed out and the solvent was reduced to ~100 mL on the rotavap. The suspension was cooled to 0° C. and the solid was collected on a Büchner funnel, rinsed with cold iPrOH and air dried for 15 min. to give a fourth lot of 1-((3-((3R,5R)-5-(4-chlorophenyl)tetrahydrofuran-3-yl)-1,2,4-oxadiazol-5-yl)methyl)-2,7-dimethyl-1H-purin-6(7H)-one (8.50 g, 99% purity by LCMS) as a light beige solid. Still not satisfied with the color of the purified material, it was dissolved in EtOAc (500 mL) and the brown solution was treated with 8 g of activated charcoal. The mixture was allowed to stir for 15 min. The suspension was filtered on celite and the cake was rinsed with EtOAc. The colorless filtrate was evaporated under reduced pressure to give a fifth lot of 1-((3-((3R,5R)-5-(4-chlorophenyl)tetrahydrofuran-3-yl)-1,2,4-oxadiazol-5-yl)methyl)-2,7-dimethyl-1H-purin-6(7H)-one (7.50 g, 99% purity by LCMS) as a white solid. Finally, the second lot (950 mg, >99% purity by LCMS) and the fifth lot (7.50 g, 99% purity by LCMS) were combined in a 200 mL RBF and iPrOH (100 mL) was added. The suspension was stirred in a 100° C. oil bath until full dissolution and water was added (3 mL). The flask was removed from oil bath and the light yellow clear solution was allowed to cool down at room temperature. The suspension was cooled in an ice bath and the solid was collected on a Buchner funnel, rinsed with cold iPrOH (20 mL) and air dried for 24 hours to give the title compound 1-((3-((3R, 5R)-5-(4-chlorophenyl)tetrahydrofuran-3-yl)-1,2,4-oxadiazol-5-yl)methyl)-2,7-dimethyl-1H-purin-6(7H)-one (7.3 g) as a white solid. LCMS: purity=99.4%, $MH^+$=427.2/429.2. $^1$H NMR (400 MHz, DMSO-d6) δ 8.18 (s, 1H), 7.46-7.33 (m, 4H), 5.63 (s, 2H), 5.00 (t, J=7.4 Hz, 1H), 4.35 (dd, J=8.4, 7.5 Hz, 1H), 3.93 (s, 3H), 3.95-3.88 (m, 1H), 3.79-3.70 (m, 1H), 2.60 (s, 3H), 2.63-2.53 (m, 1H), 2.13 (ddd, J=12.7, 8.9, 7.8 Hz, 1H).

Example 9: 1-((3-((3R, 5R)-5-(4-chlorophenyl)-tetrahydrofuran-3-yl)-1, 2, 4-oxadiazol-5-yl) methyl)-7-methyl-1H-purine-6,8(7H,9H)-dione The overall Example 9 reaction scheme is as follows:

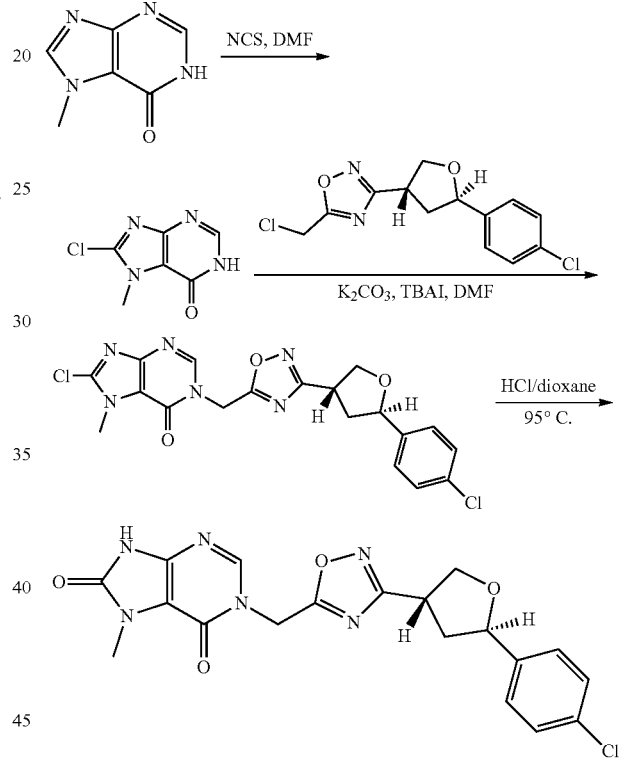

Step 1: Preparation of 8-chloro-7-methyl-1H-purin-6(7H)-one

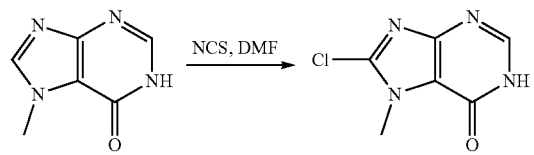

A solution of NCS (6.0 g, 44.93 mmol) and 7-methyl-1H-purin-6-one (8.7 g, 57.95 mmol) in DMF (70 mL) was stirred at room temperature overnight. The resulting solution was further purified by RP-HPLC to yield the title compound (4.7 g, 65%) as an off-white solid.

149

Step 2: Preparation of 8-chloro-1-((3-((3R, 5R)-5-(4-chlorophenyl)-tetrahydrofuran-3-yl)-1, 2, 4-oxadiazol-5-yl) methyl)-7-methyl-1H-purin-6(7H)-one

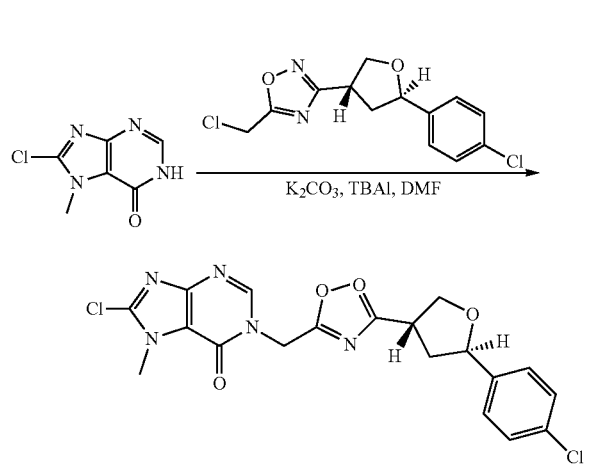

A solution of 5-(chloromethyl)-3-[(3R,5R)-5-(4-chlorophenyl)tetrahydrofuran-3-yl]-1,2,4-oxadiazole (55.0 mg, 0.18 mmol, prepared according to a similar procedure as example 1), 8-chloro-7-methyl-1H-purin-6(7H)-one (30.0 mg, 0.19 mmol), $K_2CO_3$ (51.0 mg, 0.37 mmol), and TBAI (3.4 mg, 0.01 mmol) in DMF (3 mL) was stirred at room temperature for 2 hours. The residue was purified by RP-HPLC to yield the title compound (48 mg, 67%) as a white solid.

150

Step 3: Preparation of 1-((3-((3R,5R)-5-(4-chlorophenyl)-tetrahydrofuran-3-yl)-1, 2, 4-oxadiazol-5-yl)methyl)-7-methyl-1H-purine-6,8(7H,9H)-dione

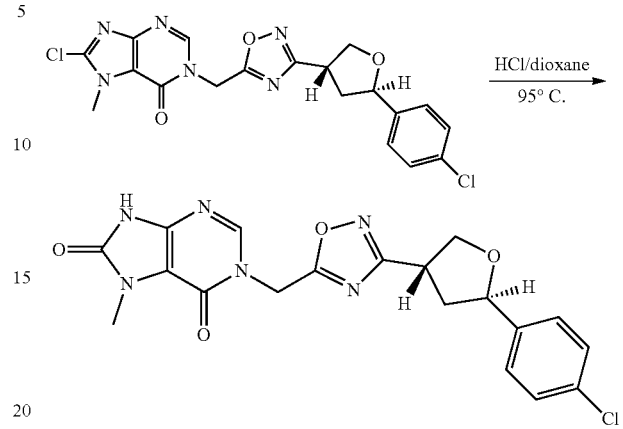

A solution of 8-chloro-1-[[3-[(3R,5R)-5-(4-chlorophenyl)tetrahydrofuran-3-yl]-1,2,4-oxadiazol-5-yl]methyl]-7-methyl-purin-6-one (230.0 mg, 0.51 mmol) in formic acid (5 mL) was stirred at 95° C. for 2 hours. The resulting solution was further purified by RP-HPLC to yield the title compound (51 mg, 23%) as a white solid. LCMS [M+H$^+$]: 429.1.

$^1$H NMR (400 MHz, DMSO-$d_6$) δ 11.88 (s, 1H), 8.41 (s, 1H), 7.39 (d, J=2.1 Hz, 4H), 5.53 (s, 2H), 5.01 (t, J=7.3 Hz, 1H), 4.36 (t, J=8.0 Hz, 1H), 3.90 (dd, J=8.5, 6.2 Hz, 1H), 3.81-3.75 (m, 1H), 2.61-2.56 (m, 1H), 2.20-2.06 (m, 1H).

The above compounds, together with additional compounds made using the above procedures with the appropriate starting materials, and are shown in Table 1, together with hTRPA1 $IC_{50}$ values for each compound.

| | Structure | Name | IC50 10 min | IC50 90 min |
|---|---|---|---|---|
| 1 | 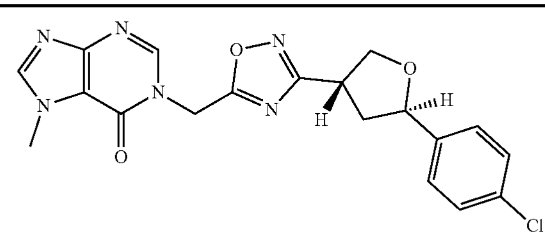 | 1-((3-((3R,5R)-5-(4-chlorophenyl)tetrahydrofuran-3-yl)-1,2,4-oxadiazol-5-yl)methyl)-7-methyl-1,7-dihydro-6H-purin-6-one | 0.00369 | 0.00088 |
| 2 | 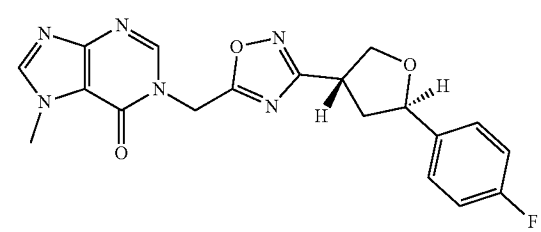 [SMILES: Cn1cnc2ncn(Cc3nc([C@@H]4CO[C@@H](c5ccc(F)cc5)C4)no3)c(=O)c21] | 1-((3-((3R,5R)-5-(4-fluorophenyl)tetrahydrofuran-3-yl)-1,2,4-oxadiazol-5-yl)methyl)-7-methyl-1,7-dihydro-6H-purin-6-one | 0.0193 | 0.0056 |
| 3 | 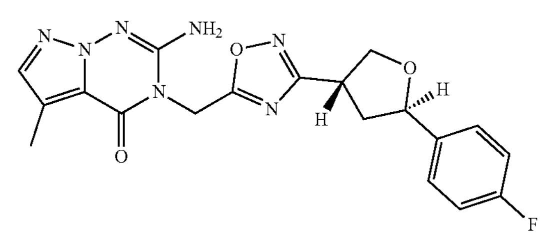 [SMILES: Cc1cnn2nc(N)n(Cc3nc([C@@H]4CO[C@@H](c5ccc(F)cc5)C4)no3)c(=O)c12] | 2-amino-3-((3-((3R,5R)-5-(4-fluorophenyl)tetrahydrofuran-3-yl)-1,2,4-oxadiazol-5-yl)methyl)-5-methylpyrazolo[5,1-f][1,2,4]triazin-4(3H)-one | 0.00502 | 0.0013 |

-continued

| | Structure | Name | IC50 10 min | IC50 90 min |
|---|---|---|---|---|
| 4 | 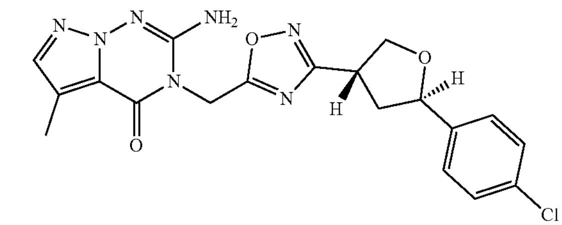 [SMILES: Cc1cnn2nc(N)n(Cc3nc([C@@H]4CO[C@@H](c5ccc(Cl)cc5)C4)no3)c(=O)c12] | 2-amino-3-((3-((3R,5R)-5-(4-chlorophenyl)tetrahydro-furan-3-yl)-1,2,4-oxadiazol-5-yl)methyl)-5-methylpyrazolo[5,1-f][1,2,4]triazin-4(3H)-one | 0.00401 | 0.00066 |
| 5 | 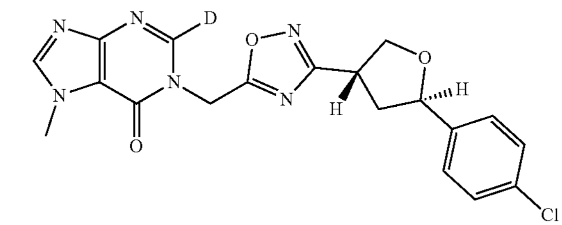 [SMILES: [2H]c1nc2ncn(C)c2c(=O)n1Cc1nc([C@@H]2CO[C@@H](c3ccc(Cl)cc3)C2)no1] | 1-((3-((3R,5R)-5-(4-chlorophenyl)tetrahydro-furan-3-yl)-1,2,4-oxadiazol-5-yl)methyl)-7-methyl-1,7-dihydro-6H-purin-6-one-2-d | 0.0176 | 0.0031 |
| 6 | 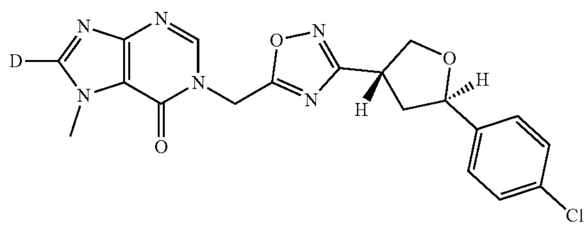 [SMILES: [2H]c1nc2ncn(Cc3nc([C@@H]4CO[C@@H](c5ccc(Cl)cc5)C4)no3)c(=O)c2n1C] | 1-((3-((3R,5R)-5-(4-chlorophenyl)tetra-hydrofuran-3-yl)-1,2,4-oxadiazol-5-yl)methyl)-7-methyl-1,7-dihydro-6H-purin-6-one-8-d | 0.0183 | 0.0043 |
| 7 | 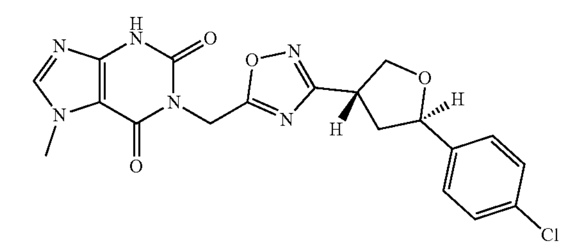 [SMILES: Cn1cnc2[nH]c(=O)n(Cc3nc([C@@H]4CO[C@@H](c5ccc(Cl)cc5)C4)no3)c(=O)c21] | 1-((3-((3R,5R)-5-(4-chlorophenyl)tetra-hydrofuran-3-yl)-1,2,4-oxadiazol-5-yl)methyl)-7-methyl-3,7-dihydro-1H-purine-2,6-dione | 0.313 | 0.023 |
| 8 | 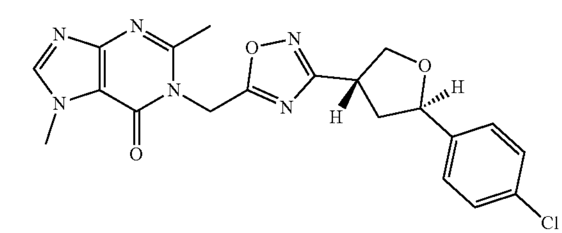 [SMILES: Cc1nc2ncn(C)c2c(=O)n1Cc1nc([C@@H]2CO[C@@H](c3ccc(Cl)cc3)C2)no1] | 1-((3-((3R,5R)-5-(4-chlorophenyl)tetra-hydrofuran-3-yl)-1,2,4-oxadiazol-5-yl)methyl)-2,7-dimethyl-1,7-dihydro-6H-purin-6-one | 0.00938 | 0.0041 |
| 9 | 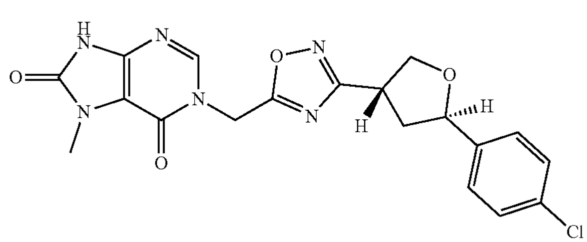 [SMILES: Cn1c(=O)[nH]c2ncn(Cc3nc([C@@H]4CO[C@@H](c5ccc(Cl)cc5)C4)no3)c(=O)c21] | 1-((3-((3R,5R)-5-(4-chlorophenyl)tetra-hydrofuran-3-yl)-1,2,4-oxadiazol-5-yl)methyl)-7-methyl-7,9-dihydro-1H-purine-6,8-dione | 0.0404 | 0.011 |

-continued

| | Structure | Name | IC50 10 min | IC50 90 min |
|---|---|---|---|---|
| 10 | 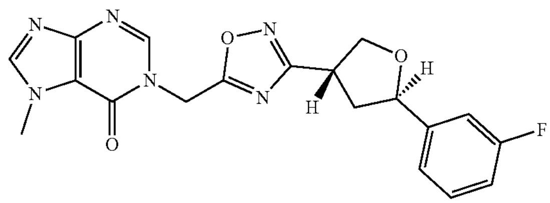 [SMILES: Cn1cnc2ncn(Cc3nc([C@@H]4CO[C@@H](c5cccc(F)c5)C4)no3)c(=O)c21] | 1-((3-((3R,5R)-5-(3-fluorophenyl)tetrahydrofuran-3-yl)-1,2,4-oxadiazol-5-yl)methyl)-7-methyl-1,7-dihydro-6H-purin-6-one | 0.0274 | 0.017 |
| 11 | 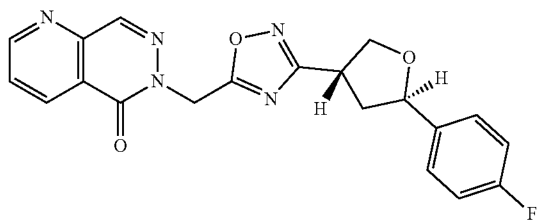 [SMILES: O=c1c2cccnc2cnn1Cc1nc([C@@H]2CO[C@@H](c3ccc(F)cc3)C2)no1] | 6-((3-((3R,5R)-5-(4-fluorophenyl)tetrahydrofuran-3-yl)-1,2,4-oxadiazol-5-yl)methyl)pyrido[2,3-d]pyridazin-5(6H)-one | 0.0166 | 0.013 |
| 12 | 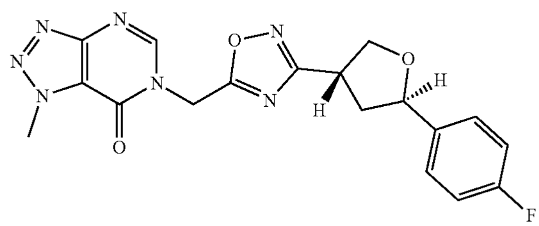 [SMILES: Cn1nnc2ncn(Cc3nc([C@@H]4CO[C@@H](c5ccc(F)cc5)C4)no3)c(=O)c21] | 6-((3-((3R,5R)-5-(4-fluorophenyl)tetrahydrofuran-3-yl)-1,2,4-oxadiazol-5-yl)methyl)-1-methyl-1,6-dihydro-7H-[1,2,3]triazolo[4,5-d]pyrimidin-7-one | 0.00755 | 0.0034 |
| 13 | 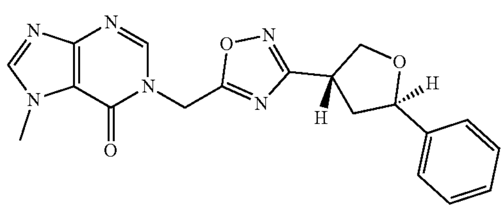 [SMILES: Cn1cnc2ncn(Cc3nc([C@@H]4CO[C@@H](c5ccccc5)C4)no3)c(=O)c21] | 7-methyl-1-((3-((3R,5R)-5-phenyltetrahydrofuran-3-yl)-1,2,4-oxadiazol-5-yl)methyl)-1,7-dihydro-6H-purin-6-one | 0.0823 | 0.033 |
| 14 | 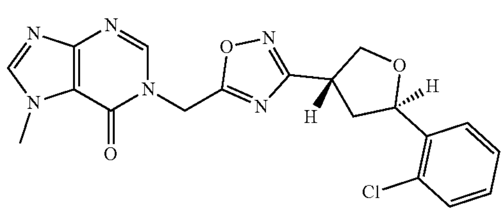 [SMILES: Cn1cnc2ncn(Cc3nc([C@@H]4CO[C@@H](c5ccccc5Cl)C4)no3)c(=O)c21] | 1-((3-((3R,5R)-5-(2-chlorophenyl)tetrahydrofuran-3-yl)-1,2,4-oxadiazol-5-yl)methyl)-7-methyl-1,7-dihydro-6H-purin-6-one | 0.335 | 0.16 |
| 15 | 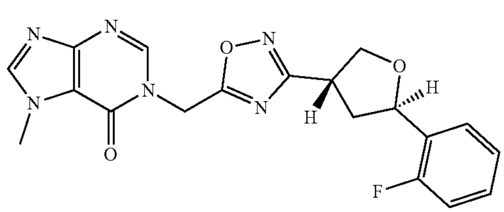 [SMILES: Cn1cnc2ncn(Cc3nc([C@@H]4CO[C@@H](c5ccccc5F)C4)no3)c(=O)c21] | 1-((3-((3R,5R)-5-(2-fluorophenyl)tetrahydrofuran-3-yl)-1,2,4-oxadiazol-5-yl)methyl)-7-methyl-1,7-dihydro-6H-purin-6-one | 0.127 | 0.059 |
| 16 | 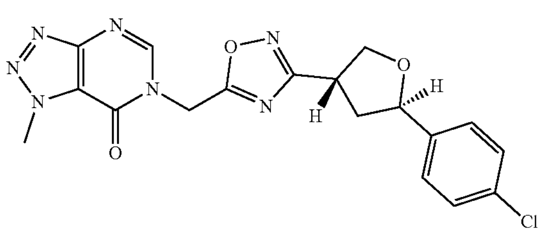 [SMILES: Cn1nnc2ncn(Cc3nc([C@@H]4CO[C@@H](c5ccc(Cl)cc5)C4)no3)c(=O)c21] | 6-((3-((3R,5R)-5-(4-chlorophenyl)tetrahydrofuran-3-yl)-1,2,4-oxadiazol-5-yl)methyl)-1-methyl-1,6-dihydro-7H-[1,2,3]triazolo[4,5-d]pyrimidin-7-one | 0.0049 | 0.0027 |

-continued

| | Structure | Name | IC50 10 min | IC50 90 min |
|---|---|---|---|---|
| 17 | 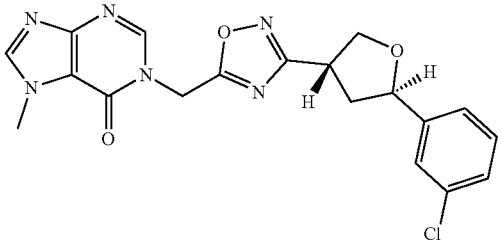 [SMILES: Cn1cnc2ncn(Cc3nc([C@@H]4CO[C@@H](c5cccc(Cl)c5)C4)no3)c(=O)c21] | 1-((3-((3R,5R)-5-(3-chlorophenyl)tetrahydro-furan-3-yl)-1,2,4-oxadiazol-5-yl)methyl)-7-methyl-1,7-dihydro-6H-purin-6-one | 0.0295 | 0.014 |
| 18 | 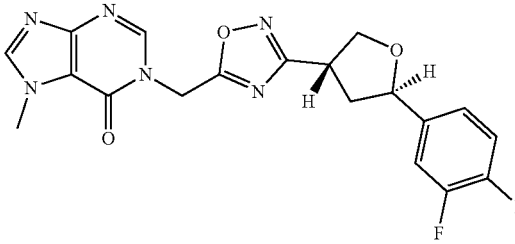 | 1-((3-((3R,5R)-5-(3,4-difluorophenyl)tetra-hydrofuran-3-yl)-1,2,4-oxadiazol-5-yl)methyl)-7-methyl-1,7-dihydro-6H-purin-6-one | 0.173 | 0.130 |
| 19 | 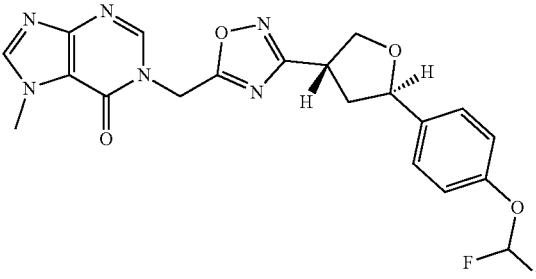 | 1-((3-((3R,5R)-5-(4-(difluoromethoxy)phenyl)tetrahydrofuran-3-yl)-1,2,4-oxadiazol-5-yl)methyl)-7-methyl-1,7-dihydro-6H-purin-6-one | 0.15 | 0.11 |
| 20 | 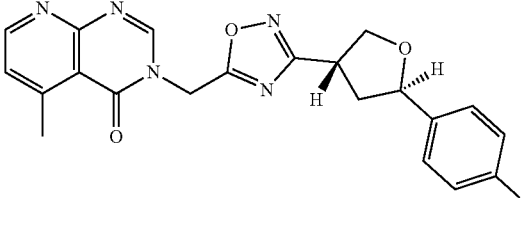 | 3-((3-((3R,5R)-5-(4-fluorophenyl)tetrahydro-furan-3-yl)-1,2,4-oxadiazol-5-yl)methyl)-5-methylpyrido[2,3-d]pyrimidin-4(3H)-one | 0.00705 | 0.0036 |
| 21 | 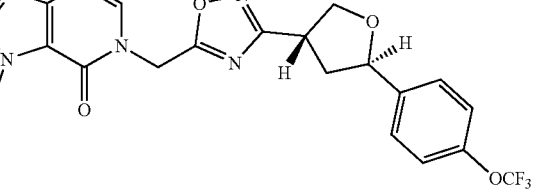 | 7-methyl-1-((3-((3R,5R)-5-(4-(trifluoromethoxy)phenyl)tetrahydro-furan-3-yl)-1,2,4-oxadiazol-5-yl)methyl)-1,7-dihydro-6H-purin-6-one | 0.0985 | 0.067 |
| 22 | 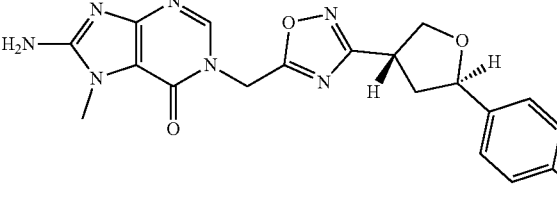 | 8-amino-1-((3-((3R,5R)-5-(4-fluorophenyl)tetrahydro-furan-3-yl)-1,2,4-oxadiazol-5-yl)methyl)-7-methyl-1,7-dihydro-6H-purin-6-one | 0.126 | 0.019 |

-continued

| | Structure | Name | IC50 10 min | IC50 90 min |
|---|---|---|---|---|
| 23 | 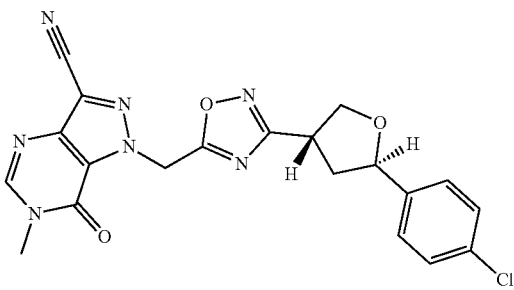 [SMILES: Cn1cnc2c(C#N)nn(Cc3nc([C@@H]4CO[C@@H](c5ccc(Cl)cc5)C4)no3)c2c1=O] | 1-((3-((3R,5R)-5-(4-chlorophenyl)tetrahydro-furan-3-yl)-1,2,4-oxadiazol-5-yl)methyl)-6-methyl-7-oxo-6,7-dihydro-1H-pyrazolo[4,3-d]pyrimidine-3-carbonitrile | 0.0457 | 0.024 |
| 24 | 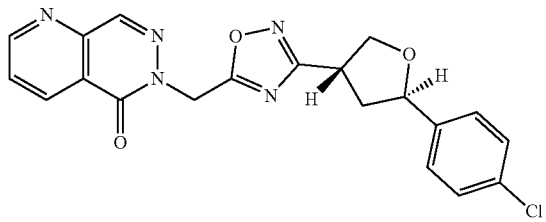 [SMILES: O=c1c2cccnc2cnn1Cc1nc([C@@H]2CO[C@@H](c3ccc(Cl)cc3)C2)no1] | 6-((3-((3R,5R)-5-(4-chlorophenyl)tetrahydro-furan-3-yl)-1,2,4-oxadiazol-5-yl)methyl)pyrido[2,3-d]pyridazin-5(6H)-one | 0.0072 | 0.0049 |
| 25 | 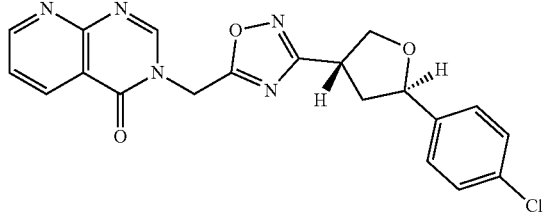 [SMILES: O=c1c2cccnc2ncn1Cc1nc([C@@H]2CO[C@@H](c3ccc(Cl)cc3)C2)no1] | 3-((3-((3R,5R)-5-(4-chlorophenyl)tetrahydro-furan-3-yl)-1,2,4-oxadiazol-5-yl)methyl)pyrido[2,3-d]pyrimidin-4(3H)-one | 0.00655 | 0.0057 |
| 26 | 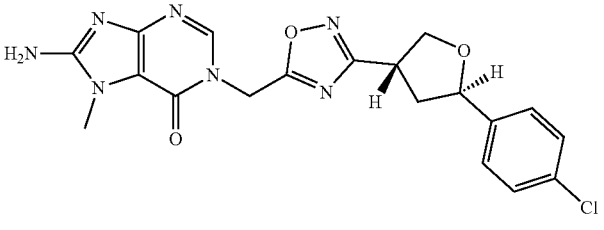 [SMILES: Cn1c(N)nc2ncn(Cc3nc([C@@H]4CO[C@@H](c5ccc(Cl)cc5)C4)no3)c(=O)c21] | 8-amino-1-((3-((3R,5R)-5-(4-chlorophenyl)tetrahydro-furan-3-yl)-1,2,4-oxadiazol-5-yl)methyl)-7-methyl-1,7-dihydro-6H-purin-6-one | 0.0587 | 0.0097 |
| 27 | 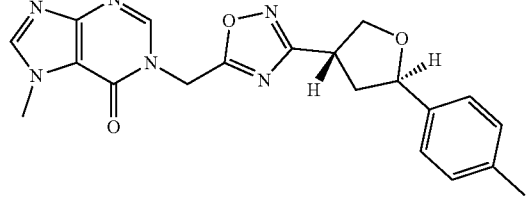 | 7-methyl-1-((3-((3R,5R)-5-(p-tolyl)tetrahydrofuran-3-yl)-1,2,4-oxadiazol-5-yl)methyl)-1,7-dihydro-6H-purin-6-one | 0.0161 | 0.0057 |
| 28 | 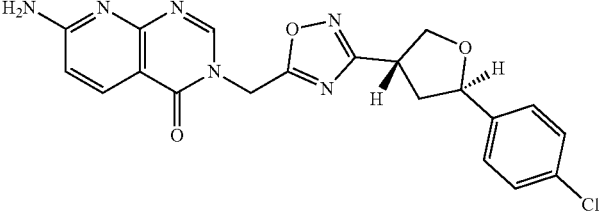 [SMILES: Nc1ccc2c(=O)n(Cc3nc([C@@H]4CO[C@@H](c5ccc(Cl)cc5)C4)no3)cnc2n1] | 7-amino-3-((3-((3R,5R)-5-(4-chlorophenyl)tetrahydro-furan-3-yl)-1,2,4-oxadiazol-5-yl)methyl)pyrido[2,3-d]pyrimidin-4(3H)-one | 0.00632 | 0.0039 |

-continued

| | Structure | Name | IC50 10 min | IC50 90 min |
|---|---|---|---|---|
| 29 | 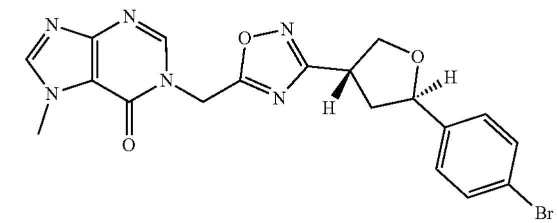 [SMILES: Cn1cnc2ncn(Cc3nc([C@@H]4CO[C@@H](c5ccc(Br)cc5)C4)no3)c(=O)c21] | 1-((3-((3R,5R)-5-(4-bromophenyl)tetra-hydrofuran-3-yl)-1,2,4-oxadiazol-5-yl)methyl)-7-methyl-1,7-dihydro-6H-purin-6-one | 0.00783 | 0.0018 |
| 30 | 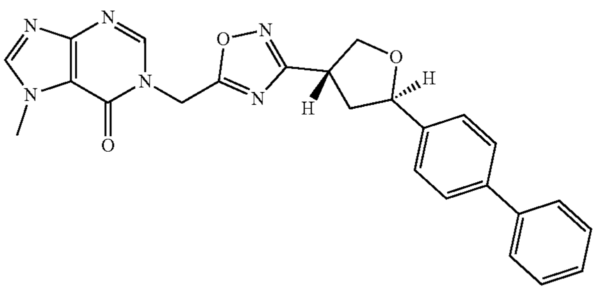 [SMILES: Cn1cnc2ncn(Cc3nc([C@@H]4CO[C@@H](c5ccc(-c6ccccc6)cc5)C4)no3)c(=O)c21] | 1-((3-((3R,5R)-5-[(1,1'-biphenyl]-4-yl)tetrahydrofuran-3-yl)-1,2,4-oxadiazol-5-yl)methyl)-7-methyl-1,7-dihydro-6H-purin-6-one | 0.623 | 0.370 |
| 31 | 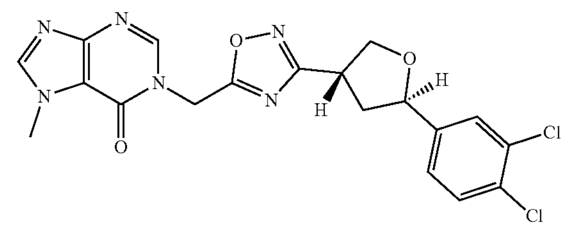 [SMILES: Cn1cnc2ncn(Cc3nc([C@@H]4CO[C@@H](c5ccc(Cl)c(Cl)c5)C4)no3)c(=O)c21] | 1-((3-((3R,5R)-5-(3,4-dichlorophenyl)tetra-hydrofuran-3-yl)-1,2,4-oxadiazol-5-yl)methyl)-7-methyl-1,7-dihydro-6H-purin-6-one | 0.0197 | 0.0078 |
| 32 | 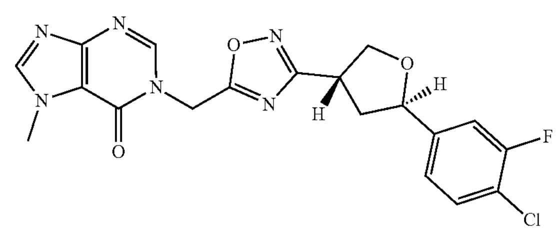 [SMILES: Cn1cnc2ncn(Cc3nc([C@@H]4CO[C@@H](c5ccc(Cl)c(F)c5)C4)no3)c(=O)c21] | 1-((3-((3R,5R)-5-(4-chloro-3-fluorophenyl)tetrahydro-furan-3-yl)-1,2,4-oxadiazol-5-yl)methyl)-7-methyl-1,7-dihydro-6H-purin-6-one | 0.00788 | 0.002 |
| 33 | 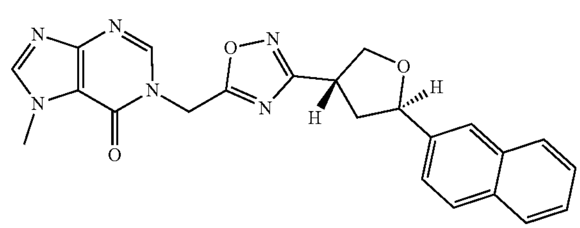 [SMILES: Cn1cnc2ncn(Cc3nc([C@@H]4CO[C@@H](c5ccc6ccccc6c5)C4)no3)c(=O)c21] | 7-methyl-1-((3-((3R,5R)-5-(naphthalen-2-yl)tetrahydrofuran-3-yl)-1,2,4-oxadiazol-5-yl)methyl)-1,7-dihydro-6H-purin-6-one | 0.00409 | 0.0024 |
| 34 | 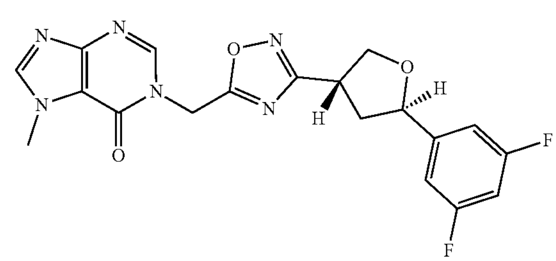 [SMILES: Cn1cnc2ncn(Cc3nc([C@@H]4CO[C@@H](c5cc(F)cc(F)c5)C4)no3)c(=O)c21] | 1-((3-((3R,5R)-5-(3,5-difluorophenyl)tetra-hydrofuran-3-yl)-1,2,4-oxadiazol-5-yl)methyl)-7-methyl-1,7-dihydro-6H-purin-6-one | 0.0635 | 0.028 |

-continued

| | Structure | Name | IC50 10 min | IC50 90 min |
|---|---|---|---|---|
| 35 | 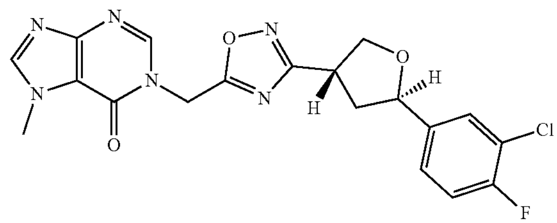 [SMILES: Cn1cnc2ncn(Cc3nc([C@@H]4CO[C@@H](c5ccc(F)c(Cl)c5)C4)no3)c(=O)c21] | 1-((3-((3R,5R)-5-(3-chloro-4-fluorophenyl)tetrahydrofuran-3-yl)-1,2,4-oxadiazol-5-yl)methyl)-7-methyl-1,7-dihydro-6H-purin-6-one | 0.0164 | 0.0036 |
| 36 | 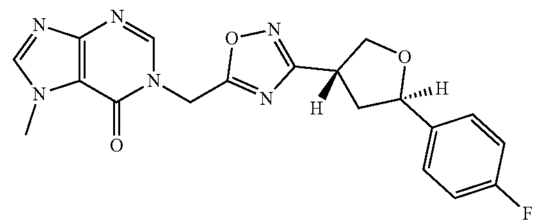 [SMILES: Cn1cnc2ncn(Cc3nc([C@@H]4CO[C@@H](c5ccc(F)cc5)C4)no3)c(=O)c21] | 1-((3-((3R,5R)-5-(4-fluorophenyl)tetrahydrofuran-3-yl)-1,2,4-oxadiazol-5-yl)methyl)-7-methyl-1,7-dihydro-6H-purin-6-one | 0.019 | 0.0066 |
| 37 | 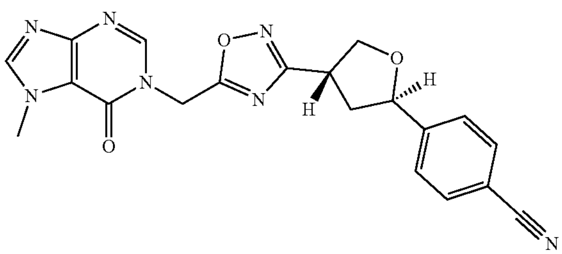 [SMILES: Cn1cnc2ncn(Cc3nc([C@@H]4CO[C@@H](c5ccc(C#N)cc5)C4)no3)c(=O)c21] | 4-((2R,4R)-4-(5-((7-methyl-6-oxo-6,7-dihydro-1H-purin-1-yl)methyl)-1,2,4-oxadiazol-3-yl)tetrahydrofuran-2-yl)benzonitrile | 0.108 | 0.052 |
| 38 | 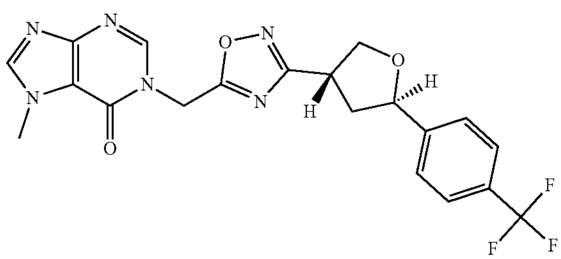 [SMILES: Cn1cnc2ncn(Cc3nc([C@@H]4CO[C@@H](c5ccc(C(F)(F)F)cc5)C4)no3)c(=O)c21] | 7-methyl-1-((3-((3R,5R)-5-(4-(trifluoromethyl)phenyl)tetrahydrofuran-3-yl)-1,2,4-oxadiazol-5-yl)methyl)-1,7-dihydro-6H-purin-6-one | 0.0464 | 0.029 |
| 39 | 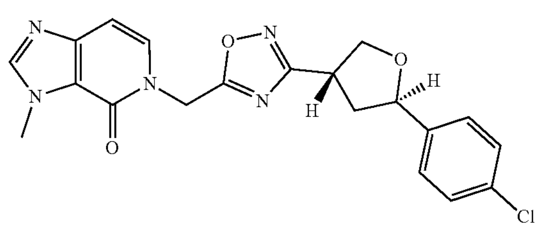 [SMILES: Cn1cnc2ccn(Cc3nc([C@@H]4CO[C@@H](c5ccc(Cl)cc5)C4)no3)c(=O)c21] | 5-((3-((3R,5R)-5-(4-chlorophenyl)tetrahydrofuran-3-yl)-1,2,4-oxadiazol-5-yl)methyl)-3-methyl-3,5-dihydro-4H-imidazo[4,5-c]pyridin-4-one | 0.00306 | 0.00042 |
| 40 | 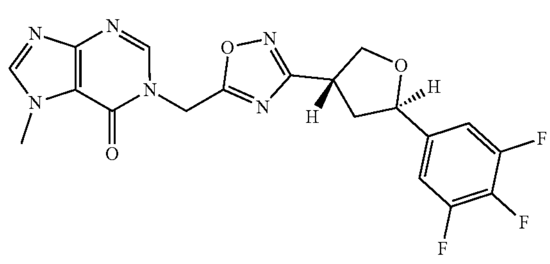 [SMILES: Cn1cnc2ncn(Cc3nc([C@@H]4CO[C@@H](c5cc(F)c(F)c(F)c5)C4)no3)c(=O)c21] | 7-methyl-1-((3-((3R,5R)-5-(3,4,5-trifluorophenyl)tetrahydrofuran-3-yl)-1,2,4-oxadiazol-5-yl)methyl)-1,7-dihydro-6H-purin-6-one | 0.0276 | 0.011 |

| | Structure | Name | IC50 10 min | IC50 90 min |
|---|---|---|---|---|
| 41 | 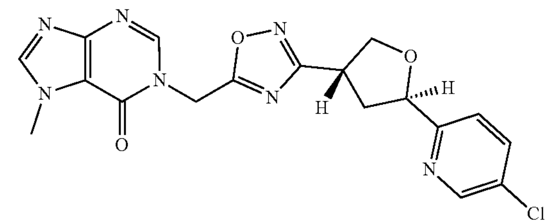 [SMILES: Cn1cnc2ncn(Cc3nc([C@@H]4CO[C@@H](c5ccc(Cl)cn5)C4)no3)c(=O)c21] | 1-((3-((3R,5R)-5-(5-chloropyridin-2-yl)tetrahydrofuran-3-yl)-1,2,4-oxadiazol-5-yl)methyl)-7-methyl-1,7-dihydro-6H-purin-6-one | 0.19 | 0.17 |
| 42 | 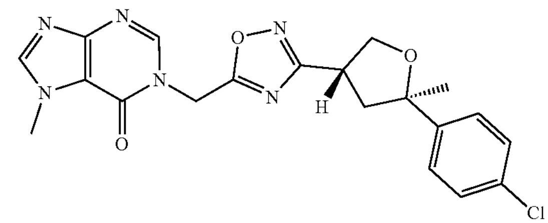 [SMILES: Cn1cnc2ncn(Cc3nc([C@@H]4CO[C@@](C)(c5ccc(Cl)cc5)C4)no3)c(=O)c21] | 1-((3-((3R,5R)-5-(4-chlorophenyl)-5-methyltetrahydrofuran-3-yl)-1,2,4-oxadiazol-5-yl)methyl)-7-methyl-1,7-dihydro-6H-purin-6-one | 3.71 | 2.2 |
| 43 | 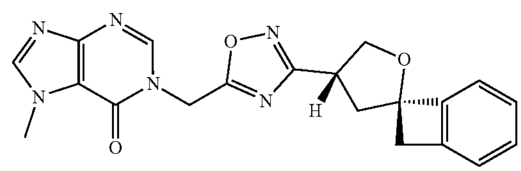 [SMILES: Cn1cnc2ncn(Cc3nc([C@@H]4CO[C@@]5(Cc6ccccc65)C4)no3)c(=O)c21] | 1-((3-((4'R,7R)-4',5'-dihydro-3'H-spiro[bicyclo[4.2.0]octane-7,2'-furan]-1(6),2,4-trien-4'-yl)-1,2,4-oxadiazol-5-yl)methyl)-7-methyl-1,7-dihydro-6H-purin-6-one | 0.278 | 0.14 |
| 44 | 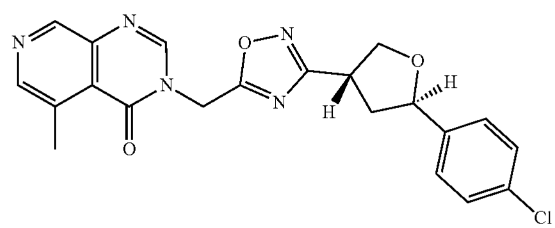 [SMILES: Cc1cncc2ncn(Cc3nc([C@@H]4CO[C@@H](c5ccc(Cl)cc5)C4)no3)c(=O)c12] | 3-((3-((3R,5R)-5-(4-chlorophenyl)tetrahydro-furan-3-yl)-1,2,4-oxadiazol-5-yl)methyl)-5-methylpyrido[3,4-d]pyrimidin-4(3H)-one | 0.0032 | 0.0013 |
| 45 | 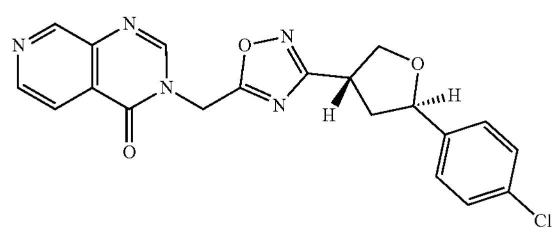 [SMILES: O=c1c2ccncc2ncn1Cc1nc([C@@H]2CO[C@@H](c3ccc(Cl)cc3)C2)no1] | 3-((3-((3R,5R)-5-(4-chlorophenyl)tetrahydro-furan-3-yl)-1,2,4-oxadiazol-5-yl)methyl)pyrido[3,4-d]pyrimidin-4(3H)-one | 0.0193 | 0.0078 |
| 46 | 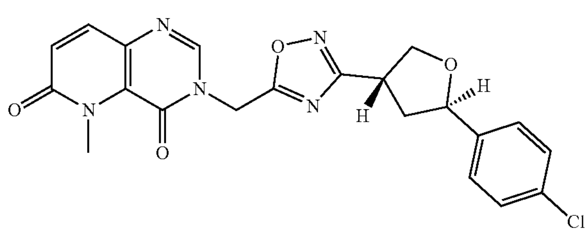 [SMILES: Cn1c(=O)ccc2ncn(Cc3nc([C@@H]4CO[C@@H](c5ccc(Cl)cc5)C4)no3)c(=O)c21] | 3-((3-((3R,5R)-5-(4-chlorophenyl)tetra-hydrofuran-3-yl)-1,2,4-oxadiazol-5-yl)methyl)-5-methyl-3,5-dihydropyrido[3,2-d]pyrimidine-4,6-dione | 0.0145 | 0.014 |
| 47 | 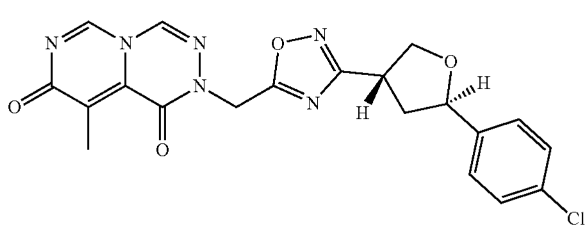 [SMILES: Cc1c(=O)ncn2cnn(Cc3nc([C@@H]4CO[C@@H](c5ccc(Cl)cc5)C4)no3)c(=O)c12] | 2-((3-((3R,5R)-5-(4-chlorophenyl)tetra-hydrofuran-3-yl)-1,2,4-oxadiazol-5-yl)methyl)-9-methyl-2H-pyrimido[1,6-d][1,2,4]triazine-1,8-dione | 0.332 | 0.24 |

-continued

| | Structure | Name | IC50 10 min | IC50 90 min |
|---|---|---|---|---|
| 48 | 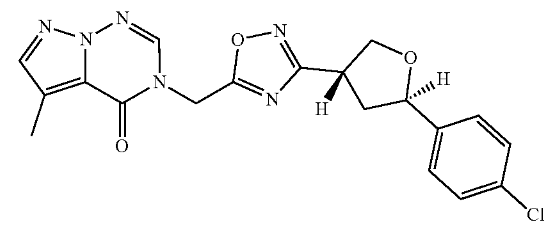 [SMILES: Cc1cnn2ncn(Cc3nc([C@@H]4CO[C@@H](c5ccc(Cl)cc5)C4)no3)c(=O)c12] | 3-((3-((3R,5R)-5-(4-chlorophenyl)tetra-hydrofuran-3-yl)-1,2,4-oxadiazol-5-yl)methyl)-5-methylpyrazolo[5,1-f][1,2,4]triazin-4(3H)-one | 0.0012 | 0.0008 |
| 49 | 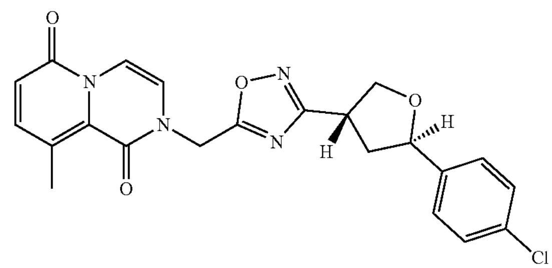 [SMILES: Cc1ccc(=O)n2ccn(Cc3nc([C@@H]4CO[C@@H](c5ccc(Cl)cc5)C4)no3)c(=O)c12] | 2-((3-((3R,5R)-5-(4-chlorophenyl)tetrahydro-furan-3-yl)-1,2,4-oxadiazol-5-yl)methyl)-9-methyl-2H-pyrido[1,2-a]pyrazine-1,6-dione | | 0.0043 |
| 50 | 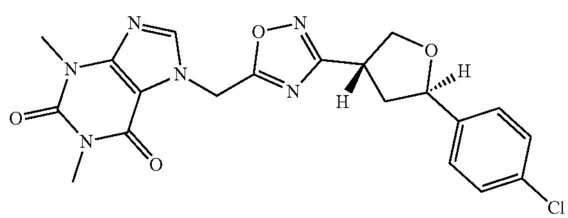 [SMILES: Cn1c(=O)c2c(ncn2Cc2nc([C@@H]3CO[C@@H](c4ccc(Cl)cc4)C3)no2)n(C)c1=O] | 7-((3-((3R,5R)-5-(4-chlorophenyl)tetrahydro-furan-3-yl)-1,2,4-oxadiazol-5-yl)methyl)-1,3-dimethyl-3,7-dihydro-1H-purine-2,6-dione | 0.0508 | 0.057 |
| 51 | 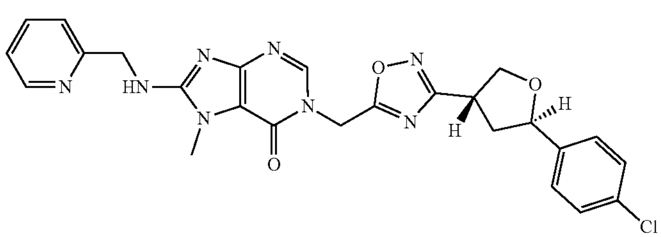 [SMILES: Cn1c(NCc2ccccn2)nc2ncn(Cc3nc([C@@H]4CO[C@@H](c5ccc(Cl)cc5)C4)no3)c(=O)c21] | 1-((3-((3R,5R)-5-(4-chlorophenyl)tetrahydro-furan-3-yl)-1,2,4-oxadiazol-5-yl)methyl)-7-methyl-8-((pyridin-2-ylmethyl)amino)-1,7-dihydro-6H-purin-6-one yl]methyl]purin-6-one | 0.0401 | 0.029 |
| 52 | 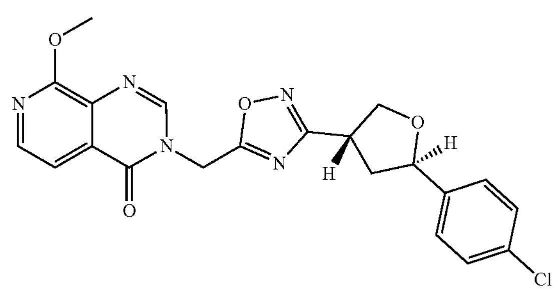 [SMILES: COc1nccc2c(=O)n(Cc3nc([C@@H]4CO[C@@H](c5ccc(Cl)cc5)C4)no3)cnc12] | 3-((3-((3R,5R)-5-(4-chlorophenyl)tetrahydro-furan-3-yl)-1,2,4-oxadiazol-5-yl)methyl)-8-methoxypyrido[3,4-d]pyrimidin-4(3H)-one | 0.0951 | 0.14 |
| 53 | 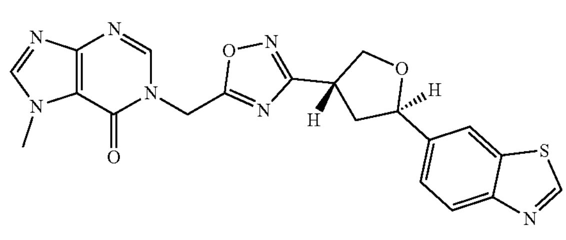 [SMILES: Cn1cnc2ncn(Cc3nc([C@@H]4CO[C@@H](c5ccc6ncsc6c5)C4)no3)c(=O)c21] | 1-((3-((3R,5R)-5-(benzo[d]thiazol-6-yl)tetrahydrofuran-3-yl)-1,2,4-oxadiazol-5-yl)methyl)-7-methyl-1,7-dihydro-6H-purin-6-one | 0.146 | 0.088 |

-continued

| | Structure | Name | IC50 10 min | IC50 90 min |
|---|---|---|---|---|
| 54 | 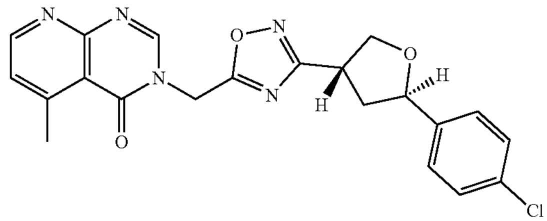 [SMILES: Cc1ccnc2ncn(Cc3nc([C@@H]4CO[C@@H](c5ccc(Cl)cc5)C4)no3)c(=O)c12] | 3-((3-((3R,5R)-5-(4-chlorophenyl)tetrahydrofuran-3-yl)-1,2,4-oxadiazol-5-yl)methyl)-5-methylpyrido[2,3-d]pyrimidin-4(3H)-one | 0.00214 | 0.00073 |
| 55 | 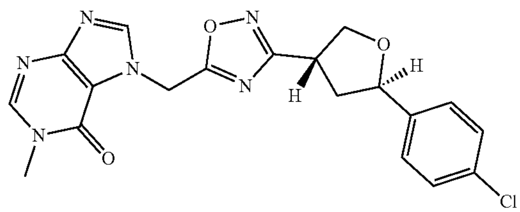 [SMILES: Cn1cnc2ncn(Cc3nc([C@@H]4CO[C@@H](c5ccc(Cl)cc5)C4)no3)c2c1=O] | 7-((3-((3R,5R)-5-(4-chlorophenyl)tetrahydrofuran-3-yl)-1,2,4-oxadiazol-5-yl)methyl)-1-methyl-1,7-dihydro-6H-purin-6-one | 0.019 | 0.012 |
| 56 | 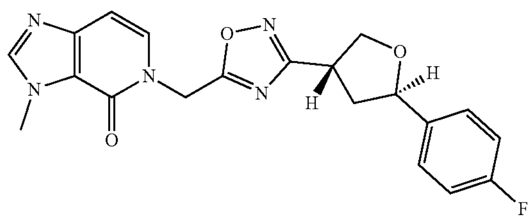 [SMILES: Cn1cnc2ccn(Cc3nc([C@@H]4CO[C@@H](c5ccc(F)cc5)C4)no3)c(=O)c21] | 5-((3-((3R,5R)-5-(4-fluorophenyl)tetrahydrofuran-3-yl)-1,2,4-oxadiazol-5-yl)methyl)-3-methyl-3,5-dihydro-4H-imidazo[4,5-c]pyridin-4-one | 0.00676 | 0.0019 |
| 57 | 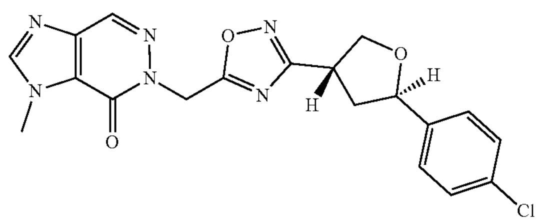 [SMILES: Cn1cnc2cnn(Cc3nc([C@@H]4CO[C@@H](c5ccc(Cl)cc5)C4)no3)c(=O)c21] | 5-((3-((3R,5R)-5-(4-chlorophenyl)tetrahydrofuran-3-yl)-1,2,4-oxadiazol-5-yl)methyl)-3-methyl-3,5-dihydro-4H-imidazo[4,5-d]pyridazin-4-one | 0.0388 | 0.018 |
| 58 | 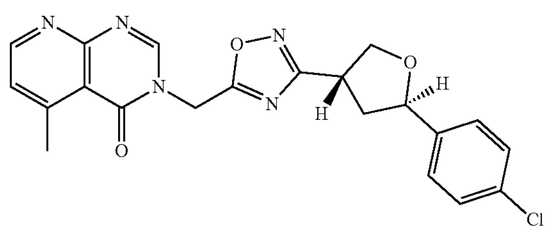 [SMILES: Cc1ccnc2ncn(Cc3nc([C@@H]4CO[C@@H](c5ccc(Cl)cc5)C4)no3)c(=O)c12] | 3-((3-((3R,5R)-5-(4-chlorophenyl)tetrahydrofuran-3-yl)-1,2,4-oxadiazol-5-yl)methyl)-5-methylpyrido[2,3-d]pyrimidin-4(3H)-one | 0.069 | 0.052 |
| 59 | 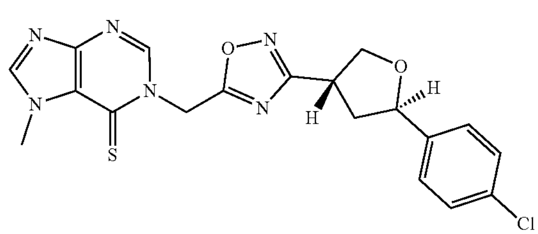 [SMILES: Cn1cnc2ncn(Cc3nc([C@@H]4CO[C@@H](c5ccc(Cl)cc5)C4)no3)c(=S)c21] | 1-((3-((3R,5R)-5-(4-chlorophenyl)tetrahydrofuran-3-yl)-1,2,4-oxadiazol-5-yl)methyl)-7-methyl-1,7-dihydro-6H-purine-6-thione | 0.00416 | 0.003 |
| 60 | 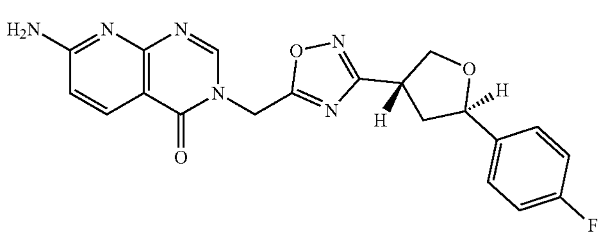 [SMILES: Nc1ccc2c(=O)n(Cc3nc([C@@H]4CO[C@@H](c5ccc(F)cc5)C4)no3)cnc2n1] | 7-amino-3-((3-((3R,5R)-5-(4-fluorophenyl)tetrahydrofuran-3-yl)-1,2,4-oxadiazol-5-yl)methyl)pyrido[2,3-d]pyrimidin-4(3H)-one | 0.0156 | 0.012 |

| | Structure | Name | IC50 10 min | IC50 90 min |
|---|---|---|---|---|
| 61 | 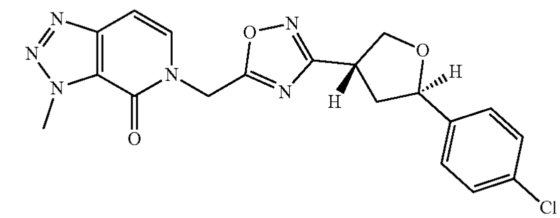 [SMILES: Cn1nnc2ccn(Cc3nc([C@@H]4CO[C@@H](c5ccc(Cl)cc5)C4)no3)c(=O)c21] | 5-((3-((3R,5R)-5-(4-chlorophenyl)tetrahydro-furan-3-yl)-1,2,4-oxadiazol-5-yl)methyl)-3-methyl-3,5-dihydro-4H-[1,2,3]triazolo[4,5-c]pyridin-4-one | 0.00465 | 0.0021 |
| 62 | 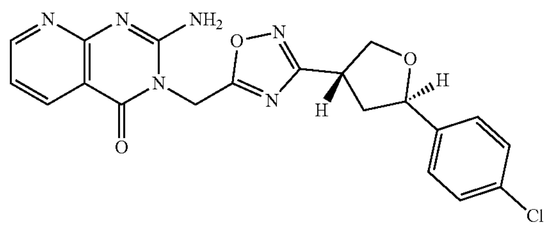 [SMILES: Nc1nc2ncccc2c(=O)n1Cc1nc([C@@H]2CO[C@@H](c3ccc(Cl)cc3)C2)no1] | 2-amino-3-((3-((3R,5R)-5-(4-chlorophenyl)tetrahydrofuran-3-yl)-1,2,4-oxadiazol-5-yl)methyl)pyrido[2,3-d]pyrimidin-4(3H)-one | 0.00829 | 0.0027 |
| 63 | 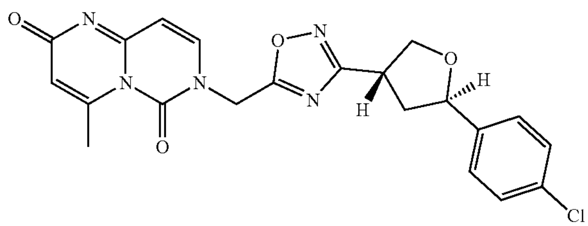 [SMILES: Cc1cc(=O)nc2ccn(Cc3nc([C@@H]4CO[C@@H](c5ccc(Cl)cc5)C4)no3)c(=O)n12] | 7-((3-((3R,5R)-5-(4-chlorophenyl)tetrahydro-furan-3-yl)-1,2,4-oxadiazol-5-yl)methyl)-4-methyl-2H-pyrimido[1,6-a]pyrimidine-2,6(7H)-dione | 0.00926 | 0.0028 |
| 64 | 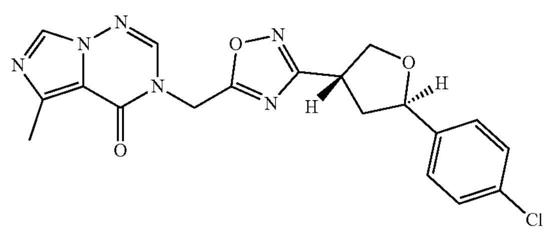 [SMILES: Cc1ncn2ncn(Cc3nc([C@@H]4CO[C@@H](c5ccc(Cl)cc5)C4)no3)c(=O)c12] | 3-((3-((3R,5R)-5-(4-chlorophenyl)tetrahydro-furan-3-yl)-1,2,4-oxadiazol-5-yl)methyl)-5-methylimidazo[1,5-f][1,2,4]triazin-4(3H)-one | 0.0206 | 0.015 |
| 65 | 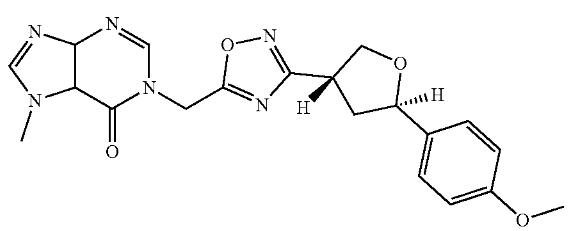 [SMILES: COc1ccc([C@H]2C[C@H](c3noc(CN4C=NC5N=CN(C)C5C4=O)n3)CO2)cc1] | 1-((3-((3R,5R)-5-(4-methoxyphenyl)tetrahydrofuran-3-yl)-1,2,4-oxadiazol-5-yl)methyl)-7-methyl-1,7-dihydro-6H-purin-6-one | 0.137 | 0.067 |
| 66 | 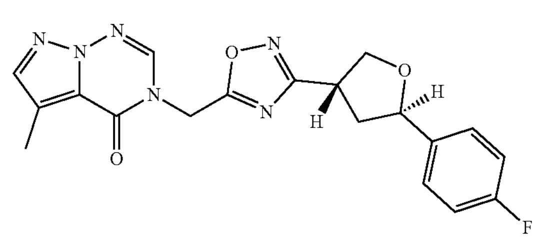 [SMILES: Cc1cnn2ncn(Cc3nc([C@@H]4CO[C@@H](c5ccc(F)cc5)C4)no3)c(=O)c12] | 3-((3-((3R,5R)-5-(4-fluorophenyl)tetrahydro-furan-3-yl)-1,2,4-oxadiazol-5-yl)methyl)-5-methylpyrazolo[5,1-f][1,2,4]triazin-4(3H)-one | 0.00847 | 0.0016 |

-continued

| | Structure | Name | IC50 10 min | IC50 90 min |
|---|---|---|---|---|
| 67 | 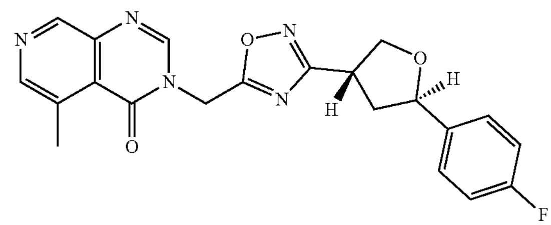 [SMILES: Cc1cncc2ncn(Cc3nc([C@@H]4CO[C@@H](c5ccc(F)cc5)C4)no3)c(=O)c12] | 3-((3-((3R,5R)-5-(4-fluorophenyl)tetrahydro-furan-3-yl)-1,2,4-oxadiazol-5-yl)methyl)-5-methylpyrido[3,4-d]pyrimidin-4(3H)-one | 0.0107 | 0.0012 |
| 68 | 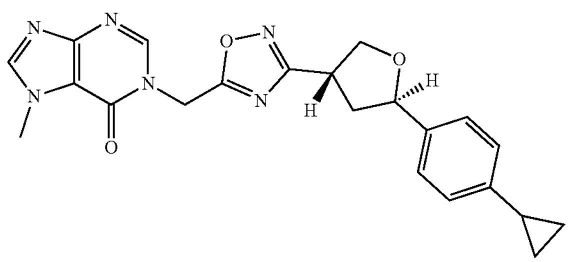 [SMILES: Cn1cnc2ncn(Cc3nc([C@@H]4CO[C@@H](c5ccc(C6CC6)cc5)C4)no3)c(=O)c21] | 1-((3-((3R,5R)-5-(4-cyclopropylphenyl)tetrahydrofuran-3-yl)-1,2,4-oxadiazol-5-yl)methyl)-7-methyl-1,7-dihydro-6H-purin-6-one | 0.046 | 0.027 |
| 69 | 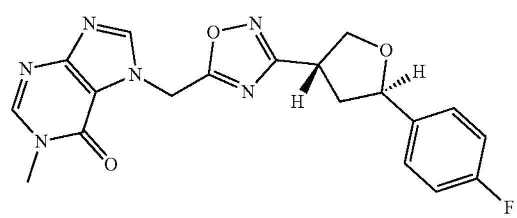 [SMILES: Cn1cnc2ncn(Cc3nc([C@@H]4CO[C@@H](c5ccc(F)cc5)C4)no3)c2c1=O] | 7-((3-((3R,5R)-5-(4-fluorophenyl)tetrahydro-furan-3-yl)-1,2,4-oxadiazol-5-yl)methyl)-1-methyl-1,7-dihydro-6H-purin-6-one | 0.0595 | 0.034 |
| 70 | 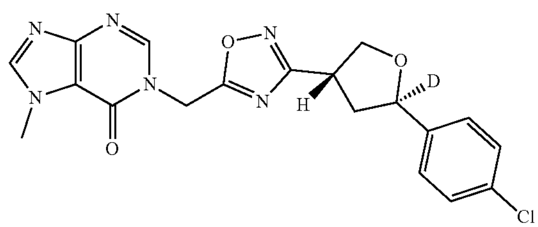 [SMILES: [2H][C@]1(c2ccc(Cl)cc2)C[C@H](c2noc(Cn3cnc4ncn(C)c4c3=O)n2)CO1] | 1-((3-((3R,5R)-5-(4-chlorophenyl)tetrahydro-furan-3-yl-5-d)-1,2,4-oxadiazol-5-yl)methyl)-7-methyl-1,7-dihydro-6H-purin-6-one | 0.00471 | 0.0012 |
| 71 | 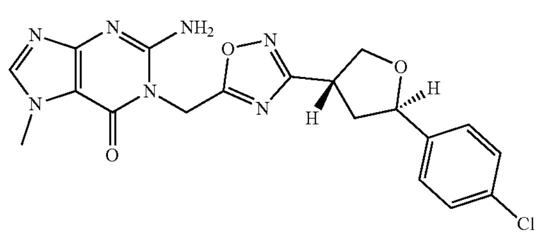 [SMILES: Cn1cnc2nc(N)n(Cc3nc([C@@H]4CO[C@@H](c5ccc(Cl)cc5)C4)no3)c(=O)c21] | 2-amino-1-((3-((3R,5R)-5-(4-chlorophenyl)tetrahydrofuran-3-yl)-1,2,4-oxadiazol-5-yl)methyl)-7-methyl-1,7-dihydro-6H-purin-6-one | 0.0184 | 0.0015 |
| 72 | 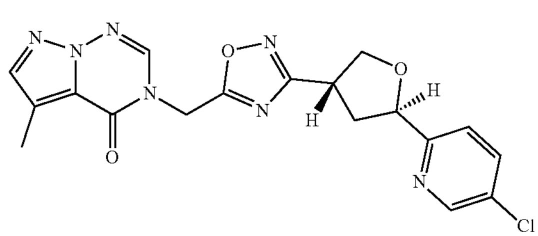 [SMILES: Cc1cnn2ncn(Cc3nc([C@@H]4CO[C@@H](c5ccc(Cl)cn5)C4)no3)c(=O)c12] | Racemic 3-((3-((3R,5R)-5-(5-chloropyridin-2-yl)tetrahydrofuran-3-yl)-1,2,4-oxadiazol-5-yl)methyl)-5-methylpyrazolo[5,1-f][1,2,4]triazin-4(3H)-one | 0.219 | 0.15 |

-continued

| | Structure | Name | IC50 10 min | IC50 90 min |
|---|---|---|---|---|
| 73 | 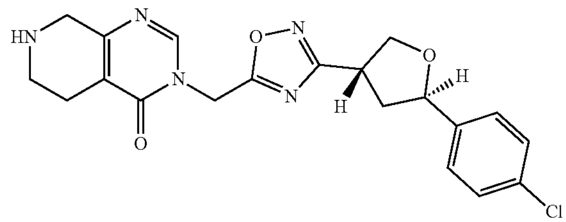 [SMILES: O=c1c2c(ncn1Cc1nc([C@@H]3CO[C@@H](c4ccc(Cl)cc4)C3)no1)CNCC2] | 3-((3-((3R,5R)-5-(4-chlorophenyl)tetrahydrofuran-3-yl)-1,2,4-oxadiazol-5-yl)methyl)-5,6,7,8-tetrahydropyrido[3,4-d]pyrimidin-4(3H)-one | — | 0.022 |
| 74 | 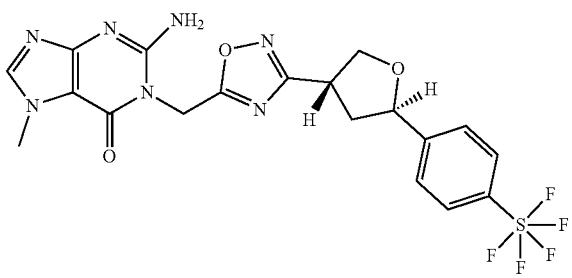 [SMILES: Cn1cnc2nc(N)n(Cc3nc([C@@H]4CO[C@@H](c5ccc(S(F)(F)(F)(F)F)cc5)C4)no3)c(=O)c21] | 2-amino-7-methyl-1-((3-((3R,5R)-5-(4-(pentafluoro-16-sulfanyl)phenyl)tetrahydrofuran-3-yl)-1,2,4-oxadiazol-5-yl)methyl)-1,7-dihydro-6H-purin-6-one | 0.17 | 0.12 |
| 75 | 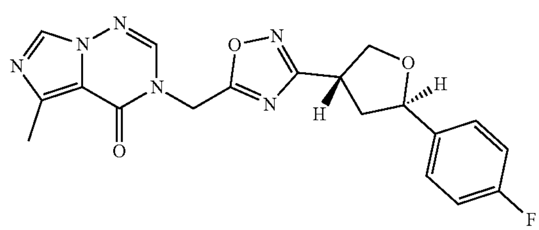 [SMILES: Cc1ncn2ncn(Cc3nc([C@@H]4CO[C@@H](c5ccc(F)cc5)C4)no3)c(=O)c12] | 3-((3-((3R,5R)-5-(4-fluorophenyl)tetrahydrofuran-3-yl)-1,2,4-oxadiazol-5-yl)methyl)-5-methylimidazo[5,1-f][1,2,4]triazin-4(3H)-one | — | 0.025 |
| 76 | 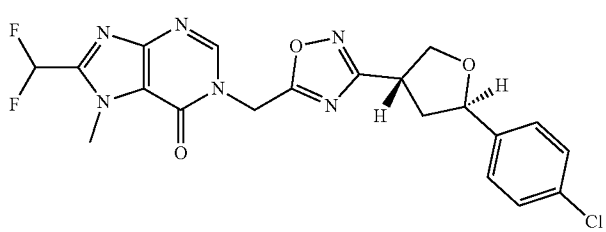 [SMILES: Cn1c(C(F)F)nc2ncn(Cc3nc([C@@H]4CO[C@@H](c5ccc(Cl)cc5)C4)no3)c(=O)c21] | 1-((3-((3R,5R)-5-(4-chlorophenyl)tetrahydrofuran-3-yl)-1,2,4-oxadiazol-5-yl)methyl)-8-(difluoromethyl)-7-methyl-1,7-dihydro-6H-purin-6-one | — | 0.011 |
| 77 | 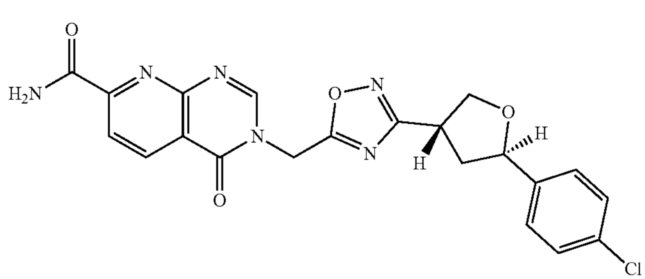 [SMILES: NC(=O)c1ccc2c(=O)n(Cc3nc([C@@H]4CO[C@@H](c5ccc(Cl)cc5)C4)no3)cnc2n1] | 3-((3-((3R,5R)-5-(4-chlorophenyl)tetrahydrofuran-3-yl)-1,2,4-oxadiazol-5-yl)methyl)-4-oxo-3,4-dihydropyrido[2,3-d]pyrimidine-7-carboxamide | — | 0.066 |

| | Structure | Name | IC50 10 min | IC50 90 min |
|---|---|---|---|---|
| 78 | 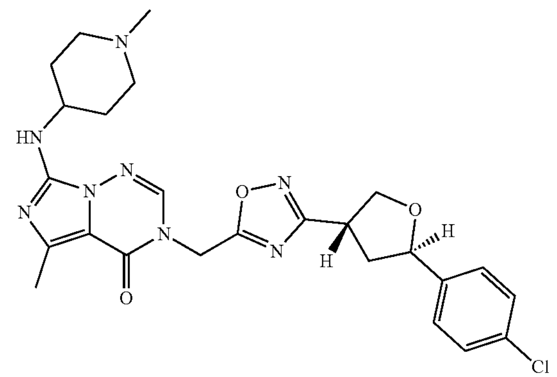 [SMILES: Cc1nc(NC2CCN(C)CC2)n2ncn(Cc3nc([C@@H]4CO[C@@H](c5ccc(Cl)cc5)C4)no3)c(=O)c12] | 3-((3-((3R,5R)-5-(4-chlorophenyl)tetrahydro-furan-3-yl)-1,2,4-oxadiazol-5-yl)methyl)-5-methyl-7-((1-methylpiperidin-4-yl)amino)imidazo[5,1-f][1,2,4]triazin-4(3H)-one | — | 0.15 |
| 79 | 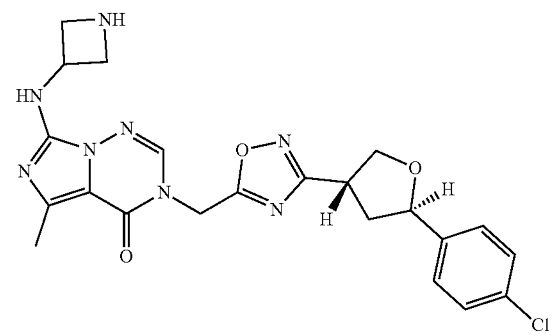 [SMILES: Cc1nc(NC2CNC2)n2ncn(Cc3nc([C@@H]4CO[C@@H](c5ccc(Cl)cc5)C4)no3)c(=O)c12] | 7-(azetidin-3-ylamino)-3-((3-((3R,5R)-5-(4-chlorophenyl)tetrahydro-furan-3-yl)-1,2,4-oxadiazol-5-yl)methyl)-5-methylimidazo[5,1-f][1,2,4]triazin-4(3H)-one | — | 0.092 |
| 80 | 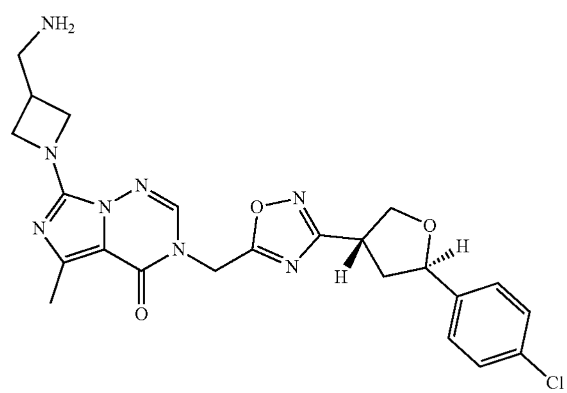 [SMILES: Cc1nc(N2CC(CN)C2)n2ncn(Cc3nc([C@@H]4CO[C@@H](c5ccc(Cl)cc5)C4)no3)c(=O)c12] | 7-(3-(aminomethyl)azetidin-1-yl)-3-((3-((3R,5R)-5-(4-chlorophenyl)tetrahydro-furan-3-yl)-1,2,4-oxadiazol-5-yl)methyl)-5-methylimidazo[5,1-f][1,2,4]triazin-4(3H)-one | — | 0.18 |
| 81 | 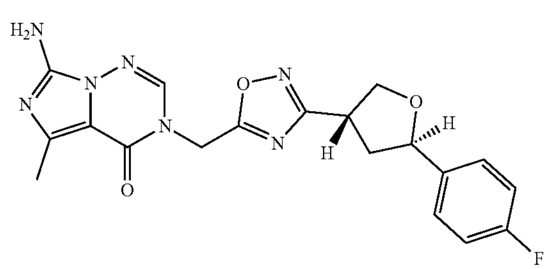 [SMILES: Cc1nc(N)n2ncn(Cc3nc([C@@H]4CO[C@@H](c5ccc(F)cc5)C4)no3)c(=O)c12] | 7-amino-3-((3-((3R,5R)-5-(4-fluorophenyl)tetrahydro-furan-3-yl)-1,2,4-oxadiazol-5-yl)methyl)-5-methyl-imidazo[5,1-f][1,2,4]triazin-4(3H)-one | — | 0.075 |

-continued

| | Structure | Name | IC50 10 min | IC50 90 min |
|---|---|---|---|---|
| 82 | 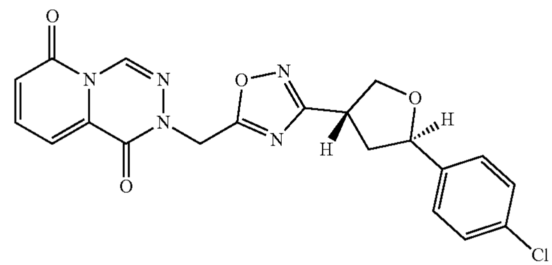 [SMILES: O=c1c2cccc(=O)n2cnn1Cc1nc([C@@H]2CO[C@@H](c3ccc(Cl)cc3)C2)no1] | 2-((3-((3R,5R)-5-(4-chlorophenyl)tetrahydrofuran-3-yl)-1,2,4-oxadiazol-5-yl)methyl)-2H-pyrido[1,2-d][1,2,4]triazine-1,6-dione | — | 0.0024 |
| 83 | 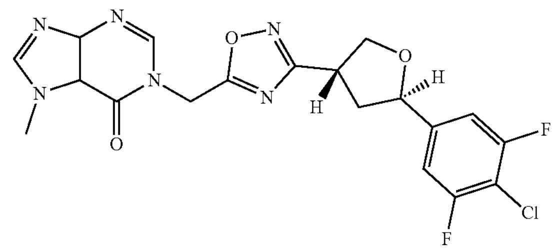 [SMILES: CN1C=NC2N=CN(Cc3nc([C@@H]4CO[C@@H](c5cc(F)c(Cl)c(F)c5)C4)no3)C(=O)C21] | 1-((3-((3R,5R)-5-(4-chloro-3,5-difluorophenyl)tetrahydrofuran-3-yl)-1,2,4-oxadiazol-5-yl)methyl)-7-methyl-1,7-dihydro-6H-purin-6-one | 0.0474 | 0.013 |
| 84 | 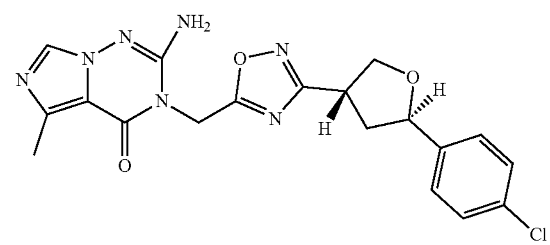 [SMILES: Cc1ncn2nc(N)n(Cc3nc([C@@H]4CO[C@@H](c5ccc(Cl)cc5)C4)no3)c(=O)c12] | 2-amino-3-((3-((3R,5R)-5-(4-chlorophenyl)tetrahydrofuran-3-yl)-1,2,4-oxadiazol-5-yl)methyl)-5-methylimidazo[5,1-f][1,2,4]triazin-4(3H)-one | 0.142 | 0.0046 |
| 85 | 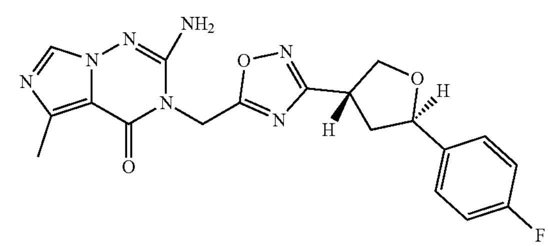 [SMILES: Cc1ncn2nc(N)n(Cc3nc([C@@H]4CO[C@@H](c5ccc(F)cc5)C4)no3)c(=O)c12] | 2-amino-3-((3-((3R,5R)-5-(4-fluorophenyl)tetrahydrofuran-3-yl)-1,2,4-oxadiazol-5-yl)methyl)-5-methylimidazo[5,1-f][1,2,4]triazin-4(3H)-one | 0.0155 | 0.006 |
| 86 | 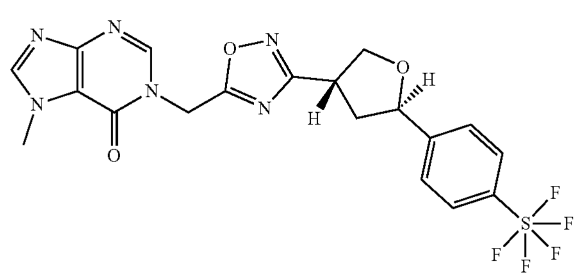 [SMILES: Cn1cnc2ncn(Cc3nc([C@@H]4CO[C@@H](c5ccc(S(F)(F)(F)(F)F)cc5)C4)no3)c(=O)c21] | 7-methyl-1-((3-((3R,5R)-5-(4-(pentafluoro-l6-sulfanyl)phenyl)tetrahydrofuran-3-yl)-1,2,4-oxadiazol-5-yl)methyl)-1,7-dihydro-6H-purin-6-one | 1.56 | 0.93 |
| 87 | 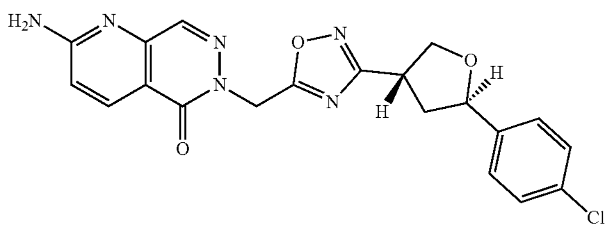 [SMILES: Nc1ccc2c(=O)n(Cc3nc([C@@H]4CO[C@@H](c5ccc(Cl)cc5)C4)no3)ncc2n1] | 2-amino-6-((3-((3R,5R)-5-(4-chlorophenyl)tetrahydrofuran-3-yl)-1,2,4-oxadiazol-5-yl)methyl)pyrido[2,3-d]pyridazin-5(6H)-one | 0.0105 | 0.0035 |

-continued

| | Structure | Name | IC50 10 min | IC50 90 min |
|---|---|---|---|---|
| 88 | 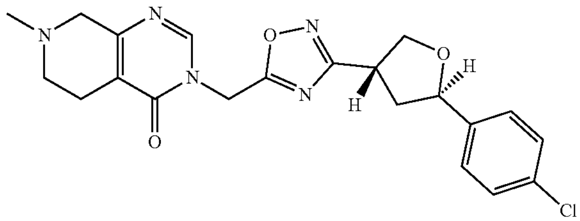 [SMILES: CN1CCc2c(ncn(Cc3nc([C@@H]4CO[C@@H](c5ccc(Cl)cc5)C4)no3)c2=O)C1] | 3-((3-((3R,5R)-5-(4-chlorophenyl)tetrahydrofuran-3-yl)-1,2,4-oxadiazol-5-yl)methyl)-7-methyl-5,6,7,8-tetrahydropyrido[3,4-d]pyrimidin-4(3H)-one | 2.72 | 0.45 |
| 89 | 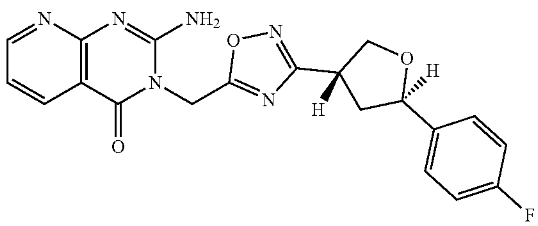 [SMILES: Nc1nc2ncccc2c(=O)n1Cc1nc([C@@H]2CO[C@@H](c3ccc(F)cc3)C2)no1] | 2-amino-3-((3-((3R,5R)-5-(4-fluorophenyl)tetrahydrofuran-3-yl)-1,2,4-oxadiazol-5-yl)methyl)pyrido[2,3-d]pyrimidin-4(3H)-one | 0.0187 | 0.0029 |
| 90 | 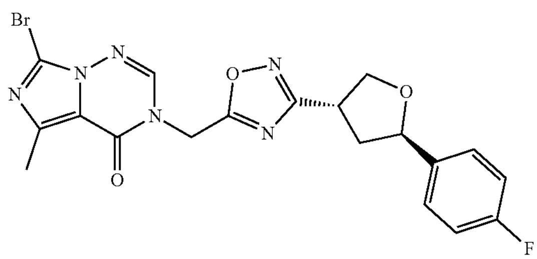 [SMILES: Cc1nc(Br)n2ncn(Cc3nc([C@@H]4CO[C@@H](c5ccc(F)cc5)C4)no3)c(=O)c12] | 7-bromo-5-methyl-3-[[3-[rac-(3R,5R)-5-(4-fluorophenyl)tetrahydrofuran-3-yl]-1,2,4-oxadiazol-5-yl]methyl]imidazo[5,1-f][1,2,4]triazin-4-one | — | 0.033 |
| 91 | 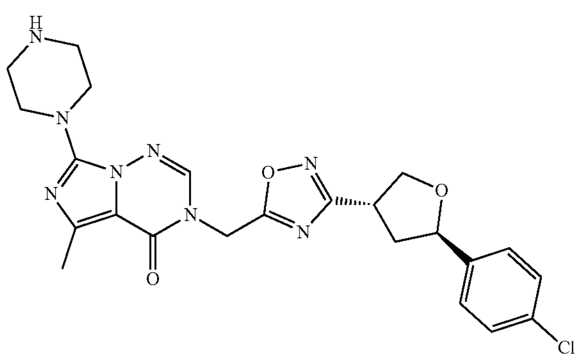 [SMILES: Cc1nc(N2CCNCC2)n2ncn(Cc3nc([C@@H]4CO[C@@H](c5ccc(Cl)cc5)C4)no3)c(=O)c12] | formic acid; 5-methyl-7-piperazin-1-yl-3-[[3-[rac-(3R,5R)-5-(4-chlorophenyl)tetrahydrofuran-3-yl]-1,2,4-oxadiazol-5-yl]methyl]imidazo[5,1-f][1,2,4]triazin-4-one | — | 0.33 |
| 92 | 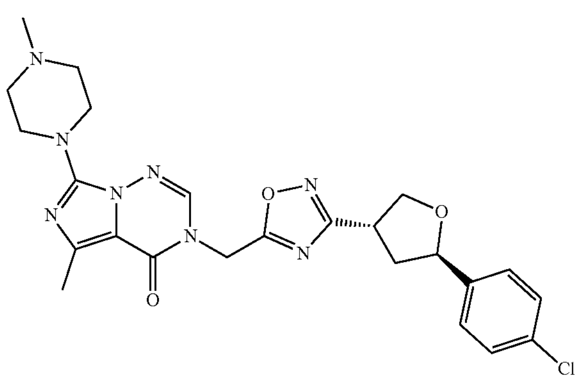 [SMILES: Cc1nc(N2CCN(C)CC2)n2ncn(Cc3nc([C@@H]4CO[C@@H](c5ccc(Cl)cc5)C4)no3)c(=O)c12] | 5-methyl-7-(4-methylpiperazin-1-yl)-3-[[3-[rac-(3R,5R)-5-(4-chlorophenyl)tetrahydrofuran-3-yl]-1,2,4-oxadiazol-5-yl]methyl]imidazo[5,1-f][1,2,4]triazin-4-one | — | 0.17 |

-continued

| | Structure | Name | IC50 10 min | IC50 90 min |
|---|---|---|---|---|
| 93 | 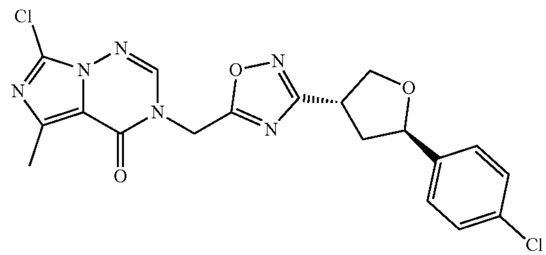 [SMILES: Cc1nc(Cl)n2ncn(Cc3nc([C@@H]4CO[C@@H](c5ccc(Cl)cc5)C4)no3)c(=O)c12] | 7-chloro-5-methyl-3-[[3-[rac-(3R,5R)-5-(4-chlorophenyl)tetrahydro-furan-3-yl]-1,2,4-oxadiazol-5-yl]methyl]imidazo[5,1-f][1,2,4]triazin-4-one | — | 0.013 |
| 94 | 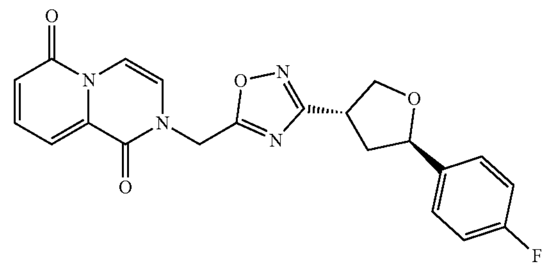 [SMILES: O=c1c2cccc(=O)n2ccn1Cc1nc([C@@H]2CO[C@@H](c3ccc(F)cc3)C2)no1] | 2-[[3-[rac-(3R,5R)-5-(4-fluorophenyl)tetrahydro-furan-3-yl]-1,2,4-oxadiazol-5-yl]methyl]pyrido[1,2-a]pyrazine-1,6-dione | — | 0.012 |
| 95 | 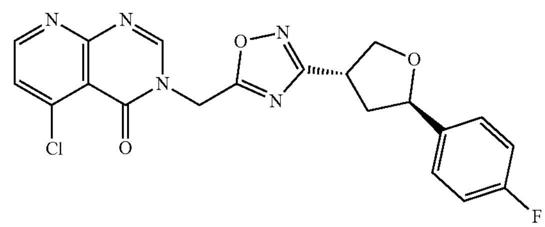 [SMILES: O=c1c2c(Cl)ccnc2ncn1Cc1nc([C@@H]2CO[C@@H](c3ccc(F)cc3)C2)no1] | 5-chloro-3-[[3-[rac-(3R,5R)-5-(4-fluorophenyl)tetrahydrofuran-3-yl]-1,2,4-oxadiazol-5-yl]methyl]pyrido[2,3-d]pyrimidin-4-one | — | 0.015 |
| 96 | 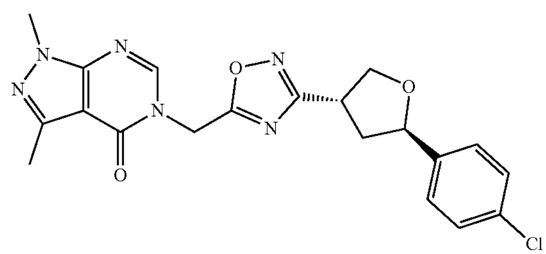 [SMILES: Cc1nn(C)c2ncn(Cc3nc([C@@H]4CO[C@@H](c5ccc(Cl)cc5)C4)no3)c(=O)c12] | 1,3-dimethyl-5-[[3-[rac-(3R,5R)-5-(4-chlorophenyl)tetrahydro-furan-3-yl]-1,2,4-oxadiazol-5-yl]methyl]pyrazolo[3,4-d]pyrimidin-4-one | — | 0.033 |
| 97 | 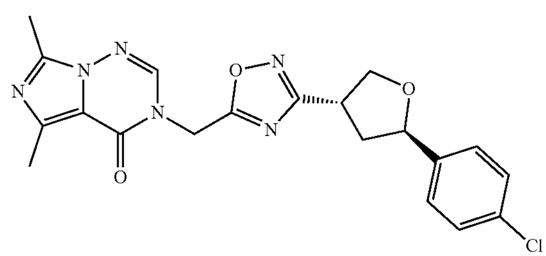 [SMILES: Cc1nc(C)n2ncn(Cc3nc([C@@H]4CO[C@@H](c5ccc(Cl)cc5)C4)no3)c(=O)c12] | 5,7-dimethyl-3-[[3-[rac-(3R,5R)-5-(4-chlorophenyl)tetrahydro-furan-3-yl]-1,2,4-oxadiazol-5-yl]methyl]imidazo[5,1-f][1,2,4]triazin-4-one | — | 0.045 |
| 98 | 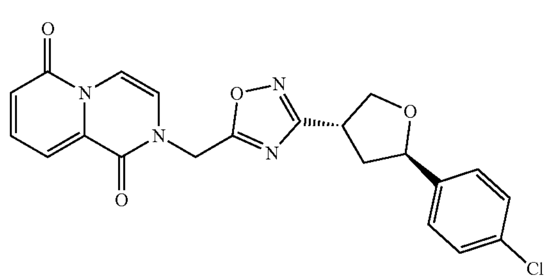 [SMILES: O=c1c2cccc(=O)n2ccn1Cc1nc([C@@H]2CO[C@@H](c3ccc(Cl)cc3)C2)no1] | 2-[[3-[rac-(3R,5R)-5-(4-chlorophenyl)tetrahydro-furan-3-yl]-1,2,4-oxadiazol-5-yl]methyl]pyrido[1,2-a]pyrazine-1,6-dione | 0.0064 | 0.004 |

-continued

| | Structure | Name | IC50 10 min | IC50 90 min |
|---|---|---|---|---|
| 99 | 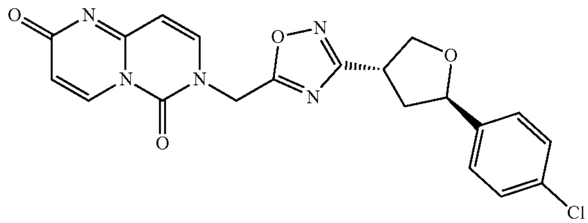 [SMILES: O=c1ccn2c(=O)n(Cc3nc([C@@H]4CO[C@@H](c5ccc(Cl)cc5)C4)no3)ccc2n1] | 7-[[3-[rac-(3R,5R)-5-(4-chlorophenyl)tetrahydro-furan-3-yl]-1,2,4-oxadiazol-5-yl]methyl]pyrimido[1,6-a]pyrimidine-2,6-dione | 0.0154 | 0.0072 |
| 100 | 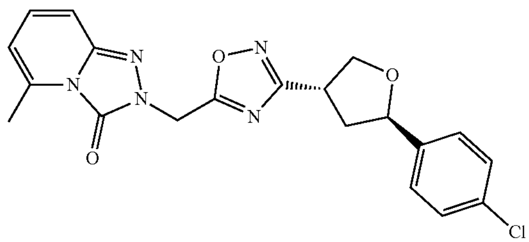 [SMILES: Cc1cccc2nn(Cc3nc([C@@H]4CO[C@@H](c5ccc(Cl)cc5)C4)no3)c(=O)n12] | 5-methyl-2-[[3-[rac-(3R,5R)-5-(4-chlorophenyl)tetrahydro-furan-3-yl]-1,2,4-oxadiazol-5-yl]methyl]-[1,2,4]triazolo[4,3-a]pyridin-3-one | 0.153 | 0.14 |
| 101 | 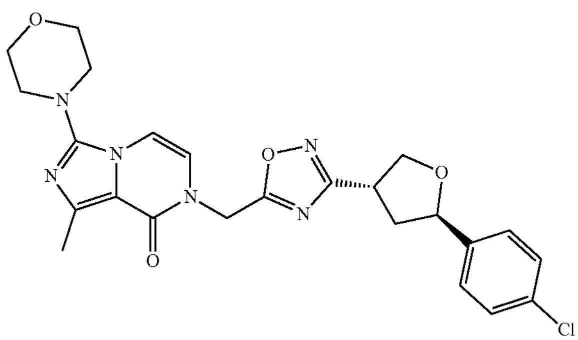 [SMILES: Cc1nc(N2CCOCC2)n2ccn(Cc3nc([C@@H]4CO[C@@H](c5ccc(Cl)cc5)C4)no3)c(=O)c12] | 5-methyl-7-morpholino-3-[[3-[rac-(3R,5R)-5-(4-chlorophenyl)tetrahydro-furan-3-yl]-1,2,4-oxadiazol-5-yl]methyl]imidazo[5,1-f][1,2,4]triazin-4-one | 0.123 | 0.096 |
| 102 | 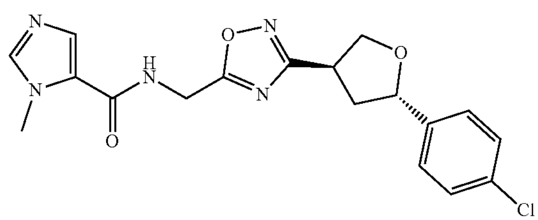 [SMILES: Cn1cncc1C(=O)NCc1nc([C@H]2CO[C@H](c3ccc(Cl)cc3)C2)no1] | 3-methyl-N-[[3-[rac-(3S,5S)-5-(4-chlorophenyl)tetrahydro-furan-3-yl]-1,2,4-oxadiazol-5-yl]methyl]imidazole-4-carboxamide | 0.0389 | 0.023 |
| 103 | 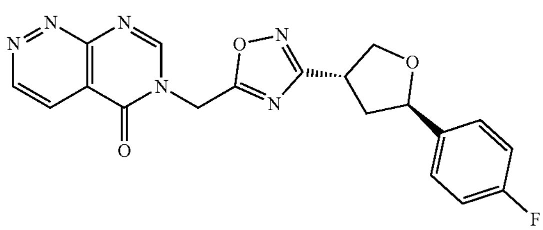 [SMILES: O=c1c2ccnnc2ncn1Cc1nc([C@@H]2CO[C@@H](c3ccc(F)cc3)C2)no1] | 6-[[3-[(3R,5R)-5-(4-fluorophenyl)tetrahydro-furan-3-yl]-1,2,4-oxadiazol-5-yl]methyl]pyrimido[4,5-c]pyridazin-5-one | 0.0717 | 0.089 |
| 104 | 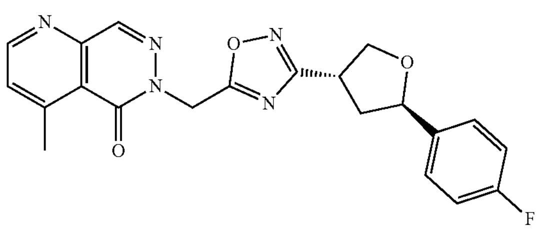 [SMILES: Cc1ccnc2cnn(Cc3nc([C@@H]4CO[C@@H](c5ccc(F)cc5)C4)no3)c(=O)c12] | 6-[[3-[(3R,5R)-5-(4-fluorophenyl)tetrahydro-furan-3-yl]-1,2,4-oxadiazol-5-yl]methyl]-4-methyl-pyrido[2,3-d]pyridazin-5-one | 0.0072 | 0.0067 |

-continued

| | Structure | Name | IC50 10 min | IC50 90 min |
|---|---|---|---|---|
| 105 | 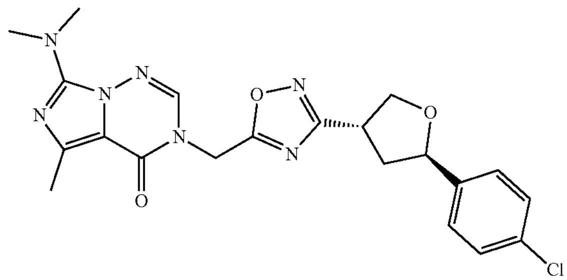 [SMILES: Cc1nc(N(C)C)n2ncn(Cc3nc([C@@H]4CO[C@@H](c5ccc(Cl)cc5)C4)no3)c(=O)c12] | 7-(dimethylamino)-5-methyl-3-[[3-[rac-(3R,5R)-5-(4-chlorophenyl)tetrahydrofuran-3-yl]-1,2,4-oxadiazol-5-yl]methyl]imidazo[5,1-f][1,2,4]triazin-4-one | 0.042 | 0.059 |
| 106 | 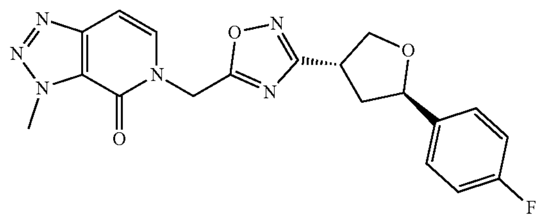 [SMILES: Cn1nnc2ccn(Cc3nc([C@@H]4CO[C@@H](c5ccc(F)cc5)C4)no3)c(=O)c21] | 3-methyl-5-[[3-[rac-(3R,5R)-5-(4-fluorophenyl)tetrahydrofuran-3-yl]-1,2,4-oxadiazol-5-yl]methyl]triazolo[4,5-c]pyridin-4-one | 0.0069 | 0.0056 |
| 107 | 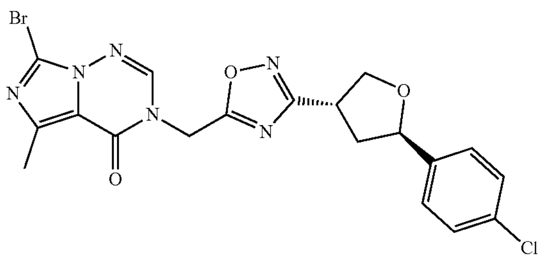 [SMILES: Cc1nc(Br)n2ncn(Cc3nc([C@@H]4CO[C@@H](c5ccc(Cl)cc5)C4)no3)c(=O)c12] | 7-bromo-5-methyl-3-[[3-[rac-(3R,5R)-5-(4-chlorophenyl)tetrahydrofuran-3-yl]-1,2,4-oxadiazol-5-yl]methyl]imidazo[5,1-f][1,2,4]triazin-4-one | 0.0008 | 0.0003 |
| 108 | 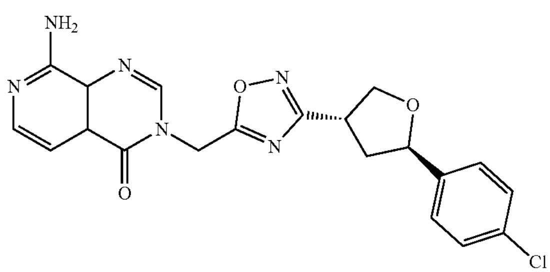 [SMILES: NC1=NC=CC2C(=O)N(Cc3nc([C@@H]4CO[C@@H](c5ccc(Cl)cc5)C4)no3)C=NC12] | 8-amino-3-[[3-[rac-(3R,5R)-5-(4-chlorophenyl)tetrahydrofuran-3-yl]-1,2,4-oxadiazol-5-yl]methyl]pyrido[3,4-d]pyrimidin-4-one | 0.0769 | 0.057 |
| 109 | 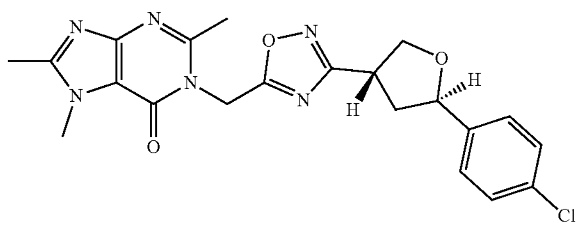 [SMILES: Cc1nc2nc(C)n(C)c2c(=O)n1Cc1nc([C@@H]2CO[C@@H](c3ccc(Cl)cc3)C2)no1] | 1-((3-((3R,5R)-5-(4-chlorophenyl)tetrahydrofuran-3-yl)-1,2,4-oxadiazol-5-yl)methyl)-2,7,8-trimethyl-1,7-dihydro-6H-purin-6-one | 0.085 | 0.062 |
| 110 | 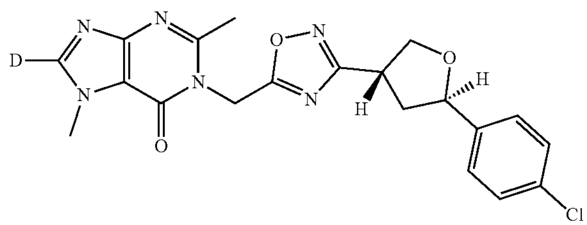 [SMILES: [2H]c1nc2nc(C)n(Cc3nc([C@@H]4CO[C@@H](c5ccc(Cl)cc5)C4)no3)c(=O)c2n1C] | 1-((3-((3R,5R)-5-(4-chlorophenyl)tetrahydrofuran-3-yl)-1,2,4-oxadiazol-5-yl)methyl)-2,7-dimethyl-1,7-dihydro-6H-purin-6-one-8-d | 0.00932 | 0.0039 |

-continued

| | Structure | Name | IC50 10 min | IC50 90 min |
|---|---|---|---|---|
| 111 | 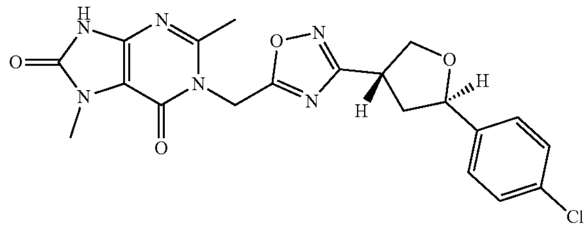 [SMILES: Cc1nc2[nH]c(=O)n(C)c2c(=O)n1Cc1nc([C@@H]2CO[C@@H](c3ccc(Cl)cc3)C2)no1] | 1-((3-((3R,5R)-5-(4-chlorophenyl)tetrahydro-furan-3-yl)-1,2,4-oxadiazol-5-yl)methyl)-2,7-dimethyl-7,9-dihydro-1H-purine-6,8-dione | 0.0858 | 0.034 |
| 112 | 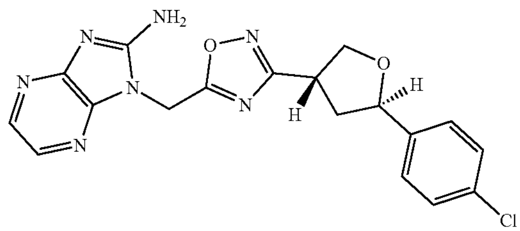 [SMILES: Nc1nc2nccnc2n1Cc1nc([C@@H]2CO[C@@H](c3ccc(Cl)cc3)C2)no1] | 1-((3-((3R,5R)-5-(4-chlorophenyl)tetrahydro-furan-3-yl)-1,2,4-oxadiazol-5-yl)methyl)-1H-imidazo[4,5-b]pyrazin-2-amine | 0.0108 | 0.0038 |
| 113 | 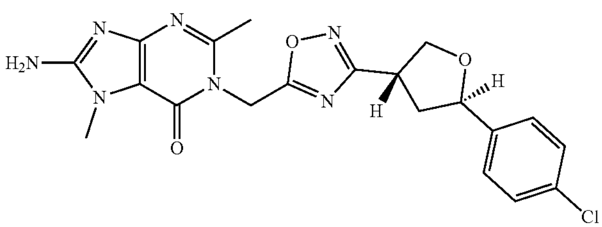 [SMILES: Cc1nc2nc(N)n(C)c2c(=O)n1Cc1nc([C@@H]2CO[C@@H](c3ccc(Cl)cc3)C2)no1] | 8-amino-2,7-dimethyl-1-[[3-[rac-(3R,5R)-5-(4-chlorophenyl)tetrahydro-furan-3-yl]-1,2,4-oxadiazol-5-yl]methyl]purin-6-one | 0.123 | 0.014 |
| 114 | 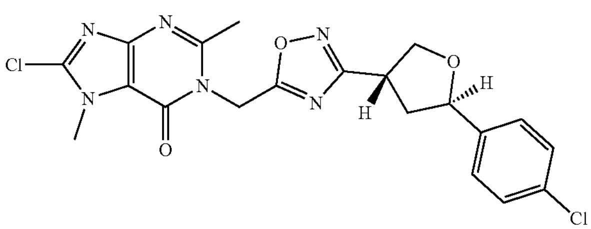 [SMILES: Cc1nc2nc(Cl)n(C)c2c(=O)n1Cc1nc([C@@H]2CO[C@@H](c3ccc(Cl)cc3)C2)no1] | 8-chloro-1-((3-((3R,5R)-5-(4-chlorophenyl)tetrahydrofuran-3-yl)-1,2,4-oxadiazol-5-yl)methyl)-2,7-dimethyl-1,7-dihydro-6H-purin-6-one | 0.0378 | 0.022 |
| 115 | 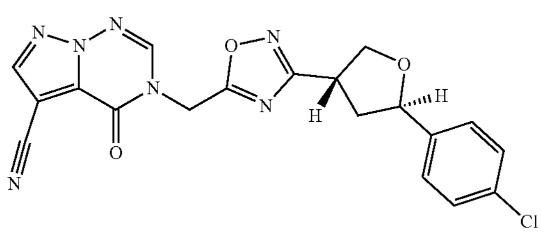 [SMILES: N#Cc1cnn2ncn(Cc3nc([C@@H]4CO[C@@H](c5ccc(Cl)cc5)C4)no3)c(=O)c12] | 3-((3-((3R,5R)-5-(4-chlorophenyl)tetrahydro-furan-3-yl)-1,2,4-oxadiazol-5-yl)methyl)-4-oxo-3,4-dihydro-pyrazolo[5,1-f][1,2,4]triazine-5-carbonitrile | 0.0949 | 0.04 |
| 116 | 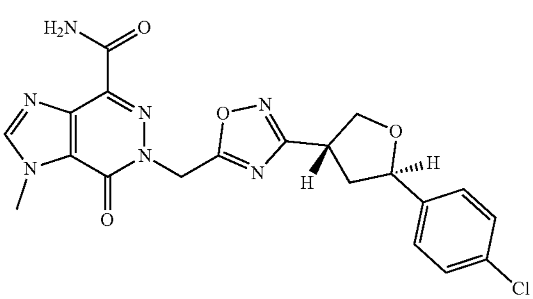 [SMILES: Cn1cnc2c(C(N)=O)nn(Cc3nc([C@@H]4CO[C@@H](c5ccc(Cl)cc5)C4)no3)c(=O)c21] | 6-((3-((3R,5R)-5-(4-chlorophenyl)tetrahydro-furan-3-yl)-1,2,4-oxadiazol-5-yl)methyl)-1-methyl-7-oxo-6,7-dihydro-1H-imidazo[4,5-d]pyridazine-4-carboxamide | 0.0765 | 0.039 |

-continued

| | Structure | Name | IC50 10 min | IC50 90 min |
|---|---|---|---|---|
| 117 | 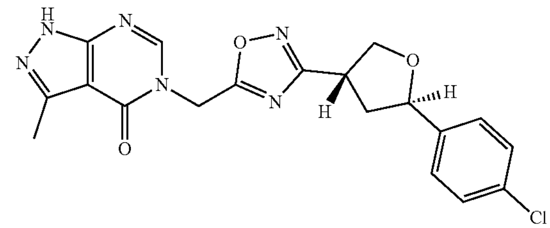 [SMILES: Cc1n[nH]c2ncn(Cc3nc([C@@H]4CO[C@@H](c5ccc(Cl)cc5)C4)no3)c(=O)c12] | 5-((3-((3R,5R)-5-(4-chlorophenyl)tetrahydro-furan-3-yl)-1,2,4-oxadiazol-5-yl)methyl)-3-methyl-1,5-dihydro-4H-pyrazolo[3,4-d]pyrimidin-4-one | 0.0113 | 0.0059 |
| 118 | 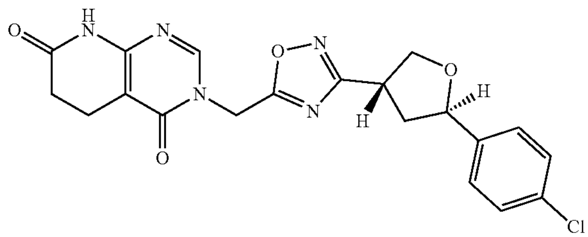 [SMILES: O=C1CCc2c(ncn(Cc3nc([C@@H]4CO[C@@H](c5ccc(Cl)cc5)C4)no3)c2=O)N1] | 3-((3-((3R,5R)-5-(4-chlorophenyl)tetrahydro-furan-3-yl)-1,2,4-oxadiazol-5-yl)methyl)-5,8-dihydropyrido[2,3-d]pyrimidine-4,7(3H,6H)-dione | 0.0964 | 0.047 |
| 119 | 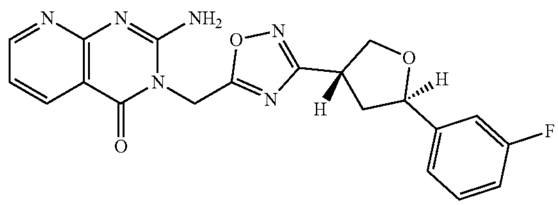 [SMILES: Nc1nc2ncccc2c(=O)n1Cc1nc([C@@H]2CO[C@@H](c3cccc(F)c3)C2)no1] | 2-amino-3-((3-((3R,5R)-5-(3-fluorophenyl)tetrahydro-furan-3-yl)-1,2,4-oxadiazol-5-yl)methyl)pyrido[2,3-d]pyrimidin-4(3H)-one | 0.0319 | 0.013 |
| 120 | 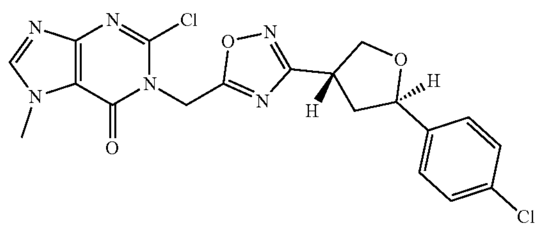 | 2-chloro-1-((3-((3R,5R)-5-(4-chlorophenyl)tetrahydro-furan-3-yl)-1,2,4-oxadiazol-5-yl)methyl)-7-methyl-1,7-dihydro-6H-purin-6-one | 0.0294 | 0.02 |
| 121 | 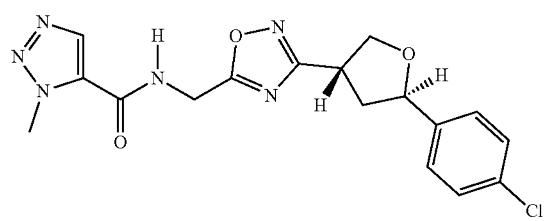 [SMILES: Cn1nncc1C(=O)NCc1nc([C@@H]2CO[C@@H](c3ccc(Cl)cc3)C2)no1] | N-((3-((3R,5R)-5-(4-chlorophenyl)tetrahydro-furan-3-yl)-1,2,4-oxadiazol-5-yl)methyl)-1-methyl-1H-1,2,3-triazole-5-carboxamide | 0.111 | 0.049 |
| 122 | 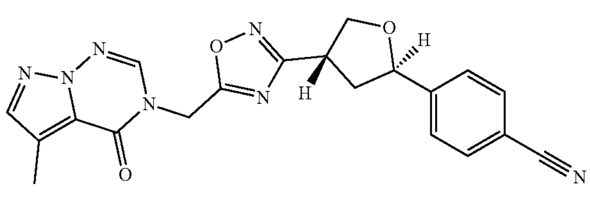 [SMILES: Cc1cnn2ncn(Cc3nc([C@@H]4CO[C@@H](c5ccc(C#N)cc5)C4)no3)c(=O)c12] | 4-((2R,4R)-4-(5-((5-methyl-4-oxopyrazolo[5,1-f][1,2,4]triazin-3(4H)-yl)methyl)-1,2,4-oxadiazol-3-yl)tetrahydrofuran-2-yl)benzonitrile | 0.0758 | 0.039 |
| 123 | 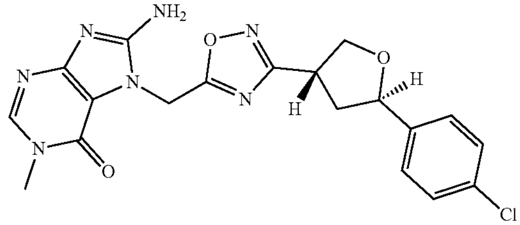 [SMILES: Cn1cnc2nc(N)n(Cc3nc([C@@H]4CO[C@@H](c5ccc(Cl)cc5)C4)no3)c2c1=O] | 8-amino-7-((3-((3R,5R)-5-(4-chlorophenyl)tetrahydro-furan-3-yl)-1,2,4-oxadiazol-5-yl)methyl)-1-methyl-1,7-dihydro-6H-purin-6-one | 0.126 | 0.017 |

-continued

| | Structure | Name | IC50 10 min | IC50 90 min |
|---|---|---|---|---|
| 124 | 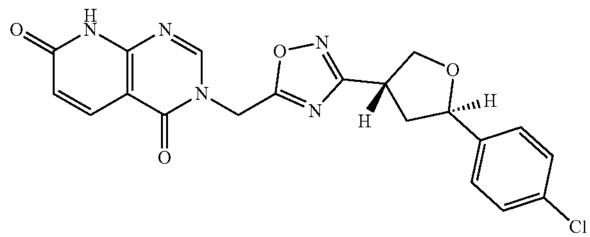 [SMILES: O=c1ccc2c(=O)n(Cc3nc([C@@H]4CO[C@@H](c5ccc(Cl)cc5)C4)no3)cnc2[nH]1] | 3-((3-((3R,5R)-5-(4-chlorophenyl)tetrahydro-furan-3-yl)-1,2,4-oxadiazol-5-yl)methyl)pyrido[2,3-d]pyrimidine-4,7(3H,8H)-dione | 0.0127 | 0.016 |
| 125 | 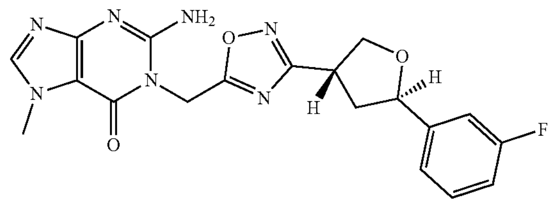 [SMILES: Cn1cnc2nc(N)n(Cc3nc([C@@H]4CO[C@@H](c5cccc(F)c5)C4)no3)c(=O)c21] | 2-amino-1-((3-((3R,5R)-5-(3-fluorophenyl)tetrahydrofuran-3-yl)-1,2,4-oxadiazol-5-yl)methyl)-7-methyl-1,7-dihydro-6H-purin-6-one | 0.0405 | 0.0031 |
| 126 | 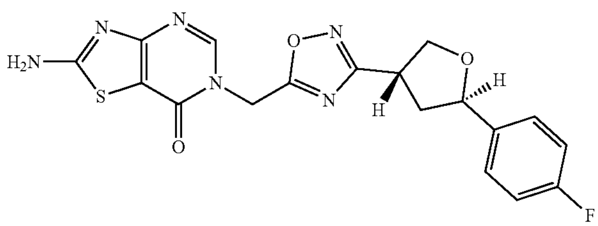 [SMILES: Nc1nc2ncn(Cc3nc([C@@H]4CO[C@@H](c5ccc(F)cc5)C4)no3)c(=O)c2s1] | 2-amino-6-((3-((3R,5R)-5-(4-fluorophenyl)tetrahydrofuran-3-yl)-1,2,4-oxadiazol-5-yl)methyl)thiazolo[4,5-d]pyrimidin-7(6H)-one | 0.0899 | 0.036 |
| 127 | 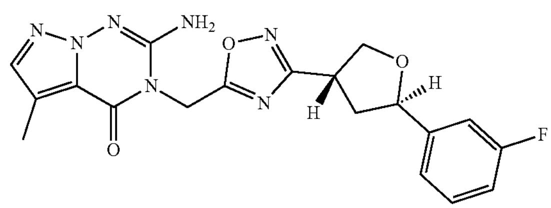 [SMILES: Cc1cnn2nc(N)n(Cc3nc([C@@H]4CO[C@@H](c5cccc(F)c5)C4)no3)c(=O)c12] | 2-amino-3-((3-((3R,5R)-5-(3-fluorophenyl)tetrahydro-3-yl)-1,2,4-oxadiazol-5-yl)methyl)-5-methylpyrazolo[5,1-f][1,2,4]triazin-4(3H)-one | 0.0179 | 0.0029 |
| 128 | 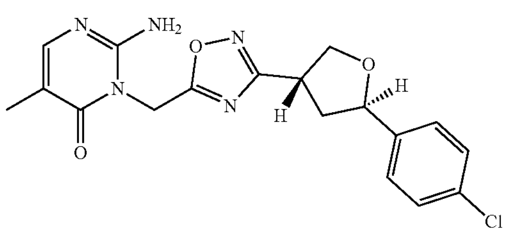 [SMILES: Cc1cnc(N)n(Cc2nc([C@@H]3CO[C@@H](c4ccc(Cl)cc4)C3)no2)c1=O] | 2-amino-3-((3-((3R,5R)-5-(4-chlorophenyl)tetra-hydrofuran-3-yl)-1,2,4-oxadiazol-5-yl)methyl)-5-methylpyrimidin-4(3H)-one | 0.146 | 0.067 |
| 129 | 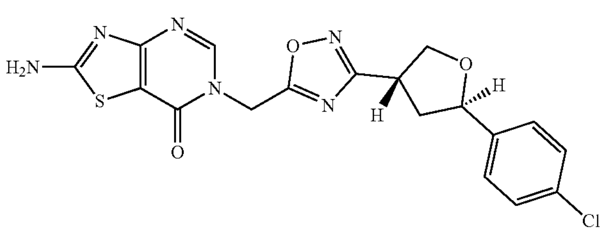 [SMILES: Nc1nc2ncn(Cc3nc([C@@H]4CO[C@@H](c5ccc(Cl)cc5)C4)no3)c(=O)c2s1] | 2-amino-6-((3-((3R,5R)-5-(4-chlorophenyl)tetrahydrofuran-3-yl)-1,2,4-oxadiazol-5-yl)methyl)thiazolo[4,5-d]pyrimidin-7(6H)-one | 0.0151 | 0.0056 |
| 130 | 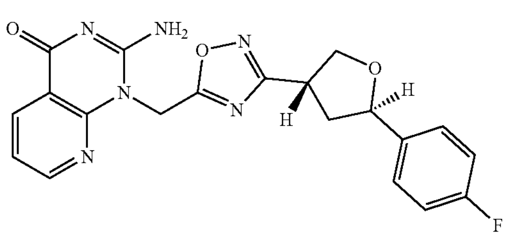 [SMILES: Nc1nc(=O)c2cccnc2n1Cc1nc([C@@H]2CO[C@@H](c3ccc(F)cc3)C2)no1] | 2-amino-1-((3-((3R,5R)-5-(4-fluorophenyl)tetra-hydrofuran-3-yl)-1,2,4-oxadiazol-5-yl)methyl)pyrido[2,3-d]pyrimidin-4(1H)-one | 0.0833 | 0.015 |

| | Structure | Name | IC50 10 min | IC50 90 min |
|---|---|---|---|---|
| 131 | 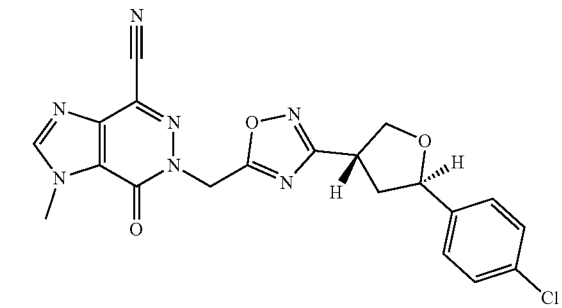 [SMILES: Cn1cnc2c(C#N)nn(Cc3nc([C@@H]4CO[C@@H](c5ccc(Cl)cc5)C4)no3)c(=O)c21] | 6-((3-((3R,5R)-5-(4-chlorophenyl)tetrahydro-furan-3-yl)-1,2,4-oxadiazol-5-yl)methyl)-1-methyl-7-oxo-6,7-dihydro-1H-imidazo[4,5-d]pyridazine-4-carbonitrile | 0.00742 | 0.0031 |
| 132 | 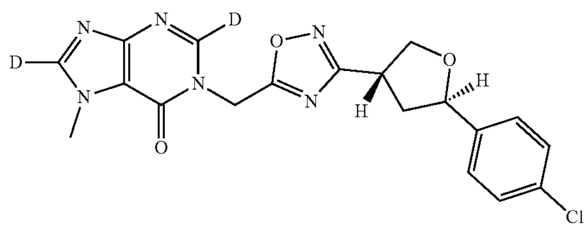 [SMILES: [2H]c1nc2nc([2H])n(C)c2c(=O)n1Cc1nc([C@@H]2CO[C@@H](c3ccc(Cl)cc3)C2)no1] | 1-((3-((3R,5R)-5-(4-chlorophenyl)tetrahydro-furan-3-yl)-1,2,4-oxadiazol-5-yl)methyl)-7-methyl-1,7-dihydro-6H-purin-6-one-2,8-d2 | 0.00743 | 0.0022 |
| 133 | 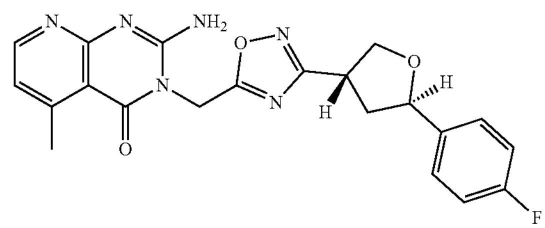 [SMILES: Cc1ccnc2nc(N)n(Cc3nc([C@@H]4CO[C@@H](c5ccc(F)cc5)C4)no3)c(=O)c12] | 2-amino-3-((3-((3R,5R)-5-(4-fluorophenyl)tetra-hydrofuran-3-yl)-1,2,4-oxadiazol-5-yl)methyl)-5-methylpyrido[2,3-d]pyrimidin-4(3H)-one | 0.0134 | 0.0014 |
| 134 | 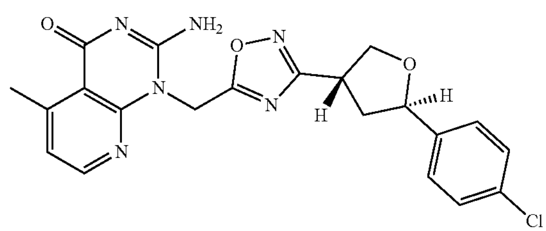 [SMILES: Cc1ccnc2c1c(=O)nc(N)n2Cc1nc([C@@H]2CO[C@@H](c3ccc(Cl)cc3)C2)no1] | 2-amino-1-((3-((3R,5R)-5-(4-chlorophenyl)tetrahydro-furan-3-yl)-1,2,4-oxadiazol-5-yl)methyl)-5-methylpyrido[2,3-d]pyrimidin-4(1H)-one | 0.02 | 0.006 |
| 135 | 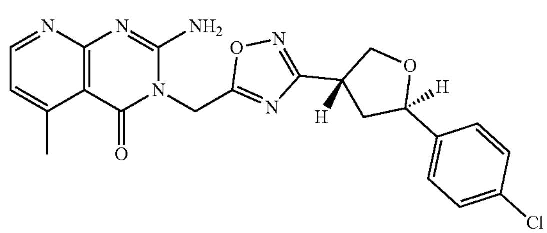 [SMILES: Cc1ccnc2nc(N)n(Cc3nc([C@@H]4CO[C@@H](c5ccc(Cl)cc5)C4)no3)c(=O)c12] | 2-amino-3-((3-((3R,5R)-5-(4-chlorophenyl)tetrahydro-furan-3-yl)-1,2,4-oxadiazol-5-yl)methyl)-5-methylpyrido[2,3-d]pyrimidin-4(3H)-one | 0.0104 | 0.0015 |
| 136 | 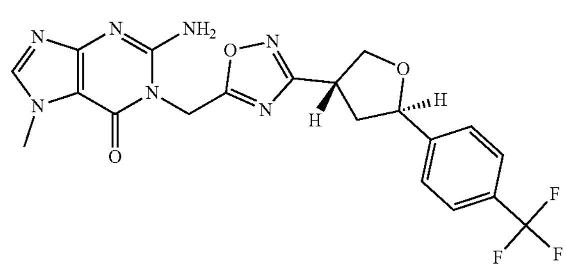 [SMILES: Cn1cnc2nc(N)n(Cc3nc([C@@H]4CO[C@@H](c5ccc(C(F)(F)F)cc5)C4)no3)c(=O)c21] | 2-amino-7-methyl-1-((3-((3R,5R)-5-(4-(trifluoromethyl)phenyl)tetrahydrofuran-3-yl)-1,2,4-oxadiazol-5-yl)methyl)-1,7-dihydro-6H-purin-6-one | 0.0973 | 0.011 |

-continued

| | Structure | Name | IC50 10 min | IC50 90 min |
|---|---|---|---|---|
| 137 | 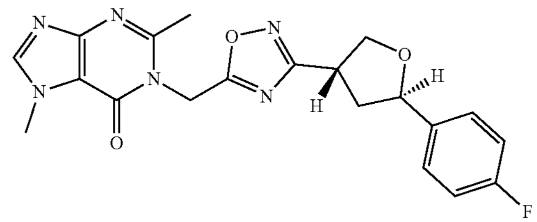 [SMILES: Cc1nc2ncn(C)c2c(=O)n1Cc1nc([C@@H]2CO[C@@H](c3ccc(F)cc3)C2)no1] | 1-((3-((3R,5R)-5-(4-fluorophenyl)tetrahydro-furan-3-yl)-1,2,4-oxadiazol-5-yl)methyl)-2,7-dimethyl-1,7-dihydro-6H-purin-6-one | 0.0641 | 0.013 |
| 138 | 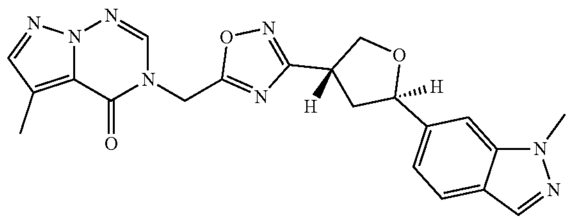 [SMILES: Cc1cnn2ncn(Cc3nc([C@@H]4CO[C@@H](c5ccc6cnn(C)c6c5)C4)no3)c(=O)c12] | 5-methyl-3-((3-((3R,5R)-5-(1-methyl-1H-indazol-6-yl)tetrahydrofuran-3-yl)-1,2,4-oxadiazol-5-yl)methyl)pyrazolo[5,1-f][1,2,4]triazin-4(3H)-one | 0.00826 | 0.0023 |
| 139 | 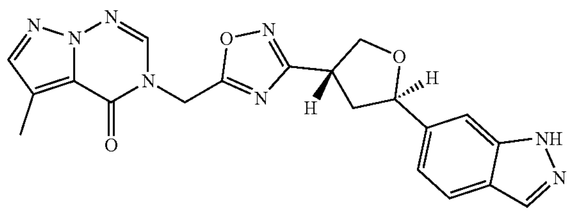 [SMILES: Cc1cnn2ncn(Cc3nc([C@@H]4CO[C@@H](c5ccc6cn[nH]c6c5)C4)no3)c(=O)c12] | 3-((3-((3R,5R)-5-(1H-indazol-6-yl)tetrahydrofuran-3-yl)-1,2,4-oxadiazol-5-yl)methyl)-5-methylpyrazolo[5,1-f][1,2,4]triazin-4(3H)-one | 0.0195 | 0.0075 |
| 140 | 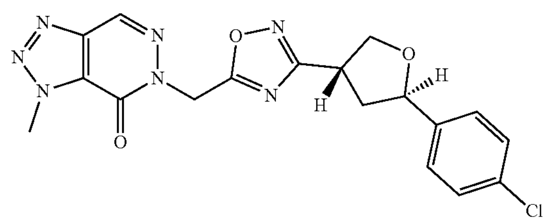 [SMILES: Cn1nnc2cnn(Cc3nc([C@@H]4CO[C@@H](c5ccc(Cl)cc5)C4)no3)c(=O)c21] | 5-((3-((3R,5R)-5-(4-chlorophenyl)tetrahydro-furan-3-yl)-1,2,4-oxadiazol-5-yl)methyl)-3-methyl-3,5-dihydro-4H-[1,2,3]triazolo[4,5-d]pyridazin-4-one | 0.0801 | 0.043 |
| 141 | 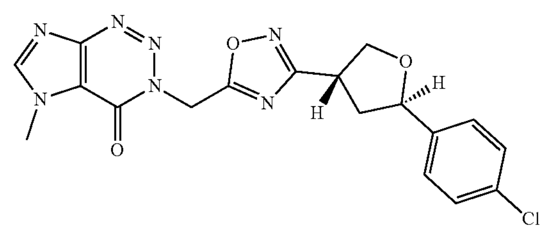 [SMILES: Cn1cnc2nnn(Cc3nc([C@@H]4CO[C@@H](c5ccc(Cl)cc5)C4)no3)c(=O)c21] | 3-((3-((3R,5R)-5-(4-chlorophenyl)tetrahydro-furan-3-yl)-1,2,4-oxadiazol-5-yl)methyl)-5-methyl-3,5-dihydro-4H-imidazo[4,5-d][1,2,3]triazin-4-one | 0.0309 | 0.011 |
| 142 | 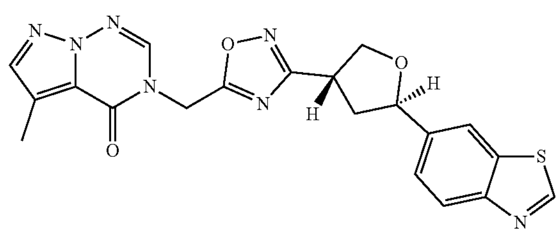 [SMILES: Cc1cnn2ncn(Cc3nc([C@@H]4CO[C@@H](c5ccc6ncsc6c5)C4)no3)c(=O)c12] | 3-((3-((3R,5R)-5-(benzo[d]thiazol-6-yl)tetrahydrofuran-3-yl)-1,2,4-oxadiazol-5-yl)methyl)-5-methylpyrazolo[5,1-f][1,2,4]triazin-4(3H)-one | 0.0817 | 0.04 |
| 143 | 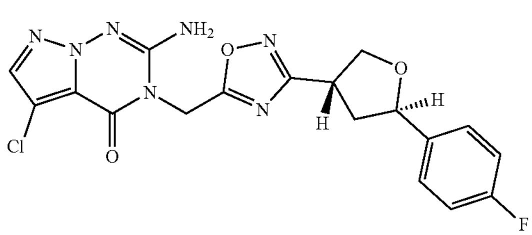 [SMILES: Nc1nn2ncc(Cl)c2c(=O)n1Cc1nc([C@@H]2CO[C@@H](c3ccc(F)cc3)C2)no1] | 2-amino-5-chloro-3-((3-((3R,5R)-5-(4-fluorophenyl)tetrahydro-furan-3-yl)-1,2,4-oxadiazol-5-yl)methyl)pyrazolo[5,1-f][1,2,4]triazin-4(3H)-one | 0.0569 | 0.0066 |

| | Structure | Name | IC50 10 min | IC50 90 min |
|---|---|---|---|---|
| 144 | 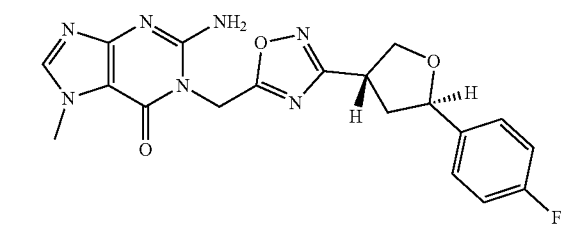 [SMILES: Cn1cnc2nc(N)n(Cc3nc([C@@H]4CO[C@@H](c5ccc(F)cc5)C4)no3)c(=O)c21] | 2-amino-1-((3-((3R,5R)-5-(4-fluorophenyl)tetrahydrofuran-3-yl)-1,2,4-oxadiazol-5-yl)methyl)-7-methyl-1,7-dihydro-6H-purin-6-one | 0.0569 | 0.0066 |
| 145 | 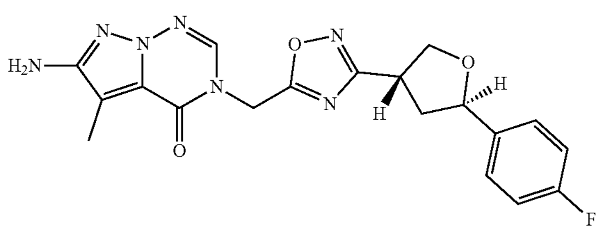 [SMILES: Cc1c(N)nn2ncn(Cc3nc([C@@H]4CO[C@@H](c5ccc(F)cc5)C4)no3)c(=O)c12] | 6-amino-3-((3-((3R,5R)-5-(4-fluorophenyl)tetrahydrofuran-3-yl)-1,2,4-oxadiazol-5-yl)methyl)-5-methylpyrazolo[5,1-f][1,2,4]triazin-4(3H)-one | 0.00928 | 0.046 |
| 146 | 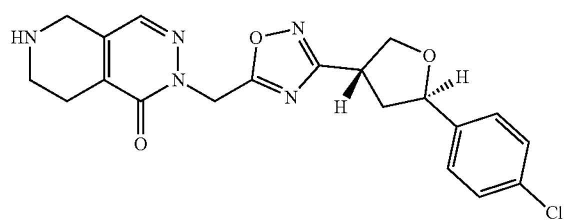 [SMILES: O=c1c2c(cnn1Cc1nc([C@@H]3CO[C@@H](c4ccc(Cl)cc4)C3)no1)CNCC2] | 2-((3-((3R,5R)-5-(4-chlorophenyl)tetrahydrofuran-3-yl)-1,2,4-oxadiazol-5-yl)methyl)-5,6,7,8-tetrahydropyrido[3,4-d]pyridazin-1(2H)-one hydrochloride | 2.6 | 0.097 |
| 147 | 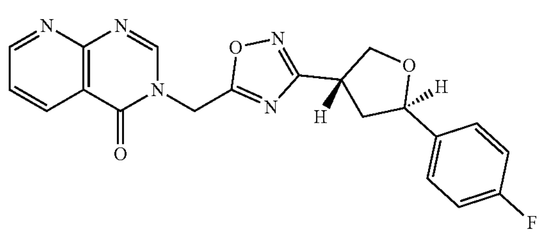 [SMILES: O=c1c2cccnc2ncn1Cc1nc([C@@H]2CO[C@@H](c3ccc(F)cc3)C2)no1] | 3-((3-((3R,5R)-5-(4-fluorophenyl)tetrahydrofuran-3-yl)-1,2,4-oxadiazol-5-yl)methyl)pyrido[2,3-d]pyrimidin-4(3H)-one | 0.107 | 0.082 |
| 148 | 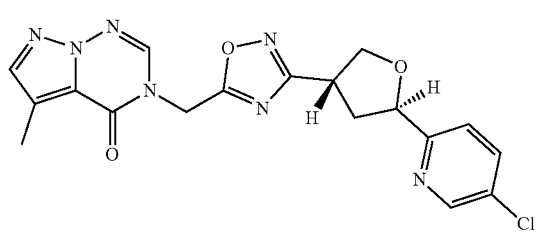 [SMILES: Cc1cnn2ncn(Cc3nc([C@@H]4CO[C@@H](c5ccc(Cl)cn5)C4)no3)c(=O)c12] | 3-((3-((3R,5R)-5-(5-chloropyridin-2-yl)tetrahydrofuran-3-yl)-1,2,4-oxadiazol-5-yl)methyl)-5-methylpyrazolo[5,1-f][1,2,4]triazin-4(3H)-one | 0.0213 | 0.014 |
| 149 | 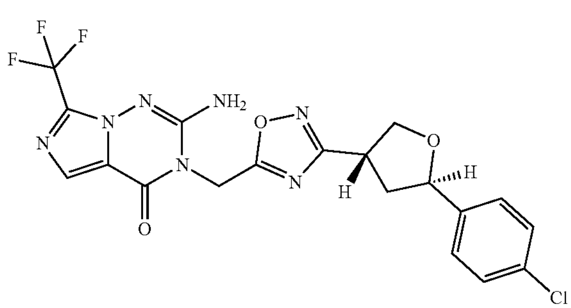 [SMILES: Nc1nn2c(C(F)(F)F)ncc2c(=O)n1Cc1nc([C@@H]2CO[C@@H](c3ccc(Cl)cc3)C2)no1] | 2-amino-3-((3-((3R,5R)-5-(4-chlorophenyl)tetrahydrofuran-3-yl)-1,2,4-oxadiazol-5-yl)methyl)-7-(trifluoromethyl)imidazo[5,1-f][1,2,4]triazin-4(3H)-one | 0.00448 | 0.0021 |

-continued

| | Structure | Name | IC50 10 min | IC50 90 min |
|---|---|---|---|---|
| 150 | 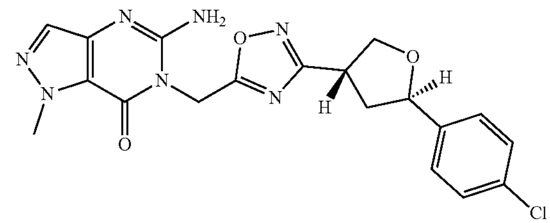 [SMILES: Cn1ncc2nc(N)n(Cc3nc([C@@H]4CO[C@@H](c5ccc(Cl)cc5)C4)no3)c(=O)c21] | 5-amino-6-((3-((3R,5R)-5-(4-chlorophenyl)tetrahydro-furan-3-yl)-1,2,4-oxadiazol-5-yl)methyl)-1-methyl-1,6-dihydro-7H-pyrazolo[4,3-d]pyrimidin-7-one | 0.00319 | 0.0017 |
| 151 | 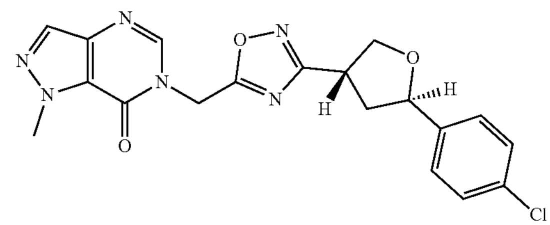 [SMILES: Cn1ncc2ncn(Cc3nc([C@@H]4CO[C@@H](c5ccc(Cl)cc5)C4)no3)c(=O)c21] | 6-((3-((3R,5R)-5-(4-chlorophenyl)tetrahydro-furan-3-yl)-1,2,4-oxadiazol-5-yl)methyl)-1-methyl-1,6-dihydro-7H-pyrazolo[4,3-d]pyrimidin-7-one | 0.047 | 0.032 |
| 152 | 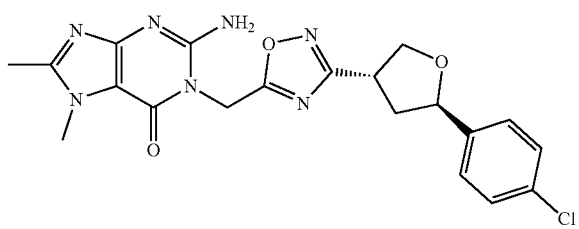 [SMILES: Cc1nc2nc(N)n(Cc3nc([C@@H]4CO[C@@H](c5ccc(Cl)cc5)C4)no3)c(=O)c2n1C] | 2-amino-7,8-dimethyl-1-[[3-[rac-(3R,5R)-5-(4-chlorophenyl)tetrahydro-furan-3-yl]-1,2,4-oxadiazol-5-yl]methyl]purin-6-one | 0.0431 | 0.0062 |
| 153 | 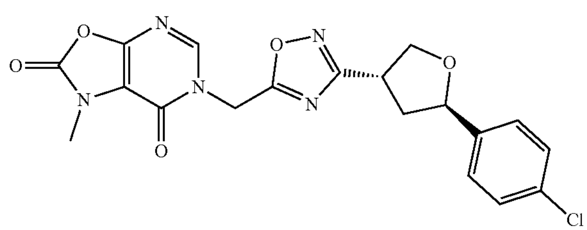 [SMILES: Cn1c(=O)oc2ncn(Cc3nc([C@@H]4CO[C@@H](c5ccc(Cl)cc5)C4)no3)c(=O)c21] | 1-methyl-6-[[3-[rac-(3R,5R)-5-(4-chlorophenyl)tetrahydro-furan-3-yl]-1,2,4-oxadiazol-5-yl]methyl]oxazolo[5,4-d]pyrimidine-2,7-dione | 0.00635 | 0.0018 |
| 154 | 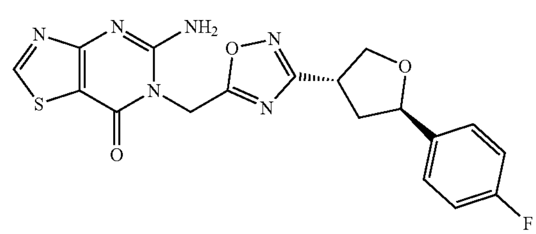 [SMILES: Nc1nc2ncsc2c(=O)n1Cc1nc([C@@H]2CO[C@@H](c3ccc(F)cc3)C2)no1] | 5-amino-6-[[3-[rac-(3R,5R)-5-(4-fluorophenyl)tetrahydro-furan-3-yl]-1,2,4-oxadiazol-5-yl]methyl]thiazolo[4,5-d]pyrimidin-7-one | | 0.0023 |
| 155 | 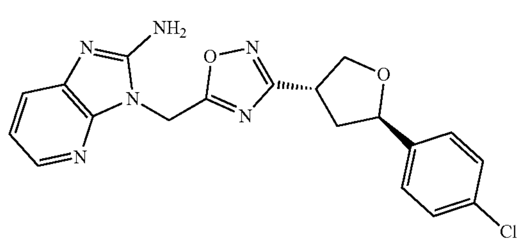 [SMILES: Nc1nc2cccnc2n1Cc1nc([C@@H]2CO[C@@H](c3ccc(Cl)cc3)C2)no1] | 3-[[3-[(3R,5R)-5-(4-chlorophenyl)tetrahydro-furan-3-yl]-1,2,4-oxadiazol-5-yl]methyl]imidazo[4,5-b]pyridin-2-amine | 0.0103 | 0.0075 |

| | Structure | Name | IC50 10 min | IC50 90 min |
|---|---|---|---|---|
| 156 | 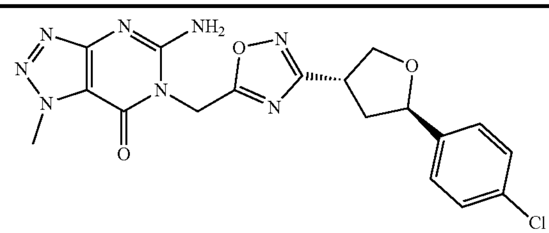 | 5-amino-1-methyl-6-[[3-[rac-(3R,5R)-5-(4-chlorophenyl)tetrahydrofuran-3-yl]-1,2,4-oxadiazol-5-yl]methyl]triazolo[4,5-d]pyrimidin-7-one | 0.0161 | 0.0021 |
| 157 | 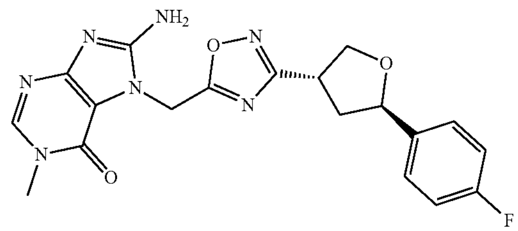 [SMILES: Cn1cnc2nc(N)n(Cc3nc([C@@H]4CO[C@@H](c5ccc(F)cc5)C4)no3)c2c1=O] | 8-amino-1-methyl-7-[[3-[rac-(3R,5R)-5-(4-fluorophenyl)tetrahydrofuran-3-yl]-1,2,4-oxadiazol-5-yl]methyl]purin-6-one | 0.470 | 0.087 |
| 158 | 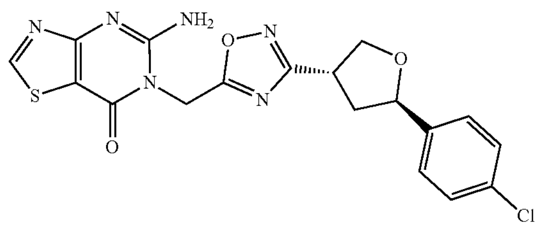 [SMILES: Nc1nc2ncsc2c(=O)n1Cc1nc([C@@H]2CO[C@@H](c3ccc(Cl)cc3)C2)no1] | 5-amino-6-[[3-[rac-(3R,5R)-5-(4-chlorophenyl)tetrahydrofuran-3-yl]-1,2,4-oxadiazol-5-yl]methyl]thiazolo[4,5-d]pyrimidin-7-one | 0.00573 | 0.0014 |

Table 2 below provides proton NMR data for the compounds of Table 1.

TABLE 2

1  $^1$H NMR (500 MHz, DMSO-d6) δ 8.46 (s, 1H), 8.24 (s, 1H), 7.42-7.36 (m, 4H), 5.57 (s, 2H), 5.01 (t, J = 7.3 Hz, 1H), 4.35 (dd, J = 8.6, 7.4 Hz, 1H), 3.96 (s, 3H), 3.90 (dd, J = 8.6, 6.3 Hz, 1H), 3.80-3.71 (m, 1H), 2.60-2.54 (m, 1H), 2.17-2.10 (m, 1H).

2  $^1$H NMR (400 MHz, DMSO-d6) δ 8.44 (s, 1H), 8.21 (d, J = 10.8 Hz, 1H), 7.38 (dd, J = 8.5, 5.7 Hz, 2H), 7.19-7.09 (m, 2H), 5.56 (s, 2H), 4.97 (t, J = 7.4 Hz, 1H), 4.39-4.28 (m, 1H), 3.93 (s, 3H), 3.87 (dd, J = 8.5, 6.3 Hz, 1H), 3.74 (dt, J = 13.9, 6.9 Hz, 1H), 2.58-2.50 (m, 1H), 2.18-2.07 (m, 1H).

3  1H NMR (400 MHz, dmso) 7.44-7.35 (m, 3H), 7.21-7.11 (m, 2H), 6.88 (s, 2H), 5.48 (s, 2H), 5.00 (t, J = 7.4 Hz, 1H), 4.36 (dd, J = 8.5, 7.4 Hz, 1H), 3.89 (dd, J = 8.5, 6.3 Hz, 1H), 3.77 (dt, J = 13.9, 6.9 Hz, 1H), 2.56 (ddd, J = 12.4, 7.0, 5.1 Hz, 1H), 2.29 (d, J = 0.4 Hz, 3H), 2.15 (ddd, J = 12.7, 8.9, 7.8 Hz, 1H)

4  1H NMR (400 MHz, dmso) 7.44-7.35 (m, 5H), 6.87 (s, 2H), 5.48 (s, 2H), 5.01 (t, J = 7.5 Hz, 1H), 4.36 (dd, J = 8.5, 7.4 Hz, 1H), 3.90 (dd, J = 8.6, 6.3 Hz, 1H), 3.77 (dd, J = 14.9, 6.3 Hz, 1H), 2.57 (ddd, J = 7.3, 6.2, 3.3 Hz, 1H), 2.29 (s, 3H), 2.20-2.08 (m, 1H)

5  1H NMR (400 MHz, DMSO-d$_6$) δ 8.22 (s, 1H), 7.42-7.28 (m, 4H), 5.55 (s, 2H), 4.99 (t, J = 7.4 Hz, 1H), 4.33 (dd, J = 8.5, 7.4 Hz, 1H), 3.93 (s, 3H), 3.88 (dd, J = 8.6, 6.3 Hz, 1H), 3.80-3.70 (m, 1H), 2.61-2.52 (m, 1H), 2.19-2.08 (m, 1H).

6  $^1$H NMR (400 MHz, DMSO-d$_6$) δ 8.44 (s, 1H), 7.47-7.28 (m, 4H), 5.56 (s, 2H), 4.99 (t, J = 7.3 Hz, 1H), 4.33 (t, J = 7.9 Hz, 1H), 3.93 (s, 3H), 3.88 (dd, J = 8.5, 6.3 Hz, 1H), 3.79-3.70 (m, 1H), 2.61-2.51 (m, 1H), 2.19-2.08 (m, 1H).

7  $^1$H NMR (400 MHz, DMSO-d$_6$) δ 12.21 (s, 1H), 8.03 (s, 1H), 7.40 (d, J = 1.3 Hz, 4H), 5.31 (s, 2H), 5.02 (t, J = 7.3 Hz, 1H), 4.36 (dd, J = 8.6, 7.4 Hz, 1H), 3.91 (dd, J = 8.6, 6.3 Hz, 1H), 3.87 (s, 3H), 3.77-3.73 (m, 1H), 2.1-2.56 (m, 1H), 2.20-2.06 (m, 1H).

8  1H NMR (400 MHz, DMSO-d6) 8.18 (d, J = 0.6 Hz, 1H), 7.47-7.28 (m, 4H), 5.63 (s, 2H), 5.00 (t, J = 7.4 Hz, 1H), 4.35 (dd, J = 8.5, 7.4 Hz, 1H), 3.93 (d, J = 0.4 Hz, 3H), 3.91 (dd, J = 8.6, 6.3 Hz, 1H), 3.79-3.70 (m, 1H), 2.60 (s, 3H), 2.62-2.54 (m, 1H), 2.13 (ddd, J = 12.7, 8.9, 7.7 Hz, 1H).

9  $^1$H NMR (400 MHz, DMSO-d$_6$) δ 11.88 (s, 1H), 8.41 (s, 1H), 7.39 (d, J = 2.1 Hz, 4H), 5.53 (s, 2H), 5.01 (t, J = 7.3 Hz, 1H), 4.36 (t, J = 8.0 Hz, 1H), 3.90 (dd, J = 8.5, 6.2 Hz, 1H), 3.81-3.75 (m, 1H), 2.61-2.56 (m, 1H), 2.20-2.06 (m, 1H)

10  $^1$H NMR (400 MHz, DMSO-d$_6$) δ 8.46 (s, 1H), 8.24 (s, 1H), 7.39-7.36 (m, 1H), 7.20-7.16 (m, 2H), 7.10 (t, J = 8.6 Hz, 1H), 5.58 (s, 2H), 5.04 (t, J = 7.3 Hz, 1H), 4.41-4.34 (m, 1H), 3.95 (s, 3H), 3.93-3.89 (m, 1H), 3.89-3.73 (m, 1H), 2.67-2.56 (m, 1H), 2.21-2.13 (m, 1H).

11  $^1$H NMR (500 MHz, DMSO-d6) δ 9.21 (dd, J = 4.6, 1.7 Hz, 1H), 8.66 (ddd, J = 8.1, 1.7, 0.7 Hz, 1H), 8.62 (d, J = 0.7 Hz, 1H), 7.93 (dd, J = 8.1, 4.6 Hz, 1H), 7.43-7.37 (m, 2H), 7.20-7.13 (m, TABLE 2-continued

| | |
|---|---|
| | 2H), 5.73 (s, 2H), 5.00 (t, J = 7.4 Hz, 1H), 4.36 (dd, J = 8.5, 7.5 Hz, 1H), 3.90 (dd, J = 8.6, 6.3 Hz, 1H), 3.81-3.74 (m, 1H), 2.56 (ddd, J = 14.0, 9.5, 6.0 Hz, 1H), 2.16 (ddd, J = 12.7, 9.0, 7.9 Hz, 1H). |
| 12 | $^1$H NMR (500 MHz, DMSO-d6) δ 8.60 (s, 1H), 7.42-7.38 (m, 2H), 7.19-7.14 (m, 2H), 5.63 (s, 2H), 5.00 (t, J = 7.4 Hz, 1H), 4.37 (s, 2H), 4.36 (dd, J = 8.5, 7.4 Hz, 2H), 3.90 (dd, J = 8.6, 6.3 Hz, 1H), 3.82-3.73 (m, 1H), 2.56 (ddd, J = 11.7, 8.4, 4.9 Hz, 1H), 2.16 (ddd, J = 12.7, 8.9, 7.8 Hz, 1H). |
| 13 | $^1$H NMR (400 MHz, DMSO-$d_6$) δ 8.46 (s, 1H), 8.24 (s, 1H), 7.39-7.30 (m, 4H), 7.33-7.23 (m, 1H), 5.58 (s, 2H), 5.00 (t, J = 7.4 Hz, 1H), 4.36-4.34 (m, 1H), 3.96 (s, 3H), 3.92-3.88 (m, 1H), 3.82-3.70 (m, 1H), 2.60-2.54 (m, 1H), 2.20-2.13 (m, 1H). |
| 14 | $^1$H NMR (400 MHz, DMSO-$d_6$) δ 8.46 (s, 1H), 8.24 (s, 1H), 7.56 (dd, J = 7.6, 1.6 Hz, 1H), 7.43 (dd, J = 7.7, 1.3 Hz, 1H), 7.40-7.26 (m, 2H), 5.59 (s, 2H), 5.27 (t, J = 7.3 Hz, 1H), 4.52-4.36 (m, 1H), 4.04-3.88 (m, 4H), 3.76-3.71 (m, 1H), 2.74-2.68 (m, 1H), 2.12-1.98 (m, 1H). |
| 15 | $^1$H NMR (400 MHz, DMSO-$d_6$) δ 8.46 (s, 1H), 8.24 (s, 1H), 7.51-7.47 (m, 1H), 7.35-7.31 (m, 1H), 7.22-7.15 (m, 2H), 5.58 (s, 2H), 5.22 (t, J = 7.4 Hz, 1H), 4.39-4.35 (m, 1H), 3.95-3.90 (m, 4H), 3.79-3.76 (m, 1H), 2.67-2.50 (m, 1H), 2.32-2.17 (m, 1H). |
| 16 | $^1$H NMR (400 MHz, CD$_3$OD) δ 8.50 (s, 1H), 7.37 (s, 4H), 5.62 (s, 2H), 5.11-5.06 (m, 1H), 4.47 (s, 3H), 4.47-4.40 (m, 1H), 4.09-4.04 (m, 1H), 3.83-3.74 (m, 1H), 2.73-2.64 (m, 1H), 2.28-2.17 (m, 1H). |
| 17 | $^1$H NMR (400 MHz, DMSO-$d_6$) δ 8.46 (s, 1H), 8.24 (s, 1H), 7.44-7.37 (m, 1H), 7.40-7.28 (m, 3H), 5.58 (s, 2H), 5.05-5.01 (m, 1H), 4.37 (dd, J = 8.5, 7.3 Hz, 1H), 3.96 (s, 3H), 3.91 (dd, J= 8.6, 6.2 Hz, 1H), 3.82-3.71 (m, 1H), 2.63-2.57 (m, 1H), 2.20-2.13 (m, 1H). |
| 18 | $^1$H NMR (400 MHz, DMSO-$d_6$) δ 8.46 (s, 1H), 8.24 (s, 1H), 7.48-7.34 (m, 2H), 7.21 (s, 1H), 5.57 (s, 2H), 5.03-5.00 (m, 1H), 4.41-4.32 (m, 1H), 3.95 (s, 3H), 3.90 (dd, J = 8.5, 6.3 Hz, 1H), 3.82-3.72 (m, 1H), 2.61-2.55 (m, 1H), 2.23-2.10 (m, 1H). |
| 19 | $^1$H NMR (400 MHz, DMSO-$d_6$) δ 8.46 (s, 1H), 8.24 (s, 1H), 7.43-7.35 (m, 2H), 7.22 (t, J = 75 Hz, 1H). 7.16-7.10 (m, 2H), 5.58 (s, 2H), 5.22 (t, J = 7.4 Hz, 1H), 4.39-4.35 (m, 1H), 3.96 (s, 3H), 3.93-3.88 (m, 1H), 3.81-3.72 (m, 1H), 2.61-2.57 (m, 1H), 2.19-2.13 (m, 1H). |
| 20 | $^1$H NMR (400 MHz, DMSO-$d_6$) δ 8.77 (d,J = 4.8 Hz, 1H), 8.70 (s, 1H), 7.41-7.34 (m, 3H), 7.14 (t, J = 8.9 Hz, 2H), 5.52 (s, 2H), 4.97 (t, J = 7.4 Hz, 1H), 4.36-4.30 (m, 1H), 3.87 (dd, J = 8.5, 6.3 Hz, 1H), 3.75 (dt, J = 13.7, 6.8 Hz, 1H), 2.74 (s, 3H), 2.58-2.51 (m, 1H), 2.17-2.08 (m, 1H). |
| 21 | $^1$H NMR (400 MHz, DMSO-$d_6$) δ 8.46 (s, 1H), 8.24 (s, 1H), 7.49 (d, J = 8.6 Hz, 2H), 7.34 (d, J = 8.0 Hz, 2H), 5.58 (s, 2H), 5.06 (t, J = 7.3 Hz, 1H), 4.37 (dd, J = 8.4, 7.5 Hz, 1H), 4.03-3.86 (m, 4H), 3.82-3.69 (m, 1H), 2.63-2.57 (m, 1H), 2.24-2.10 (m, 1H). |
| 22 | $^1$H NMR (500 MHz, DMSO-d6) δ 8.27 (s, 1H), 7.44-7.34 (m, 2H), 7.19-7.12 (m, 2H), 6.83 (s, 2H), 5.49 (s, 2H), 5.00 (t, J = 7.3 Hz, 1H), 4.36 (dd, J = 8.5, 7.5 Hz, 1H), 3.89 (dd, J = 8.6, 6.3 Hz, 1H), 3.82-3.68 (m, 1H), 2.56 (ddd, J = 12.4, 7.1, 5.1 Hz, 1H), 2.18-2.09 (m, 1H). |
| 23 | $^1$H NMR (300 MHz, DMSO-$d_6$) δ 8.49 (s, 1H), 7.47-7.34 (m, 4H), 6.34 (s, 2H), 5.01 (t, J = 7.3 Hz, 1H), 4.37-4.30 (m, 1H), 3.91-3.86 (m, 1H), 3.76 (d, J = 7.2 Hz, 1H), 3.53 (s, 3H), 2.64-2.52 (m, 1H), 2.15-2.11 (m, 1H). |
| 24 | $^1$H NMR (300 MHz, DMSO-$d_6$) δ 9.22 (dd, J = 4.6, 1.7 Hz, 1H), 8.71-8.59 (m, 2H), 7.93 (dd, J = 8.1, 4.6 Hz, 1H), 7.42-7.35 (m, 4H), 5.74 (s, 2H), 5.02 (t, J = 7.4 Hz, 1H), 4.38-4.33 (m, 1H), 3.93-3.80 (m, 1H), 3.78-3.71 (m, 1H), 2.64-2.55 (m, 1H), 2.23-2.06 (m, 1H). |
| 25 | $^1$H NMR (300 MHz, DMSO-$d_6$) δ 9.05 (dd, J = 4.6, 2.0 Hz, 1H), 8.78 (s, 1H), 8.58 (dd, J = 7.9, 2.0 Hz, 1H), 7.65 (dd, J = 7.9, 4.6 Hz, 1H), 7.46-7.33 (m, 4H), 5.61 (s, 2H), 5.01 (t, J = 7.4 Hz, 1H), 4.36 (dd, J = 8.5, 7.3 Hz, 1H), 3.91 (dd, J = 8.5, 6.3 Hz, 1H), 3.81-3.72 (m, 1H), 2.61-2.49 (m, 1H), 2.19-2.10 (m, 1H). |
| 26 | $^1$H NMR (400 MHz, DMSO-$d_6$) δ 8.26 (s, 1H), 7.41-7.34 (m, 4H), 6.82 (s, 2H), 5.49 (s, 2H), 5.01 (t, J = 7.2 Hz, 1H), 4.35 (t, J = 8.0 Hz, 1H), 3.92-3.88 (m, 1H), 3.78-3.71 (m, 1H), 3.62 (s, 3H), 2.61-2.54 (m, 1H), 2.17-2.10 (m, 1H). |
| 27 | $^1$H NMR (400 MHz, DMSO-$d_6$) δ 8.46 (s, 1H), 8.24 (s, 1H), 7.23 (d, J = 7.7 Hz, 2H), 7.15 (d, J= 7.7 Hz, 2H), 5.57 (s, 2H), 4.95 (t, J = 7.4 Hz, 1H), 4.34 (t, J = 8.0 Hz, 1H), 3.96 (s, 3H), 3.89-3.80 (m, 1H), 3.76-3.73 (m, 1H), 2.77-2.58 (m, 1H), 2.28 (s, 3H), 2.17-2.12 (m, 1H). |
| 28 | $^1$H NMR (400 MHz, DMSO-$d_6$) δ 8.51 (s, 1H), 8.01 (d, J = 8.7 Hz, 1H), 7.44-7.33 (m, 4H), 7.18 (s, 2H), 6.61 (d, J = 8.8 Hz, 1H), 5.47 (s, 2H), 5.01 (t, J = 7.4 Hz, 1H), 4.35 (dd, J = 8.5, 7.3 Hz, 1H), 3.90 (dd, J = 8.6, 6.3 Hz, 1H), 3.81-3.70 (m, 1H), 2.60-2.54 (m, 1H), 2.20-2.05 (m, 1H). |
| 29 | $^1$H NMR (400 MHz, DMSO-d6) δ 8.45 (s, 1H), 8.24 (s, 1H), 7.59-7.47 (m, 2H), 7.36-7.23 (m, 2H), 5.57 (s, 2H), 4.99 (t, J = 7.3 Hz, 1H), 4.35 (dd, J = 8.6, 7.4 Hz, 1H), 3.95 (s, 3H), 3.90 (dd, J = 8.6, 6.3 Hz, 1H), 3.81-3.69 (m, 1H), 2.57 (ddd, J = 12.5, 7.1, 5.1 Hz, 1H), 2.14 (ddd, J = 12.7, 8.9, 7.6 Hz, 1H). |
| 30 | $^1$H NMR (400 MHz, DMSO-d6) δ 8.47 (s, 1H), 8.24 (s, 1H), 7.69-7.60 (m, 4H), 7.51-7.41 (m, 4H), 7.40-7.31 (m, 1H), 5.59 (s, 2H), 5.06 (t, J = 7.4 Hz, 1H), 4.39 (dd, J = 8.5, 7.4 Hz, 1H), 3.96 (s, 3H), 3.93 (dd, J = 8.6, 6.2 Hz, 1H), 3.85-3.73 (m, 1H), 2.60 (ddd, J = 12.4, 7.1, 5.1 Hz, 1H), 2.21 (ddd, J = 12.7, 9.0, 7.7 Hz, 1H). |
| 31 | 1H NMR (400 MHz, dmso) δ 8.45 (s, 1H), 8.24 (d, J = 0.5 Hz, 1H), 7.62-7.59 (m, 2H), 7.35 (ddd, J = 8.4, 2.1, 0.6 Hz, 1H), 5.57 (s, 2H), 5.03 (t, J = 7.3 Hz, 1H), 4.36 (dd, J = 8.5, 7.4 Hz, 1H), 3.95 (s, 3H), 3.91 (dd, J = 8.5, 6.3 Hz, 1H), 3.79-3.72 (m, 1H), 2.60 (ddd, J = 12.7, 7.3, 5.4 Hz, 1H), 2.16 (ddd, J = 12.7, 8.8, 7.4 Hz, 1H). |
| 32 | 1H NMR (400 MHz, dmso) δ 8.45 (s, 1H), 8.24 (s, 1H), 7.58-7.53 (m, 1H), 7.40 (dd, J = 10.6, 1.7 Hz, 1H), 7.25-7.21 (m, 1H), 5.57 (s, 2H), 5.04 (t, J = 7.2 Hz, 1H), 4.36 (dd, J = 8.5, 7.4 Hz, 1H), 3.95 (s, 3H), 3.91 (dd, J = 8.5, 6.3 Hz, 1H), 3.80-3.71 (m, 1H), 2.60 (ddd, J = 12.7, 7.2, 5.4 Hz, 1H), 2.16 (ddd, J = 12.7, 8.7, 7.4 Hz, 1H). |
| 33 | $^1$H NMR (400 MHz, DMSO-$d_6$) δ 8.47 (s, 1H), 8.24 (s, 1H), 7.94-7.85 (m, 4H), 7.56-7.45 (m, 3H), 5.59 (s, 2H), 5.19 (t, J = 7.4 Hz, 1H), 4.44 (dd, J = 8.5, 7.4 Hz, 1H), 3.97 (dd, J = 8.6, 6.3 Hz, 1H), 3.96 (s, 3H), 3.88-3.78 (m, 1H), 2.68-2.62 (m, 1H), 2.33-2.27 (m, 1H). |

TABLE 2-continued

| | |
|---|---|
| 34 | 1H NMR (400 MHz, DMSO) δ 8.46 (s, 1H), 8.25 (d, J = 0.5 Hz, 1H), 7.18-7.05 (m, 3H), 5.57 (s, 2H), 5.05 (t, J = 7.2 Hz, 1H), 4.36 (dd, J = 8.5, 7.3 Hz, 1H), 3.95 (d, J = 0.5 Hz, 3H), 3.94-3.87 (m, 1H), 3.79-3.70 (m, 1H), 2.61 (ddd, J = 12.8, 7.4, 5.5 Hz, 1H), 2.16 (ddd, J = 12.8, 8.7, 7.3 Hz, 1H). |
| 35 | $^1$H NMR (400 MHz, DMSO-$d_6$) δ 8.46 (s, 1H), 8.24 (s, 1H), 7.57 (dd, J = 7.5, 1.5 Hz, 1H), 7.43-7.34 (m, 2H), 5.58 (s, 2H), 5.02 (t, J = 7.3 Hz, 1H), 4.37 (dd, J = 8.5, 7.3 Hz, 1H), 3.95 (s, 3H), 3.90 (dd, J = 8.5, 6.3 Hz, 1H), 3.80-3.73 (m, 1H), 2.62-2.55 (m, 1H), 2.23-2.05 (m, 1H). |
| 36 | $^1$H NMR (400 MHz, DMSO-$d_6$) δ 8.46 (s, 1H), 8.24 (s, 1H), 7.44-7.35 (m, 2H), 7.18-7.11 (m, 2H), 5.58 (s, 2H), 5.00 (t, J = 7.4 Hz, 1H), 4.36 (m, 1H), 3.95 (s, 3H), 3.89-3.78 (m, 1H), 3.77-3.73 (m, 1H), 2.59-2.50 (m, 1H), 2.18-2.07 (m, 1H). |
| 37 | $^1$H NMR (400 MHz, DMSO-$d_6$) δ 8.46 (s, 1H), 8.24 (d, J = 0.7 Hz, 1H), 7.86-7.78 (m, 2H), 7.60-7.52 (m, 2H), 5.58 (s, 2H), 5.11 (t, J = 7.4 Hz, 1H), 4.39-4.35 (m, 1H), 3.96-3.92 (m, 4H), 3.79-3.72 (m, 1H), 2.67-2.61 (m, 1H), 2.18-2.13 (m, 1H). |
| 38 | $^1$H NMR (300 MHz, DMSO-$d_6$) δ 8.47 (s, 1H), 8.25 (s, 1H), 7.72 (d, J = 8.2 Hz, 2H), 7.59 (d, J = 8.2 Hz, 2H), 5.59 (s, 2H), 5.13 (t, J = 7.4 Hz, 1H), 4.39 (dd, J = 8.6, 7.3 Hz, 1H), 3.99-3.92 (m, 4H), 3.82-3.73 (m, 1H), 2.70-2.61 (m, 1H), 2.25-2.05 (m, 1H). |
| 39 | $^1$H NMR (300 MHz, DMSO-$d_6$) δ 8.17 (s, 1H), 7.57 (d, J = 7.3 Hz, 1H), 7.42-7.36 (m, 4H), 6.73 (d, J = 7.3 Hz, 1H), 5.53 (s, 2H), 5.02 (t, J = 7.4 Hz, 1H), 4.39-4.33 (m, 1H), 3.99 (s, 3H), 3.91-3.86 (m, 1H), 3.77-3.70 (m, 1H), 2.66-2.50 (m, 1H), 2.18-2.12 (m, 1H). |
| 40 | 1H NMR (400 MHz, dmso) δ 8.45 (s, 1H), 8.24 (d, J = 0.5 Hz, 1H), 7.37-7.29 (m, 2H), 5.57 (s, 2H), 5.03 (t, J = 7.3 Hz, 1H), 4.37 (dd, J = 8.5, 7.3 Hz, 1H), 3.95 (s, 3H), 3.90 (dd, J = 8.5, 6.3 Hz, 1H), 3.79-3.70 (m, 1H), 2.63-2.55 (m, 1H), 2.21-2.11 (m, 1H). |
| 41 | 1H NMR (400 MHz, dmso) δ 8.60-8.57 (m, 1H), 8.46 (s, 1H), 8.24 (s, 1H), 7.94 (dd, J = 8.4, 2.5 Hz, 1H), 7.51 (d, J = 8.4 Hz, 1H), 5.57 (s, 2H), 5.10 (t, J = 7.0 Hz, 1H), 4.33 (dd, J = 8.4, 7.3 Hz, 1H), 3.98-3.92 (m, 4H), 3.79-3.70 (m, 1H), 2.62-2.54 (m, 1H), 2.42-2.31 (m, 1H). |
| 42 | 1H NMR (400 MHz, dmso) δ 8.40 (s, 1H), 8.23 (s, 1H), 7.41-7.36 (m, 2H), 7.35-7.31 (m, 2H), 5.49 (s, 2H), 4.30 (t, J = 7.6 Hz, 1H), 3.93 (s, 3H), 3.92-3.81 (m, 2H), 2.64 (dd, J = 12.6, 8.0 Hz, 1H), 2.21 (dd, J = 12.5, 8.7 Hz, 1H), 1.45 (s, 3H). |
| 43 | 1H NMR (400 MHz, DMSO) 1H NMR (400 MHz, DMSO) 8.47 (s, 1H), 8.25 (s, 1H), 7.26 (td, J = 7.4, 1.1 Hz, 1H), 7.19-7.14 (m, 1H), 7.13-7.07 (m, 1H), 7.05-7.01 (m, 1H), 5.59 (s, 2H), 4.23 (t, J = 8.3 Hz, 1H), 4.02 (dd, J = 8.5, 6.6 Hz, 1H), 3.95 (s, 3H), 3.90-3.80 (m, 1H), 3.38 (d, J = 13.9 Hz, 1H), 3.23 (d, J = 13.9 Hz, 1H), 2.65 (dd, J = 12.7, 8.4 Hz, 1H), 2.39 (dd, J = 12.7, 7.4 Hz, 1H). |
| 44 | $^1$H NMR (400 MHz, DMSO-$d_6$) δ 8.93 (s, 1H), 8.63 (s, 1H), 8.53 (s, 1H), 7.43-7.34 (m, 4H), 5.55 (s, 2H), 5.00 (t, J = 7.3 Hz, 1H), 4.35 (dd, J = 8.6, 7.3 Hz, 1H), 3.90 (dd, J = 8.6, 6.2 Hz, 1H), 3.79-3.74 (m 1H), 2.70 (s, 3H), 2.61-2.54 (m, 1H), 2.17-2.08 (m, 1H). |
| 45 | $^1$H NMR (400 MHz, DMSO-$d_6$) δ 9.15 (d, J = 0.9 Hz, 1H), 8.75 (d, J = 5.2 Hz, 1H), 8.69 (s, 1H), 8.02 (dd, J = 5.2, 0.9 Hz, 1H), 7.43-7.33 (m, 4H), 5.61 (s, 2H), 5.00 (t, J = 7.3 Hz, 1H), 4.34 (dd, J = 8.6, 7.4 Hz, 1H), 3.89 (dd, J = 8.6, 6.2 Hz, 1H), 3.79-3.72 (m, 1H), 2.62-2.53 (m, 1H), 2.17-2.09 (m, 1H). |
| 46 | 1H NMR (400 MHz, dmso) δ 8.50 (s, 1H), 7.76 (d, J = 9.6 Hz, 1H), 7.42-7.36 (m, 4H), 6.97 (d, J = 9.7 Hz, 1H), 5.55 (s, 2H), 5.01 (t, J = 7.3 Hz, 1H), 4.36 (dd, J = 8.5, 7.4 Hz, 1H), 3.90 (dd, J = 8.5, 6.3 Hz, 1H), 3.86 (s, 3H), 3.80-3.73 (m, 1H), 2.57 (ddd, J = 12.5, 7.1, 5.2 Hz, 1H), 2.14 (ddd, J = 12.7, 8.9, 7.7 Hz, 1H). |
| 47 | 1H NMR (400 MHz, dmso) δ 9.50 (s, 1H), 8.72 (s, 1H), 7.43-7.36 (m, 4H), 5.55 (s, 2H), 5.01 (t, J = 7.4 Hz, 1H), 4.36 (dd, J = 8.5, 7.4 Hz, 1H), 3.91 (dd, J = 8.6, 6.2 Hz, 1H), 3.81-3.73 (m, 1H), 2.58 (ddd, J = 12.4, 7.1, 5.1 Hz, 1H), 2.40 (s, 3H), 2.14 (ddd, J = 12.7, 8.9, 7.7 Hz, 1H). |
| 48 | $^1$H NMR (400 MHz, DMSO-$d_6$) δ 8.42 (s, 1H), 7.77 (s, 1H), 7.44-7.34 (m, 4H), 5.49 (s, 2H), 5.01 (t, J = 7.3 Hz, 1H), 4.36 (dd, J = 8.6, 7.4 Hz, 1H), 3.91 (dd, J = 8.6, 6.2 Hz, 1H), 3.83-3.71 (m, 1H), 2.61-2.55 (m, 1H), 2.36 (s, 3H), 2.18-2.08 (m, 1H). |
| 49 | $^1$H NMR (400 MHz, DMSO-$d_6$) δ 7.69 (d, J = 6.5 Hz, 1H), 7.58 (d, J = 9.4 Hz, 1H), 7.44-7.35 (m, 4H), 7.15 (d, J = 6.5 Hz, 1H), 6.78 (d, J = 9.3 Hz, 1H), 5.35 (s, 2H), 5.02 (t, J = 7.3 Hz, 1H), 4.37 (dd, J = 8.6, 7.4 Hz, 1H), 3.92 (dd, J = 8.6, 6.3 Hz, 1H), 3.83-3.72 (m, 1H), 2.64-2.55 (m, 1H), 2.56 (s, 3H), 2.19-2.11 (m, 1H). |
| 50 | $^1$H NMR (400 MHz, DMSO-$d_6$) δ 8.26 (s, 1H), 7.44-7.34 (m, 4H), 5.95 (s, 2H), 5.00 (t, J = 7.3 Hz, 1H), 4.35 (dd, J = 8.6, 7.4 Hz, 1H), 3.89 (dd, J = 8.5, 6.2 Hz, 1H), 3.81-3.70 (m, 1H), 3.46 (s, 3H), 3.18 (s, 3H), 2.61-2.51 (m, 1H), 2.17-2.07 (m, 1H). |
| 51 | 1H NMR (400 MHz, dmso) δ 8.54-8.50 (m, 1H), 8.28 (s, 1H), 7.79-7.71 (m, 2H), 7.43-7.36 (m, 5H), 7.29-7.24 (m, 1H), 5.50 (s, 2H), 5.01 (t, J = 7.4 Hz, 1H), 4.65 (d, J = 5.9 Hz, 2H), 4.35 (dd, J = 8.6, 7.4 Hz, 1H), 3.89 (dd, J = 8.6, 6.3 Hz, 1H), 3.79-3.70 (m, 1H), 3.71 (s, 3H), 2.61-2.53 (m, 1H), 2.18-2.07 (m, 1H). |
| 52 | 1H NMR (400 MHz, dmso) δ 8.62 (s, 1H), 8.24 (d, J = 5.4 Hz, 1H), 7.54 (d, J = 5.4 Hz, 1H), 7.41-7.35 (m, 4H), 5.60 (s, 2H), 4.99 (t, J = 7.4 Hz, 1H), 4.34 (dd, J = 8.6, 7.4 Hz, 1H), 4.03 (s, 3H), 3.88 (dd, J = 8.5, 6.3 Hz, 1H), 3.79-3.71 (m, 1H), 2.59-2.52 (m, 1H), 2.17-2.08 (m, 1H). Dimethyl |
| 53 | 1H NMR (400 MHz, dmso) δ 9.37 (s, 1H), 8.47 (s, 1H), 8.25 (d, J = 0.5 Hz, 1H), 8.17-8.16 (m, 1H), 8.05 (d, J = 8.5 Hz, 1H), 7.54-7.51 (m, 2H), 5.59 (s, 2H), 5.18 (t, J = 7.3 Hz, 1H), 4.42 (dd, J = 8.5, 7.4 Hz, 1H), 3.97-3.93 (m, 4H), 3.85-3.77 (m, 1H), 2.64 (ddd, J = 12.6, 7.2, 5.3 Hz, 1H), 2.24 (ddd, J = 12.7, 8.8, 7.5 Hz, 1H). |
| 54 | 1H NMR (400 MHz, dmso) δ8.77 (d, J = 4.8 Hz, 1H), 8.70 (s, 1H), 7.40-7.34 (m, 5H), 5.52 (s, 2H), 4.98 (t, J = 7.4 Hz, 1H), 4.33 (dd, J = 8.5, 7.4 Hz, 1H), 3.88 (dd, J = 8.6, 6.3 Hz, 1H), 3.78-3.71 (m, 1H), 2.74 (d, J = 0.6 Hz, 3H), 2.55 (ddd, J = 12.4, 7.1, 5.1 Hz, 1H), 2.11 (ddd, J = 12.7, 8.9, 7.7 Hz, 1H). |
| 55 | $^1$H NMR (400 MHz, DMSO-$d_6$) δ 8.39 (s, 1H), 8.34 (s, 1H), 7.44-7.33 (m, 4H), 6.02 (s, 2H), 4.99 (t, J = 7.4 Hz, 1H), 4.34 (dd, J = 8.6, 7.3 Hz, 1H), 3.88 (dd, J = 8.6, 6.2 Hz, 1H), 3.80-3.69 (m, 1H), 3.46 (s, 3H), 2.60-2.51 (m, 1H), 2.19-2.05 (m, 1H). |
| 56 | $^1$H NMR (400 MHz, DMSO-$d_6$) δ 8.17 (s, 1H), 7.57 (d, J = 7.3 Hz, 1H), 7.45-7.36 (m, 2H), 7.22-7.11 (m, 2H), 6.72 (d, J = 7.3 Hz, 1H), 5.53 (s, 2H), 5.00 (t, J = 7.4 Hz, 1H), 4.38-4.33 (m, 1H), 3.98 (s, 3H), 3.90-3.79 (m, 1H), 3.82-3.74 (m, 1H), 2.56-2.49 (m, 1H), 2.18-2.15 (m, 1H). |

| | |
|---|---|
| 57 | 1H NMR (400 MHz, cdcl3) δ 8.36 (s, 1H), 7.90 (s, 1H), 7.35-7.27 (m, 4H), 5.65 (s, 2H), 5.10 (t, J = 7.3 Hz, 1H), 4.43 (dd, J = 8.8, 7.6 Hz, 1H), 4.17 (s, 3H), 4.08 (dd, J = 8.8, 6.8 Hz, 1H), 3.77-3.67 (m, 1H), 2.74-2.65 (m, 1H), 2.24-2.13 (m, 1H). |
| 58 | 1H NMR (400 MHz, dmso) δ68.77 (d, J = 4.8 Hz, 1H), 8.70 (s, 1H), 7.40-7.34 (m, 5H), 5.52 (s, 2H), 4.98 (t, J = 7.4 Hz, 1H), 4.33 (dd, J = 8.5, 7.4 Hz, 1H), 3.88 (dd, J = 8.6, 6.3 Hz, 1H), 3.78-3.71 (m, 1H), 2.74 (d, J = 0.6 Hz, 3H), 2.55 (ddd, J = 12.4, 7.1, 5.1 Hz, 1H), 2.11 (ddd, J = 12.7, 8.9, 7.7 Hz, 1H). |
| 59 | 1H NMR (400 MHz, dmso) δ 8.86 (s, 1H), 8.47 (s, 1H), 7.41-7.36 (m, 4H), 6.03 (s, 2H), 4.99 (t, J = 7.3 Hz, 1H), 4.34 (dd, J = 8.5, 7.5 Hz, 1H), 4.18 (s, 3H), 3.87 (dd, J = 8.6, 6.3 Hz, 1H), 3.78-3.70 (m, 1H), 2.55 (ddd, J = 10.5, 6.2, 4.2 Hz, 1H), 2.13 (ddd, J = 12.7, 8.8, 7.7 Hz, 1H). |
| 60 | $^1$H NMR (400 MHz, DMSO-$d_6$) δ 8.51 (s, 1H), 8.01 (d, J = 8.7 Hz, 1H), 7.44-7.36 (m, 2H), 7.21-7.11 (m, 4H), 6.61 (d, J = 8.7 Hz, 1H), 5.47 (s, 2H), 4.99 (t, J = 7.4 Hz, 1H), 4.35 (dd, J = 8.6, 7.4 Hz, 1H), 3.89 (dd, J = 8.5, 6.3 Hz, 1H), 3.82-3.70 (m, 1H), 2.61-2.51 (m, 1H), 2.18-2.11 (m, 1H). |
| 61 | $^1$H NMR (400 MHz, DMSO-$d_6$) δ 7.68 (d, J = 7.5 Hz, 1H), 7.42-7.35 (m, 4H), 7.00 (d, J = 7.4 Hz, 1H), 5.58 (s, 2H), 5.01 (t, J = 7.3 Hz, 1H), 4.39 (s, 3H), 4.35 (dd, J = 8.6, 7.3 Hz, 1H), 3.90 (dd, J = 8.5, 6.3 Hz, 1H), 3.82 ? |
| 62 | $^1$H NMR (400 MHz, DMSO-$d_6$) δ 8.83 (dd, J = 4.4, 2.1 Hz, 1H), 8.28 (dd, J = 8.0, 2.1 Hz, 1H), 7.42-7.37 (m, 4H), 7.22-7.19 (m, 2H).7.16-7.04 (brs, 1H), 5.89 (s, 2H), 5.03 (t, J = 7.4 Hz, 1H), 4.39 (dd, J = 8.6, 7.4 Hz, 1H), 3.96 (dd, J = 8.6, 6.2 Hz, 1H), 3.87- 3.77(m, 1H), 2.65-2.59 (m, 1H), 2.20-2.08 (m, 1H). |
| 63 | 1H NMR (400 MHz, dmso) δ 7.85 (d, J = 7.8 Hz, 1H), 7.42-7.37 (m, 4H), 6.25 (d, J = 7.8 Hz, 1H), 6.10 (d, J = 1.0 Hz, 1H), 5.39 (s, 2H), 5.02 (t, J = 7.3 Hz, 1H), 4.37 (dd, J = 8.5, 7.4 Hz, 1H), 3.92 (dd, J = 8.6, 6.2 Hz, 1H), 3.82-3.75 (m, 1H), 2.62-2.56 (m, 1H), 2.55 (d, J = 0.9 Hz, 3H), 2.16 (ddd, J = 12.7, 8.9, 7.7 Hz, 1H). |
| 64 | 1H NMR (400 MHz, DMSO-d6): δ 8.41 (s, 1H), 8.24 (s, 1H), 7.43-7.32 (m, 4H), 5.41 (s, 2H), 5.01 (t, J = 7.4 Hz, 1H), 4.36 (dd, J = 8.5, 7.4 Hz, 1H), 3.91 (dd, J = 8.6, 6.3 Hz, 1H), 3.82-3.71 (m, 1H), 2.58 (ddd, J = 12.5, 7.1, 5.2 Hz, 1H), 2.47 (s, 3H), 2.14 (ddd, J = 12.7, 8.9, 7.7 Hz, 1H). |
| 65 | $^1$H NMR (400 MHz, DMSO-$d_6$) δ 8.46 (s, 1H), 8.24 (s, 1H), 7.32-7.22 (m, 2H), 6.94-6.85 (m, 2H), 5.57 (s, 2H), 4.92 (t, J = 7.4 Hz, 1H), 4.33 (dd, J = 8.5, 7.4 Hz, 1H), 3.95 (s, 3H), 3.86 (dd, J = 8.5, 6.3 Hz, 1H), 3.82-3.69 (m, 1H), 3.74 (s, 3H), 2.56-2.39 (m, 1H), 2.15 (ddd, J = 12.7, 9.0, 7.9 Hz, 1H). |
| 66 | 1H NMR (400 MHz, DMSO-d6) δ 8.41 (s, 1H), 7.76 (s, 1H), 7.44-7.35 (m, 2H), 7.21-7.11 (m, 2H), 5.48 (s, 2H), 5.00 (t, J = 7.4 Hz, 1H), 4.36 (dd, J = 8.5, 7.3 Hz, 1H), 3.90 (dd, J = 8.5, 6.3 Hz, 1H), 3.78 (ddt, J = 9.0, 7.3, 5.7 Hz, 1H), 2.56 (ddd, J = 12.4, 7.0, 5.0 Hz, 1H), 2.36 (s, 3H), 2.15 (ddd, J = 12.8, 9.0, 7.8 Hz, 1H). |
| 67 | 1H NMR (400 MHz, DMSO-d6) δ 8.93 (s, 1H), 8.63 (s, 1H), 8.53 (d, J = 1.0 Hz, 1H), 7.44-7.34 (m, 2H), 7.23-7.11 (m, 2H), 5.55 (s, 2H), 4.99 (t, J = 7.4 Hz, 1H), 4.35 (dd, J = 8.5, 7.3 Hz, 1H), 3.89 (dd, J = 8.5, 6.3 Hz, 1H), 3.82-3.71 (m, 1H), 2.70 (s, 3H), 2.56 (ddd, J = 12.4, 7.0, 5.0 Hz, 1H), 2.15 (ddd, J = 12.7, 8.9, 7.7 Hz, 1H). |
| 68 | $^1$H NMR (400 MHz, DMSO-$d_6$) δ 8.45 (s, 1H), 8.24 (s, 1H), 7.26-7.17 (m, 2H), 7.08-6.99 (m, 2H), 5.57 (s, 2H), 4.93 (t, J = 7.4 Hz, 1H), 4.33 (dd, J = 8.5, 7.4 Hz, 1H), 3.95 (s, 3H), 3.87 (dd, J = 8.5, 6.3 Hz, 1H), 3.81-3.68 (m, 1H), 2.57-2.45 (m, 1H), 2.13 (ddd, J = 12.7, 9.0, 7.8 Hz, 1H), 1.89 (tt, J = 8.4, 5.1 Hz, 1H), 0.99-0.85 (m, 2H), 0.71-0.56 (m, 2H). |
| 69 | $^1$H NMR (400 MHz, DMSO-$d_6$) δ 8.39 (s, 1H), 8.34 (s, 1H), 7.44-7.34 (m, 2H), 7.21-7.11 (m, 2H), 6.02 (s, 2H), 4.98 (t, J = 7.4 Hz, 1H), 4.34 (dd, J = 8.5, 7.4 Hz, 1H), 3.87 (dd, J = 8.5, 6.2 Hz, 1H), 3.81-3.70 (m, 1H), 3.46 (s, 3H), 2.55-2.51 (m, 1H), 2.20-2.05 (m, 1H). |
| 70 | 1H NMR (400 MHz, dmso) 8.46 (s, 1H), 8.25 (s, 1H), 7.42-7.36 (m, 4H), 5.57 (s, 2H), 4.35 (dd, J = 8.5, 7.4 Hz, 1H), 3.95 (s, 3H), 3.89 (dd, J = 8.5, 6.3 Hz, 1H), 3.79-3.71 (m, 1H), 2.56 (dd, J = 12.7, 5.2 Hz, 1H), 2.13 (m, J = 12.7, 8.9 Hz 1H). |
| 71 | 1H NMR (400 MHz, dmso) 7.92 (s, 1H), 7.45-7.28 (m, 4H), 6.86 (s, 2H), 5.46 (s, 2H), 5.00 (t, J = 7.3 Hz, 1H), 4.34 (dd, J = 8.5, 7.4 Hz, 1H), 3.88 (dd, J = 8.5, 6.3 Hz, 1H), 3.81 (s, 3H), 3.73 (dt, J = 13.6, 6.6 Hz, 1H), 2.56 (ddd, J = 12.5, 7.1, 5.2 Hz, 1H), 2.12 (ddd, J = 12.7, 8.9, 7.7 Hz, 1H). |
| 72 | 1H NMR (400 MHz, DMSO-d6) δ 8.58 (d, J = 2.5 Hz, 1H), 8.41 (s, 1H), 7.93 (dd, J = 8.4, 2.5 Hz, 1H), 7.76 (s, 1H), 7.51 (d, J = 8.4 Hz, 1H), 5.48 (s, 2H), 5.11 (t, J = 7.0 Hz, 1H), 4.34 (dd, J = 8.6, 7.1 Hz, 1H), 3.96 (dd, J = 8.5, 6.0 Hz, 1H), 3.76 (ddd, J = 13.7, 8.1, 6.0 Hz, 1H), 2.59 (ddd, J = 13.1, 7.5, 5.7 Hz, 1H), 2.44-2.32 (m, 1H), 2.36 (s, 3H). |
| 73 | $^1$H NMR (400 MHz, DMSO-$d_6$) δ 8.45 (s, 1H), 7.44-7.37 (m, 4H), 5.44 (s, 2H), 5.01 (t, J = 7.2 Hz, 1H), 4.36 (t, J = 7.6 Hz, 1H), 3.91-3.88 (m, 1H), 3.76-3.74 (m, 1H), 3.59 (s, 2H), 2.87-2.82 (m, 2H), 2.61-2.52 (m, 1H), 2.34-2.27 (s, 2H), 2.17-2.06 (m, 1H). |
| 74 | $^1$H NMR (400 MHz, DMSO-d6) δ 7.93 (s, 1H), 7.88 (d,J = 8.9 Hz, 2H), 7.59 (d, J = 8.5 Hz, 2H), 6.88 (s, 2H), 5.48 (s, 2H), 5.13 (t, J = 7.3 Hz, 1H), 4.38 (dd, J = 8.4, 7.4 Hz, 1H), 3.95 (dd, J = 8.5, 6.2 Hz, 1H), 3.83 (s, 3H), 3.79-3.72 (m, 1H), 2.69-2.63 (m, 1H), 2.17 (dd, J = 12.6, 8.7, 7.5 Hz, 1H) |
| 75 | 1H NMR (400 MHz, DMSO-d6) δ 8.40 (s, 1H), 8.24 (s, 1H), 7.45-7.35 (m, 2H), 7.22-7.11 (m, 2H), 5.41 (s, 2H), 5.00 (t, J = 7.3 Hz, 1H), 4.36 (dd, J = 8.6, 7.4 Hz, 1H), 3.90 (dd, J = 8.5, 6.2 Hz, 1H), 3.83-3.72 (m, 1H), 2.57 (ddd, J = 12.3, 7.1, 5.1 Hz, 1H), 2.47 (s, 3H), 2.16 (ddd, J =z 12.6, 8.9, 7.7 Hz, 1H). |
| 76 | 1H NMR (400 MHz, dmso) δ 8.55 (s, 1H), 7.54-7.23 (m, 5H), 5.60 (s, 2H), 5.01 (t, J = 7.4 Hz, 1H), 4.35 (dd, J = 8.6, 7.4 Hz, 1H), 4.08 (s, 3H), 3.90 (dd, J = 8.6, 6.3 Hz, 1H), 3.80-3.71 (m, 1H), 2.61-2.53 (m, 1H), 2.18-2.09 (m, 1H). |
| 77 | 1H NMR (400 MHz, dmso) δ 8.84 (s, 1H), 8.73 (d, J = 8.1 Hz, 1H), 8.29 (s, 1H), 8.19 (d, J = 8.1 Hz, 1H), 7.93 (s, 1H), 7.42-7.34 (m, 4H), 5.61 (s, 2H), 5.00 (t, J = 7.3 Hz, 1H), 4.35 (dd, J = 8.6, 7.4 Hz, 1H), 3.90 (dd, J = 8.6, 6.2 Hz, 1H), 3.81-3.71 (m, 1H), 2.62-2.56 (m, 1H), 2.20-2.07 (m, 1H). |
| 78 | 1H NMR (400 MHz, dmso) δ 7.94 (s, 1H), 7.43-7.36 (m, 4H), 6.58 (d, J = 8.2 Hz, 1H), 5.29 (s, 2H), 5.02 (t, J = 7.3 Hz, 1H), 4.39-4.33 (m, 1H), 3.91 (dd, J = 8.5, 6.3 Hz, 1H), 3.81-3.71 (m, 1H), 3.63-3.49 (m, 1H), 2.79-2.67 (m, 2H), 2.63-2.53 (m, 1H), 2.34 (s, 3H), 2.20-2.10 (m, 4H), 1.98-1.86 (m, 2H), 1.85-1.76 (m, 2H), 1.68-1.52 (m, 2H). |

| | |
|---|---|
| 79 | — |
| 80 | $^1$H NMR (400 MHz, dmso) δ 7.89 (s, 1H), 7.44 ? 7.36 (m, 4H), 5.29 (s, 2H), 5.02 (t, J = 7.3 Hz, 1H), 4.36 (dd, J = 8.5, 7.5 Hz, 1H), 4.18-4.11 (m, 2H), 3.94-3.83 (m, 3H), 3.81-3.72 (m, 1H), 2.77-2.72 (m, 2H), 2.72-2.65 (m, 1H), 2.63-2.55 (m, 1H), 2.34 (s, 3H), 2.20-2.10 (m, 4H), |
| 81 | 1H NMR (400 MHz, DMSO-d6): δ 7.93 (s, 1H), 7.43-7.36 (m, 2H), 7.21-7.13 (m, 2H), 6.49 (s, 2H), 5.29 (s, 2H), 5.01 (t, J = 7.4 Hz, 1H), 4.36 (dd, J = 8.5, 7.4 Hz, 1H), 3.90 (dd, J = 8.5, 6.3 Hz, 1H), 3.82-3.72 (m, 1H), 2.57 (ddd, J = 12.3, 7.0, 5.0 Hz, 1H), 2.32 (s, 3H), 2.16 (ddd, J = 12.7, 8.9, 7.8 Hz, 1H) |
| 82 | 1H NMR (400 MHz, dmso) 8.66 (s, 1H), 7.81 (dd, J = 9.4, 7.0 Hz, 1H), 7.42-7.36 (m, 4H), 7.18 (d, J = 7.0 Hz, 1H), 6.89 (d, J = 9.0 Hz, 1H), 5.48 (s, 2H), 5.02 (t, J = 7.4 Hz, 1H), 4.40-4.34 (m, 1H), 3.92 (dd, J = 8.6, 6.3 Hz, 1H), 3.78 (dt, J = 18.9, 6.9 Hz, 1H), 2.59 (ddd, J = 12.4, 7.1, 5.1 Hz, 1H), 2.21-2.09 (m, 1H). |
| 83 | $^1$H NMR (400 MHz, DMSO) δ 8.45 (s, 1H), 8.24 (s, 1H), 7.32 (d, J = 8.4 Hz, 2H), 5.57 (s, 2H), 5.07 (t, J = 7.1 Hz, 1H), 4.37 (t, J = 7.9 Hz, 1H), 3.98-3.86 (m, 4H), 3.80-3.69 (m, 1H), 2.67-2.56 (m, 1H), 2.23-2.10 (m, 1H). |
| 84 | 1H NMR (400 MHz, dmso):. δ 8.00 (s, 1H), 7.42-7.36 (m, 4H), 6.73 (s, 2H), 5.43 (s, 2H), 5.01 (t, J = 7.4 Hz, 1H), 4.36 (dd, J = 8.5, 7.3 Hz, 1H), 3.91 (dd, J = 8.5, 6.3 Hz, 1H), 3.80-3.72 (m, 1H), 2.61-2.54 (m, 1H), 2.41 (s, 3H), 2.14 (dddd, J = 12.8, 8.8, 7.5 Hz, 1H). |
| 85 | 1H NMR (400 MHz, dmso): δ 8.00 (s, 1H), 7.43-7.37 (m, 2H), 7.20-7.13 (m, 2H), 6.73 (s, 2H), 5.43 (s, 2H), 5.00 (t, J = 7.4 Hz, 1H), 4.36 (dd, J = 8.5, 7.4 Hz, 1H), 3.90 (dd, J = 8.5, 6.3 Hz, 1H), 3.80-3.73 (m, 1H), 2.56 (ddd, J = 12.4, 7.0, 5.1 Hz, 1H), 2.42 (s, 3H), 2.16 (ddd, J = 12.7, 8.9, 7.8 Hz, 1H). |
| 86 | 1H NMR (400 MHz, DMSO-d6):<br>δ 8.46 (s, 1H), 8.24 (s, 1H), 7.90-7.84 (m, 2H), 7.58 (d, J = 8.4 Hz, 2H), 5.58 (s, 2H), 5.12 (t, J = 7.3 Hz, 1H), 4.38 (dd, J = 8.5, 7.4 Hz, 1H), 3.99-3.90 (m, 4H), 3.81-3.70 (m, 1H), 2.65 (ddd, J = 12.6, 7.3, 5.2 Hz, 1H), 2.17 (ddd, J = 12.7, 8.7, 7.5 Hz, 1H). |
| 87 | 1H NMR (400 MHz, DMSO-$d_6$) & 8.08 (s, 1H), 8.07 (d, J = 8.4 Hz, 1H), 7.41-7.39 (m, 4H), 7.36 (s, 2H), 6.87 (d, J = 9.2 Hz, 1H), 5.60 (s, 2H), 5.01 (t, J = 7.2 Hz, 1H), 4.37-4.33 (m, 1H), 3.92-3.88 (m, 1H), 3.83-3.72 (m, 1H), 2.57-2.51 (m, 1H), 2.15-2.07 (m, 1H). |
| 88 | 1H NMR (400 MHz, DMSO-$d_6$) δ 8.47 (s, 1H), 7.41-7.37 (m, 4H), 5.45 (s, 2H), 5.01 (t, J = 7.2 Hz, 1H), 4.36 (t, J = 8.0 Hz, 1H), 3.90 (dd, J = 8.4, 6.0 Hz, 1H), 3.79-3.74 (m, 1H), 3.30 (s, 2H), 2.60-2.53 (m, 3H), 2.44-2.43 (m, 2H), 2.33 (s, 3H), 2.17-2.13 (m, 1H). |
| 89 | 1H NMR (400 MHz, DMSO-$d_6$) δ 8.72 (dd, J = 4.6, 1.8 Hz, 1H), 8.25 (dd, J = 8.0, 2.1 Hz, 1H), 7.58 (s, 2H), 7.40-7.37 (m, 2H), 7.17-7.13 (m, 3H), 5.53 (s, 2H), 4.99 (t, J = 7.3 Hz, 1H), 4.35 (t, J = 7.9 Hz, 1H), 3.88 (dd, J = 8.5, 6.3 Hz, 1H), 3.80-3.72 (m, 1H), 2.61-2.51 (m, 1H), 2.16-2.13 (m, 1H). |
| 90 | 1H NMR (400 MHz, DMSO-d6)d 8.35 (s, 1H), 7.44-7.36 (m, 2H), 7.21-7.12 (m, 2H), 5.42 (s, 2H), 5.00 (t, J = 7.3 Hz, 1H), 4.36 (dd, J = 8.5, 7.4 Hz, 1H), 3.91 (dd, J = 8.6, 6.3 Hz, 1H), 3.81-3.75 (m, 1H), 2.60-2.53 (m, 1H), 2.47 (s, 3H), 2.16 (ddd, J = 12.7, 9.0, 7.9 Hz, 1H) |
| 91 | 1H NMR (400 MHz, DMSO-d6) 8.21 (s, 1H), 7.97 (s, 1H), 7.43-7.31 (m, 4H), 5.31 (s, 2H), 5.00 (t, J = 7.4 Hz, 1H), 4.34 (dd, J = 8.5, 7.4 Hz, 1H), 3.89 (dd, J = 8.6, 6.3 Hz, 1H), 3.78-3.70 (m, 1H), 3.47-3.41 (m, 4H), 2.86-2.80 (m, 4H), 2.61-2.52 (m, 1H), 2.35 (s, 3H), 2.12 (ddd, J = 12.9, 8.9, 7.8 Hz, 1H). NH and OH are missing in the broad water signal at ~3.3 ppm. |
| 92 | 1H NMR (400 MHz, DMSO-d6) 7.98 (s, 1H), 7.42-7.33 (m, 4H), 5.31 (s, 2H), 5.00 (t, J = 7.4 Hz, 1H), 4.34 (dd, J = 8.5, 7.5 Hz, 1H), 3.90 (dd, J = 8.6, 6.3 Hz, 1H), 3.81-3.69 (m, 1H), 3.55-3.44 (m, 4H), 2.57 (ddd, J = 12.4, 7.0, 5.1 Hz, 1H), 2.45-2.39 (m, 4H), 2.36 (s, 3H), 2.20 (s, 3H), 2.17-2.08 (m, 1H). |
| 93 | 1H NMR (400 MHz, DMSO-d6) 8.34 (s, 1H), 7.41-7.33 (m, 4H), 5.41 (s, 2H), 5.00 (t, J = 7.4 Hz, 1H), 4.34 (dd, J = 8.5, 7.4 Hz, 1H), 3.90 (dd, J = 8.6, 6.2 Hz, 1H), 3.80-3.69 (m, 1H), 2.56 (ddd, J = 12.5, 7.1, 5.2 Hz, 1H), 2.45 (s, 3H), 2.18-2.06 (m, 1H). |
| 94 | 1H NMR (400 MHz, dmso) 7.76-7.70 (m, 2H), 7.40 (dd, J = 8.6, 5.6 Hz, 2H), 7.27-7.22 (m, 2H), 7.20-7.12 (m, 2H), 6.82 (dd, J = 9.2, 1.2 Hz, 1H), 5.43 (s, 2H), 5.00 (t, J = 7.4 Hz, 1H), 4.39-4.32 (m, 1H), 3.90 (dd, J = 8.5, 6.3 Hz, 1H), 3.77 (dt, J = 13.6, 6.8 Hz, 1H), 2.56 (ddd, J = 10.9, 7.9, 4.4 Hz, 1H), 2.20-2.10 (m, 1H). |
| 95 | 1H NMR (400 MHz, dmso) 8.87 (d, J = 5.2 Hz, 1H), 8.80 (s, 1H), 7.71 (d, J = 5.1 Hz, 1H), 7.39 (dd, J = 8.7, 5.7 Hz, 2H), 7.16 (t, J = 8.9 Hz, 2H), 5.55 (s, 2H), 4.99 (t, J = 7.4 Hz, 1H), 4.39-4.32 (m, 1H), 3.89 (dd, J = 8.5, 6.3 Hz, 1H), 3.83-3.71 (m, 1H), 2.56 (ddd, J = 12.4, 7.0, 5.1 Hz, 1H), 2.20-2.09 (m, 1H). |
| 96 | 1H NMR (400 MHz, dmso) 8.50 (s, 1H), 7.40-7.34 (m, 4H), 5.50 (s, 2H), 4.99 (t, J = 7.4 Hz, 1H), 4.33 (dd, J = 8.5, 7.4 Hz, 1H), 3.88 (dd, J = 8.6, 6.3 Hz, 1H), 3.84 (s, 3H), 3.73 (dt, J = 13.8, 6.7 Hz, 1H), 2.55 (ddd, J = 12.5, 7.1, 5.1 Hz, 1H), 2.39 (s, 3H), 2.12 (ddd, J = 12.7, 8.9, 7.7 Hz, 1H). |
| 97 | 1H NMR (400 MHz, DMSO-d6) 8.22 (s, 1H), 7.46-7.30 (m, 4H), 5.40 (s, 2H), 5.01 (t, J = 7.3 Hz, 1H), 4.36 (dd, J = 8.5, 7.4 Hz, 1H), 3.91 (dd, J = 8.6, 6.3 Hz, 1H), 3.83-3.70 (m, 1H), 2.58 (ddd, J = 12.5, 7.1, 5.2 Hz, 1H), 2.48 (s, 3H), 2.43 (s, J = 2.9 Hz, 3H), 2.14 (ddd, J = 12.7, 8.9, 7.7 Hz, 1H). |
| 98 | 1H NMR (400 MHz, dmso) 7.76-7.69 (m, 2H), 7.43-7.35 (m, 4H), 7.24 (d, J = 6.7, 1.5 Hz, 2H), 6.82 (dd, J = 9.2, 1.2 Hz, 1H), 5.43 (s, 2H), 5.01 (t, J = 7.4 Hz, 1H), 4.36 (dd, J = 8.5, 7.4 Hz, 1H), 3.91 (dd, J = 8.6, 6.3 Hz, 1H), 3.76 (dt, J = 13.5, 6.7 Hz, 1H), 2.58 (ddd, J = 12.5, 7.1, 5.2 Hz, 1H), 2.14 (ddd, J = 12.7, 8.9, 7.7 Hz, 1H). |
| 99 | 1H NMR (400 MHz, dmso) 8.39 (d, J = 8.1 Hz, 1H), 7.92 (d, J = 7.9 Hz, 1H), 7.43-7.37 (m, 4H), 6.33 (d, J = 7.9 Hz, 1H), 6.26 (d, J = 8.0 Hz, 1H), 5.48 (s, 2H), 5.02 (t, J = 7.4 Hz, 1H), 4.37 (dd, J = 8.5, 7.4 Hz, 1H), 3.92 (dd, J = 8.5, 6.2 Hz, 1H), 3.82-3.75 (m, 1H), 2.59 (ddd, J = 12.5, 7.1, 5.1 Hz, 1H), 2.15 (ddd, J = 12.7, 8.8, 7.7 Hz, 1H). |
| 100 | 1H NMR (400 MHz, dmso) 7.43-7.37 (m, 4H), 7.09 (dd, J = 9.5, 6.5 Hz, 1H), 7.01 (d, J = 9.5 Hz, 1H), 6.29 (dt, J = 6.5, 1.1 Hz, 1H), 5.48 (s, 2H), 5.02 (t, J = 7.4 Hz, 1H), 4.37 (dd, J = 8.5, 7.4 Hz, 1H), 3.92 (dd, J = 8.5, 6.3 Hz, 1H), 3.82-3.75 (m, 1H), 2.69 (s, 3H), 2.59 (ddd, J = 12.5, 7.1, 5.1 Hz, 1H), 2.15 (ddd, J = 12.7, 9.0, 7.8 Hz, 1H). |
| 101 | 1H NMR (400 MHz, DMSO-d6) 8.00 (s, 1H), 7.43-7.27 (m, 4H), 5.32 (s, 2H), 4.99 (t, J = 7.3 Hz, 1H), 4.34 (dd, J = 8.5, 7.5 Hz, 1H), 3.89 (dd, J = 8.5, 6.3 Hz, 1H), 3.79-3.71 (m, 1H), 3.72- |

TABLE 2-continued

| | |
|---|---|
| | 3.66 (m, 4H), 3.52-3.45 (m, 4H), 2.56 (ddd, J = 12.4, 7.0, 5.1 Hz, 1H), 2.36 (s, 3H), 2.17-2.08 (m, 1H). |
| 102 | $^1$H NMR (400 MHz, DMSO-d$_6$) δ 9.12 (t, J = 5.6 Hz, 1H), 7.79 (s, 1H), 7.68 (s, 1H), 7.42-7.37 (m, 4H), 5.03 (t, J = 7.4 Hz, 1H), 4.70 (d, J = 5.6 Hz, 2H), 4.40-4.36 (m, 1H), 3.95-3.91 (m, 1H), 3.80 (s, 3H), 3.77-3.73(m, 1H), 2.63-2.57(m, 1H), 2.19-2.12 (m, 1H). |
| 103 | — |
| 104 | 1H NMR (400 MHz, DMSO-d6) δ 8.97 (d, J = 4.7 Hz, 1H), 8.50 (s, 1H), 7.69 (dd, J = 4.9, 1.0 Hz, 1H), 7.45-7.35 (m, 2H), 7.21-7.11 (m, 2H), 5.66 (s, 2H), 5.00 (t, J = 7.4 Hz, 1H), 4.36 (dd, J = 8.6, 7.4 Hz, 1H), 3.90 (dd, J = 8.5, 6.3 Hz, 1H), 3.83-3.72 (m, 1H), 2.83 (d, J = 0.8 Hz, 3H), 2.57 (ddd, J = 12.3, 7.0, 5.0 Hz, 1H), 2.15 (ddd, J = 12.7, 9.0, 7.8 Hz, 1H). |
| 105 | 1H NMR (400 MHz, DMSO-d6) 7.96 (s, 1H), 7.45-7.35 (m, 4H), 5.31 (s, 2H), 5.02 (t, J = 7.4 Hz, 1H), 4.36 (dd, J = 8.5, 7.4 Hz, 1H), 3.92 (dd, J = 8.6, 6.3 Hz, 1H), 3.83-3.71 (m, 1H), 3.08 (s, 6H), 2.59 (ddd, J = 12.5, 7.1, 5.2 Hz, 1H), 2.37 (s, 3H), 2.15 (ddd, J = 12.7, 8.9, 7.7 Hz, 1H). |
| 106 | $^1$H NMR (400 MHz, DMSO-d$_6$) δ 7.68 (d, J = 7.5 Hz, 1H), 7.44-7.35 (m, 2H), 7.16 (t, J = 8.9 Hz, 2H), 7.00 (d, J = 7.4 Hz, 1H), 5.58 (s, 2H), 5.00 (t, J = 7.4 Hz, 1H), 4.39 (s, 3H), 4.35 (dd, J = 8.5, 7.5 Hz, 1H), 3.89 (dd, J = 8.5, 6.3 Hz, 1H), 3.81-3.71 (m, 1H), 2.56 (ddd, J = 12.4, 7.0, 5.1 Hz, 1H), 2.15 (ddd, J = 12.7, 8.9, 7.8 Hz, 1H). |
| 107 | 1H NMR (400 MHz, DMSO-d6) 8.35 (s, 1H), 7.44-7.34 (m, 4H), 5.42 (s, 2H), 5.01 (t, J = 7.3 Hz, 1H), 4.36 (dd, J = 8.5, 7.4 Hz, 1H), 3.91 (dd, J = 8.6, 6.3 Hz, 1H), 3.83-3.73 (m, 1H), 2.58 (ddd, J = 12.4, 7.0, 5.1 Hz, 1H), 2.47 (s, 3H), 2.19-2.08 (m, 1H). |
| 108 | 1H NMR (400 MHz, dmso) 8.55 (s, 1H), 7.99 (d, J = 5.4 Hz, 1H), 7.41-7.35 (m, 4H), 7.00 (d, J = 5.4 Hz, 1H), 6.86 (s, 2H), 5.56 (s, 2H), 5.00 (t, J = 7.4 Hz, 1H), 4.35 (dd, J = 8.5, 7.4 Hz, 1H), 3.89 (dd, J = 8.6, 6.3 Hz, 1H), 3.79-3.72 (m, 1H), 2.56 (ddd, J = 12.5, 7.1, 5.2 Hz, 1H), 2.13 (ddd, J = 12.7, 8.9, 7.7 Hz, 1H). |
| 109 | $^1$H NMR (300 MHz, DMSO-d$_6$) δ 7.39 (m, 4H), 5.63 (s, 2H), 5.01 (t, J = 7.3 Hz, 1H), 4.35 (dd, J = 8.6, 7.4 Hz, 1H), 3.98-3.82 (m, 4H), 3.75 (m, 1H), 2.63-2.53 (m, 4H), 2.45 (s, 3H), 2.13 (m, 1H). |
| 110 | $^1$H NMR (300 MHz, DMSO-d$_6$) δ 7.46-7.33 (m, 4H), 5.64 (s, 2H), 5.01 (t, J = 7.4 Hz, 1H), 4.35 (dd, J = 8.5, 7.4 Hz, 1H), 3.94 (s, 3H), 3.95-3.86 (m, 1H), 3.83-3.70 (m, 1H), 2.61 (s, 3H), 2.66-2.51 (m, 1H), 2.14 (m, 1H). |
| 111 | $^1$H NMR (400 MHz, DMSO-d$_6$) δ 11.74 (s, 1H), 7.44-7.35 (m, 4H), 5.60 (s, 2H), 5.01 (t, J = 7.3 Hz, 1H), 4.35 (dd, J = 8.6, 7.4 Hz, 1H), 3.96-3.88 (m, 1H), 3.81-3.70 (m, 1H), 3.37 (s, 3H), 2.64-2.53 (m, 1H), 2.57 (s, 3H), 2.14 (m, 1H). |
| 112 | 1H NMR (400 MHz, dmso) 7.99 (d, J = 3.1 Hz, 1H), 7.75 (d, J = 3.1 Hz, 1H), 7.70 (s, 2H), 7.42-7.34 (m, 4H), 5.67 (s, 2H), 4.98 (t, J = 7.3 Hz, 1H), 4.37-4.30 (m, 1H), 3.87 (dd, J = 8.5, 6.2 Hz, 1H), 3.78-3.70 (m, 1H), 2.58-2.52 (m, 1H), 2.17-2.08 (m, 1H). |
| 113 | $^1$H NMR (300 MHz, DMSO-d$_6$) δ 7.40 (m, 4H), 6.81 (s, 2H), 5.57 (s, 2H), 5.01 (t, J = 7.3 Hz, 1H), 4.36 (dd, J = 8.5, 7.4 Hz, 1H), 3.91 (m, 1H), 3.83-3.70 (m, 1H), 3.61 (s, 3H), 2.66-2.53 (m, 1H), 2.52 (s, 3H), 2.14 (m, 1H). |
| 114 | $^1$H NMR (300 MHz, DMSO-d$_6$) δ 7.46-7.33 (m, 4H), 5.65 (s, 2H), 5.01 (t, J = 7.3 Hz, 1H), 4.35 (dd, J = 8.6, 7.4 Hz, 1H), 3.91 (dd, J = 8.5, 6.3 Hz, 1H), 3.90 (s, 3H), 3.75 (m, 1H), 2.62 (s, 3H), 2.61-2.53 (m, 1H), 2.14 (m, 1H). |
| 115 | $^1$H NMR (400 MHz, DMSO-d$_6$) δ 8.75 (s, 1H), 8.61 (s, 1H), 7.44-7.34 (m, 4H), 5.57 (s, 2H), 5.02 (t, J = 7.3 Hz, 1H), 4.37 (dd, J = 8.6, 7.4 Hz, 1H), 3.93 (dd, J = 8.6, 6.2 Hz, 1H), 3.84-3.72 (m, 1H), 2.61-2.56 (m, 1H), 2.16-2.12 (m, 1H). |
| 116 | $^1$H NMR (400 MHz, DMSO-d$_6$) δ 8.54 (s, 1H), 8.44 (d, J = 10.2 Hz, 1H), 8.07 (s, 1H), 7.39 (d, J = 1.1 Hz, 4H), 5.76 (s, 2H), 5.01 (t, J = 7.4 Hz, 1H), 4.36 (dd, J = 8.6, 7.4 Hz, 1H), 4.06 (s, 3H), 3.92 (dd, J = 8.6, 6.3 Hz, 1H), 3.82-3.72 (m, 1H), 2.64-2.55 (m, 1H), 2.20-2.08 (m, 1H). |
| 117 | 1H NMR (400 MHz, dmso) 8.41 (s, 1H), 7.43-7.35 (m, 4H), 5.49 (s, 2H), 5.01 (t, J = 7.4 Hz, 1H), 4.39-4.32 (m, 1H), 3.90 (dd, J = 8.5, 6.3 Hz, 1H), 3.80-3.71 (m, 1H), 2.61-2.53 (m, 1H), 2.46 (s, 3H), 2.19-2.09 (m, 1H). |
| 118 | 1H NMR (400 MHz, dmso) 10.55 (s, 1H), 8.49 (s, 1H), 7.52-7.24 (m, 4H), 5.41 (d, J = 14.2 Hz, 2H), 5.02 (t, J = 7.3 Hz, 1H), 4.39-4.28 (m, 1H), 3.91 (dd, J = 8.5, 6.3 Hz, 1H), 3.76 (dt, J = 13.5, 6.9 Hz, 1H), 2.70-2.54 (m, 4H), 2.49-2.47 (m, 1H), 2.24-2.05 (m, 1H). |
| 119 | $^1$H NMR (400 MHz, DMSO-d$_6$) δ 8.72 (dd, J = 4.6, 2.1 Hz, 1H), 8.25 (dd, J = 7.8, 2.1 Hz, 1H), 7.58 (s, 2H), 7.38 (m, 1H), 7.21-7.04 (m, 4H), 5.53 (s, 2H), 5.03 (t, J = 7.3 Hz, 1H), 4.36 (dd, J = 8.5, 7.3 Hz, 1H), 3.90 (dd, J = 8.6, 6.2 Hz, 1H), 3.75 (m, 1H), 2.59 (m, 1H), 2.16 (m, 1H). |
| 120 | 1H NMR (400 MHz, DMSO-d6): 8.58 (d, J = 0.4 Hz, 1H), 7.47-7.32 (m, 4H), 5.94 (s, 2H), 5.03 (t, J = 7.4 Hz, 1H), 4.39 (dd, J = 8.5, 7.4 Hz, 1H), 4.01 (d, J = 0.4 Hz, 3H), 3.95 (dd, J = 8.6, 6.1 Hz, 1H), 3.88-3.76 (m, 1H), 2.64-2.54 (m, 1H), 2.23-2.10 (m, 1H). |
| 121 | 1H NMR (400 MHz, dmso) 9.68 (s, 1H), 8.30 (s, 1H), 7.45-7.36 (m, 4H), 5.03 (t, J = 7.4 Hz, 1H), 4.78 (s, 2H), 4.42-4.34 (m, 1H), 4.21 (s, 3H), 3.93 (dd, J = 8.5, 6.3 Hz, 1H), 3.82-3.72 (m, 1H), 2.65-2.56 (m, 1H), 2.20-2.11 (m, 1H) |
| 122 | $^1$H NMR (400 MHz, DMSO-d$_6$) δ 8.42 (s, 1H), 7.85-7.79 (m, 2H), 7.77 (s, 1H), 7.59-7.52 (m, 2H), 5.49 (s, 2H), 5.11 (t, J = 7.3 Hz, 1H), 4.38 (dd, J = 8.6, 7.3 Hz, 1H), 3.95 (dd, J = 8.6, 6.2 Hz, 1H), 3.82-3.71 (m, 1H), 2.70-2.60 (m, 1H), 2.35 (s, 3H), 2.15 (m, 1H). |
| 123 | 1H NMR (400 MHz, dmso) 8.14 (s, 1H), 7.42-7.32 (m, 4H), 7.00 (s, 2H), 5.74 (s, 2H), 5.07-4.94 (m, 1H), 4.41-4.29 (m, 1H), 3.88 (dt, J = 18.5, 9.3 Hz, 1H), 3.81-3.65 (m, 1H), 3.43-3.38 (m, 3H), 2.56 (ddd, J = 12.4, 7.1, 5.2 Hz, 1H), 2.19-2.07 (m, 1H). |
| 124 | 1H NMR (400 MHz, dmso) 8.66 (s, 1H), 7.89 (d, J = 9.5 Hz, 1H), 7.43-7.36 (m, 4H), 6.41 (d, J = 9.5 Hz, 1H), 5.51 (s, 2H), 5.01 (t, J = 7.4 Hz, 1H), 4.35 (dd, J = 8.5, 7.4 Hz, 1H), 3.90 (dd, J = 8.6, 6.3 Hz, 1H), 3.80-3.72 (m, 1H), 2.57 (ddd, J = 12.5, 7.1, 5.2 Hz, 1H), 2.18-2.10 (m, 1H). |
| 125 | $^1$H NMR (400 MHz, DMSO-d$_6$) δ 7.95 (d, J = 3.0 Hz, 1H), 7.42-7.36 (m, 1H), 7.22-7.15 (m, 2H), 7.15-7.05 (m, 1H), 6.90 (s, 2H), 5.47 (s, 2H), 5.04 (t, J = 7.3 Hz, 1H), 4.36 (dd, J = 8.5, 7.3 Hz, 1H), 3.91 (dd, J = 8.5, 6.2 Hz, 1H), 3.83 (s, 3H), 3.81-3.71 (m, 1H), 2.63-2.56 (m, 1H), 2.20-2.13 (m, 1H). |
| 126 | 1H NMR (400 MHz, dmso) 8.50 (s, 1H), 8.34 (s, 2H), 7.43-7.37 (m, 2H), 7.19-7.13 (m, 2H), 5.51 (s, 2H), 4.99 (t, J = 7.4 Hz, 1H), 4.35 (dd, J = 8.5, 7.4 Hz, 1H), 3.89 (dd, J = 8.5, 6.3 Hz, 1H), 3.77 (ddd, J = 18.7, 7.9, 5.7 Hz, 1H), 2.55 (ddd, J = 12.3, 7.0, 5.1 Hz, 1H), 2.15 (ddd, J = 12.7, 8.9, 7.8 Hz, 1H). |

TABLE 2-continued

| | |
|---|---|
| 127 | ¹H NMR (400 MHz, DMSO-d₆) δ 7.95 (d, J = 3.0 Hz, 1H), 7.39 (m, 1H), 7.22-7.15 (m, 2H), 7.15-7.05 (m, 1H), 6.90 (s, 2H), 5.47 (s, 2H), 5.04 (t, J = 7.3 Hz, 1H), 4.36 (dd, J = 8.5, 7.3 Hz, 1H), 3.91 (dd, J = 8.5, 6.2 Hz, 1H), 3.83 (s, 3H), 3.81-3.71 (m, 1H), 2.60 (m, 1H), 2.17 (m, 1H). |
| 128 | 1H NMR (400 MHz, dmso) 7.54-7.52 (m, 1H), 7.43- 7.37 (m, 4H), 7.11 (s, 2H), 5.39 (s, 2H), 5.02 (t, J = 7.4 Hz, 1H), 4.39-4.33 (m, 1H), 3.90 (dd, J = 8.5, 6.3 Hz, 1H), 3.80-3.72 (m, 1H), 2.61-2.54 (m, 1H), 2.19-2.10 (m, 1H), 1.80 (d, J = 0.9 Hz, 3H). |
| 129 | 1H NMR (400 MHz, dmso) 8.50 (s, 1H), 8.33 (s, 2H), 7.43-7.35 (m, 4H), 5.51 (s, 2H), 5.01 (t, J = 7.3 Hz, 1H), 4.39-4.32 (m, 1H), 3.90 (dd, J = 8.5, 6.3 Hz, 1H), 3.83-3.70 (m, 1H), 2.57 (ddd, J = 12.6, 7.1, 5.3 Hz, 1H), 2.20-2.08 (m, 1H). |
| 130 | 1H NMR (400 MHz, DMSO-d₆) 8.53 (dd, J = 4.8, 1.9 Hz, 1H), 8.28 (dd, J = 7.6, 1.9 Hz, 1H), 7.68 (br. s, 2H), 7.42-7.35 (m, 2H), 7.33 (dd, J = 7.6, 4.8 Hz, 1H), 7.20-7.11 (m, 2H), 5.79 (s, 2H), 4.98 (t, J = 7.4 Hz, 1H), 4.33 (dd, J = 8.5, 7.4 Hz, 1H), 3.86 (dd, J = 8.5, 6.2 Hz, 1H), 3.80-3.67 (m, 1H), 2.56-2.52 (m, 1H), 2.19-2.07 (m, 1H). |
| 131 | ¹H NMR (400 MHz, DMSO-d₆) δ 8.52 (s, 1H), 7.45-7.35 (m, 4H), 5.85 (s, 2H), 5.01 (t, J = 7.4 Hz, 1H), 4.37-4.33 (m, 1H), 4.07 (s, 3H), 3.92-3.89 (m, 1H), 3.86-3.72 (m, 1H), 2.60-2.53 (m, 1H), 2.20-2.06 (m, 1H). |
| 132 | ¹H NMR (400 MHz, DMSO-d₆) δ 7.45-7.35 (m, 4H), 5.58 (s, 2H), 5.01 (t, J = 7.4 Hz, 1H), 4.36 (t, J = 7.9 Hz, 1H), 3.96 (s, 3H), 3.91 (dd, J = 8.6, 6.3 Hz, 1H), 3.76 (t, J = 7.4 Hz, 1H), 2.61-2.56 (m, 1H), 2.17-2.12 (m, 1H). |
| 133 | 1H NMR (400 MHz, DMSO-d6) 8.48 (d, J = 4.8 Hz, 1H), 7.46 (s, 2H), 7.43-7.36 (m, 2H), 7.20-7.12 (m, 2H), 6.93 (dd, J = 4.8, 0.8 Hz, 1H), 5.47 (s, 2H), 5.00 (t, J = 7.3 Hz, 1H), 4.36 (dd, J = 8.5, 7.4 Hz, 1H), 3.89 (dd, J = 8.5, 6.3 Hz, 1H), 3.81-3.72 (m, 1H), 2.64 (d, J = 0.5 Hz, 3H), 2.56 (ddd, J = 12.4, 7.0, 5.1 Hz, 1H), 2.15 (ddd, J = 12.7, 8.9, 7.8 Hz, 1H). |
| 134 | 1H NMR (500 MHz, DMSO-d6) 8.48 (s, 1H, formate proton), 8.32 (d, J = 5.0 Hz, 1H), 7.61 (s, 2H), 7.43-7.33 (m, 4H), 7.14 (d, J = 5.0 Hz, 1H), 5.75 (s, 2H), 4.99 (t, J = 7.4 Hz, 1H), 4.33 (dd, J = 8.5, 7.4 Hz, 1H), 3.86 (dd, J = 8.5, 6.3 Hz, 1H), 3.79-3.67 (m, 1H), 2.75 (s, 3H), 2.54 (ddd, J = 8.9, 7.1, 3.4 Hz, 1H), 2.12 (ddd, J = 12.7, 8.9, 7.7 Hz, 1H). |
| 135 | 1H NMR (500 MHz, DMSO-d6) 8.48 (d, J = 4.8 Hz, 1H), 7.48 (s, 2H), 7.41-7.35 (m, 4H), 6.94-6.90 (m, 1H), 5.48 (s, 2H), 5.01 (t, J = 7.4 Hz, 1H), 4.35 (dd, J = 8.5, 7.5 Hz, 1H), 3.90 (dd, J = 8.6, 6.3 Hz, 1H), 3.81-3.70 (m, 1H), 2.64 (s, 3H), 2.58 (ddd, J = 12.5, 7.1, 5.2 Hz, 1H), 2.14 (ddd, J = 12.7, 8.8, 7.7 Hz, 1H). |
| 136 | ¹H NMR (300 MHz, DMSO-d₆) δ 7.95 (s, 1H), 7.72 (d, J = 8.2 Hz, 2H), 7.59 (d, J = 8.1 Hz, 2H), 6.91 (s, 2H), 5.49 (s, 2H), 5.13 (t, J = 7.4 Hz, 1H), 4.45-4.34 (m, 1H), 3.95 (dd, J = 8.5, 6.2 Hz, 1H), 3.84 (s, 4H), 2.61-2.56 (m, 1H), 2.17-2.12 (m, 1H). |
| 137 | 1H NMR (400 MHz, dmso) 8.16 (s, 1H), 7.40-7.34 (m, 2H), 7.17-7.10 (m, 2H), 5.61 (s, 2H), 4.97 (t, J = 7.4 Hz, 1H), 4.32 (dd, J = 8.5, 7.5 Hz, 1H), 3.91 (s, 3H), 3.87 (dd, J = 8.6, 6.3 Hz, 1H), 3.78-3.68 (m, 1H), 2.57 (d, J = 3.8 Hz, 3H), 2.53 (ddd, J = 10.1, 7.7, 4.2 Hz, 1H), 2.12 (ddd, J = 12.7, 8.9, 7.8 Hz, 1H). |
| 138 | 1H NMR (400 MHz, cd3od) 8.22 (s, 1H), 7.98-7.96 (m, 1H), 7.76-7.72 (m, 1H), 7.69 (s, 1H), 7.58-7.55 (m, 1H), 7.21-7.13 (m, 1H), 5.49 (s, 2H), 5.27 (t, J = 7.4 Hz, 1H), 4.51 (dd, J = 8.7, 7.4 Hz, 1H), 4.13 (dd, J = 8.7, 6.3 Hz, 1H), 4.07 (s, 3H), 3.88-3.79 (m, 1H), 2.80-2.72 (m, 1H), 2.47-2.44 (m, 3H), 2.37-2.28 (m, 1H). |
| 139 | 1H NMR (400 MHz, dmso) 13.01 (s, 1H), 8.43 (s, 1H), 8.03 (s, 1H), 7.77 (s, 1H), 7.72 (d, J = 8.3 Hz, 1H), 7.50-7.47 (m, 1H), 7.11-7.07 (m, 1H), 5.49 (s, 2H), 5.14 (t, J = 7.3 Hz, 1H), 4.41 (dd, J = 8.5, 7.3 Hz, 1H), 3.95 (dd, J = 8.6, 6.3 Hz, 1H), 3.85-3.76 (m, 1H), 2.68-2.59 (m, 1H), 2.36 (s, 3H), 2.27-2.17 (m, 1H). |
| 140 | ¹H NMR (400 MHz, DMSO-d₆) δ 8.89 (s, 1H), 7.44-7.35 (m, 4H), 5.74 (s, 2H), 5.01 (t, J = 7.4 Hz, 1H), 4.44 (s, 3H), 4.36 (dd, J = 8.6, 7.4 Hz, 1H), 3.91 (dd, J = 8.6, 6.3 Hz, 1H), 3.82-3.71 (m, 1H), 2.61-2.56 (m, 1H), 2.20-2.05 (m, 1H). |
| 141 | 1H NMR (500 MHz, DMSO-d6): Clean product. 8.54 (s, 1H), 7.45-7.30 (m, 4H), 6.00 (s, 2H), 5.01 (t, J = 7.4 Hz, 1H), 4.36 (dd, J = 8.5, 7.4 Hz, 1H), 4.02 (s, 3H), 3.91 (dd, J = 8.6, 6.3 Hz, 1H), 3.80-3.71 (m, 1H), 2.58 (ddd, J = 12.6, 7.1, 5.2 Hz, 1H), 2.14 (ddd, J = 12.7, 8.9, 7.7 Hz, 1H). |
| 142 | 1H NMR (400 MHz, dmso) 9.35 (s, 1H), 8.41 (s, 1H), 8.15-8.13 (m, 1H), 8.04 (d, J = 8.4 Hz, 1H), 7.75 (s, 1H), 7.51 (dd, J = 8.6, 1.6 Hz, 1H), 5.48 (s, 2H), 5.17 (t, J = 7.2 Hz, 1H), 4.43-4.38 (m, 1H), 3.94 (dd, J = 8.5, 6.3 Hz, 1H), 3.85-3.77 (m, 1H), 2.67-2.60 (m, 1H), 2.34 (s, 3H), 2.27-2.19 (m, 1H). |
| 143 | 1H NMR (400 MHz, dmso) 7.75 (s, 1H), 7.44-7.36 (m, 2H), 7.21-7.12 (m, 2H), 7.10 (s, 2H), 5.48 (s, 2H), 5.00 (t, J = 7.4 Hz, 1H), 4.41-4.31 (m, 1H), 3.90 (dd, J = 8.5, 6.3 Hz, 1H), 3.82-3.72 (m, 1H), 2.62-2.51 (m, 1H), 2.21-2.10 (m, 1H). |
| 144 | 1H NMR (400 MHz, DMSO-d6) δ 7.93 (s, 1H), 7.45-7.35 (m, 2H), 7.21-7.11 (m, 2H), 6.87 (s, 2H), 5.48 (s, 2H), 5.00 (t, J = 7.3 Hz, 1H), 4.35 (dd, J = 8.5, 7.4 Hz, 1H), 3.89 (dd, J = 8.5, 6.3 Hz, 1H), 3.83 (s, 3H), 3.81-3.70 (m, 1H), 2.56 (ddd, J = 12.3, 7.0, 5.0 Hz, 1H), 2.15 (ddd, J = 12.7, 9.0, 7.7 Hz, 1H). |
| 145 | ¹H NMR (400 MHz, DMSO-d6) 8.15 (s, 1H), 7.43-7.35 (m, 2H), 7.21-7.11 (m, 2H), 6.23 (t, J = 6.1 Hz, 1H), 5.44 (d, J = 4.8 Hz, 2H), 4.99 (t, J = 7.4 Hz, 1H), 4.77 (t, J = 6.2 Hz, 1H), 4.35 (t, J = 8.0 Hz, 1H), 3.89 (dd, J = 8.6, 6.3 Hz, 1H), 3.77 (t, J = 7.5 Hz, 1H), 2.15 (s, 4H), 1.23 (s, 1H). |
| 146 | ¹H NMR (400 MHz, DMSO-d6) 9.68 (s, 2H), 7.96 (s, 1H), 7.40 (d, J = 1.7 Hz, 4H), 5.64 (s, 2H), 5.01 (t, J = 7.4 Hz, 1H), 4.40-4.29 (m, 1H), 4.18 (s, 2H), 3.91 (dd, J = 8.6, 6.2 Hz, 1H), 3.83-3.73 (m, 1H), 3.34 (d, J = 5.9 Hz, 2H), 2.72 (t, J = 6.1 Hz, 2H), 2.61-2.55 (m, 1H), 2.21-2.09 (m, 1H). |
| 147 | 1H NMR (400 MHz, dmso) 9.03 (dd, J = 4.6, 2.0 Hz, 1H), 8.77 (s, 1H), 8.57 (dd, J = 7.9, 2.0 Hz, 1H), 7.63 (dd, J = 7.9, 4.6 Hz, 1H), 7.43-7.35 (m, 2H), 7.19-7.12 (m, 2H), 5.60 (s, 2H), 4.99 (t, J = 7.4 Hz, 1H), 4.35 (dd, J = 8.5, 7.4 Hz, 1H), 3.88 (dd, J = 8.5, 6.3 Hz, 1H), 3.82-3.72 (m, 1H), 2.60-2.51 (m, 1H), 2.19-2.10 (m, 1H). |
| 148 | 1H NMR (400 MHz, DMSO-d6) δ 8.58 (d, J = 2.5 Hz, 1H), 8.41 (s, 1H), 7.93 (dd, J = 8.4, 2.5 Hz, 1H), 7.76 (s, 1H), 7.51 (d, J = 8.4 Hz, 1H), 5.48 (s, 2H), 5.11 (t, J = 7.0 Hz, 1H), 4.34 (t, J = 7.9 Hz, 1H), 3.96 (dd, J = 8.5, 6.0 Hz, 1H), 3.76 (ddd, J = 13.6, 8.0, 6.0 Hz, 1H), 2.59 (ddd, J = 13.1, 7.6, 5.8 Hz, 1H), 2.44-2.32 (m, 1H), 2.36 (s, 3H). |

TABLE 2-continued 149  1H NMR (400 MHz, DMSO-d6) 7.88 (s, 1H), 7.42-7.36 (m, 4H), 7.34 (s, 2H), 5.49 (s, 2H),
     5.01 (t, J = 7.4 Hz, 1H), 4.35 (dd, J = 8.4, 7.4 Hz, 1H), 3.90 (dd, J = 8.5, 6.3 Hz, 1H), 3.80-3.69
     (m, 1H), 2.57 (ddd, J = 12.5, 7.1, 5.2 Hz, 1H), 2.19-2.07 (m, 1H).
150  1H NMR (400 MHz, dmso) 7.57 (s, 1H), 7.43-7.35 (m, 4H), 6.78 (s, 2H), 5.50 (s, 2H), 5.01 (t, J =
     7.4 Hz, 1H), 4.35 (dd, J = 8.5, 7.4 Hz, 1H), 4.08 (s, 3H), 3.90 (dd, J = 8.5, 6.3 Hz, 1H), 3.81-
     3.69 (m, 1H), 2.62-2.53 (m, 1H), 2.20-2.09(m, 1H).
151  1H NMR (400 MHz, dmso) 8.34 (s, 1H), 8.06 (s, 1H), 7.44-7.33 (m, 4H), 5.59 (s, 2H), 5.01 (t, J =
     7.3 Hz, 1H), 4.38-4.32 (m, 1H), 4.19 (s, 3H), 3.93-3.87(m, 1H), 3.80-3.71 (m, 1H), 2.63-2.53
     (m, 1H), 2.19-2.08 (m, 1H).
152  1H NMR (400 MHz, dmso) 7.43-7.35 (m, 4H), 6.83 (s, 2H), 5.46 (s, 2H), 5.01 (t, J = 7.4 Hz,
     1H), 4.39-4.32 (m, 1H), 3.90 (dd, J = 8.5, 6.3 Hz, 1H), 3.77 (s, 3H), 3.79-3.69 (m, 1H), 2.61-
     2.53 (m, 1H), 2.36 (s, 3H), 2.18-2.09 (m, 1H)
153  $^1$H NMR (400 MHz, DMSO-d$_6$) δ 8.59 (s, 1H), 7.42-7.37 (m, 4H), 5.60 (s, 2H), 5.01 (t, J = 7.2
     Hz 1H) 4.38-4.34 (m, 1H) 3.93-3.89 (m, 1H) 3.80-3.73 (m, 1H) 3.39 (s, 3H) 2.61-2.54
     (m, 1H), 2.18-2.10 (m, 1H).
154  1H NMR (400 MHz, dmso) 9.47 (s, 1H), 7.52 (s, 2H), 7.43-7.36 (m, 2H), 7.19-7.12 (m, 2H),
     5.52 (s, 2H) 5.00 (t, J = 7.5 Hz, 1H) 4.38-4.32 (m, 1H) 3.89 (dd, J = 8.5, 6.3 Hz, 1H), 3.81-
     3.72 (m, 1H), 2.59-2.52 (m, 1H), 2.20-2.11 (m, 1H).
155  1H NMR (400 MHz, DMSO-d6) δ 7.83 (dd, J = 5.0, 1.4 Hz, 1H), 7.46 (dd, J = 7.7, 1.4 Hz, 1H),
     7.43-7.33 (m, 4H), 7.01 (dd, J = 7.7, 5.0 Hz, 1H), 6.98 (s, 2H), 5.65 (s, 2H), 5.00 (t, J = 7.4 Hz,
     1H), 4.34 (dd, J = 8.5, 7.3 Hz, 1H), 3.88 (dd, J = 8.5, 6.2 Hz, 1H), 3.80-3.68 (m, 1H), 2.61-
     2.51 (m, 1H), 2.12 (ddd, J = 12.7, 8.9, 7.6 Hz, 1H).
156  $^1$H NMR (400 MHz, DMSO-d$_6$) δ 7.41-7.36 (m, 4H), 7.30 (s, 2H), 5.50 (s, 2H), 5.01 (t, J = 7.2
     Hz, 1H), 4.37-4.33 (m, 1H), 4.23 (s, 3H), 3.91-3.87 (m, 1H), 3.78-3.73 (m, 1H), 2.60-2.54
     (m, 1H), 2.17-2.10 (m, 1H).
157  1H NMR (400 MHz, dmso) 8.14 (s, 1H), 7.39 (dd, J = 8.5, 5.6 Hz, 2H), 7.16 (t, J = 8.9 Hz, 2H),
     7.00 (s, 2H) 5.74 (s, 2H) 4.99 (t, J = 7.3 Hz, 1H) 4.39-4.31 (m, 1H) 3.88 (dd, J = 8.5, 6.2 Hz,
     1H), 3.80-3.71 (m, 1H), 3.40 (s, 3H), 2.58-2.51 (m, 1H), 2.19-2.10 (m, 1H).
158  1H NMR (400 MHz, dmso) 9.47 (s, 1H), 7.52 (s, 2H), 7.43-7.35 (m, 4H), 5.52 (s, 2H), 5.01 (t, J =
     7.4 Hz, 1H), 4.39-4.32 (m, 1H), 3.90 (dd, J = 8.5, 6.3 Hz, 1H), 3.81-3.71 (m, 1H), 2.61-2.53
     (m, 1H), 2.19-2.09 (m, 1H).

$IC_{50}$ Determinations of Exemplified Compounds

The $IC_{50}$ (effective concentration) of compounds on the human TRPA1 channel was determined using a FLIPR Tetra instrument. CHO cells expressing TRPA1 were plated into 384-well plates, incubated overnight at 37° C., and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 10 minutes or 90 minutes at room temperature prior to adding agonist. Following this incubation, about an $EC_{80}$ concentration of cinnamaldehyde (75) was added to active the channels and block of cinnamaldehyde induced calcium influx was measured.

The $IC_{50}$ results were fit with a standard Hill function, keeping the Hill coefficient (n) fixed to 1.5. Fixing the Hill coefficient will generally reduce variability of the $IC_{50}$ determination. The $IC_{50}$ results were individually examined to make sure the MIN and MAX points were set correctly prior to validation of the results.

The $IC_{50}$ (hTRPA1 $IC_{50}$ (micromolar)) results for compounds of the present disclosure are shown in Table 1 above where "hTRPA1" refers to hTRPA1 CHO Ca2+ MAX EVO ($IC_{50}$).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of formula I,

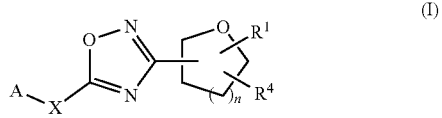

or a pharmaceutically acceptable salt thereof, wherein:

A is selected from:

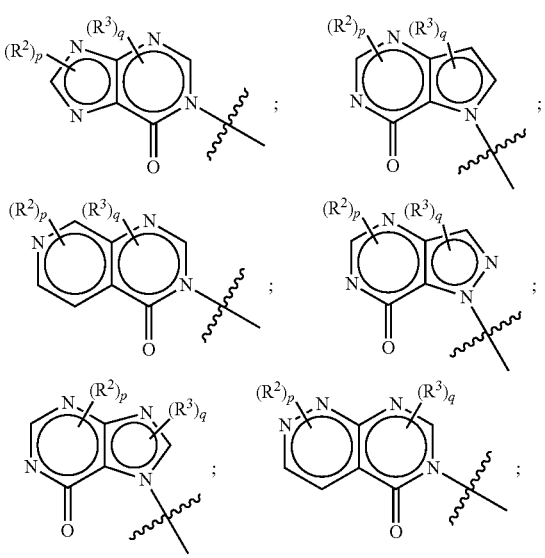

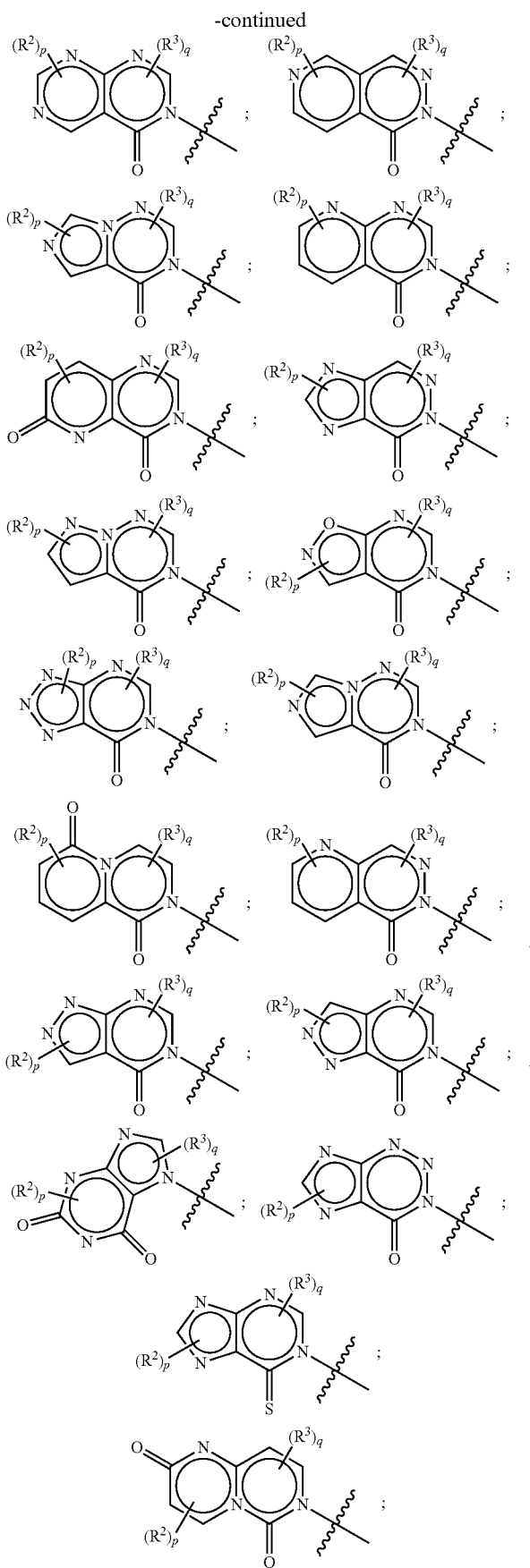
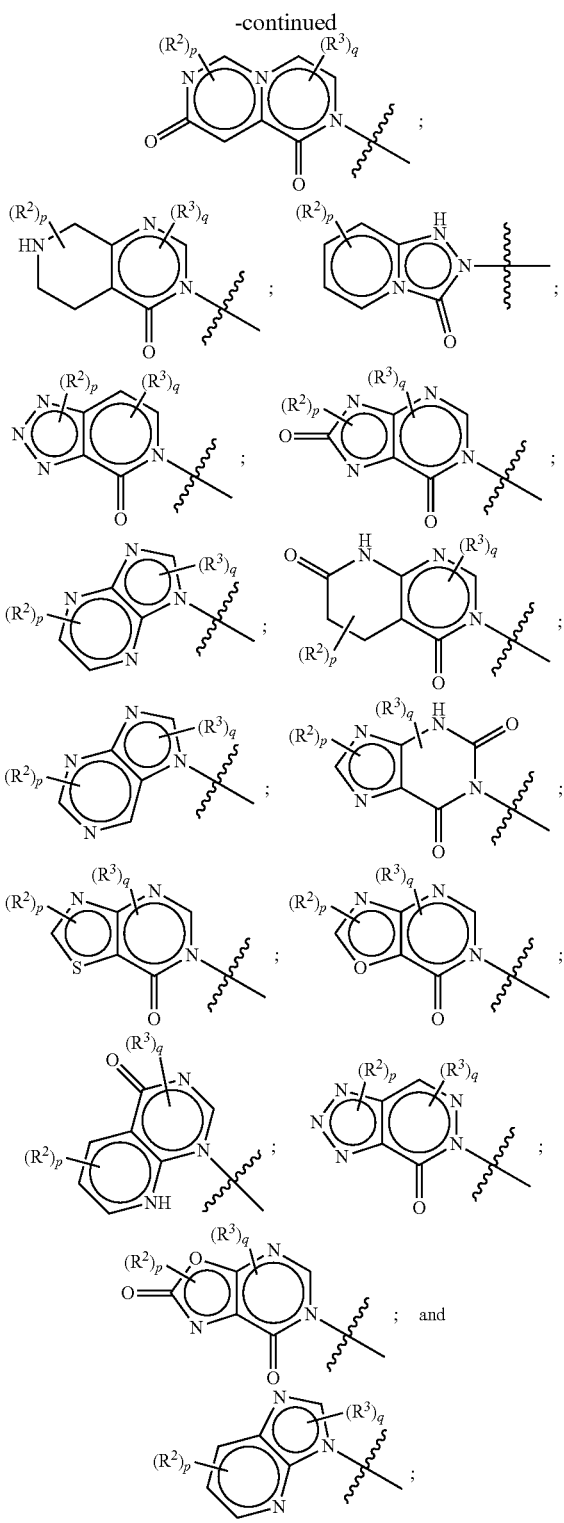
X is; a bond; $C_{1-4}$ alkylene; —O—; —S—; —SO$_2$—; or —N(R$^a$)—;
n is: 0, 1, 2 or 3;
R$^a$ is H or $C_{1-6}$ alkyl which may be unsubstituted or substituted one or more times with halo;
R$^1$ is: H; or $C_{1-6}$alkyl; and
each R$^2$ is independently: H; D; —$C_{1-4}$ alkyl; —$C_{1-4}$ haloalkyl; $C_{1-4}$ alkoxy; —CN, halo; halo-$C_{1-}$ ₄alkoxy; —OH; —SO₂—C₁₋₄alkyl; —C₁₋₄CN, C₁₋₄ aldehyde; C₁₋₄ ketone; benzylamino; or NR¹⁴R¹⁵—;

each R³ is independently: H; D: —C₁₋₄ alkyl; —C₁₋₄ haloalkyl; —CN; NR¹⁴R¹⁵; or halo;

R⁴ is: substituted or unsubstituted phenyl; substituted or unsubstituted heteroaryl; or substituted or unsubstituted naphthyl;

or R¹ and R⁴ may together form an unsubstituted or substituted C₃₋₆cylcoalkyl fused to a substituted or unsubstituted phenyl; substituted or unsubstituted heteroaryl; or substituted or unsubstituted naphthyl, p is 0, 1 or 2;

q is 0 or 1;

R¹⁴ and R¹⁵ are each independently: H; substituted or unsubstituted —C₁₋₄ alkyl; substituted or unsubstituted —C(O)—C₁₋₄ alkyl; substituted or unsubstituted C₃₋₆ cycloalkyl; substituted or unsubstituted 3- to 6-membered heterocycloalkyl; substituted or unsubstituted —C₁₋₄ heteroalkyl; —C(O)NR¹⁶R¹⁷; substituted or unsubstituted alkyl-C(O)NR¹⁶R¹⁷; substituted or unsubstituted phenyl; or substituted or unsubstituted benzyl;

or R¹⁴ and R¹⁵ together with the atoms to which they are attached may form a 4-, 5-, 6- or 7-membered ring that optionally includes one additional heteroatom selected from O, N and S; and R¹⁶ and R¹⁷ each are independently H and C₁₋₄ alkyl.

2. The compound of claim 1, or a pharmaceutically acceptable salt thereof, wherein A is:

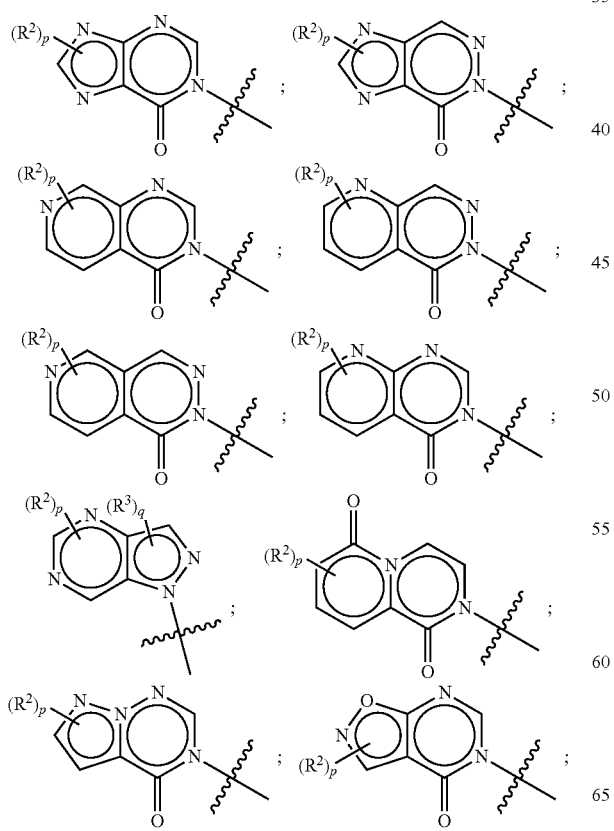

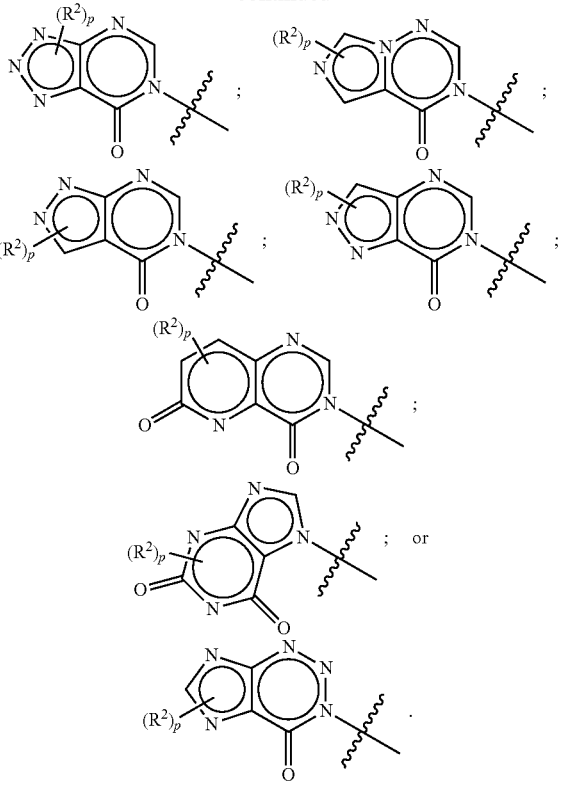

3. The compound of claim 1, or a pharmaceutically acceptable salt thereof, wherein A is:

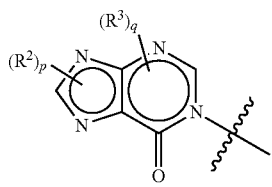

4. The compound of claim 1, or a pharmaceutically acceptable salt thereof, wherein each R² is independently; H; —CH₃; CN; -halo; —NH₂; —NHCH₃; NHCH₂CH₃; —NHCH₂CH₂CH₂OH; —NHCH₂CH₂OCH₃; —NHC(O)CH₃; —NHCH₂C(O)N(CH₃)₂;

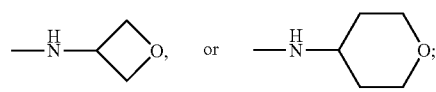

and p is 0 or 1.

5. The compound of claim 1, or a pharmaceutically acceptable salt thereof, wherein A is:

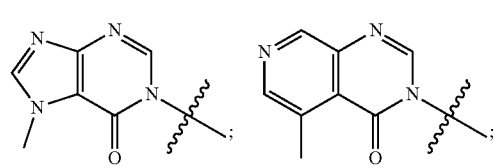

221
-continued
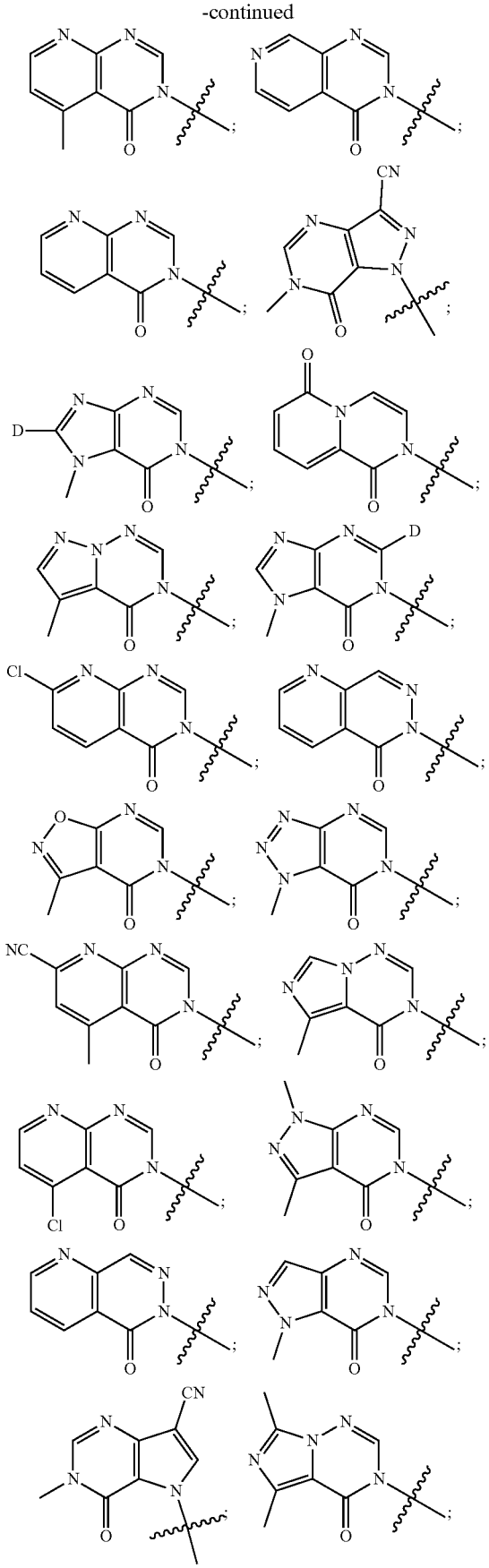
222
-continued
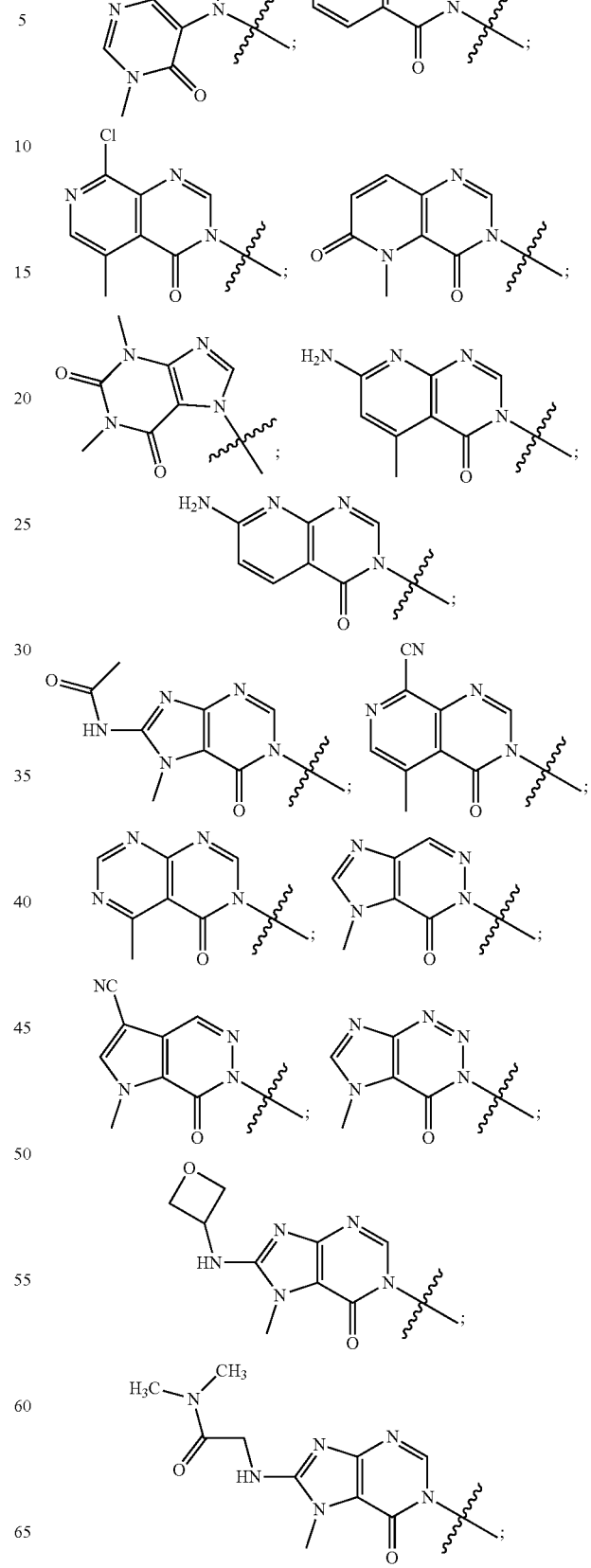

223
-continued
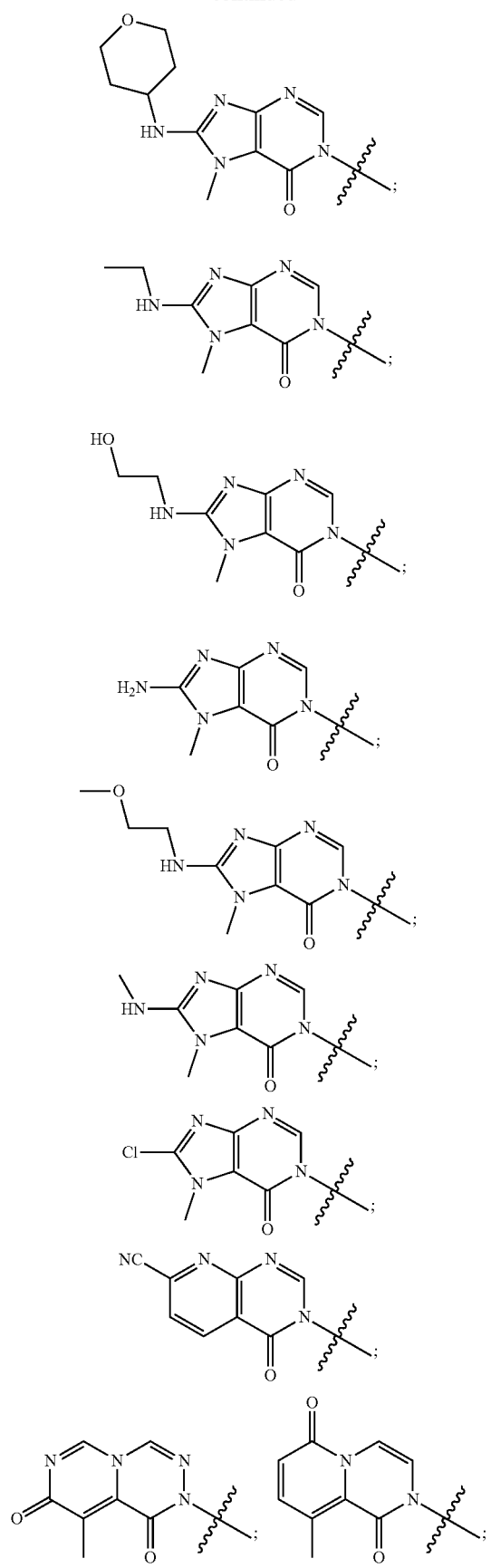
224
-continued
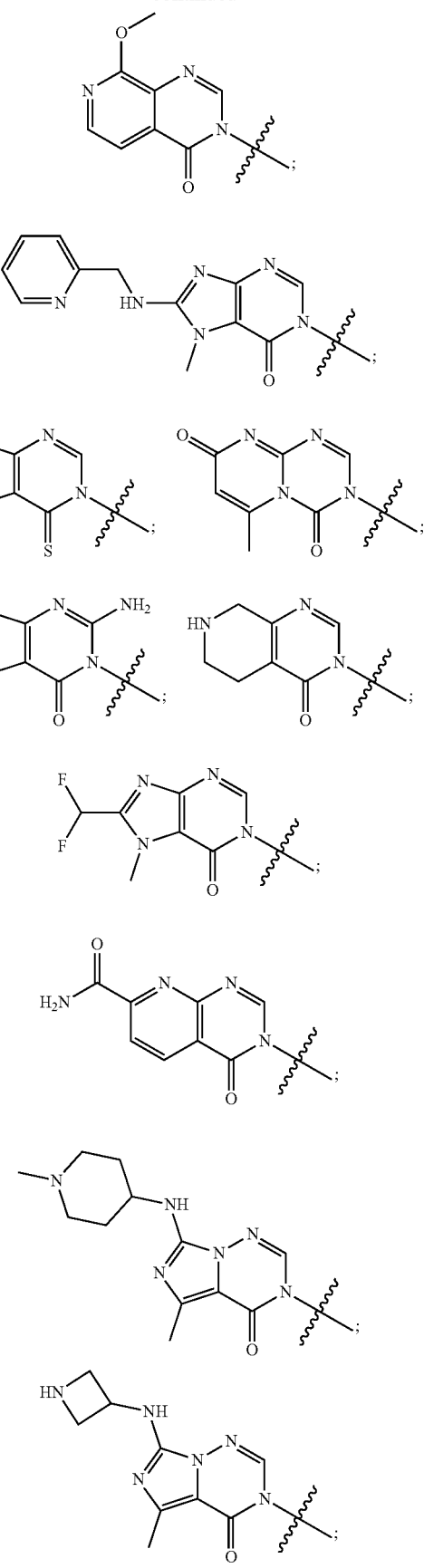

225
-continued
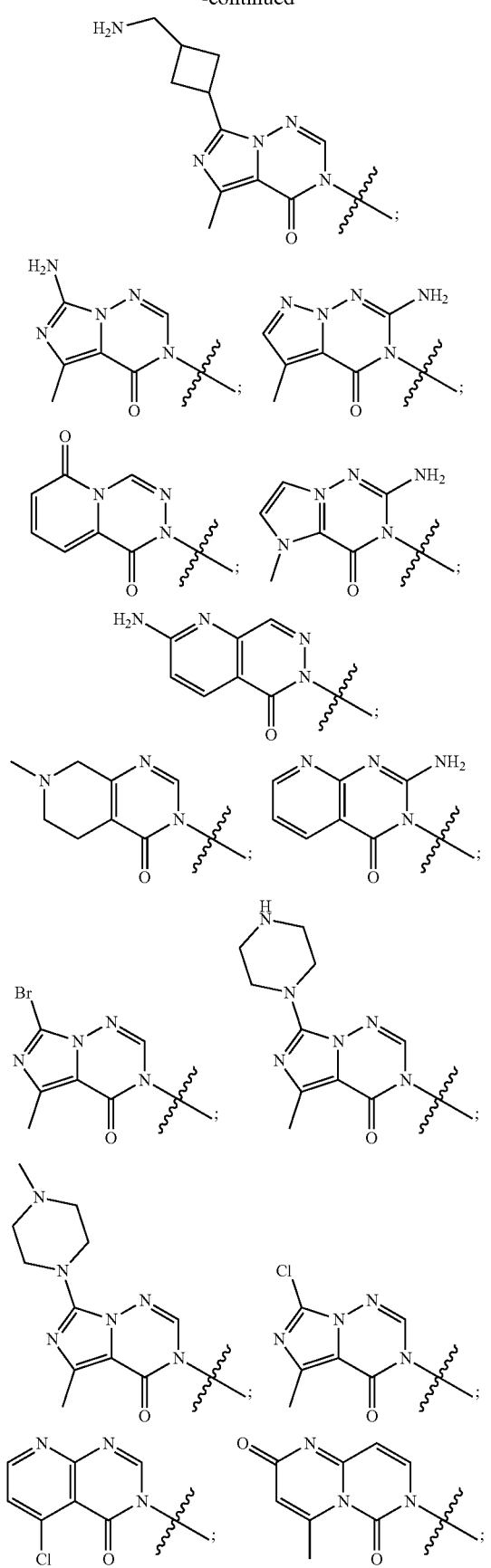
226
-continued
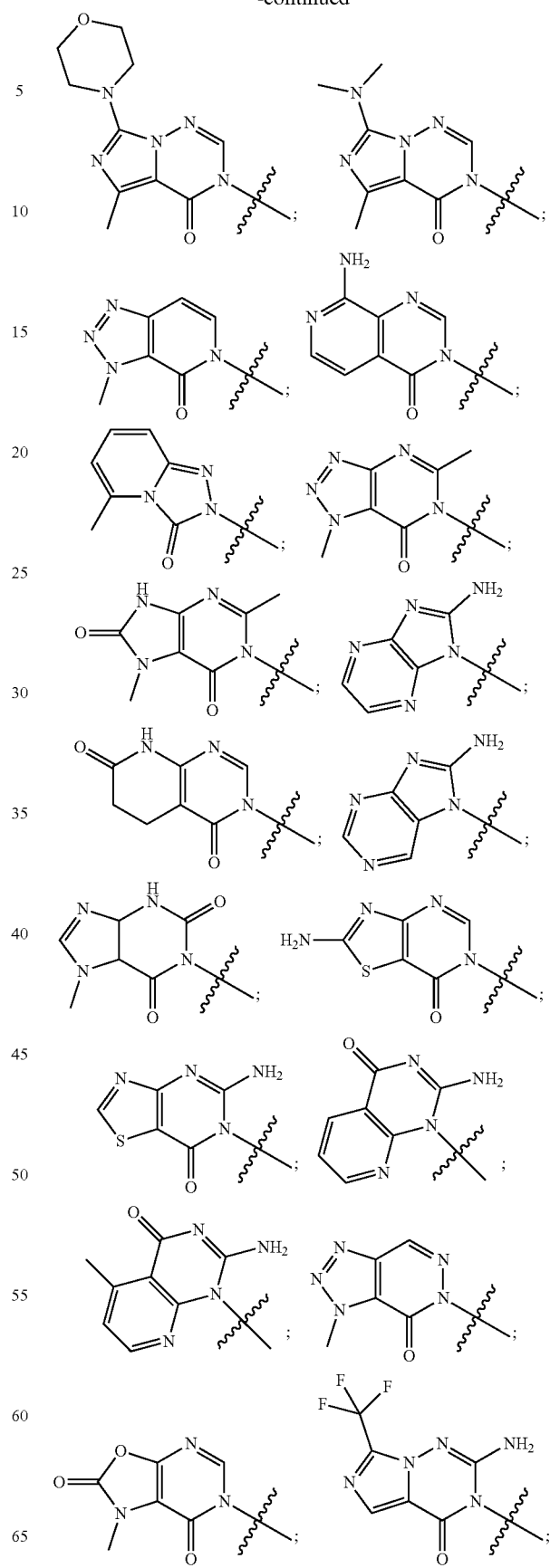

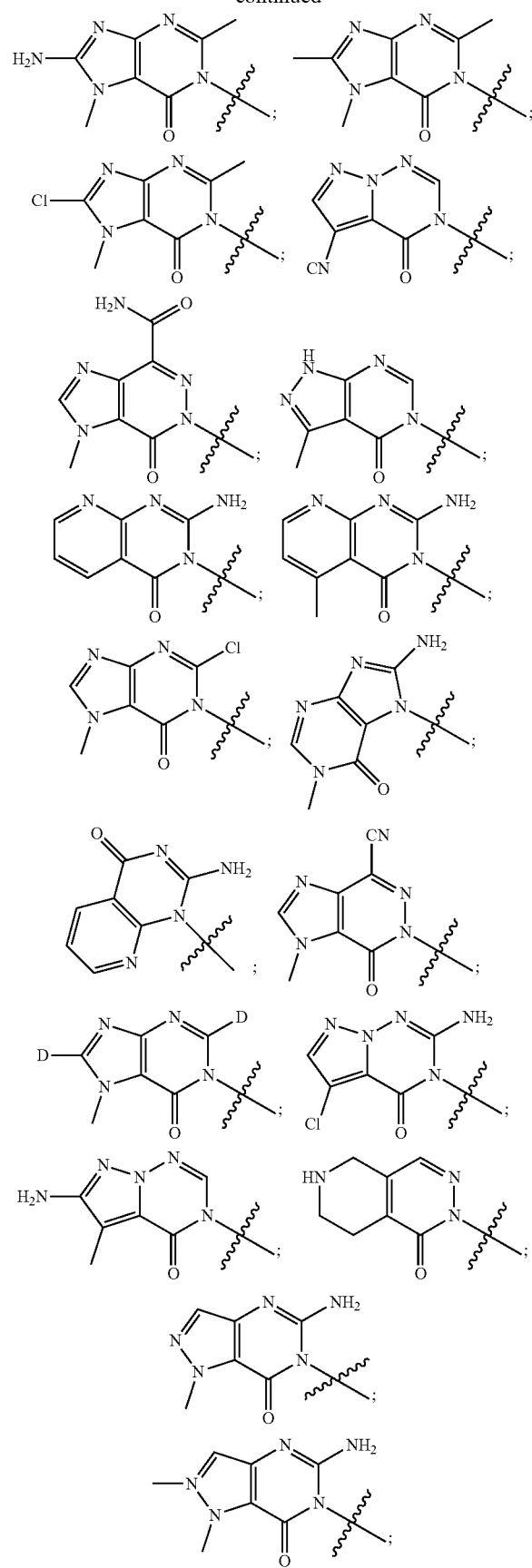
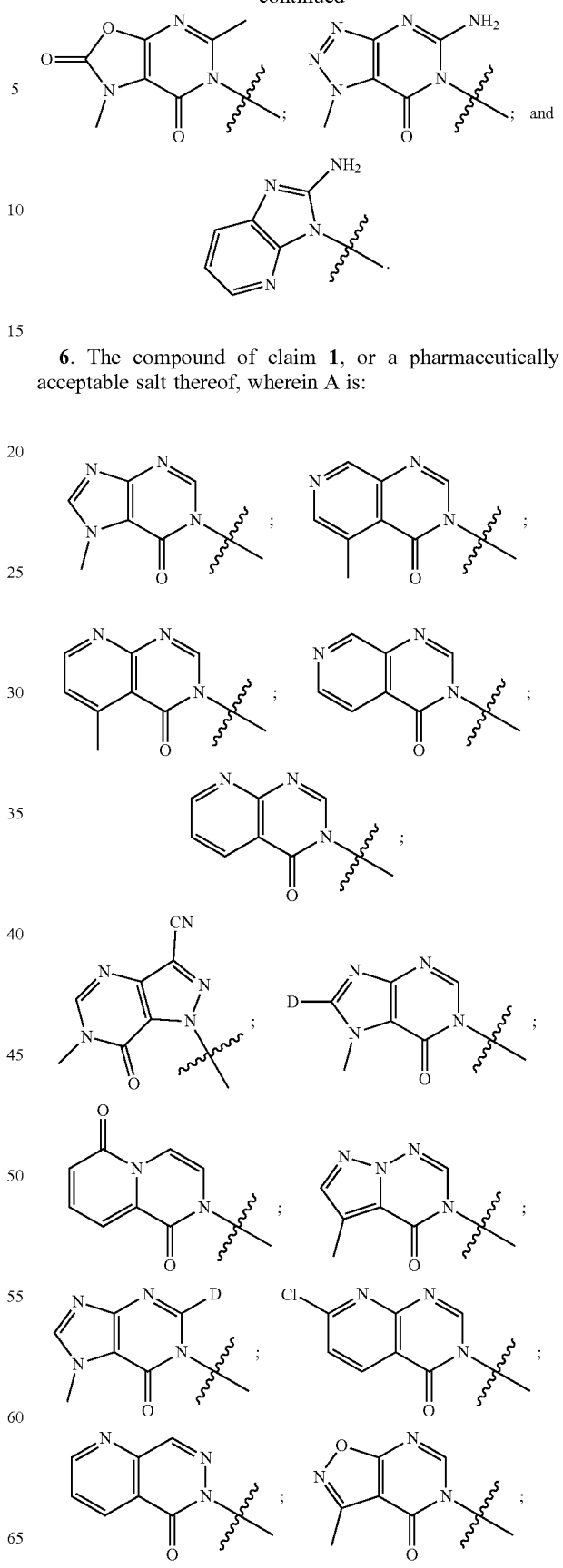
6. The compound of claim 1, or a pharmaceutically acceptable salt thereof, wherein A is:

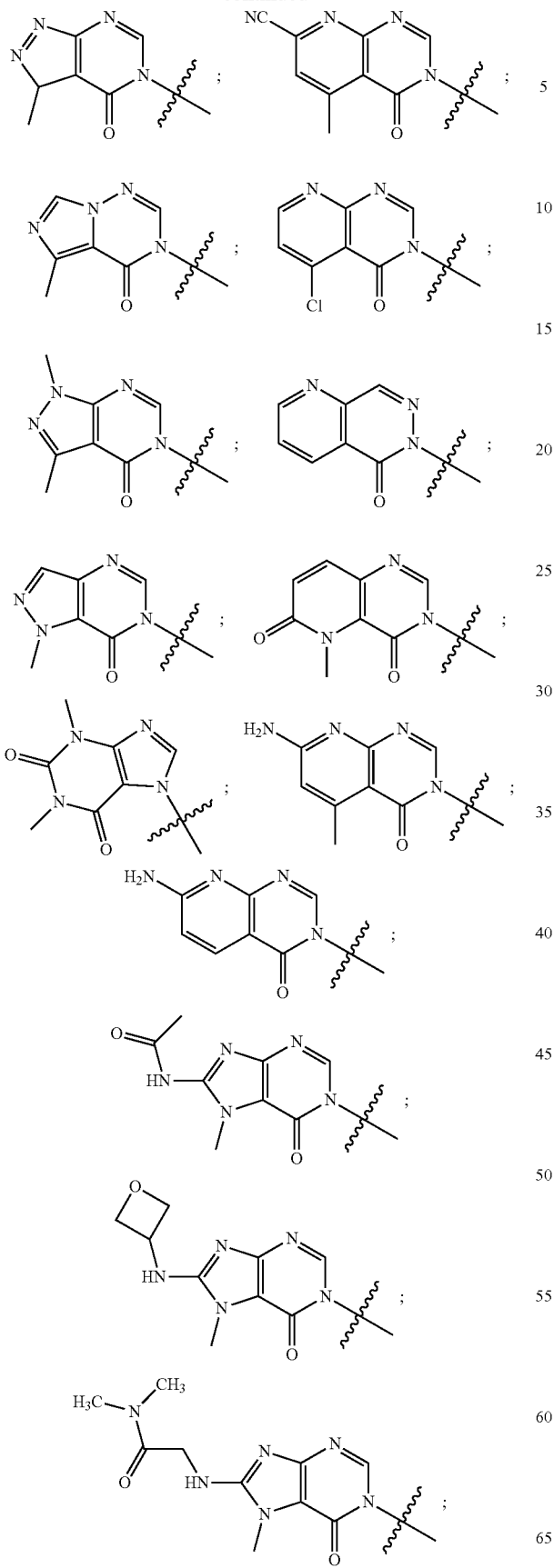
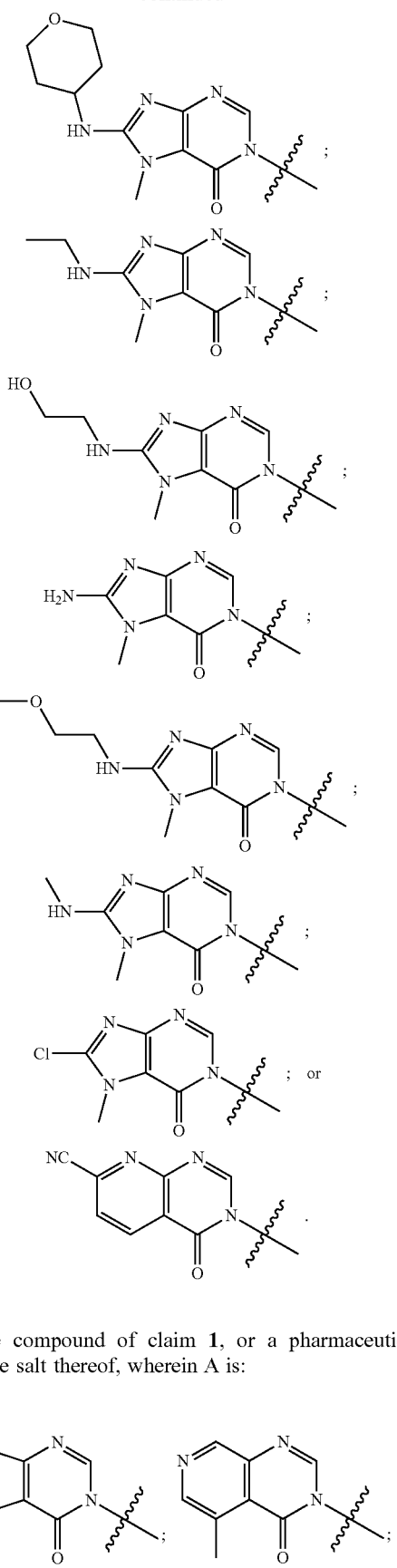
7. The compound of claim 1, or a pharmaceutically acceptable salt thereof, wherein A is:
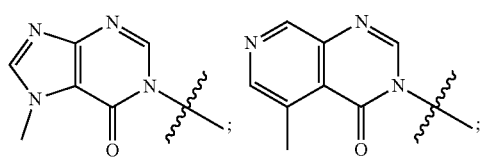

-continued

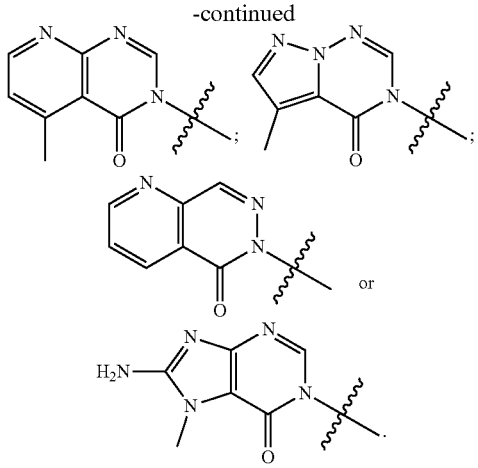

8. The compound of claim 1, or a pharmaceutically acceptable salt thereof, wherein A is:

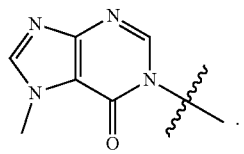 [SMILES: *n1cnc2ncn(C)c2c1=O]

9. The compound of claim 1, or a pharmaceutically acceptable salt thereof, wherein X is methylene.

10. The compound of claim 1, or a pharmaceutically acceptable salt thereof, wherein $R^4$ is:

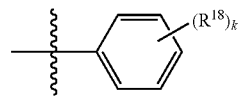

wherein:
each $R^{18}$ is independently selected from H, halogen, —OH, —$C_{1-4}$ alkyl, —$C_{1-4}$ haloalkyl, —CN, halo, $C_{1-4}$ haloalkoxy, $C_{1-4}$ alkoxy, —$SO_2$—$C_{1-4}$alkyl, —$C_{1-4}$CN, $C_{1-4}$ aldehyde, —$SF_5$, $C_{1-4}$ ketone, unsubstituted or substituted $C_{3-6}$ cycloalkyl, unsubstituted or substituted phenyl, unsubstituted or substituted heteroaryl, fused aryl, and fused heteroaryl; and
k is from 0 to 3.

11. The compound claim 10 or a pharmaceutically acceptable salt thereof, wherein each $R^{18}$ is independently: H; Cl; —$OCHF_2$; —OCF; —$OCH_3$; or —CN.

12. The compound claim 10, or a pharmaceutically acceptable salt thereof, wherein each $R^{18}$ is independently fluoro or chloro.

13. The compound of claim 1, or a pharmaceutically acceptable salt thereof, wherein $R^4$ is:

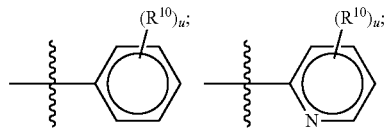

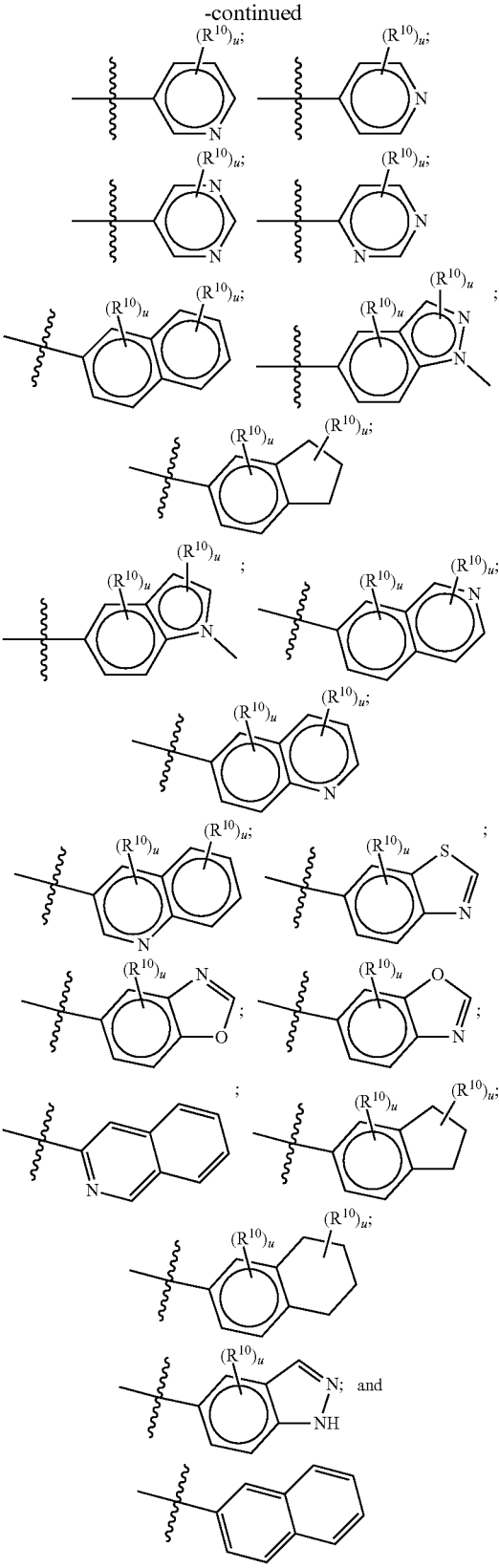

wherein:
each $R^{10}$ is independently: H; halogen; —CN; —OH; $C_{1-4}$ alkyl; substituted or unsubstituted $C_{3-6}$ cycloalkyl; C$_{1-4}$ haloalkyl; C$_{1-4}$ haloalkoxy; C$_{1-4}$ alkoxy; —SO$_2$—C$_{1-4}$ alkyl; C$_{1-4}$ CN; C$_{1-4}$ aldehyde; C$_{1-4}$ ketone; —S—C$_{1-4}$ haloalkyl; substituted or unsubstituted 5- to 6-membered heteroaryl; substituted or unsubstituted 4- to 6-membered hetercycloalkyl; or substituted or unsubstituted C$_{5-6}$ aryl; and each u is independently 0, 1, 2 or 3.

14. The compound of claim 1, or a pharmaceutically acceptable salt thereof, wherein R$^4$ is:

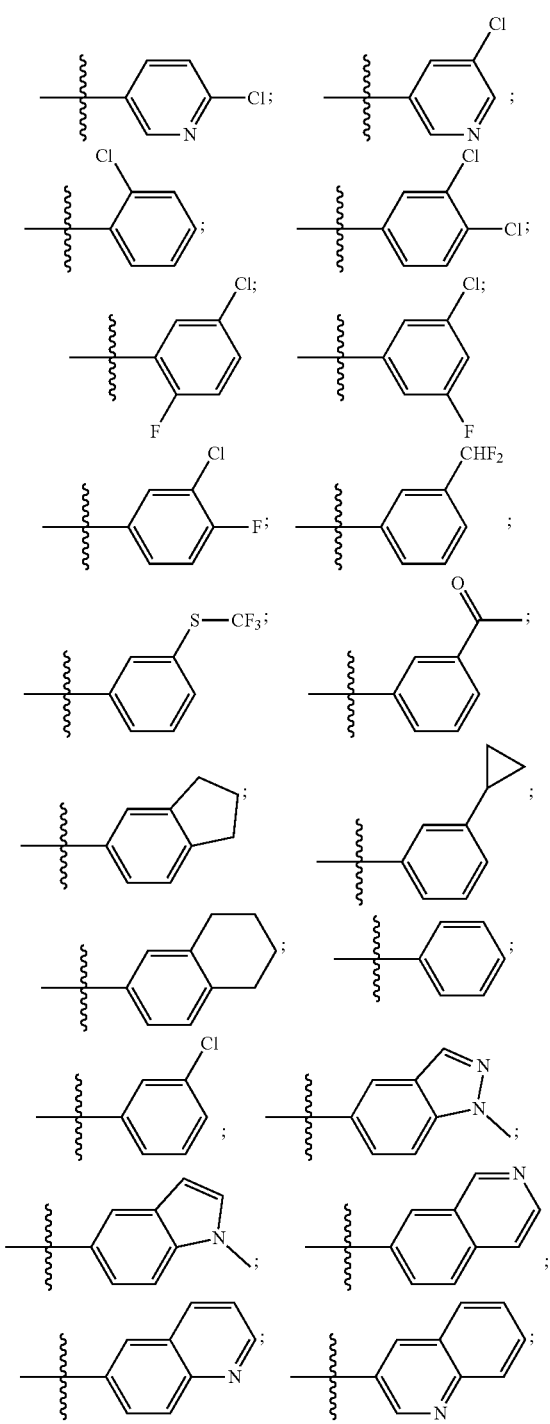
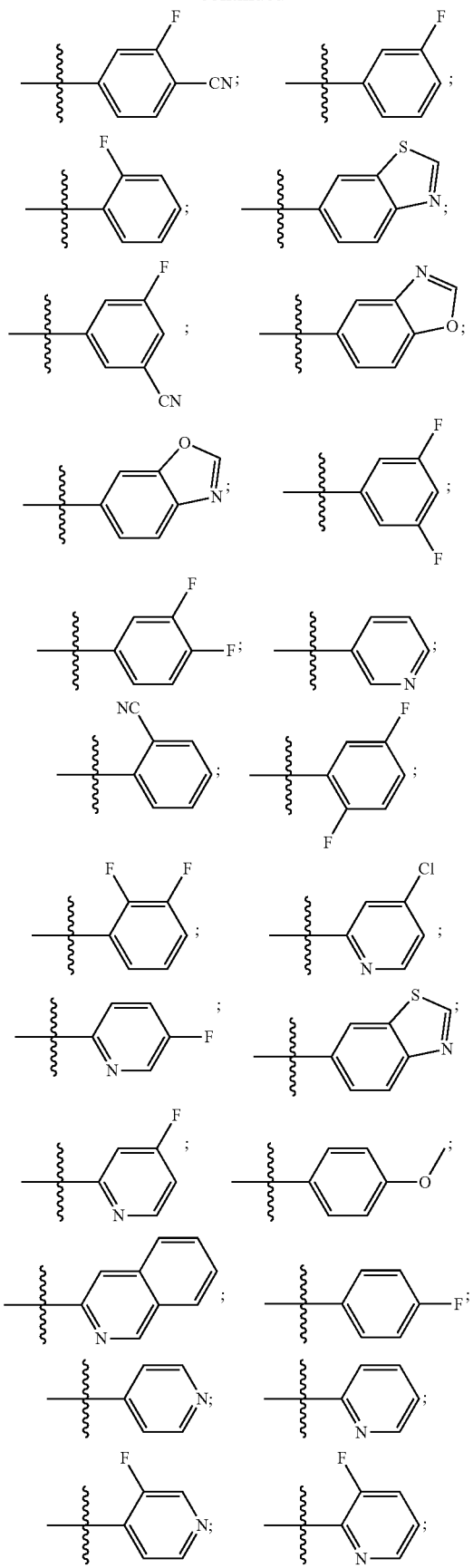

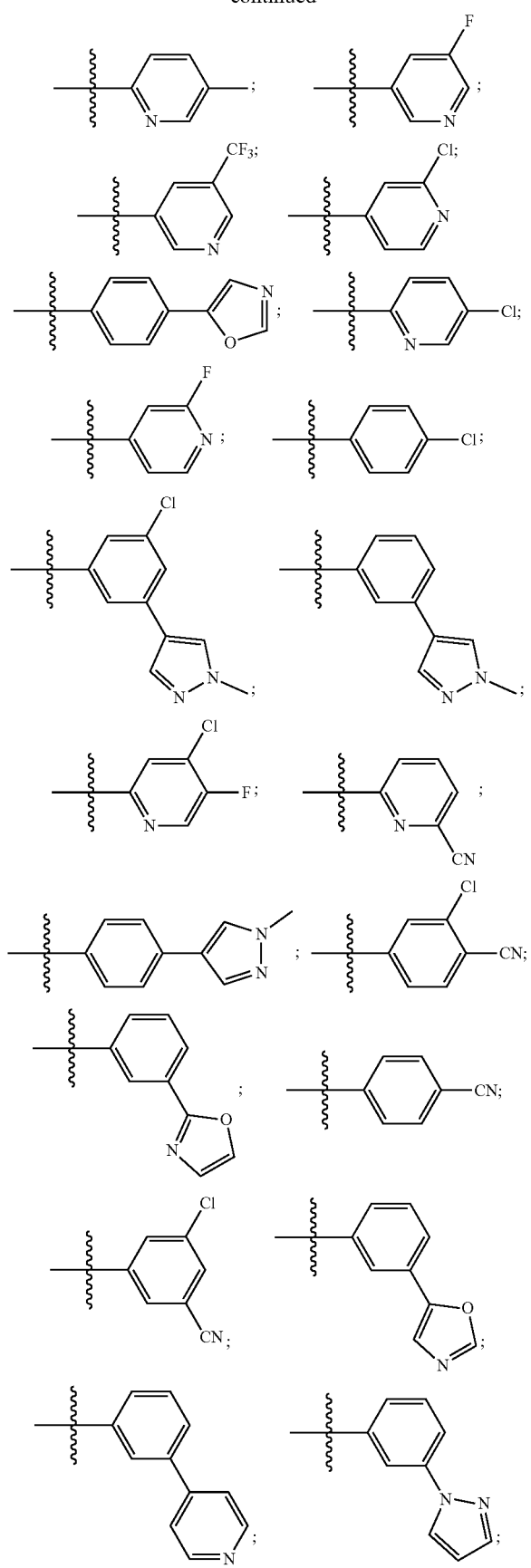
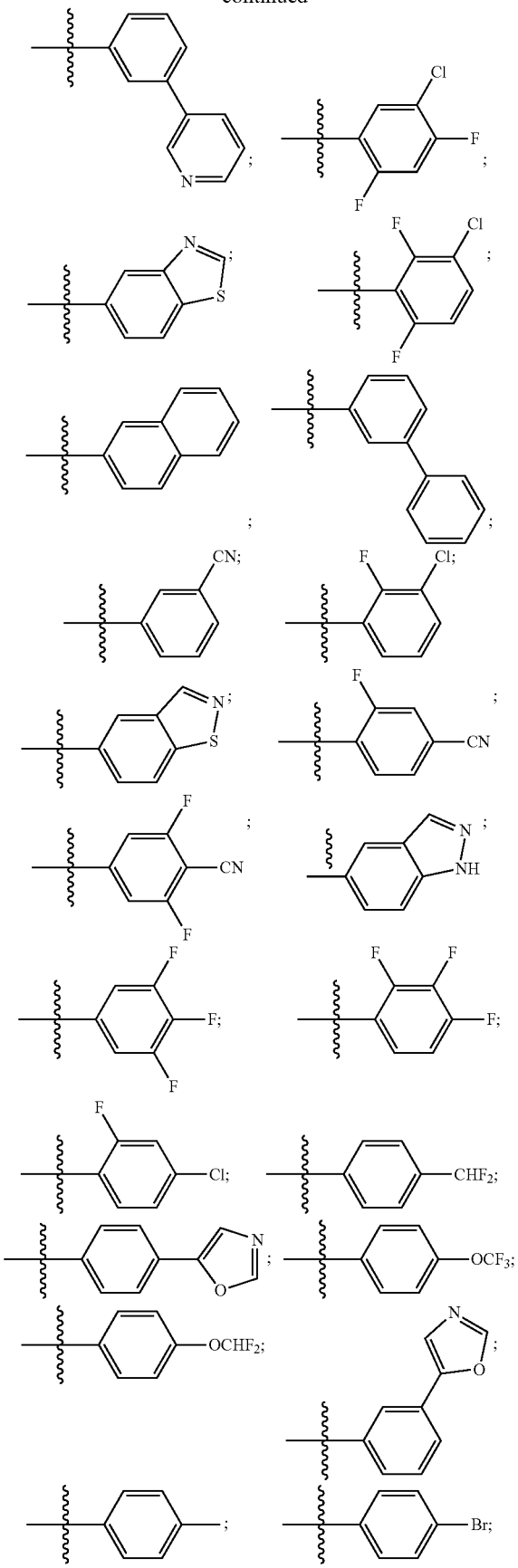

-continued

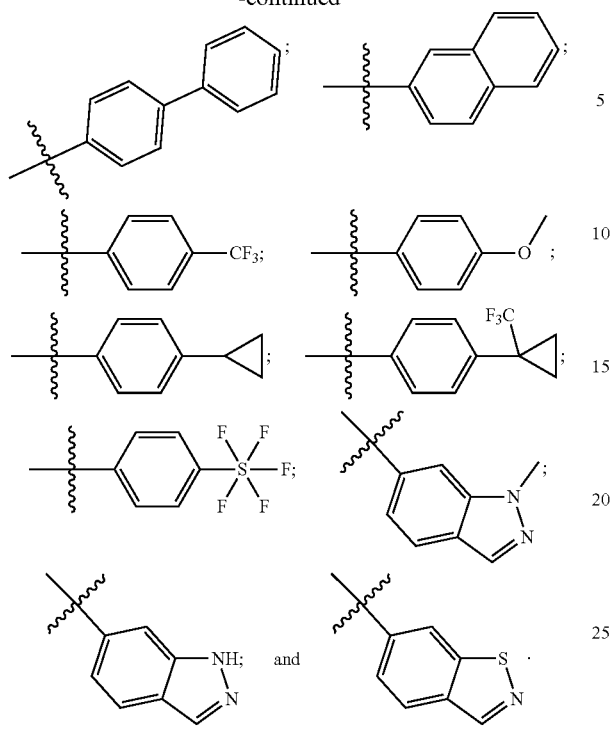

15. The compound of claim 1, or a pharmaceutically acceptable salt thereof, wherein the compound of formula (I) is a compound of formula (II)

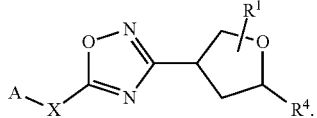

16. A compound of formula (IVa) or formula (IVb), or a pharmaceutically acceptable salt thereof,

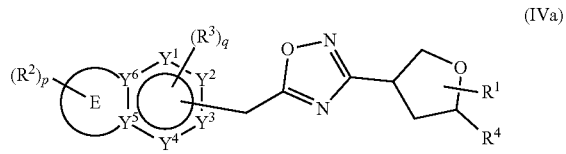
(IVa)

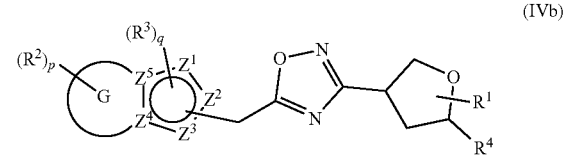
(IVb)

wherein:
- E is a five membered or a six membered heteroaryl ring wherein one ring carbon atom is optionally substituted with oxo;
- G is a six membered heteroaryl ring having one ring carbon atom substituted with oxo;

one to three of $Y^1$, $Y^2$, $Y^3$, $Y^4$, $Y^5$ and $Y^6$ are nitrogen, and the other of $Y^1$, $Y^2$, $Y^3$, $Y^4$, $Y^5$, and $Y^6$ are carbon, and one of $Y^1$, $Y^2$, $Y^3$ and $Y^4$ may be —C(O)— or —C(S)—;

one or two of $Z^1$, $Z^2$, $Z^3$, $Z^4$ and $Z^5$ are nitrogen and the other of $Z^1$, $Z^2$, $Z^3$, $Z^4$ and $Z^5$ are carbon;

$R^1$ is: H; or $C_{1-6}$alkyl;

each $R^2$ is independently; H; D; —$C_{1-4}$ alkyl; —$C_{1-4}$ haloalkyl; —CN; halo; halo$C_{1-4}$ alkoxy; $C_{1-4}$ alkoxy; —OH; —$SO_2$—$C_{1-4}$ alkyl; $C_{1-4}$ aldehyde; $C_{1-4}$ ketone; benzylamino; or $NR^{14}R^{15}$;

each $R^3$ is independently: H; D; alkyl; —$C_{1-4}$ haloalkyl; —CN; halo; or $NR^{14}R^{15}$;

$R^4$ is: substituted or unsubstituted phenyl; substituted or unsubstituted heteroaryl; or substituted or unsubstituted naphthyl;

or $R^1$ and $R^4$ may together form an unsubstituted or substituted $C_{3-6}$cycloalkyl fused to a substituted or unsubstituted phenyl; substituted or unsubstituted heteroaryl; or substituted or unsubstituted naphthyl, p is 0, 1 or 2;

q is 0 or 1;

$R^{14}$ and $R^{15}$ are each independently: H; substituted or unsubstituted —$C_{1-4}$ alkyl; substituted or unsubstituted —C(O)—$C_{1-4}$ alkyl; substituted or unsubstituted $C_{3-6}$ cycloalkyl; substituted or unsubstituted 3- to 6-membered heterocycloalkyl; substituted or unsubstituted —$C_{1-4}$ heteroalkyl; —C(O)$N^{16}R^{17}$; substituted or unsubstituted —$C_{1-4}$ alkyl-C(O)$NR^{16}R^{17}$; substituted or unsubstituted phenyl; or substituted or unsubstituted benzyl;

or $R^{14}$ and $R^{15}$ together with the atoms to which they are attached may form a 4-, 5-, 6- or 7-membered ring that optionally includes one additional heteroatom selected from O, N and S; and $R^{16}$ and $R^{17}$ each are independently H and $C_{1-4}$ alkyl.

17. The compound of claim 16, or a pharmaceutically acceptable salt thereof, wherein the compound of formula (I) is a compound of formula (Va)

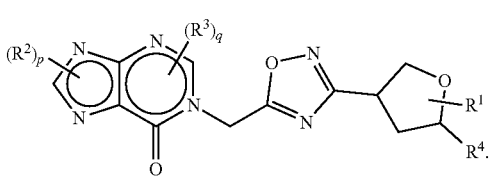
(Va)

18. The compound of claim 17 or a pharmaceutically acceptable salt thereof, wherein the compound is a compound of formula (VIc) or formula (VId)

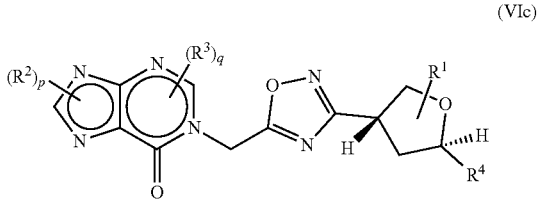
(VIc)

-continued

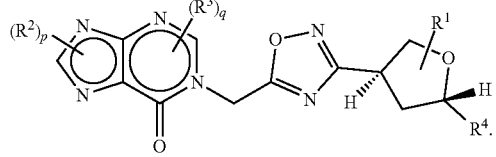
(VId)

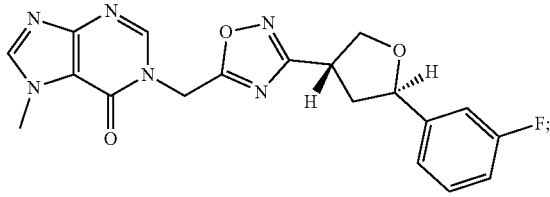

19. The compound of claim 17, or a pharmaceutically acceptable salt thereof, wherein the compound is a compound of formula (VIIc) or formula (VIId)

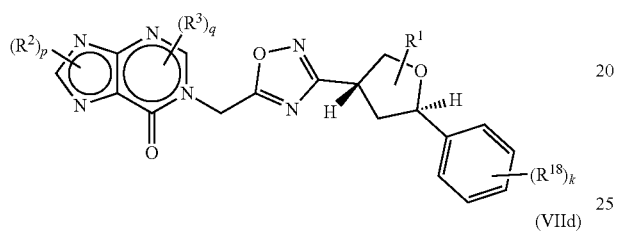
(VIIc)

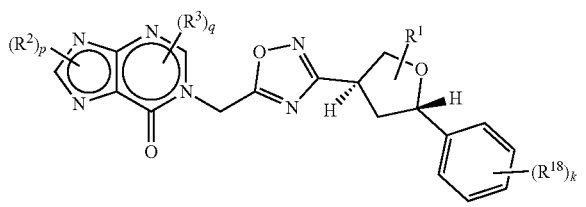
(VIId)

wherein:
  each $R^{18}$ is independently selected from H, halogen, —OH, —$C_{1-4}$ alkyl, —$C_{1-4}$ haloalkyl, —CN, halo, $C_{1-4}$ haloalkoxy, $C_{1-4}$ alkoxy, —$SO_2$—$C_{1-4}$alkyl, —$C_{1-4}$CN, $C_{1-4}$ aldehyde, —$SF_5$, $C_{1-4}$ ketone, unsubstituted or substituted $C_{3-6}$cycloalkyl, unsubstituted or substituted phenyl, unsubstituted or substituted heteroaryl, fused aryl, and fused heteroaryl; and
  k is from 0 to 3.

20. A compound selected from:

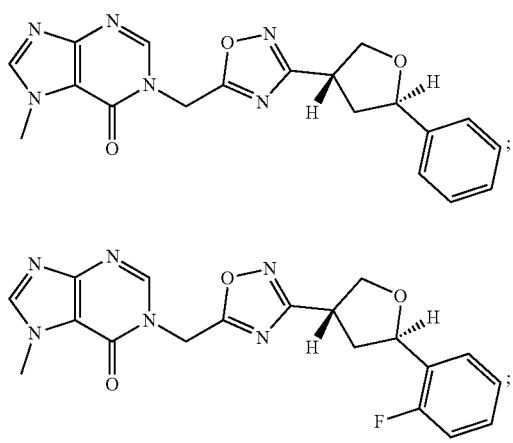

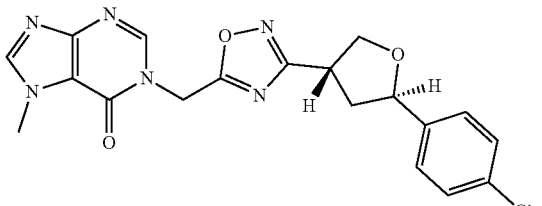

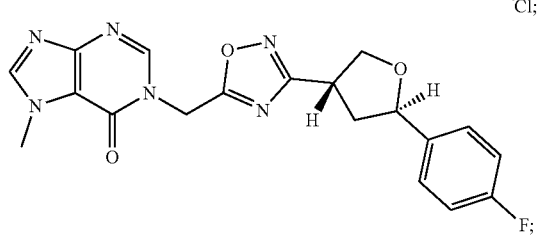

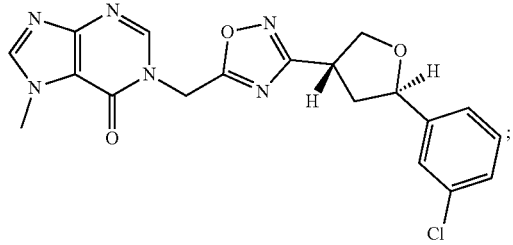

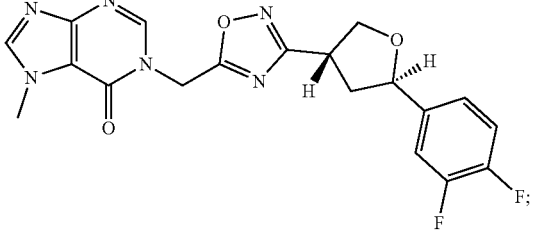

241
-continued
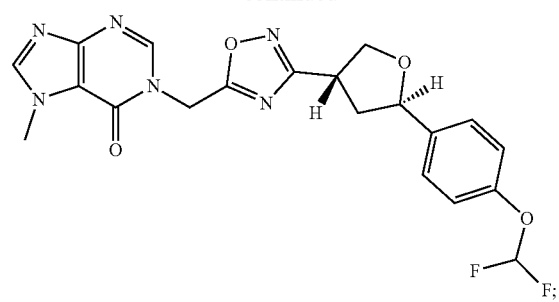
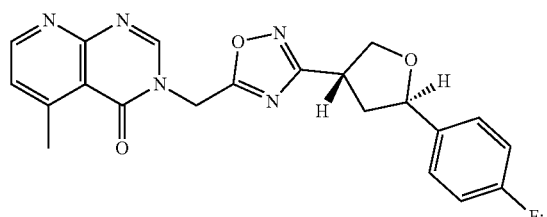
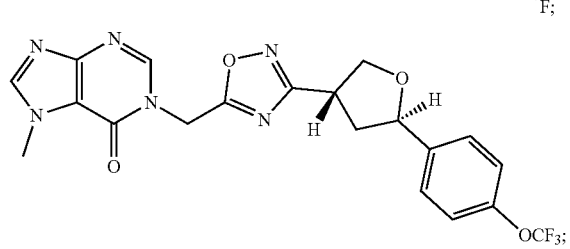
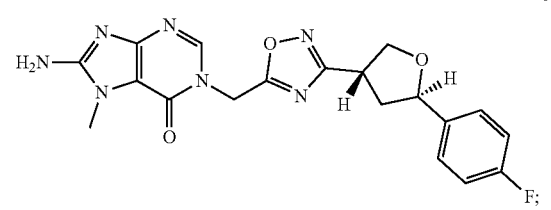
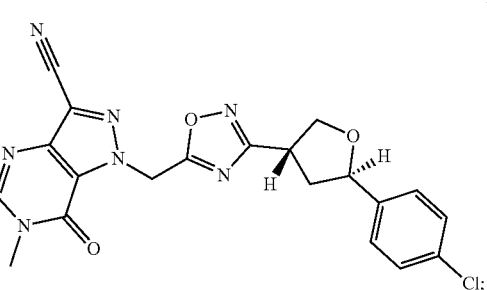
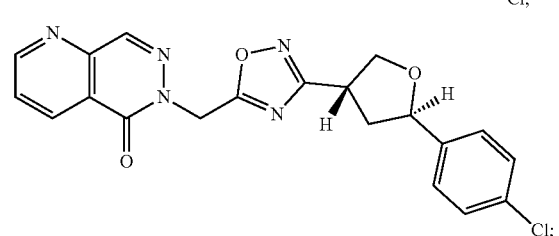
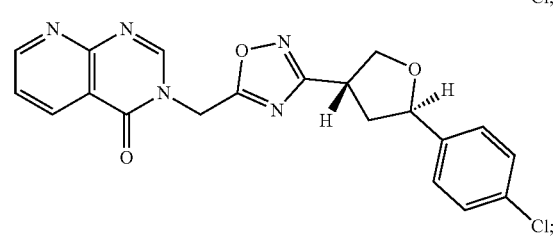
242
-continued
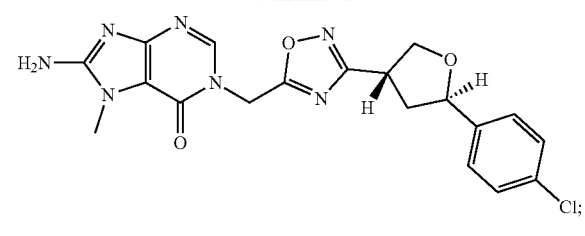
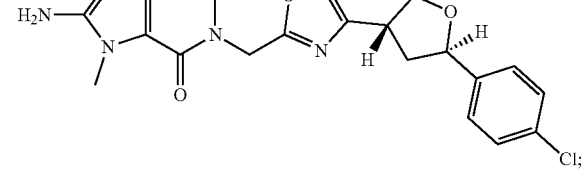
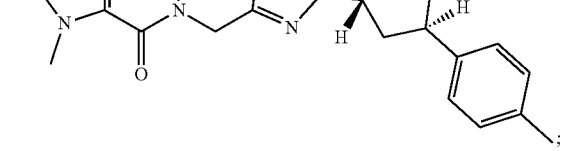
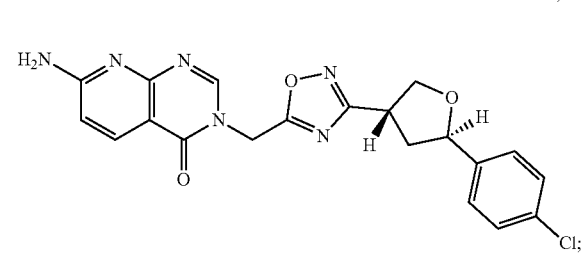
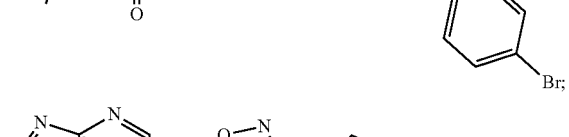
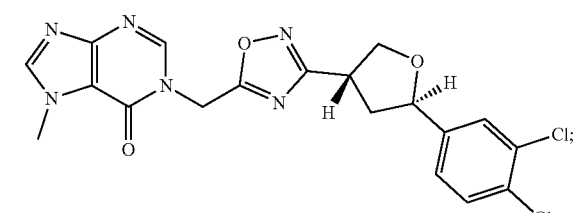
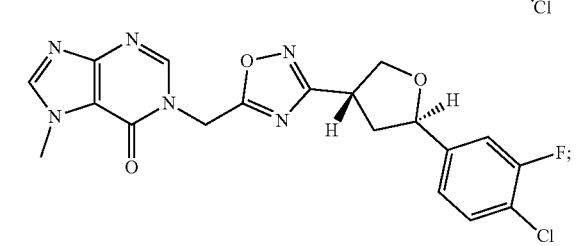

243
-continued
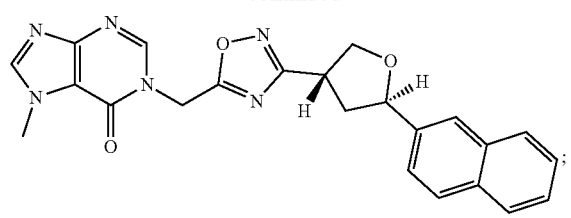
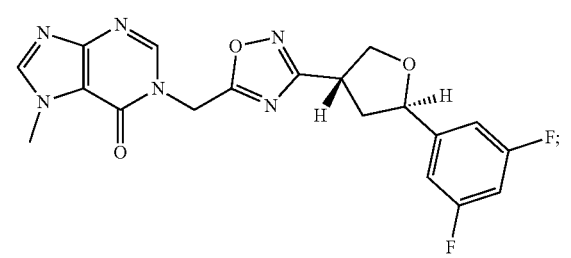
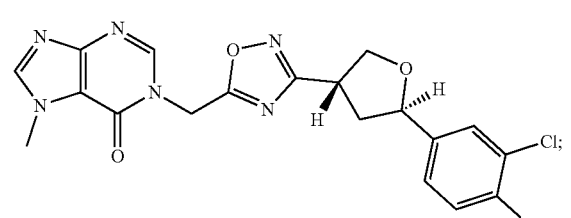
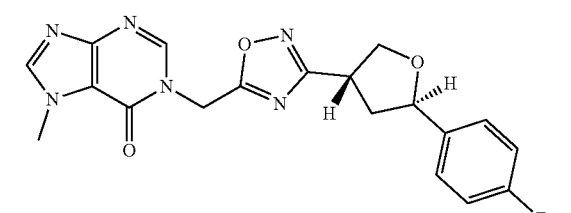
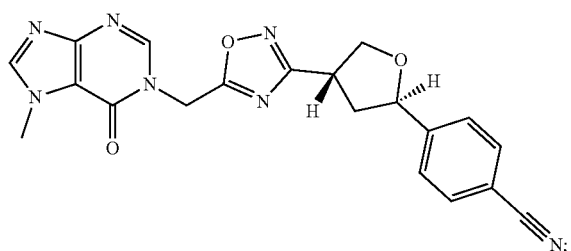
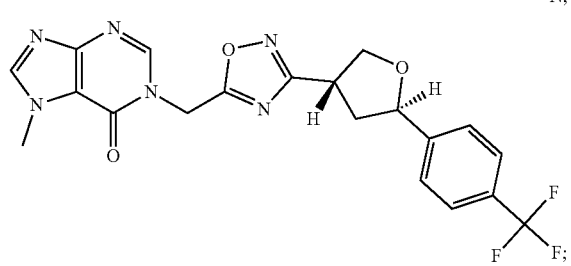
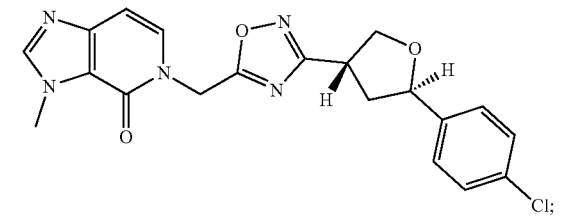
244
-continued
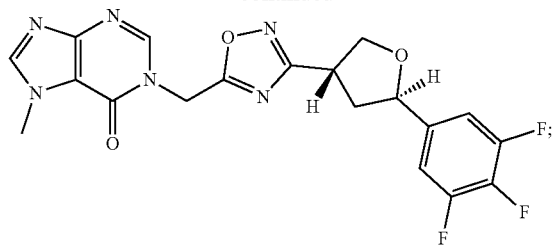
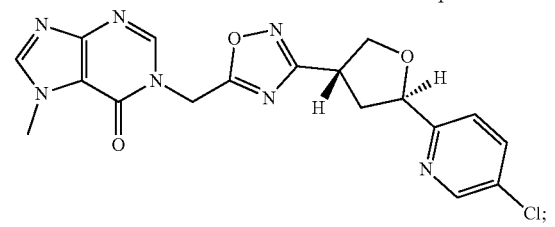
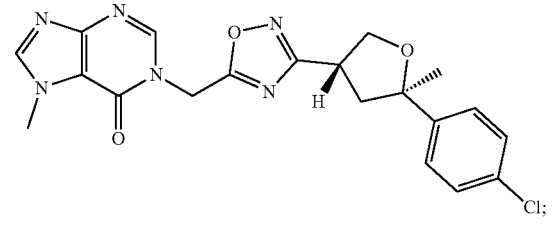
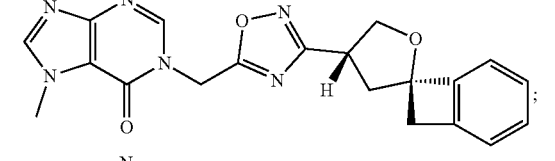
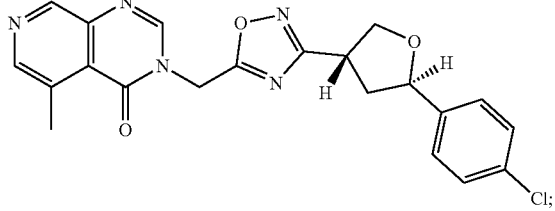
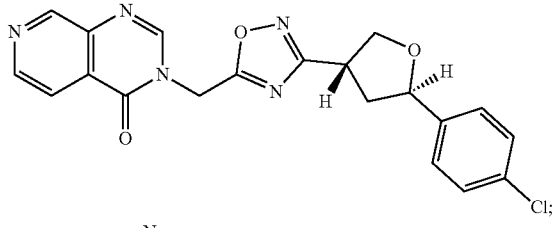
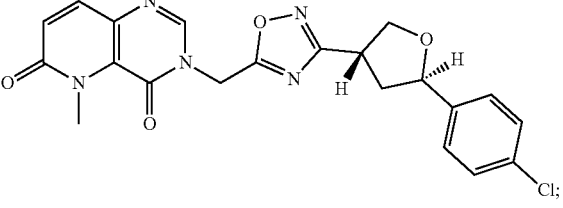
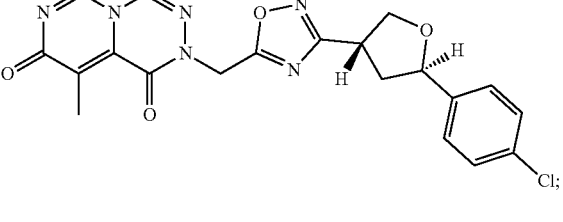

-continued
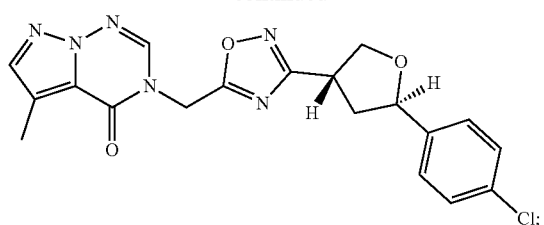
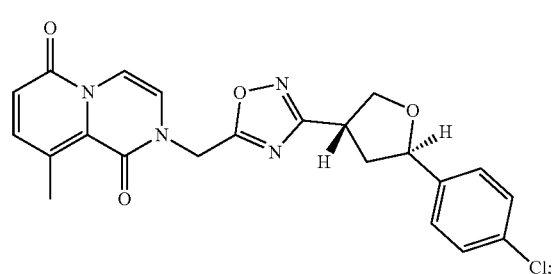
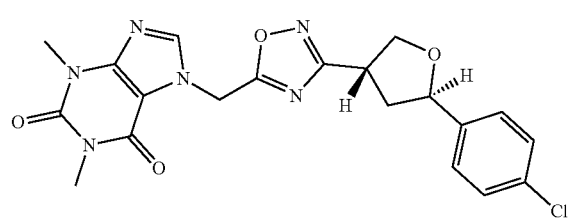
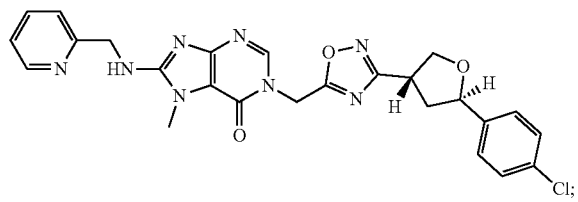
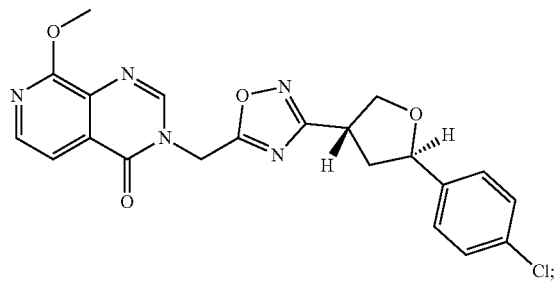
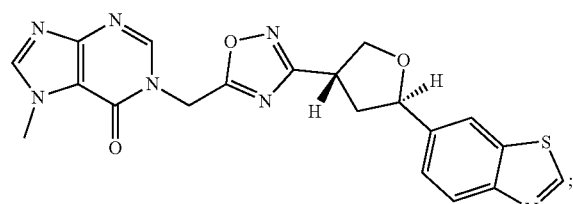
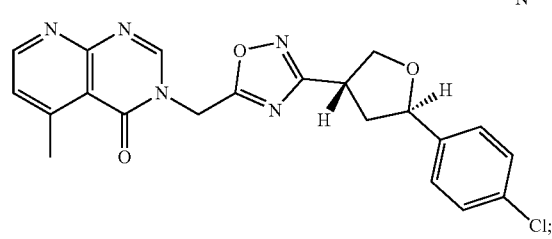
-continued
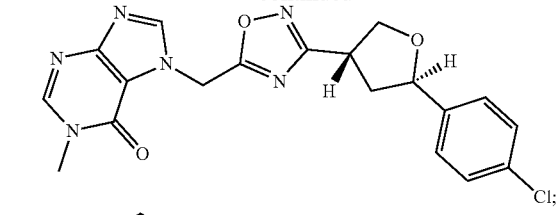
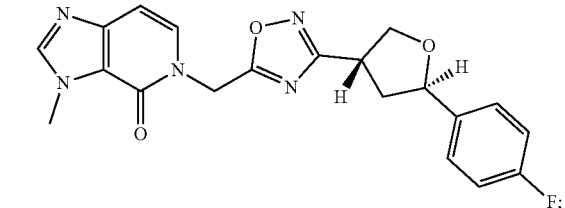
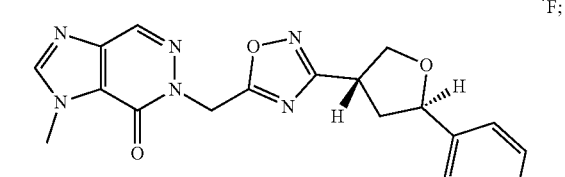
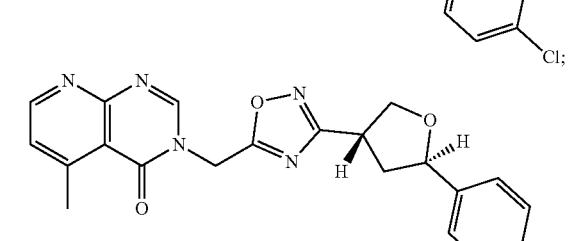
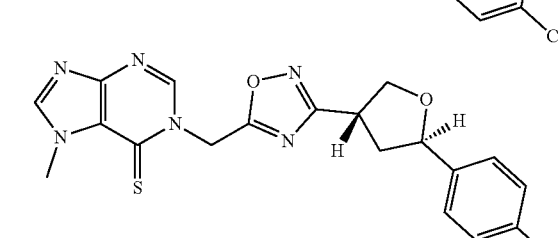
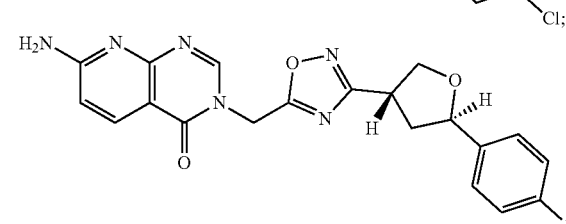
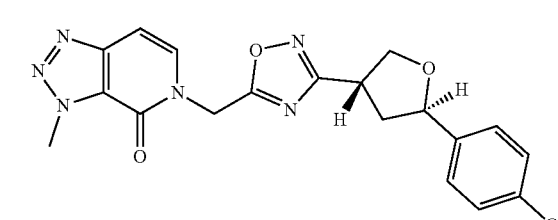
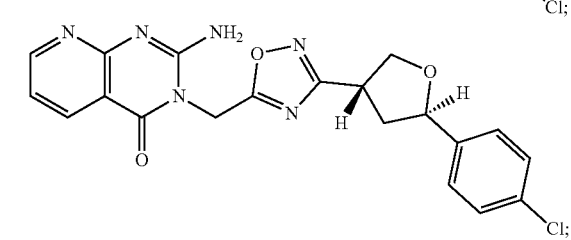

247
-continued
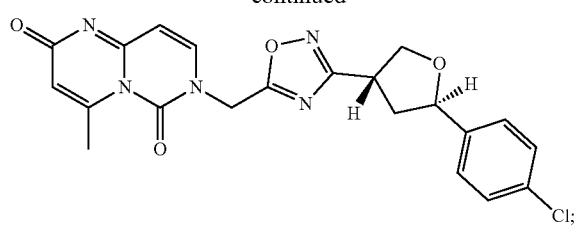
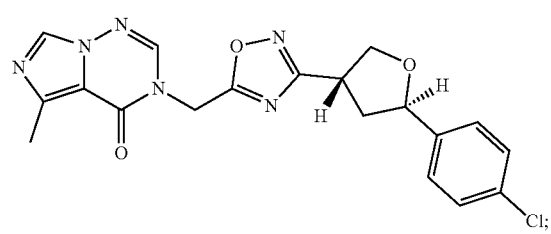
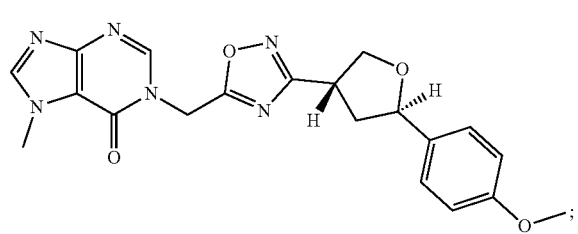
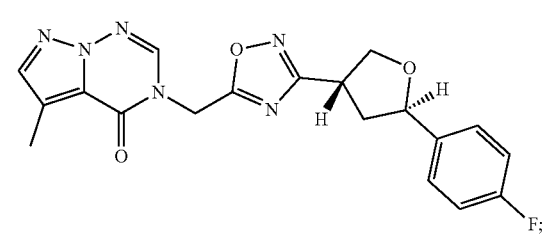
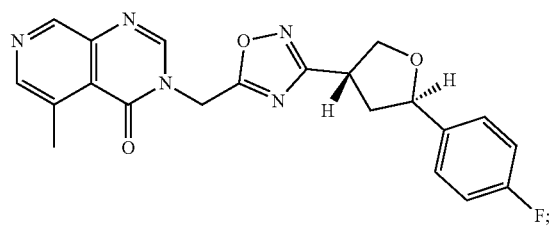
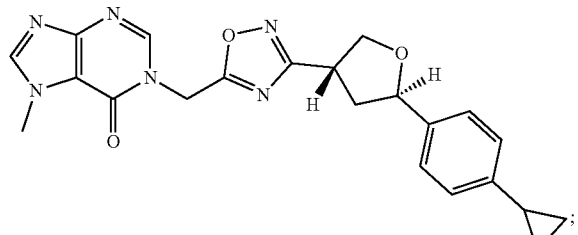
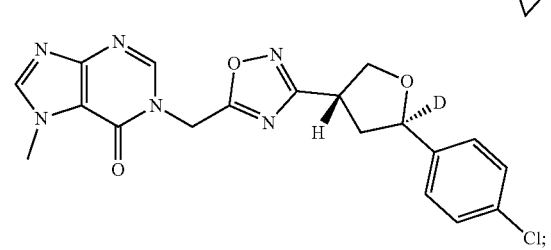
248
-continued
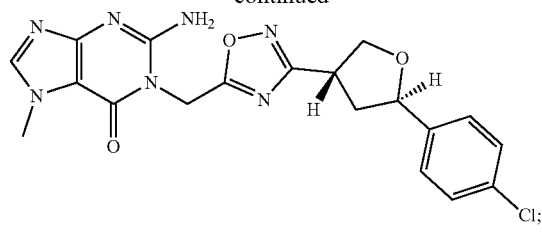
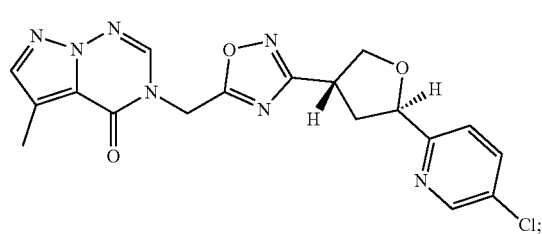
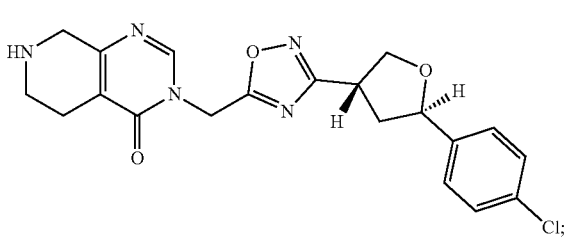
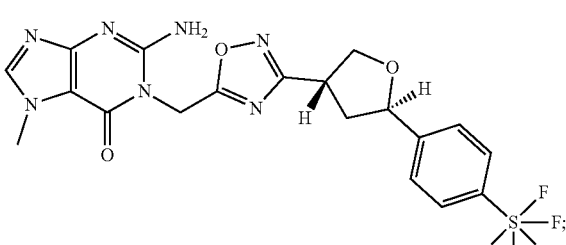
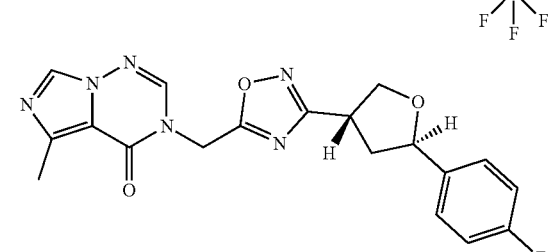
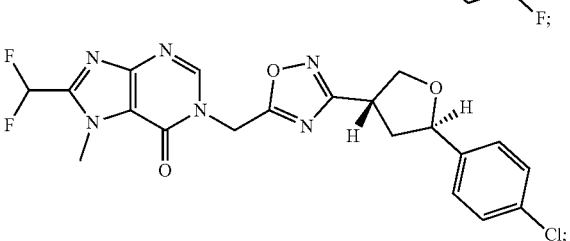
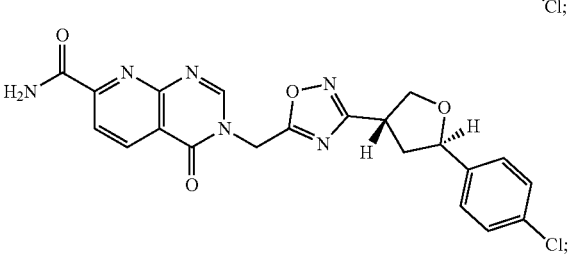

249
-continued
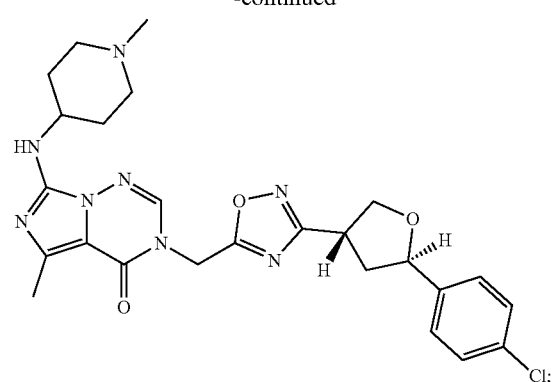
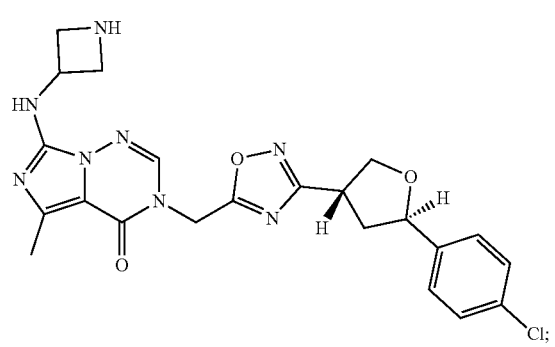
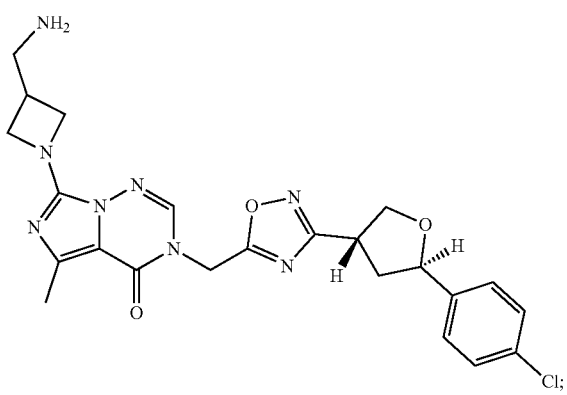
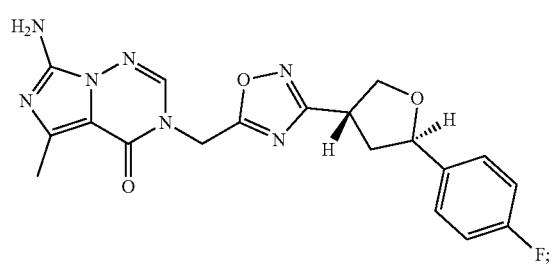
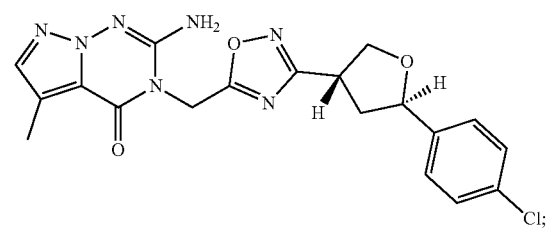
250
-continued
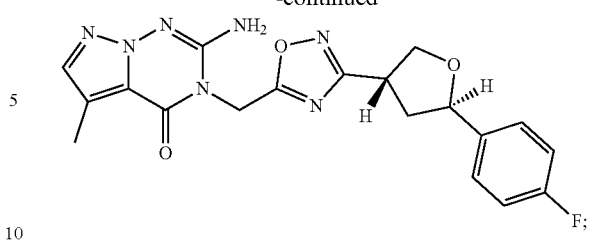
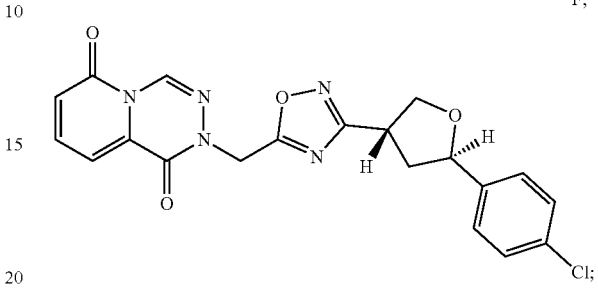
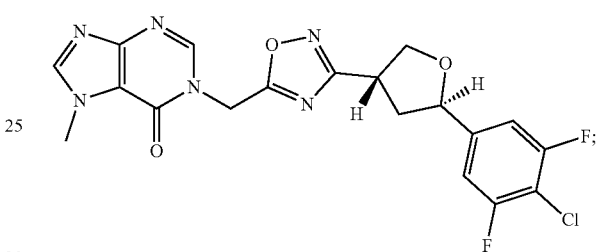
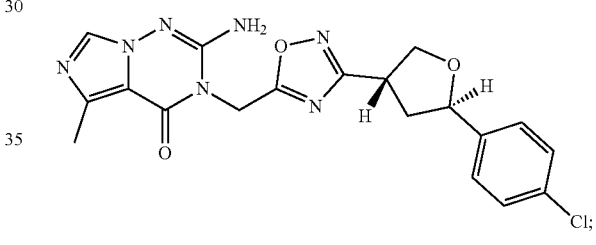
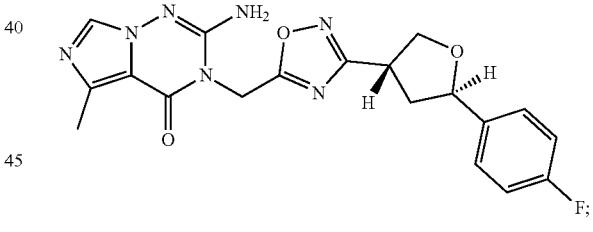
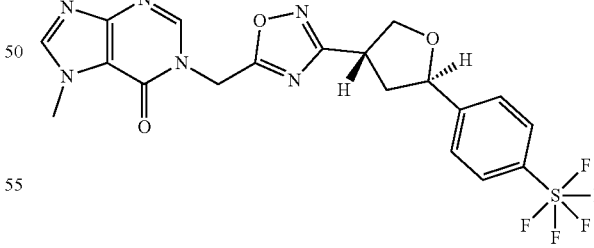
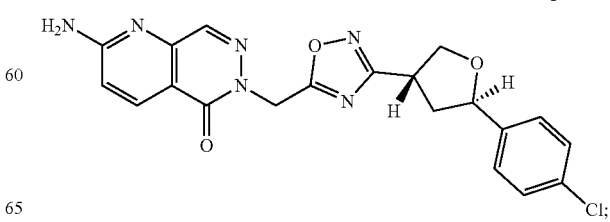

251
-continued
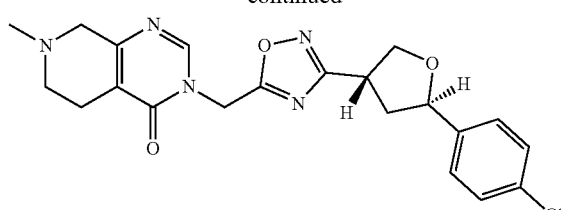
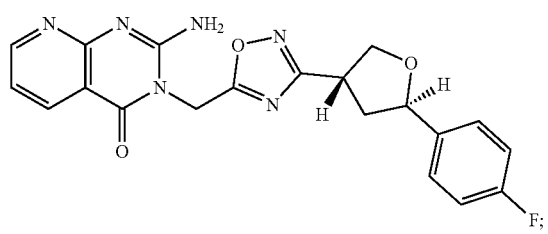
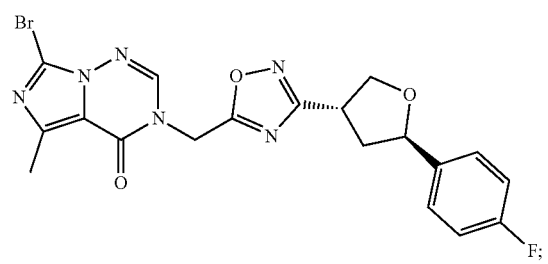
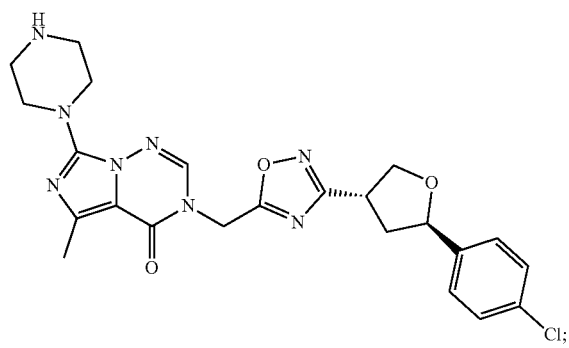
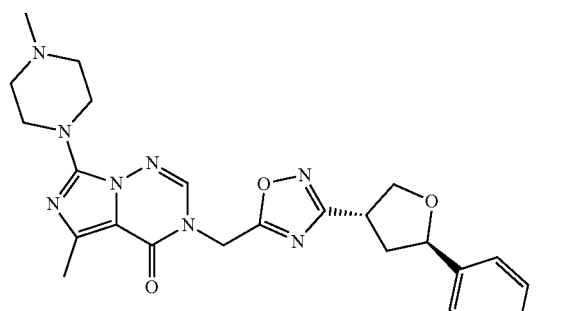
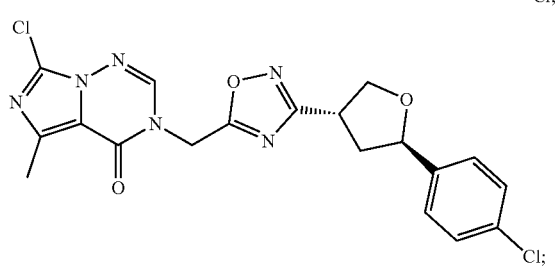
252
-continued
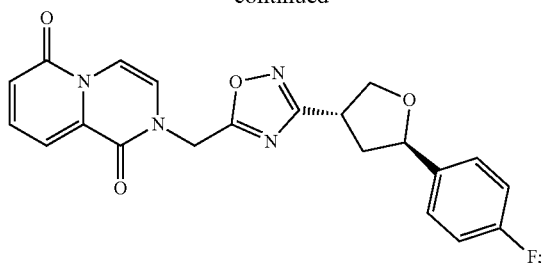
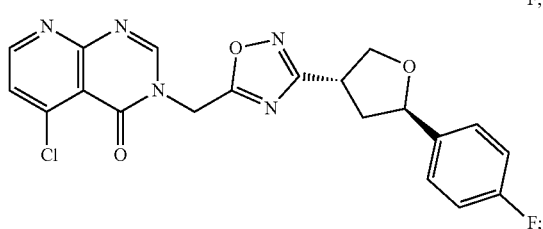
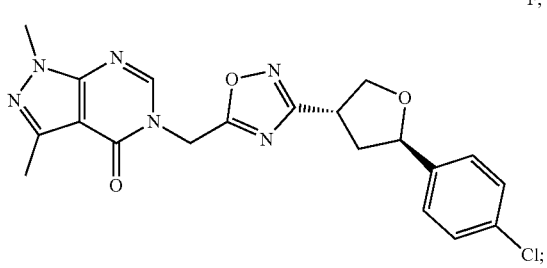
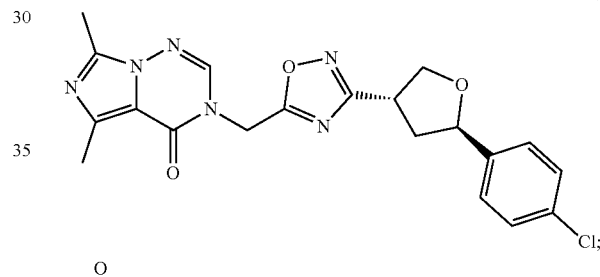
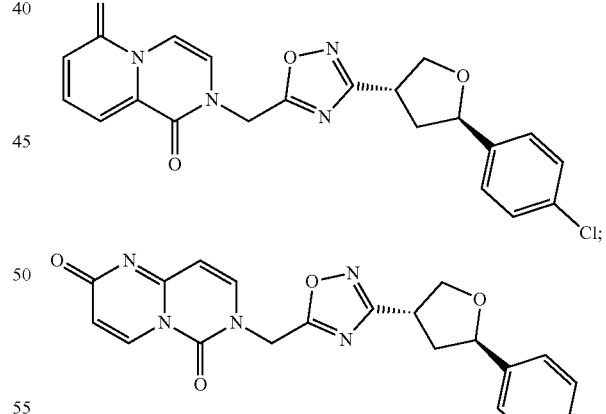
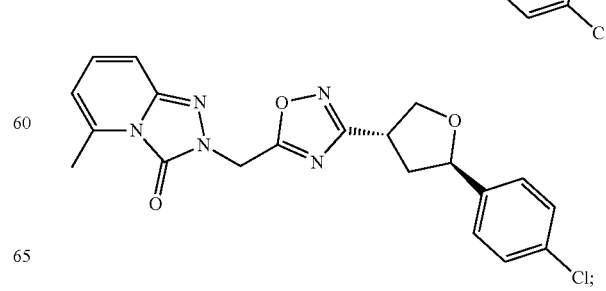

253
-continued
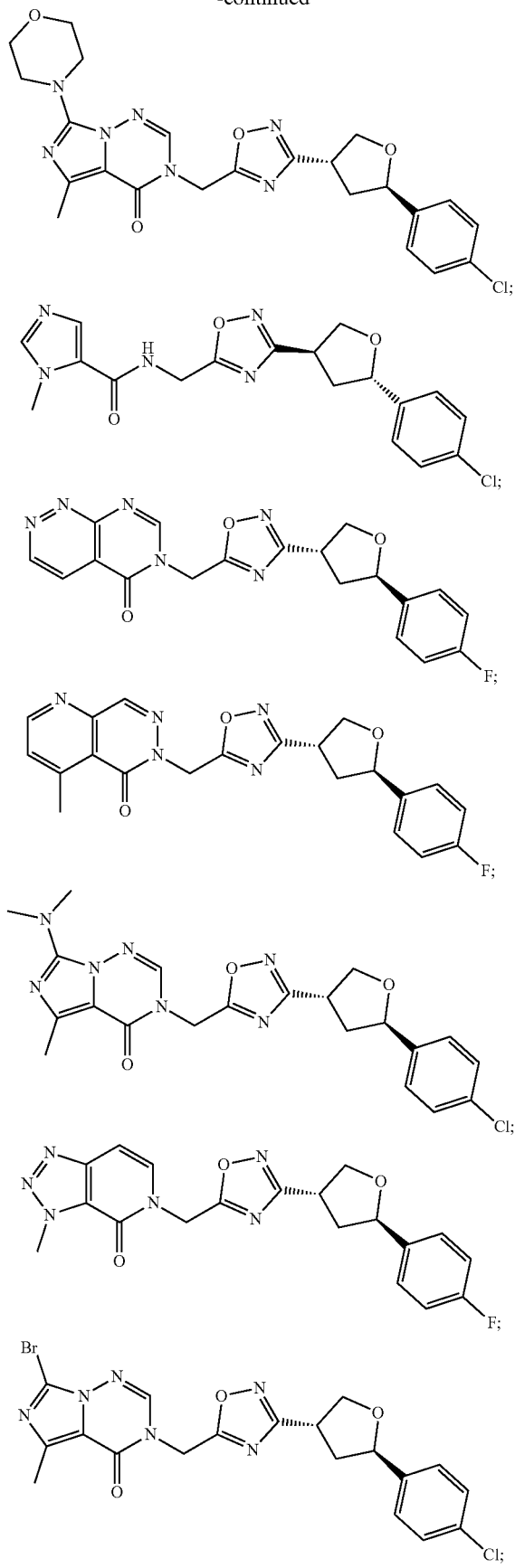
254
-continued
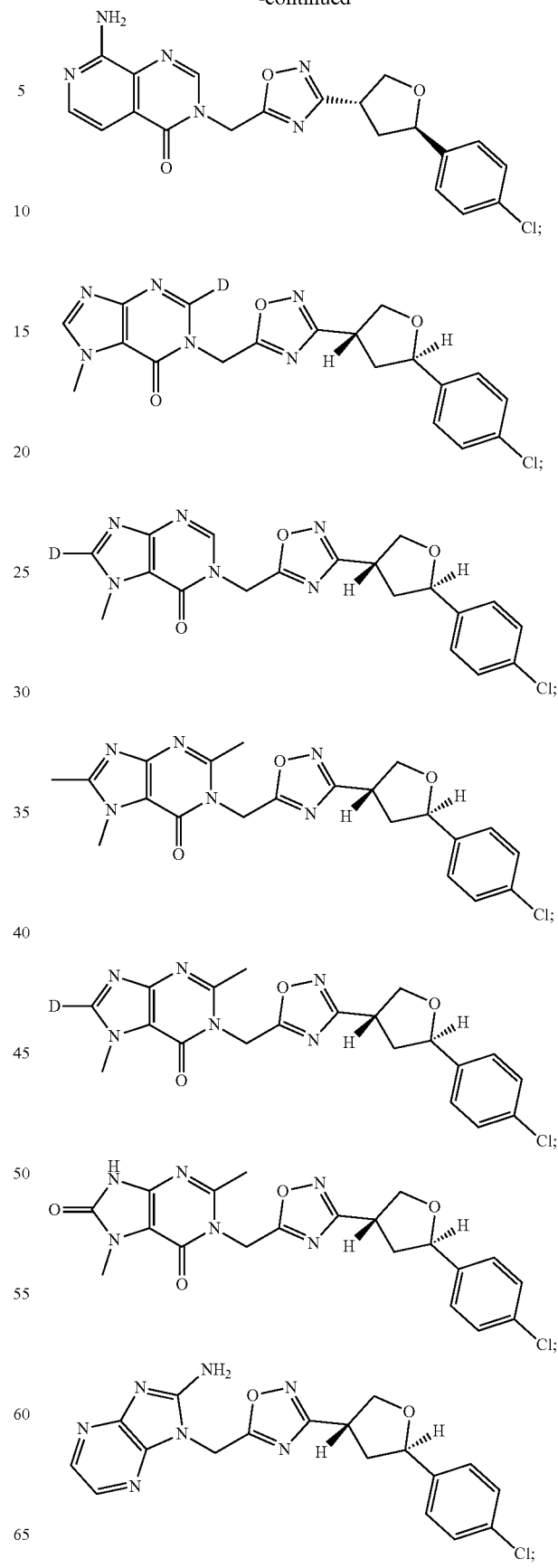

255
-continued
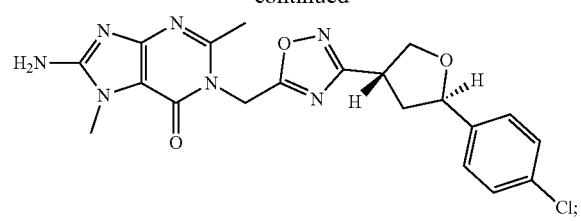
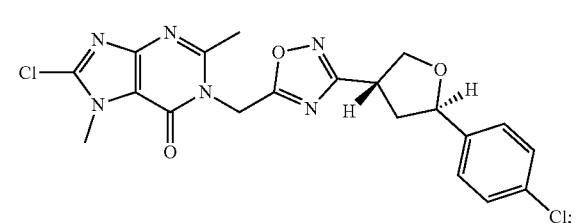
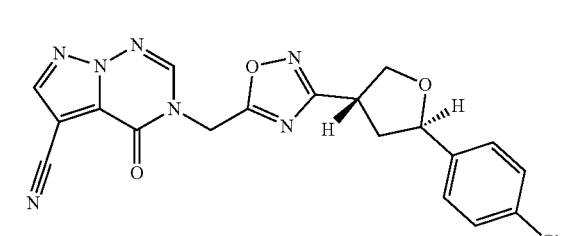
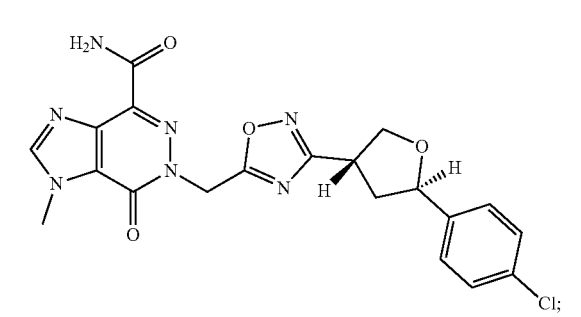
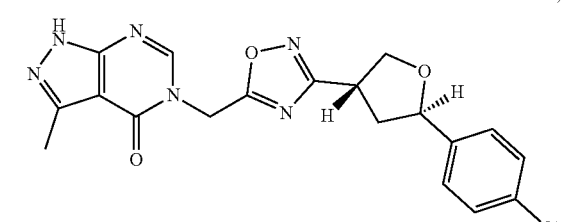
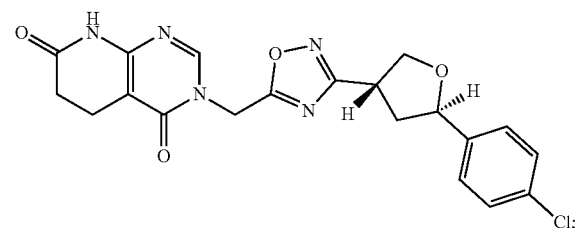
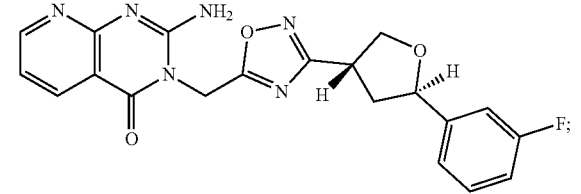
256
-continued
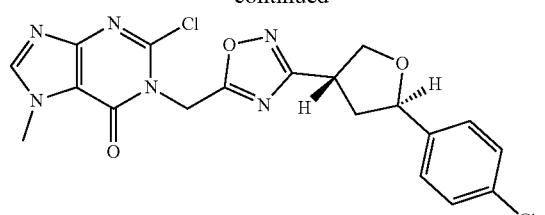
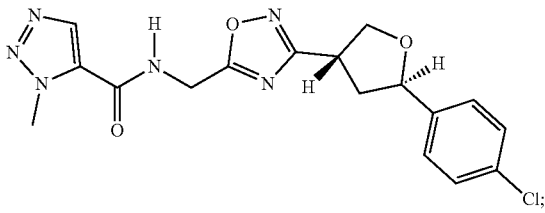
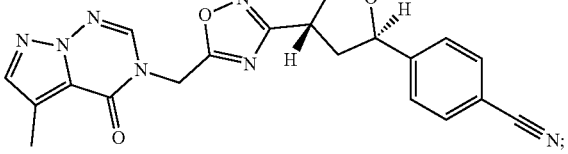
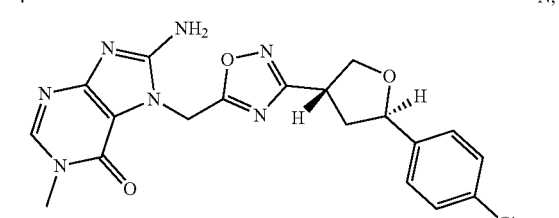
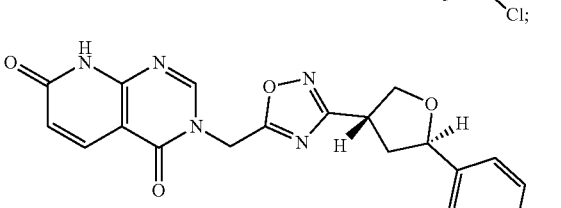
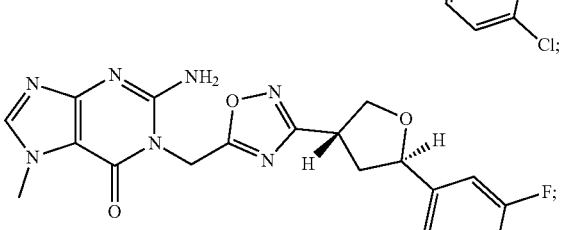
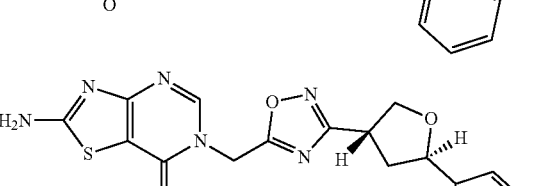
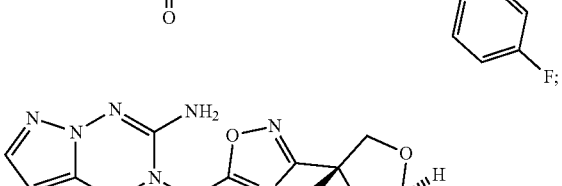
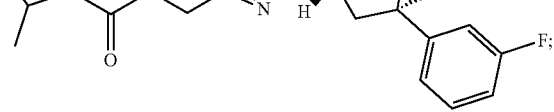

257
-continued
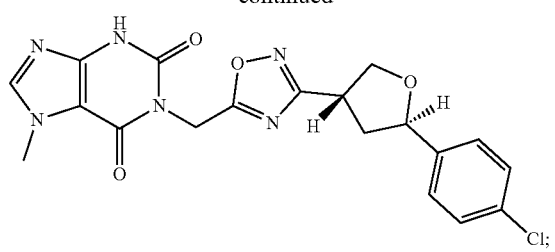
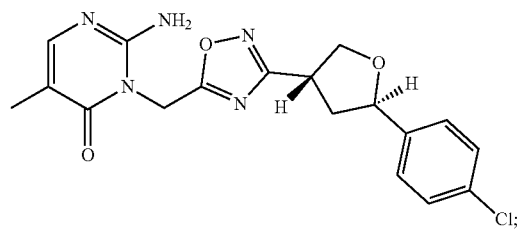
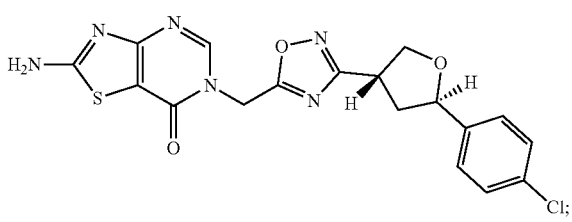
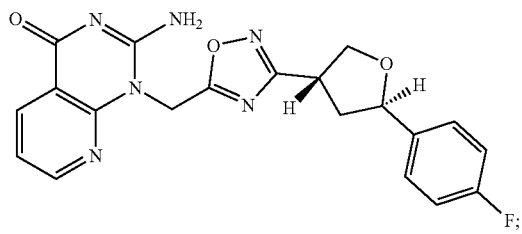
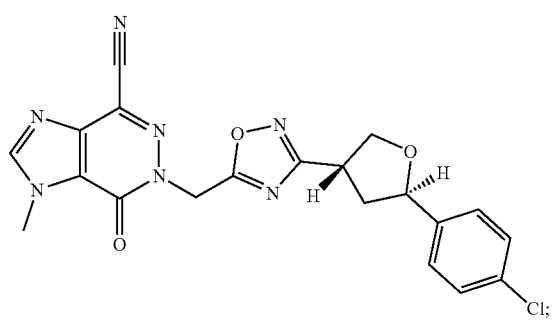
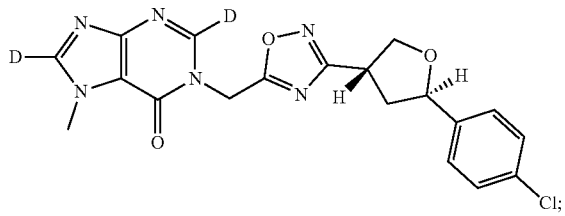
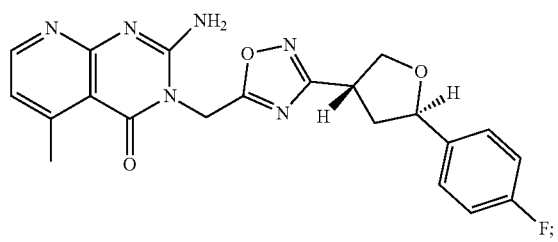
258
-continued
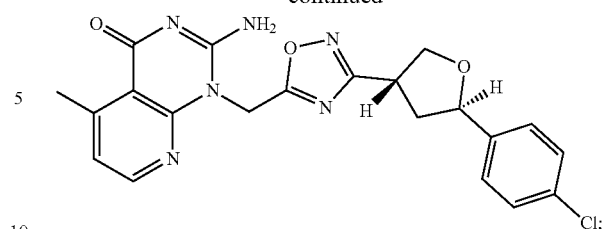
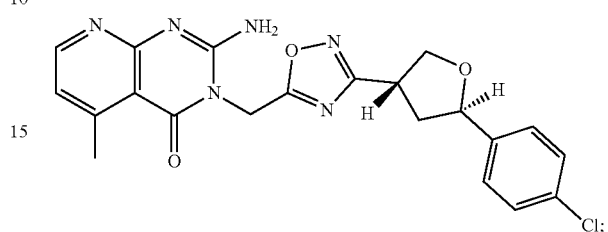
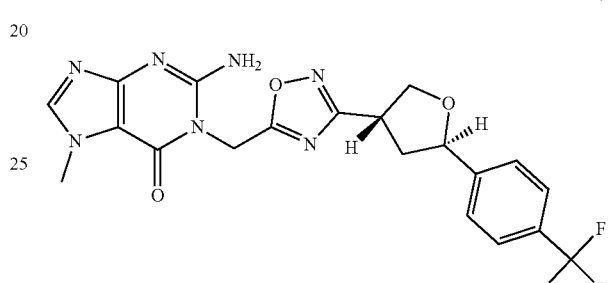
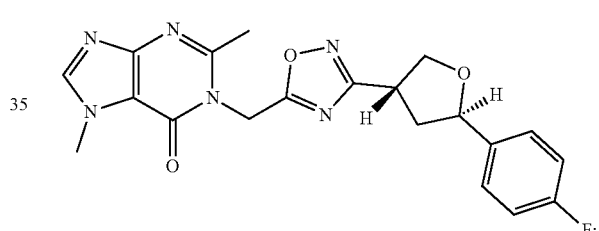
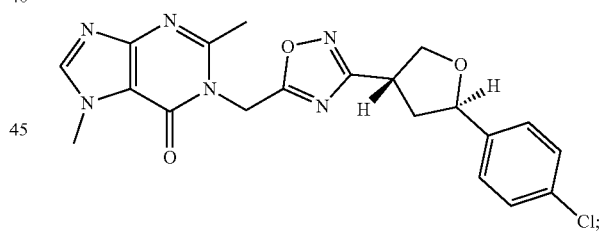
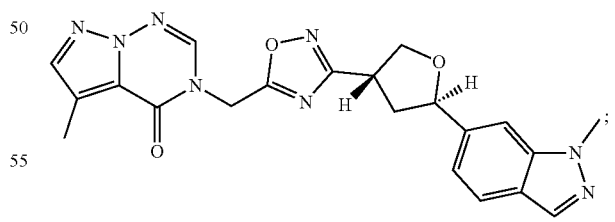
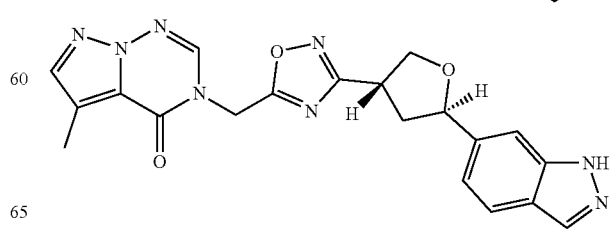

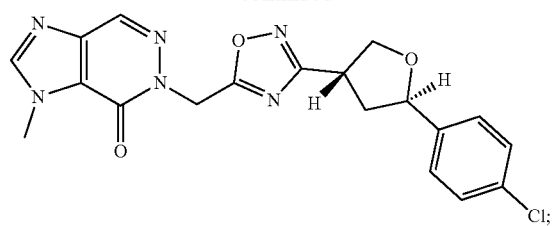
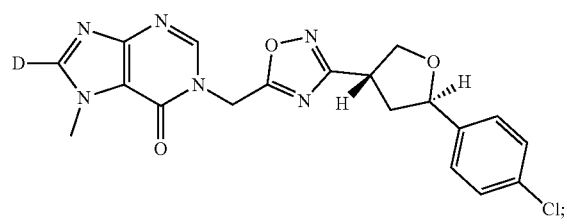
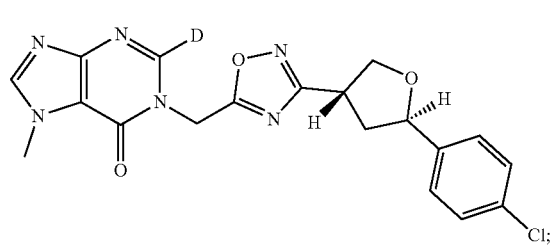
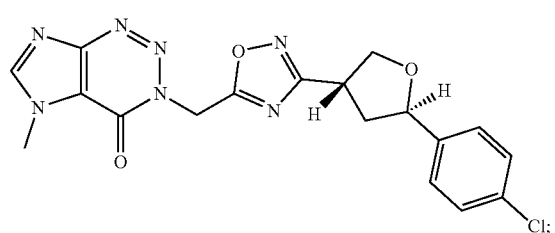
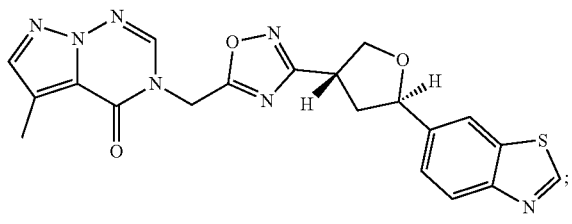
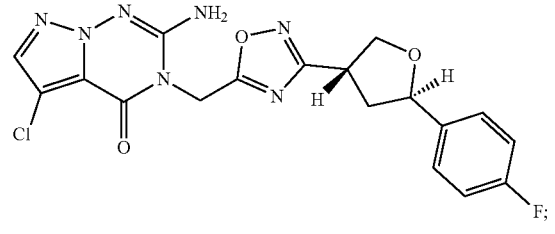
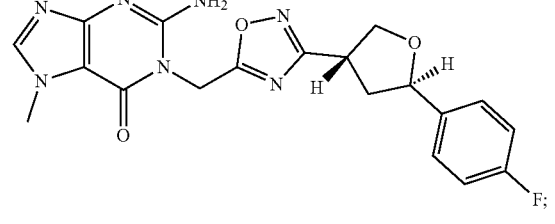
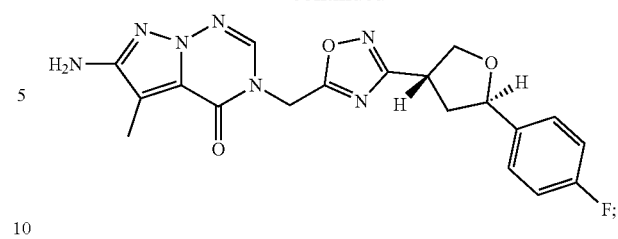
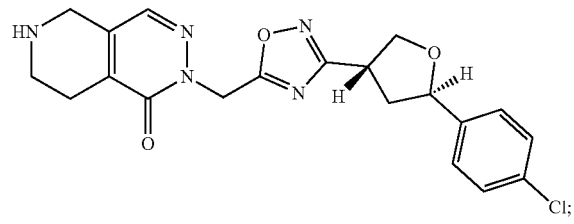
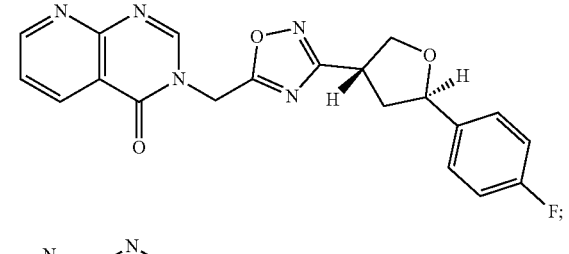
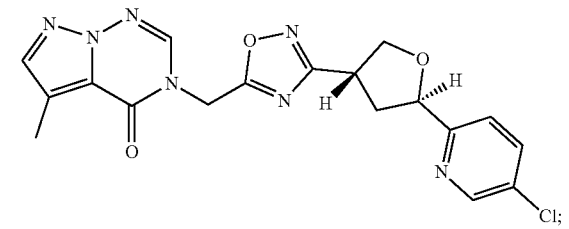
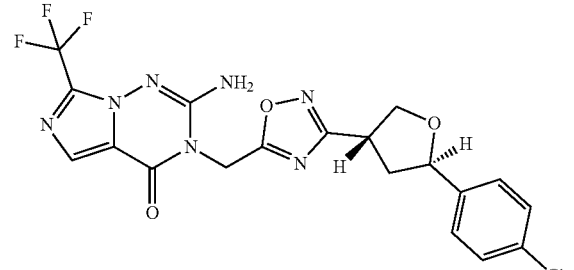
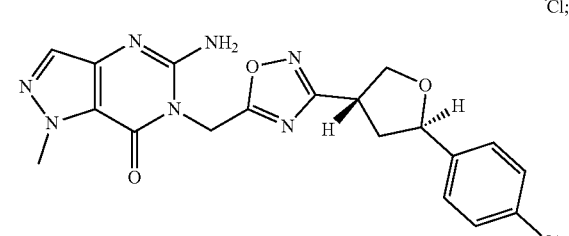
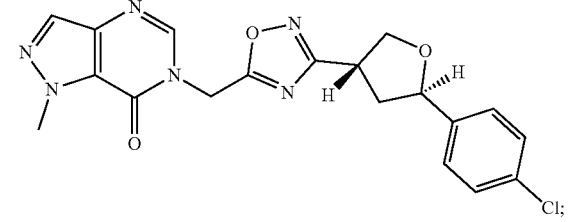

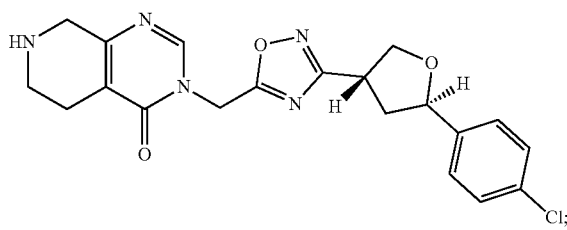

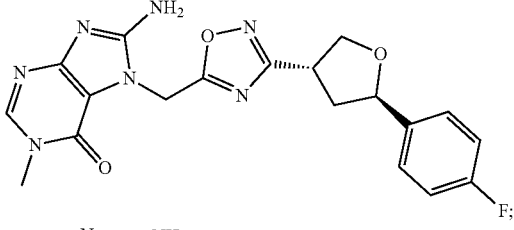

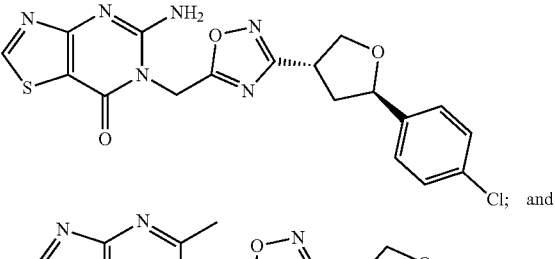

or a pharmaceutical salt thereof.

21. A pharmaceutical composition, comprising a compound as described in claim 1 or a pharmaceutically acceptable salt thereof, and a pharmaceutically acceptable carrier, diluent or excipient.

22. The compound of claim 1, or a pharmaceutical salt thereof, wherein A is:

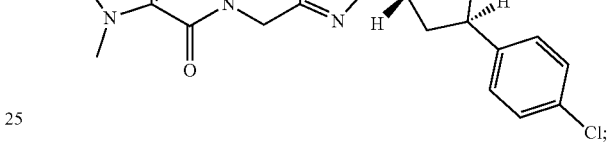

23. The compound of claim 3, or a pharmaceutical salt thereof, wherein A is:

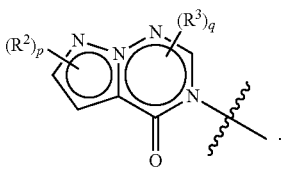

24. The compound of claim 3, or a pharmaceutical salt thereof, wherein A is:

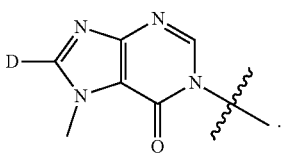 [SMILES: *n1cnc2nc([2H])n(C)c2c1=O]

25. The compound of claim 3, or a pharmaceutical salt thereof, wherein A is:

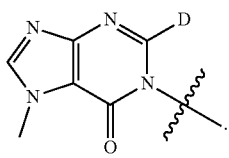 [SMILES: *n1c([2H])nc2ncn(C)c2c1=O]

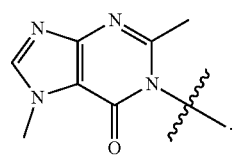
26. The compound of claim 3, or a pharmaceutical salt thereof, wherein A is:
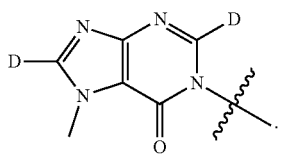
27. The compound of claim 3, or a pharmaceutical salt thereof, wherein A is:
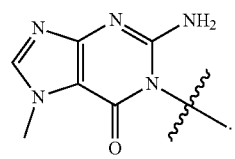 [SMILES: *n1c(N)nc2ncn(C)c2c1=O]
28. The compound of claim 22, or a pharmaceutical salt thereof, wherein A is:
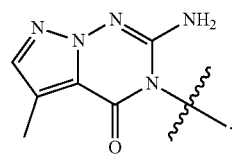 [SMILES: *n1c(N)nn2ncc(C)c2c1=O]
29. The compound of claim 20, wherein the compound is selected from:
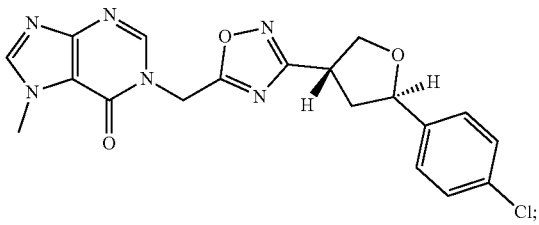
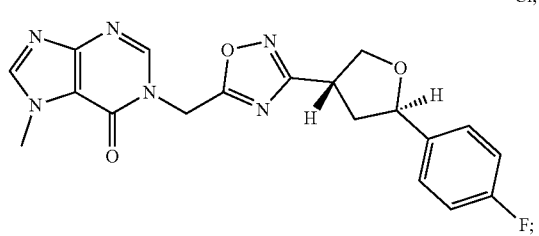
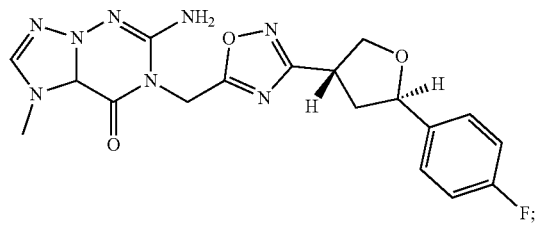
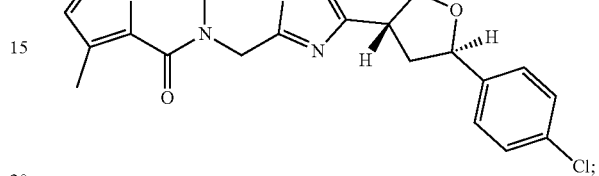
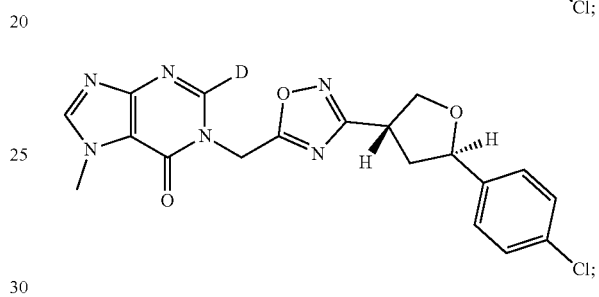
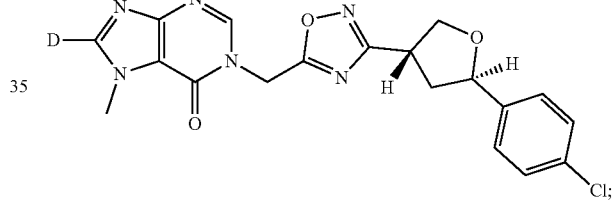
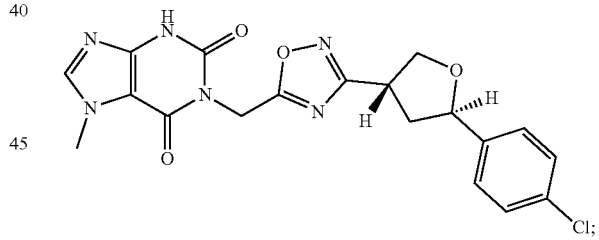
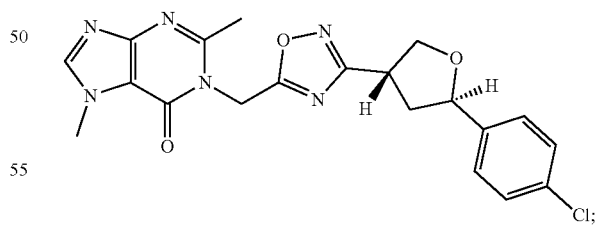
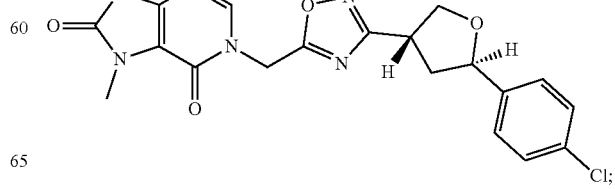

265
-continued
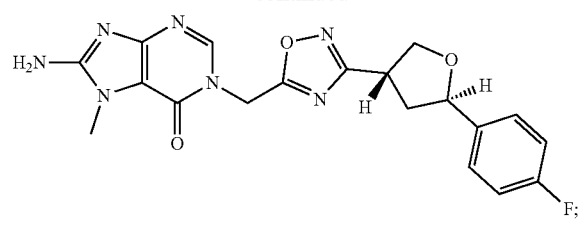
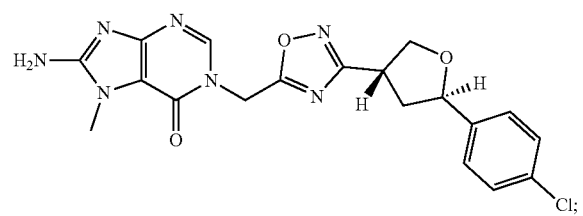
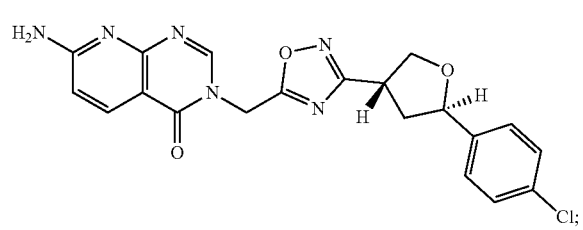
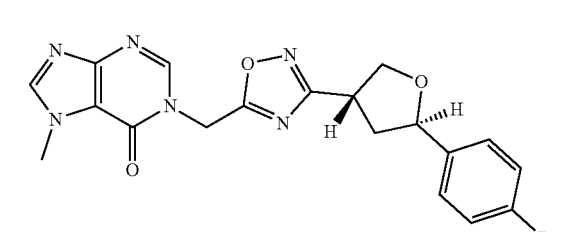
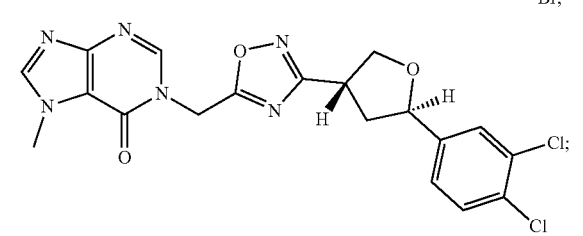
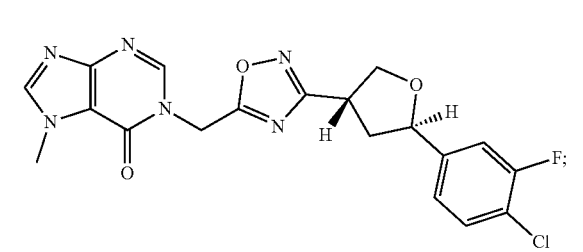
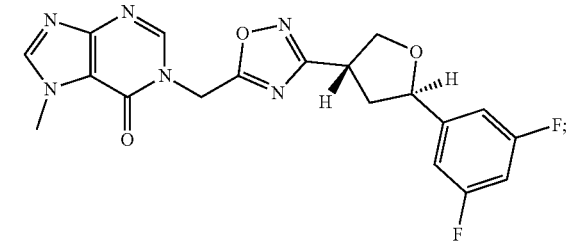
266
-continued
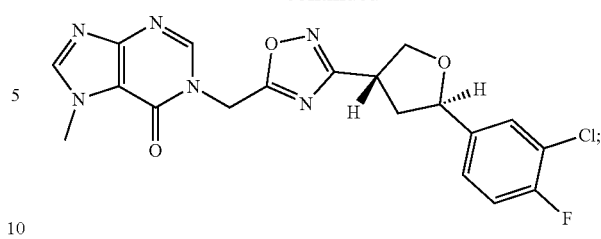
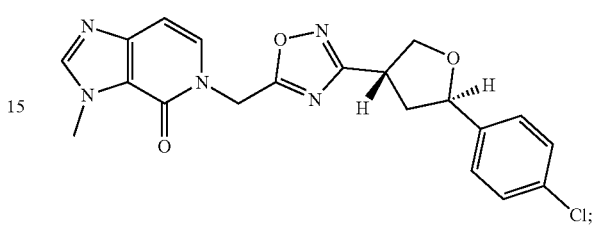
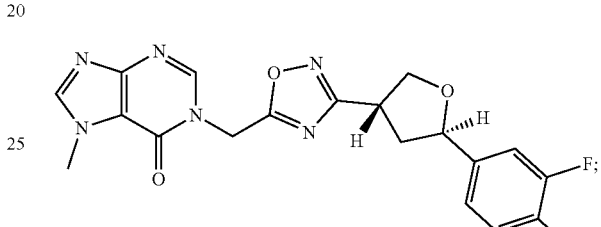
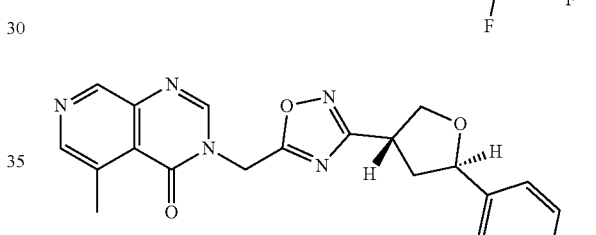
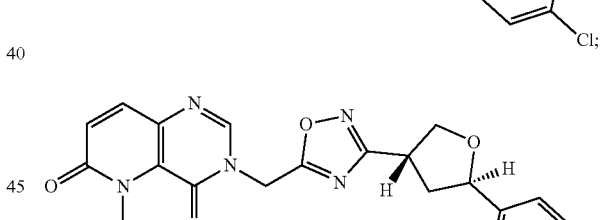
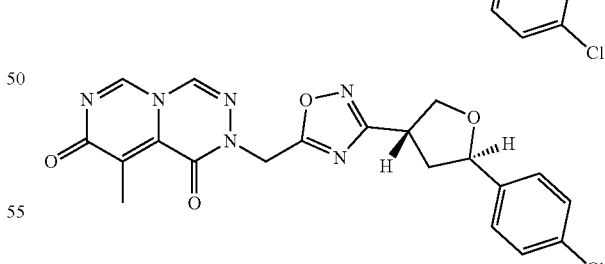
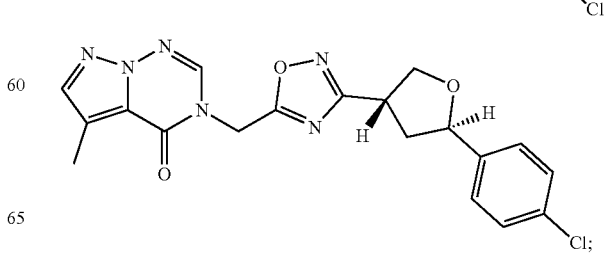

267
-continued
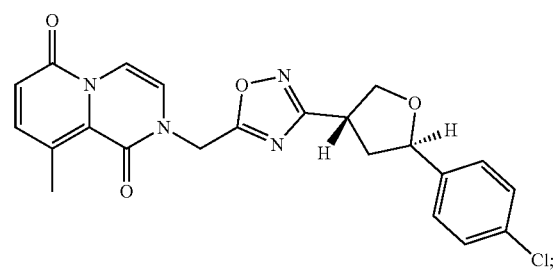
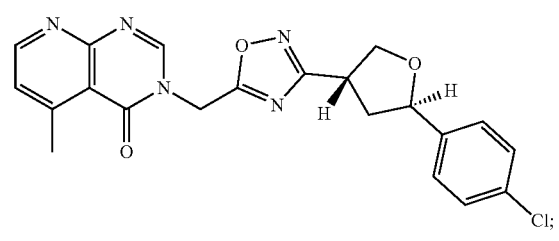
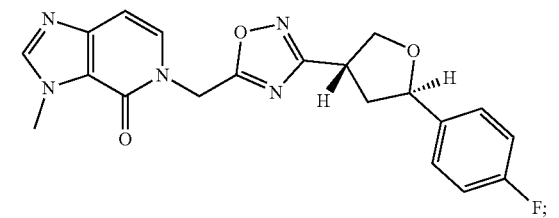
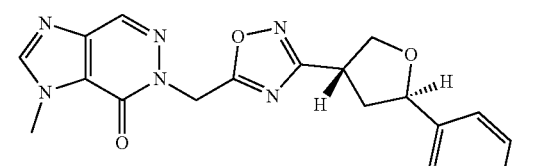
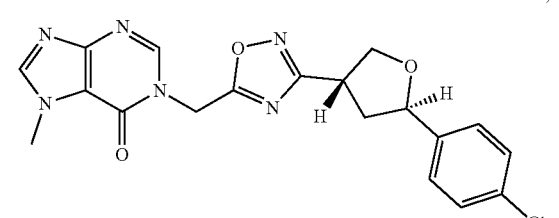
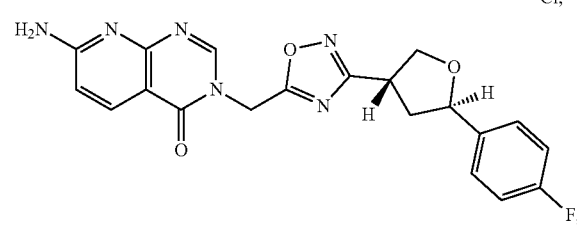
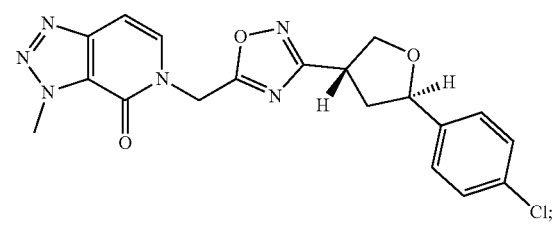
268
-continued
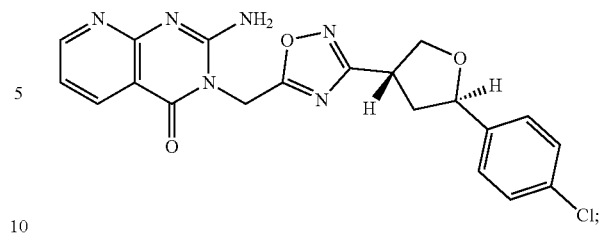
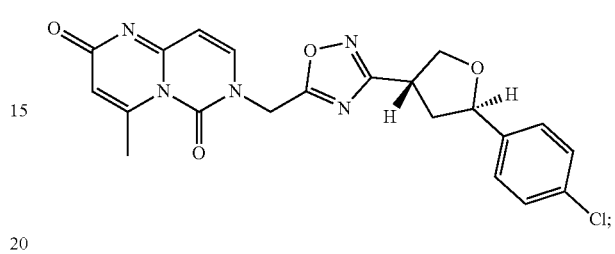
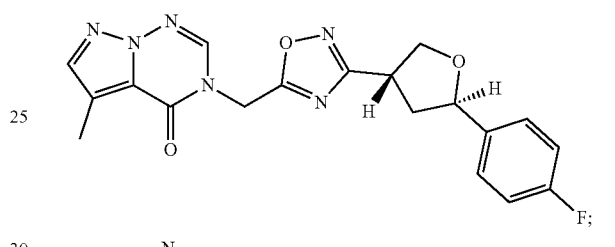
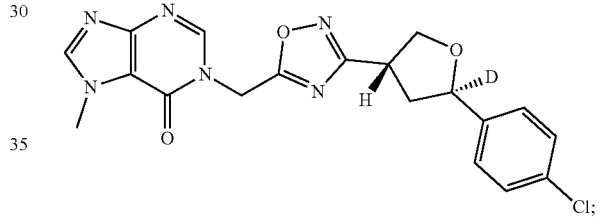
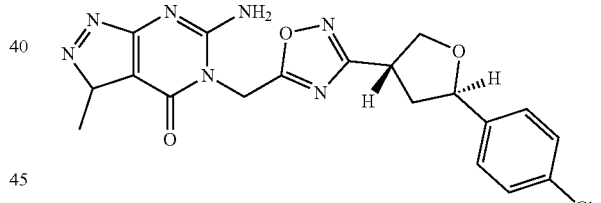
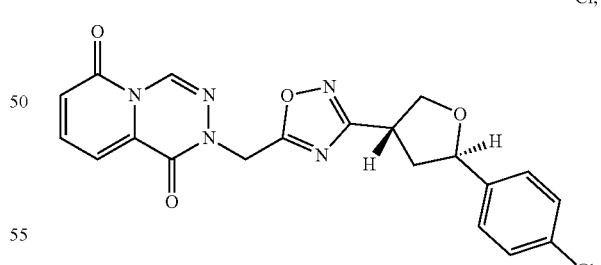
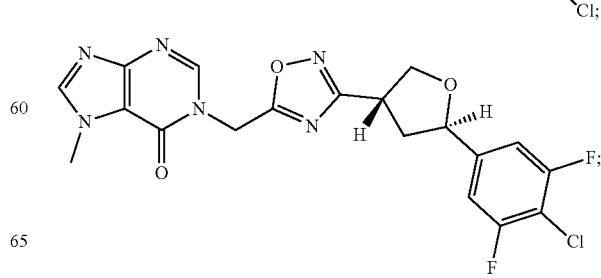

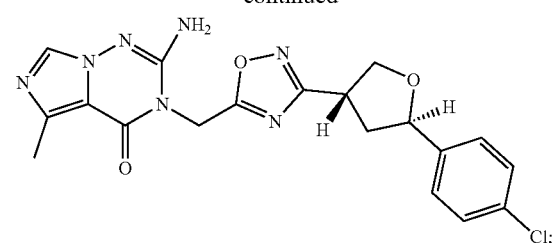
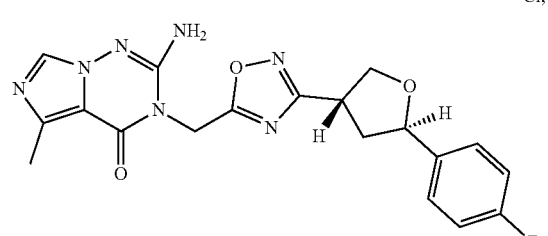
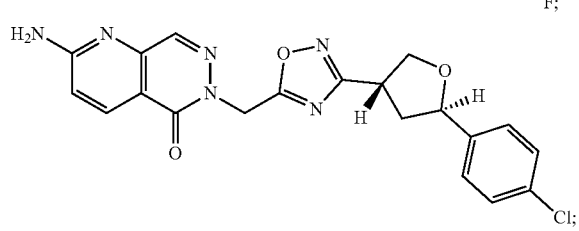
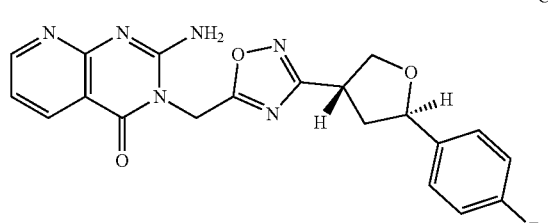
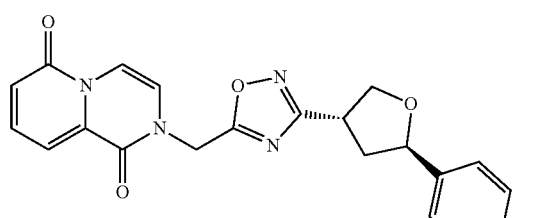
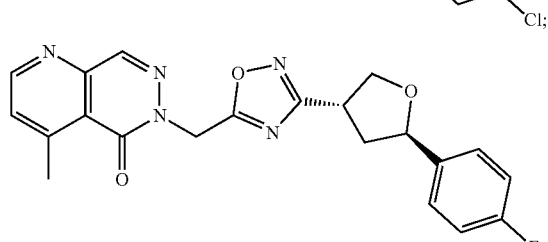
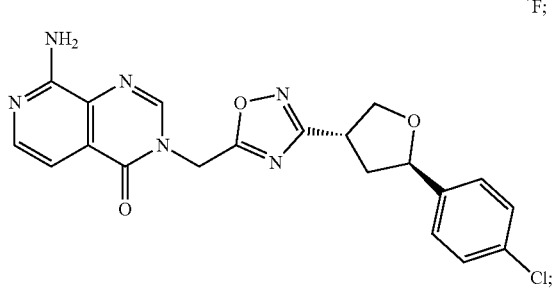
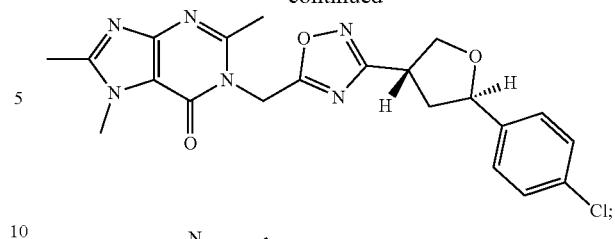
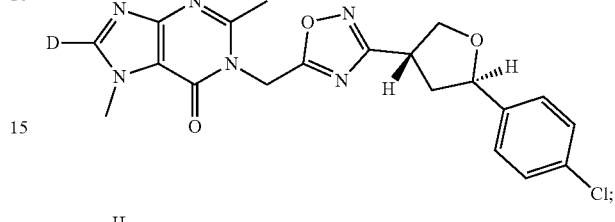
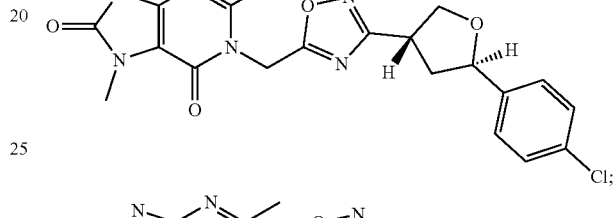
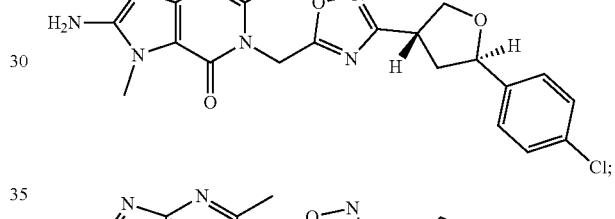
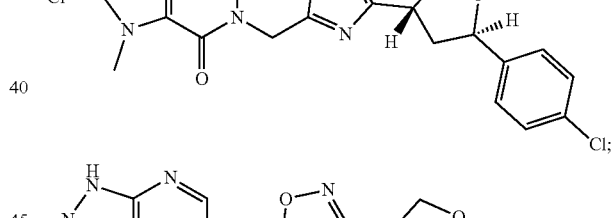
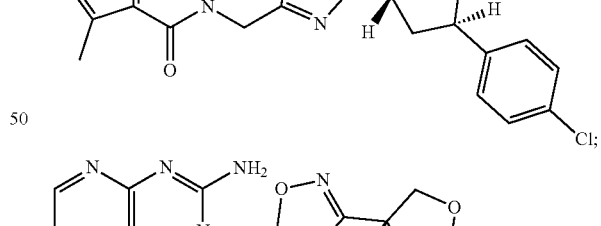
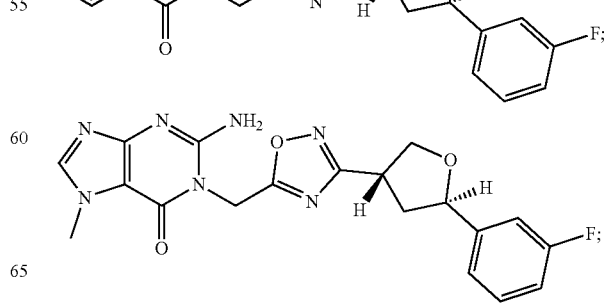

271
-continued
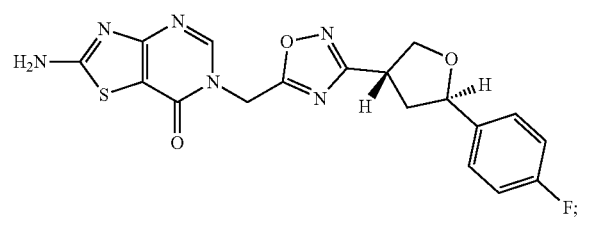
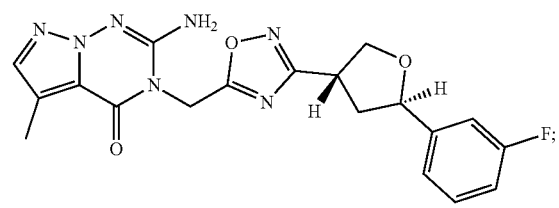
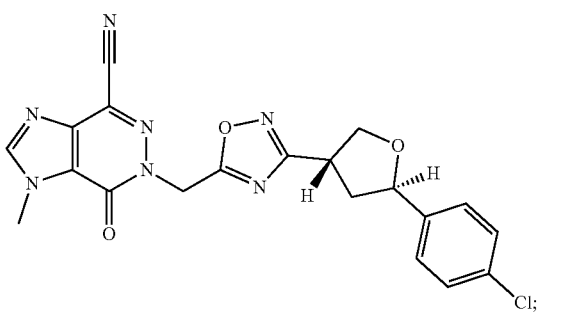
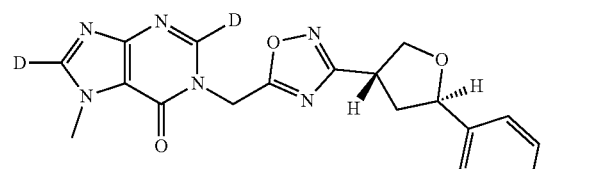
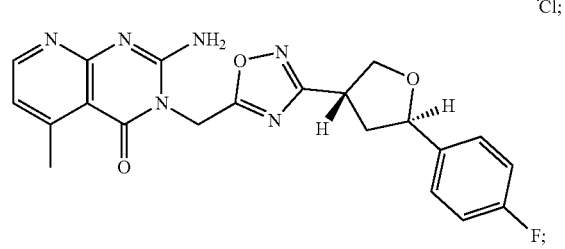
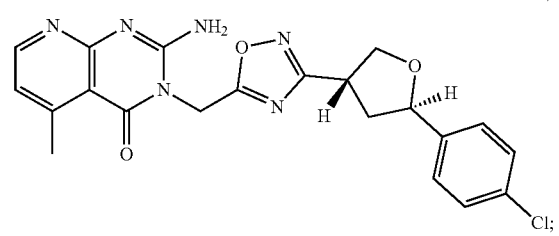
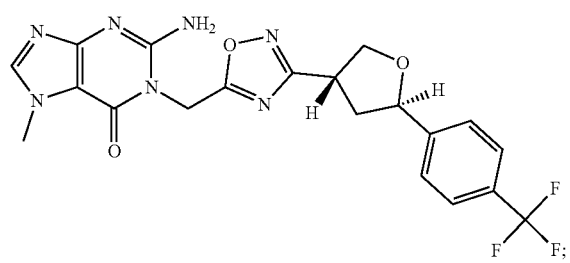
272
-continued
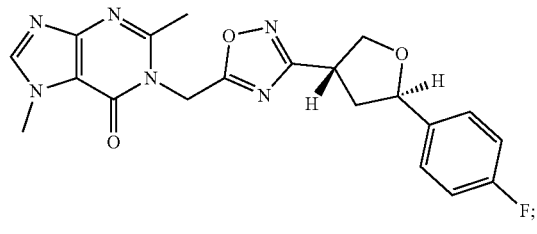
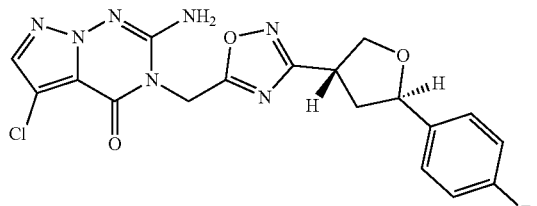
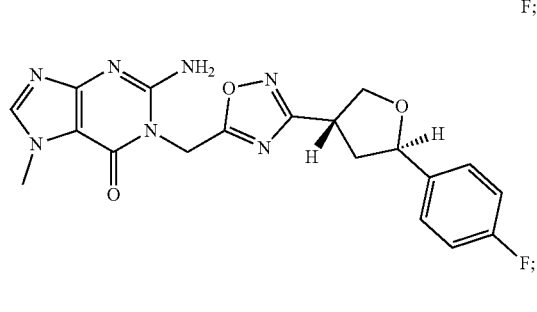
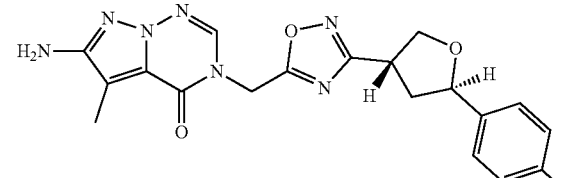
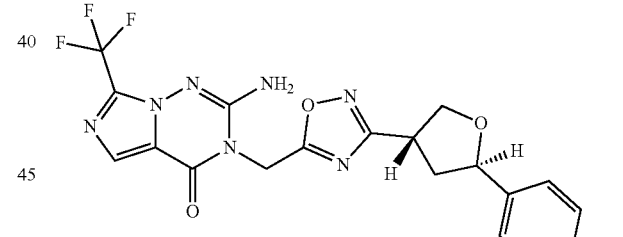
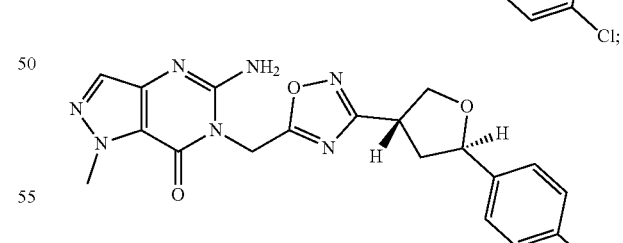
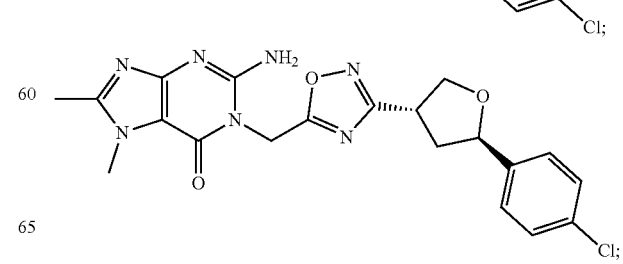

or a pharmaceutically acceptable salt thereof.

30. The compound of claim 20, wherein the compound is selected from:

275
-continued
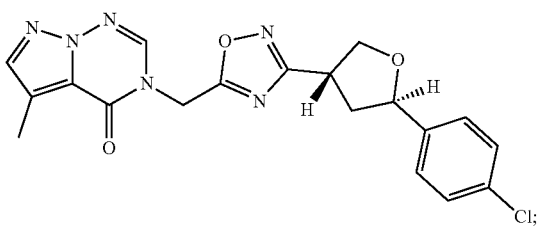
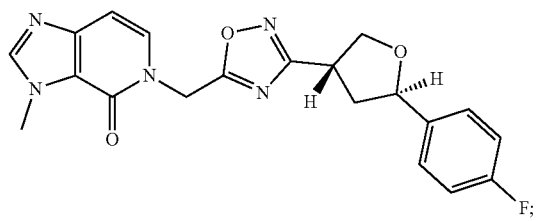
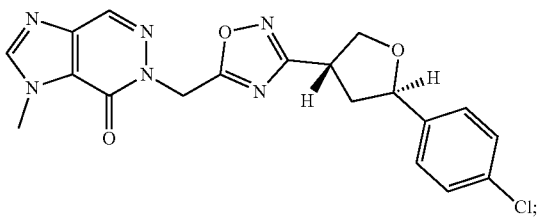
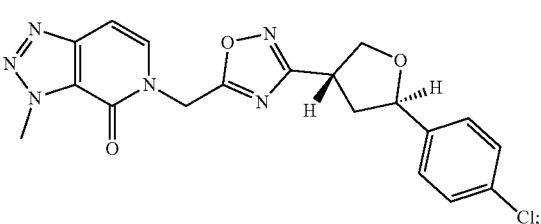
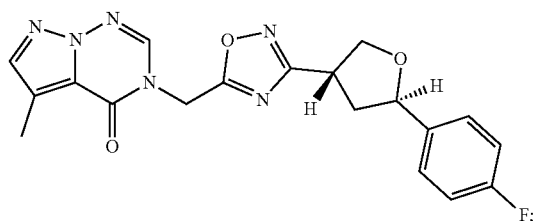
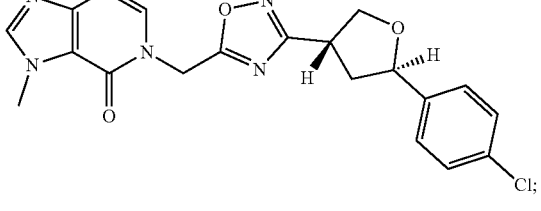
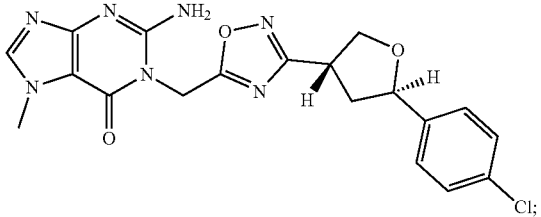
276
-continued
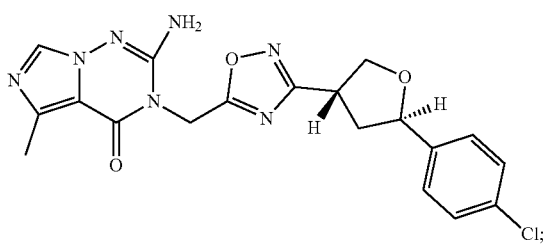

277
-continued
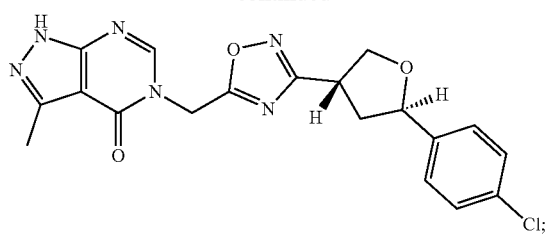
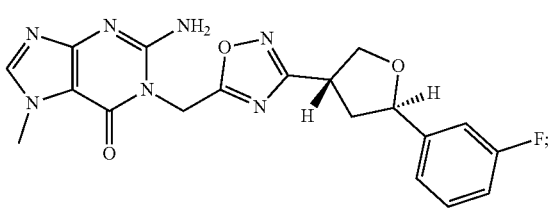
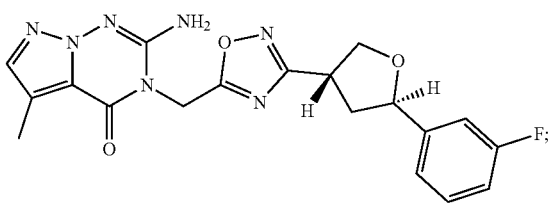
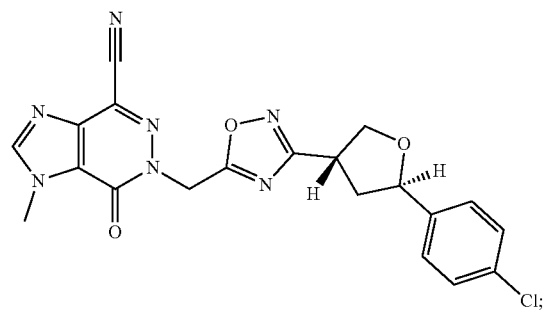
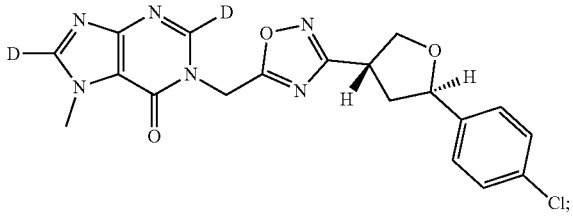
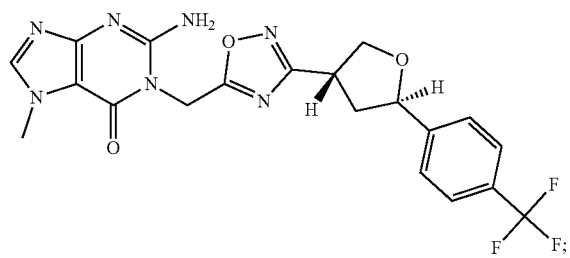
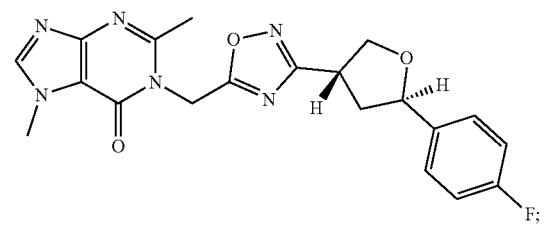
278
-continued
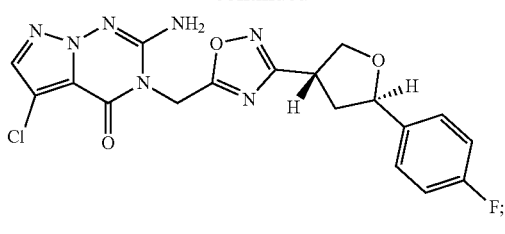
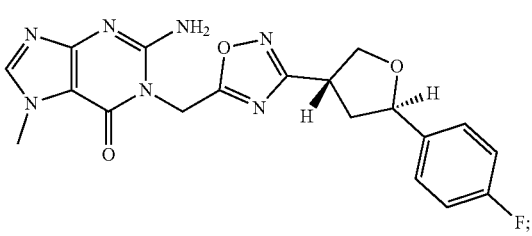
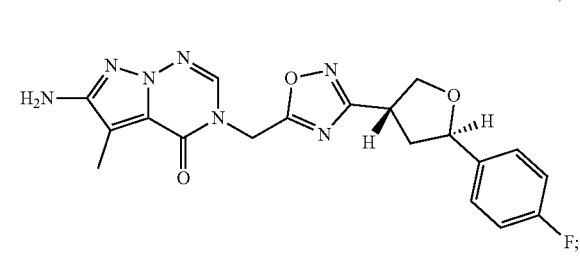
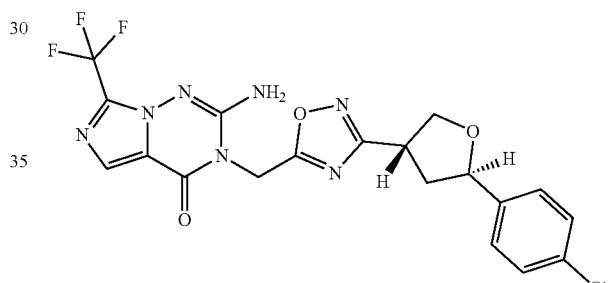
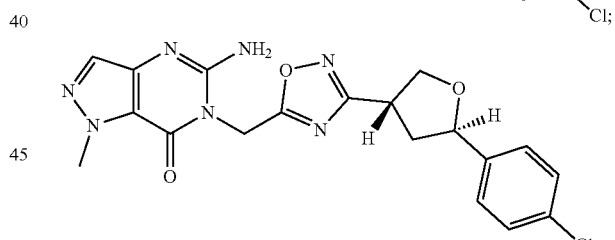
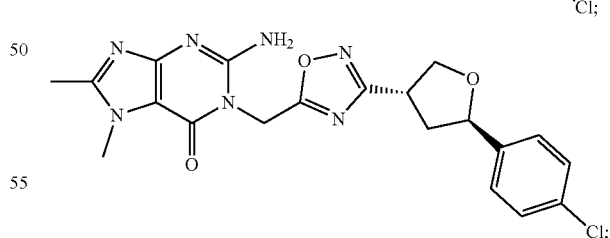
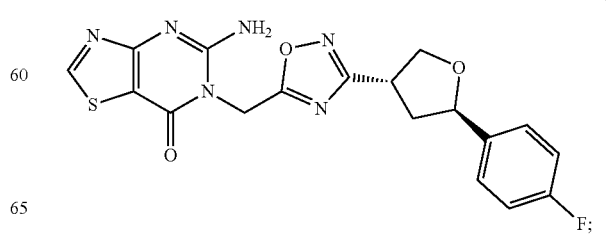

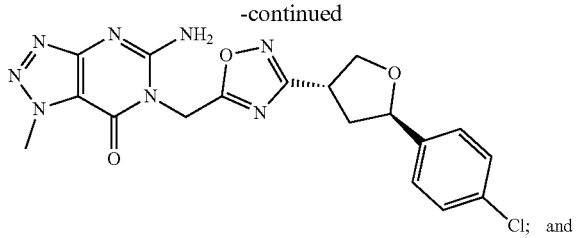
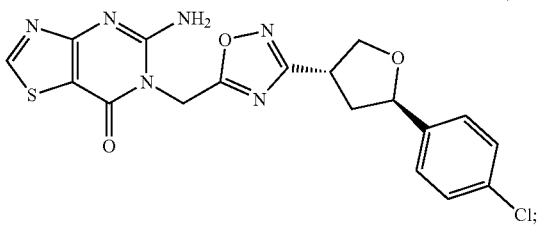
or a pharmaceutically acceptable salt thereof.
31. The compound of claim 20, wherein the compound is selected from:
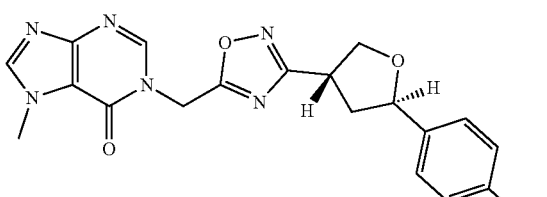
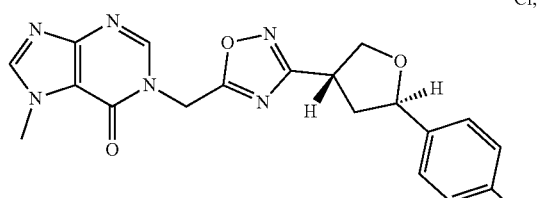
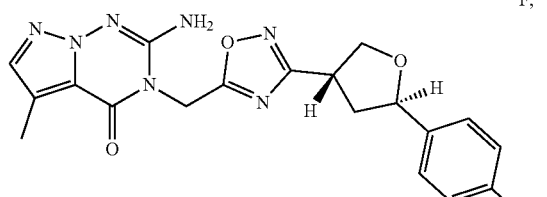
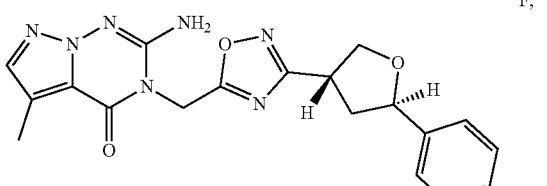
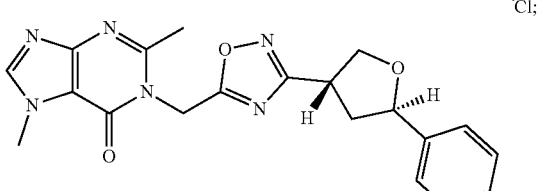
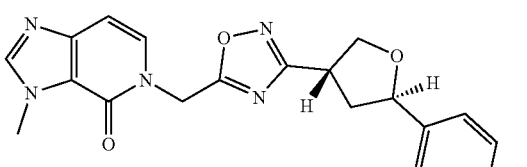
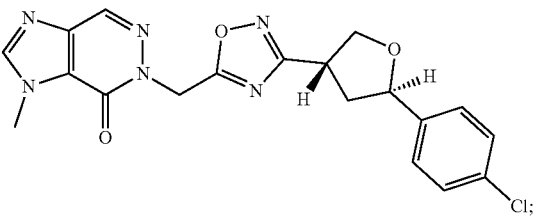
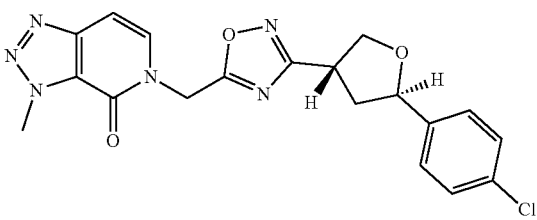
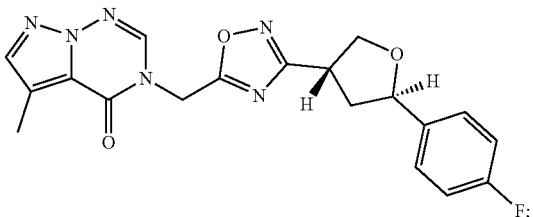
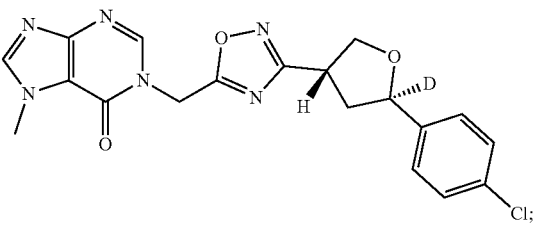

-continued
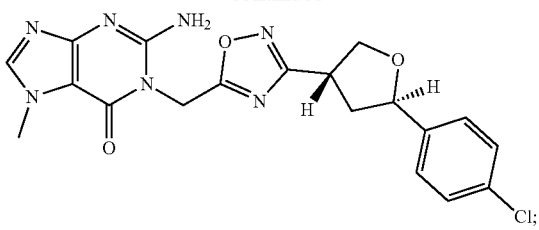
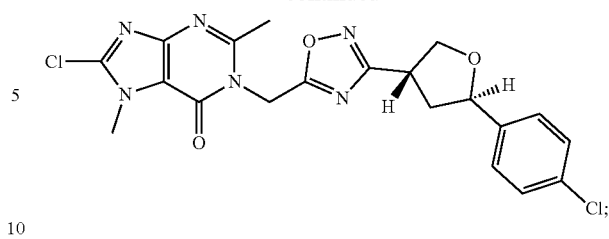
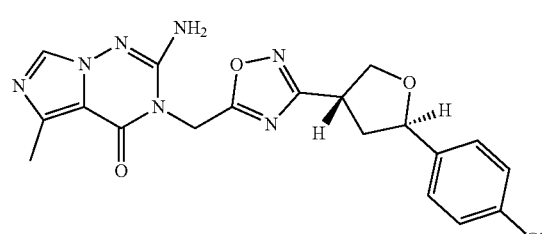
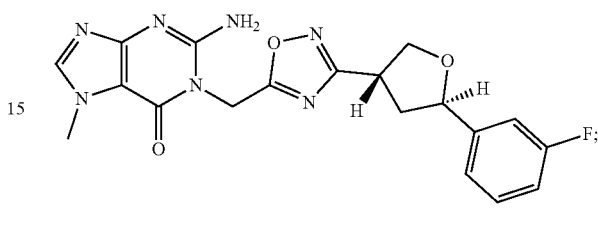
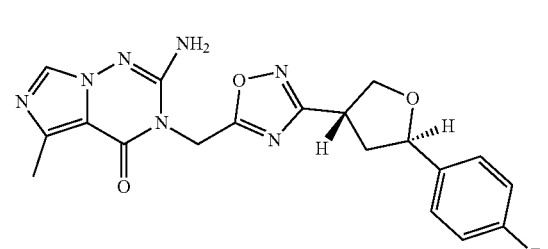
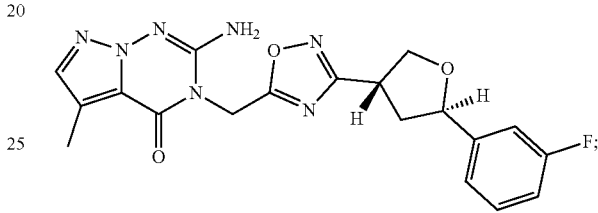
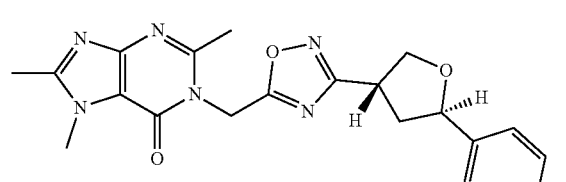
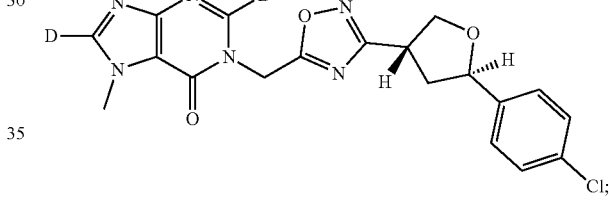
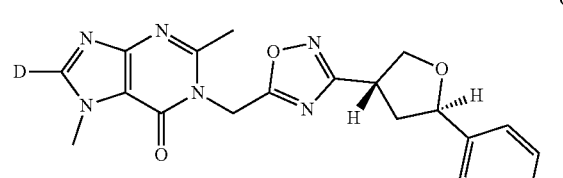
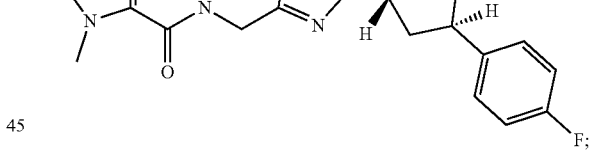
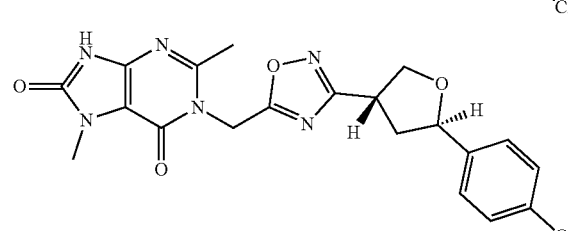
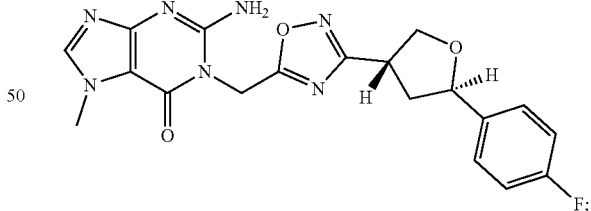
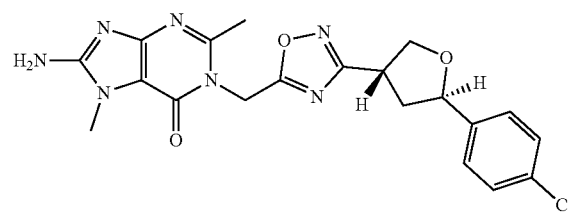
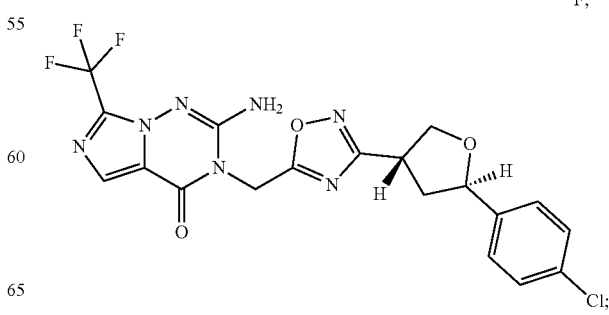

-continued

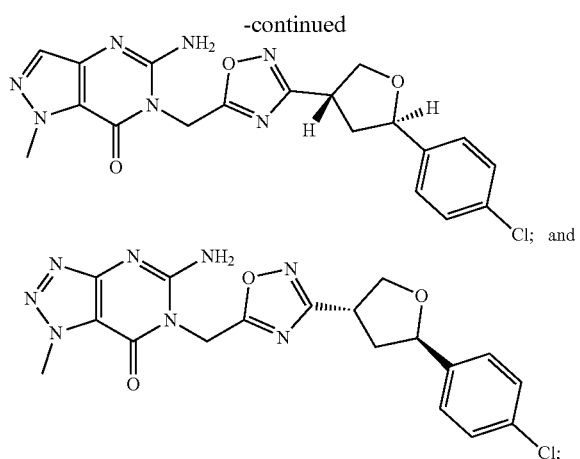

Cl; and

Cl;

or a pharmaceutically acceptable salt thereof.

32. The compound

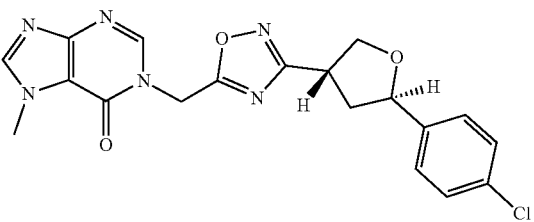 [SMILES: Cn1cnc2ncn(Cc3nc([C@@H]4CO[C@@H](c5ccc(Cl)cc5)C4)no3)c(=O)c21]

or a pharmaceutically acceptable salt thereof.

33. The compound

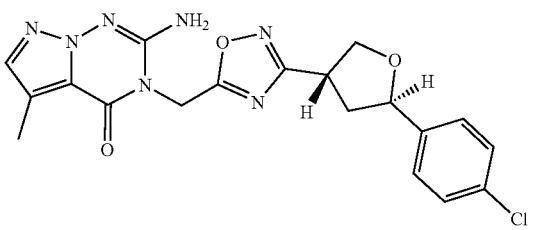 [SMILES: Cc1cnn2nc(N)n(Cc3nc([C@@H]4CO[C@@H](c5ccc(Cl)cc5)C4)no3)c(=O)c12]

or a pharmaceutically acceptable salt thereof.

34. The compound

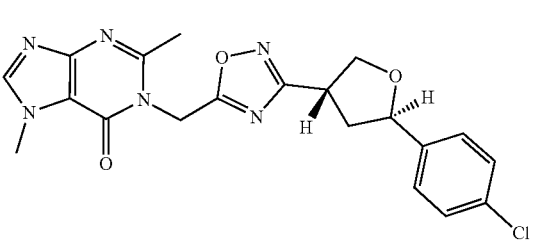 [SMILES: Cc1nc2ncn(C)c2c(=O)n1Cc1nc([C@@H]2CO[C@@H](c3ccc(Cl)cc3)C2)no1]

or a pharmaceutically acceptable salt thereof.

35. The compound

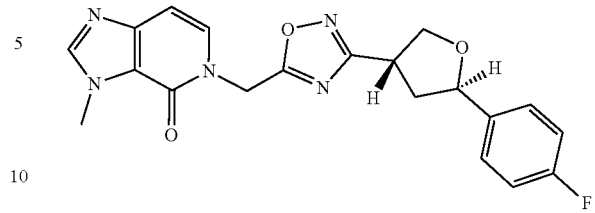

or a pharmaceutically acceptable salt thereof.

36. The compound

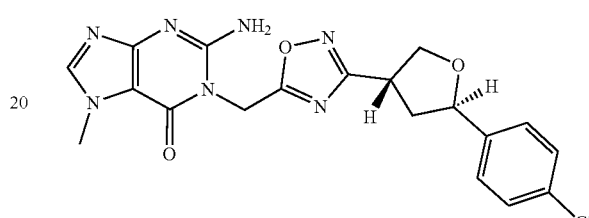

or a pharmaceutically acceptable salt thereof.

37. The compound

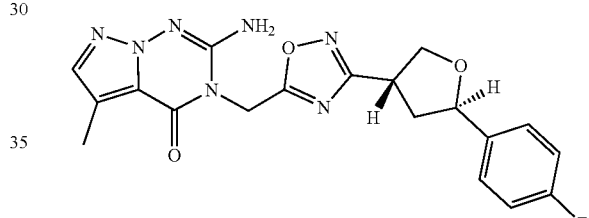

or a pharmaceutically acceptable salt thereof.

38. The compound

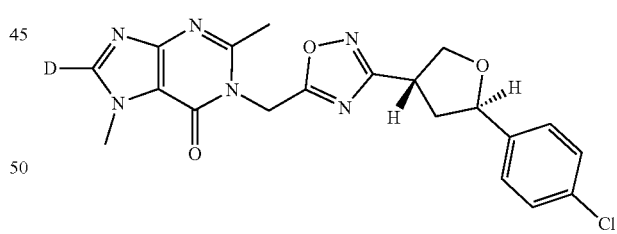

or a pharmaceutically acceptable salt thereof.

* * * * *